(12) United States Patent
Wustrow et al.

(10) Patent No.: US 9,868,722 B2
(45) Date of Patent: Jan. 16, 2018

(54) MONOCYCLIC PYRIMIDINE/PYRIDINE COMPOUNDS AS INHIBITORS OF P97 COMPLEX

(71) Applicant: Cleave Biosciences, Inc., Burlingame, CA (US)

(72) Inventors: David Wustrow, Los Gatos, CA (US); Han-Jie Zhou, Foster City, CA (US)

(73) Assignee: Cleave Biosciences, Inc., Burlingame, CA (US)

( * ) Notice: Subject to any disclaimer, the term of this patent is extended or adjusted under 35 U.S.C. 154(b) by 0 days.

(21) Appl. No.: 15/103,828

(22) PCT Filed: Dec. 10, 2014

(86) PCT No.: PCT/US2014/069598
§ 371 (c)(1),
(2) Date: Jun. 10, 2016

(87) PCT Pub. No.: WO2015/089218
PCT Pub. Date: Jun. 18, 2015

(65) Prior Publication Data
US 2016/0304495 A1  Oct. 20, 2016

Related U.S. Application Data

(60) Provisional application No. 61/929,382, filed on Jan. 20, 2014, provisional application No. 61/914,084, filed on Dec. 10, 2013.

(51) Int. Cl.
*C07D 403/04* (2006.01)
*A61K 31/506* (2006.01)

(52) U.S. Cl.
CPC .......... *C07D 403/04* (2013.01); *A61K 31/506* (2013.01)

(58) Field of Classification Search
CPC .......................... C07D 403/04; A61K 31/506
USPC ................................ 544/328; 514/256, 275
See application file for complete search history.

(56) References Cited

U.S. PATENT DOCUMENTS

| 2006/0030612 A1 | 2/2006 | Steffan et al. |
| 2008/0085898 A1 | 4/2008 | Lu et al. |
| 2011/0237590 A1 | 9/2011 | Kitamura et al. |
| 2016/0332990 A1 | 11/2016 | Zhou et al. |

FOREIGN PATENT DOCUMENTS

| CN | 106458996 A | 2/2017 |
| EP | 0640599 A1 | 3/1995 |
| EP | 2338888 A1 | 6/2011 |
| IN | 201617026874 A | 8/2016 |
| JP | 2004303057 A | 10/2004 |
| JP | 2017505812 A | 2/2017 |
| KR | 1020010091827 A | 10/2001 |
| KR | 1020020020316 A | 3/2002 |
| KR | 1020030009830 A | 2/2003 |
| TW | 201605832 A | 2/2016 |
| TW | 201605833 A | 2/2016 |
| WO | WO-2008040753 A1 | 4/2008 |
| WO | WO-2010072823 A1 | 7/2010 |
| WO | WO-2011101161 A1 | 8/2011 |
| WO | WO-2011115804 A1 | 9/2011 |
| WO | WO-2011140527 A2 | 11/2011 |
| WO | WO-2014015291 A1 | 1/2014 |
| WO | WO-2015089218 A1 | 6/2015 |
| WO | WO-2015109285 A1 | 7/2015 |

OTHER PUBLICATIONS

Gura et al., Systems for identifying new drugs are often faulty, Science, 278:1041-1042, 1997.*
Johnson et al., Relationships between drug activity in NCI preclinical in vitro and in vivo models and early clinical trials, British Journal of Cancer, 84(10):1424-1431,2001.*
Pearce et al., Failure modes in anticancer drug discovery and development, Cancer Drug Design and Discovery Edited by Stephen Neidle, Chapter 18, pp. 424-435 (2008).*
Simone, Oncology: Introduction, Cecil Textbook of Medicine, 20th Edition, vol. 1, pp. 1004-1101 O, 1995.*
Database Registry, Ref. No. 1360239-22-0, Chemical Abstracts Service, Columbus, OH (Mar. 7, 2012), 1 p.
International Application Serial No. PCT/US2014/069598, International Preliminary Report on Patentability dated Feb. 26, 2016, 10 pgs.
International Application Serial No. PCT/US2014/069598, International Search Report dated Mar. 4, 2015, 6 pgs.
International Application Serial No. PCT/US2014/069598, Written Opinion dated Mar. 4, 2015, 7 pgs.
International Application Serial No. PCT/US2014/069598, Written Opinion dated Nov. 11, 2015, 9 pgs.
International Application Serial No. PCT/US2015/011921, International Preliminary Report on Patentability dated Apr. 11, 2016, 13 pgs.
International Application Serial No. PCT/US2015/011921, International Search Report dated Mar. 30, 2015, 6 pgs.
International Application Serial No. PCT/US2015/011921, Written Opinion dated Mar. 30, 2015, 9 pgs.
International Application Serial No. PCT/US2015/011921,Written Opinion dated Feb. 11, 2016, 8 pgs.
Taiwanese Application Serial No. 103143184, Notice of Preliminary Rejection dated Apr. 15, 2015, 7 pgs.
Chou, Tsui-Fen, et al., "Structure-Activity Relationship Study Reveals ML240 and ML241 as Potent and Selective Inhibitors of p97 ATPase", ChemMedChem, 8(2), (2013), 297-312.

(Continued)

*Primary Examiner* — Deepak Rao
(74) *Attorney, Agent, or Firm* — Schwegman Lundberg & Woessner. P.A.

(57) ABSTRACT

Monocyclic pyrimidine and pyridine compounds having a benzyl amine substituent at the 4 position and a 5:6 bicyclic heteroaryl substituent at the 2 position of the pyrimidine or pyridine ring as well as optional aliphatic, functional and/or aromatic components substituted at other positions of the ring are disclosed. These compounds are inhibitors of the AAA proteasome complex containing p97 and are effective medicinal agents for treatment of diseases associated with p97 bioactivity such as cancer.

12 Claims, No Drawings

(56) References Cited

OTHER PUBLICATIONS

Chou, Tsui-Fen, et al., "Structure-Activity Relationship Study Reveals ML240 and ML241 as Potent and Selective Inhibitors of p97 ATPase", ChemMedChem, 8(2), Supporting Information: table S9; compound S164 [retrieved on Feb. 23, 2015]., Retrieved from the Internet: <URL: http://onlinelibrary.wiley.com/store/10.1002/cmdc.201200520/asset/supinfo/cmdc_201200520_sm_miscellaneous_information.pdf?v=1&s=7106b4bdbaf65d12e11c89ab243b44199f715810 >, (Jan. 11, 2013), 175 p.

U.S. Appl. No. 15/112,659, Non Final Office Action dated Apr. 28, 2017, 13 pgs.

U.S. Appl. No. 15/112,659, Response dated Apr. 11, 2017 to Restriction Requirement dated Mar. 24, 2017, 26 pgs.

U.S. Appl. No. 15/112,659, Restriction Requirement dated Mar. 24, 2017, 8 pgs.

Australian Application Serial No. 2015206292, First Examiner Report dated Jan. 27, 2017, 4 pgs.

Australian Application Serial No. 2015206292, Response to First Examiner Report dated Apr. 20, 2017, 51 pgs.

European Application Serial No. 15705122.8 Response to Communication pursuant to Rules 161(1) and 162 EPC dated Apr. 5, 2017, 24 pgs.

New Zealand Application Serial No. 722624, Office Action dated Feb. 15, 2017, 4 pgs.

Haines, D.S., "p97-Containing Complexes in Proliferation Control and Cancer: Emerging Culprits or Guilt by Association?", Genes & Cancer, 1(7), (2010), 753-763.

Vekaria, P.H., et al., "Targeting p97 to Disrupt Protein Homeostasis in Cancer", Frontiers in Oncology, 6, (Aug. 2016), 8 pgs.

* cited by examiner

MONOCYCLIC PYRIMIDINE/PYRIDINE COMPOUNDS AS INHIBITORS OF P97 COMPLEX

CLAIM OF PRIORITY

This application is a U.S. National Stage Filing under 35 U.S.C. 371 from International Application No. PCT/US2014/069598, filed on Dec. 10, 2014, and published as WO 2015/089218 A1 on Jun. 18, 2015, which claims the benefit of priority under 35 U.S.C. §119(e) to U.S. Provisional Patent Application No. 61/929,382, filed on Jan. 20, 2014, and which claims the benefit of priority under 35 U.S.C. §119(e) to U.S. Provisional Patent Application No. 61/914,084, filed on Dec. 10, 2013, each of which is hereby incorporated by reference herein in its entirety.

BACKGROUND OF THE INVENTION

The AAA (ATPase Associated with a variety of Activities) ATPase p97 having the descriptive name, Valosin containing protein, is conserved across all eukaryotes and is essential for life in budding yeast (Giaever, G., et. al. *Nature* (2002) 418, 387-391) and mice (Muller, J. M. et al. *Biochem. Biophys. Res. Commun.* (2007) 354, 459-465). Humans bearing reduction-of-function alleles of p97 are afflicted with a syndrome that includes inclusion body myopathy and frontotemporal lobar degeneration (Weihl, C. et al. *Hum. Mol. Genet.* (2006) 15, 189-199). Loss-of-function studies in model organisms indicate that p97 plays a critical role in a broad array of cellular processes including Golgi membrane reassembly (Rabouille, C. et al. *Cell* (1995) 82, 905-914), membrane transport (Ye, Y. et al *Nature* (2001) 414, 652-656; Ye, Y. et al. *Nature* (2004) 429, 841-847) degradation of misfolded membrane and secretory proteins by the ubiquitin-proteasome system (UPS) (Golbik, R. et al. *Biol. Chem.* (1999) 380, 1049-1062; Richly, H. et al. *Cell* (2005) 120, 73-84), regulation of myofibril assembly (Janiesch, P. C. et al. *Nat. Cell Biol.* (2007) 9, 379-390), and cell division (Cao, K. et al. *Cell* (2003) 115, 355-367). The broad range of cellular functions for this protein is thought to derive from its ability to unfold proteins or disassemble protein complexes. The mechanochemical activity of p97 is linked to substrate proteins by an array of at least 14 UBX domain adapters that bind p97, as well as the non-UBX domain adaptors Ufd1 and Np14 (Meyer, H. H. et al. *EMBO J.* (2000) 19, 2181-2192).

The sequence of p97 reveals three domains (N-domain, D1 ATPase domain, and D2 ATPase domain) joined by linker regions. X-ray crystallography of p97 revealed that it forms a homohexamer of 97 kilodalton subunits that assemble to form two stacked rings. The two rings are formed by the ATPase domains (Huyton, T. et al., *Struct. Biol.* (2003) 144, 337-348; DeLaBarre, B. et al. *Nat. Struct. Biol.* (2003) 10, 856-863). The 'top' ring is formed by a hexamer of the D1 domains, whereas the 'bottom' ring is formed by a hexamer of the D2 domains. The N-domain extends outward from the D1 domain ring. Although it is clear that the D2 domain hydrolyzes ATP in vitro, the level of D1-specific ATPase activity reported by different investigators varies. Nevertheless, genetic studies in yeast suggest that ATP hydrolysis by both the D1 and D2 domains is essential for the function of p97 (Song, C. et al. *J. Biol. Chem.* (2003) 278, 3648-3655; Ye, Y. et al. *J. Cell Biol.* (2004) 162, 71-84). Binding of ATP to the D1 domain is also required for assembly of p97 (Wang, Q. et al. *Biochem. Biophys. Res. Commun.* (2003) 300, 253-260). Although ATP hydrolysis by the D2 domain is not required for assembly of p97 hexamer, it is thought that ATP hydrolysis by the D2 domain is a substrate conversion, resulting in their unfolding or dissociation from bound partners.

A prominent cellular function for p97 that has received considerable scrutiny is its role in the turnover of misfolded secretory proteins via the UPS (ubiquitin proteasome system). In this process, which is known as ERAD (for endoplasmic reticulum-associated degradation), proteins that fail to fold within the ER are retrotranslocated in a p97-dependent manner into the cytoplasm where they are degraded by the UPS (Ye, Y. et al. *Nature* (2004) 429, 841-847). In this process, p97 is thought to mediate extraction of substrates from the ER membrane. The complex p97 is also required for the turnover of cytosolic substrates of the UPS (Janiesch, P. C. et al. *Nat. Cell Biol.* (2007) 9, 379-390; Cao, K. et al. *Cell* (2003) 115, 355-367; Fu, X. et al. *J. Cell Biol.* (2003) 163, 21-26), although its role in turnover of cytosolic proteins is less understood.

The Valosin containing protein, p97, represents a suitable target for cancer therapeutics. The complex p97 and its function are essential for continued cellular viability, and so drugs that inhibit it should be antiproliferative. In other words, inhibition of p97 will cause undesirable protein concentration within the target cell. A consequential cellular reaction is often apoptosis or at least amelioration of cellular growth and mitosis. Also, p97 is known to be overproduced in multiple cancers (Yamamoto, S. et al. *Ann. Surg. Oncol.* (2005) 12, 925-934; Yamamoto, S. et al. *Clin. Cancer Res.* (2004) 10, 5558-5565; Yamamoto, S. et al. *Ann. Surg. Oncol.* (2004) 11, 697-704; Yamamoto, S. et al. *Ann. Surg. Oncol.* (2004) 11, 165-172) suggesting that its activity may be rate-limiting for the development of at least some cancers. p97 is known to be essential for ERAD (Carvalho, P. et al. *Cell* (2006) 126, 361-373), and recent studies suggest that cancer cells may be particularly dependent upon ERAD (Boelens, J. et al. *In Vivo* (2007) 21, 215-226). Furthermore, p97 has been linked to the turnover of IκB and consequent activation of NF-kB (Dai, R. M. et al. *J. Biol. Chem.* (1998) 273, 3562-3573). NF-kB activity is important for the survival of some tumor cells, particularly in multiple myeloma (Keats, J. J. et. al. *Cancer Cell* (2007) 12, 131-144; Annunziata, C. M. et. al. *Cancer Cell* (2007) 12, 115-130). It has been suggested that bortezomib is active in multiple myeloma due to its ability to block turnover of proteins via the ERAD pathway and its ability to block turnover of IkB, thereby squelching the activity of NF-kB. Given that p97 is implicated in both ERAD and IkB turnover but otherwise has a more restricted role in the UPS compared to the proteasome itself, drugs that target p97 may retain much of the efficacy of bortezomib but with less toxicity. In addition, compounds intersecting with the p97 complex are disclosed in PCT/US2011/035654, filed May 6, 2011 and published as WO2011/140527 on Nov. 10, 2011.

Goals of the Invention

Thus, there is a need to develop compounds suitable for inhibition of p97 activity and for methods of inhibiting the activity of p97 using such compounds. There is a need to develop such compounds for use in treatment of neoplastic malconditions.

SUMMARY OF THE INVENTION

These and other needs are met by aspects of the present invention, one of which is directed to a monocyclic ring scaffold having pyrimidine or pyridine as the ring scaffold and optionally having one or more substituents bonded to the ring. In various embodiments, the monocyclic ring scaffolds are substituted at least at the 2 position by a heteroaryl group. In further embodiments, the monocyclic ring scaffolds are also substituted meta to the heteroaryl group by an arylalkyl amine group. For the pyrimidine scaffold, this meta substitution places the arylalkyl amine group at the 4 position. For the pyridine scaffold, this meta substitution places the arylalkyl amine group either at the 4 position, i.e., para to the nitrogen, or at the 6 position so that the heteroaryl and arylalkyl amine groups are both ortho to the pyridine nitrogen.

In another aspect of the invention, the monocyclic scaffold compounds of the invention have an ability to inhibit Valosin containing protein p97 and to ameliorate, diminish, shrink, moderate and/or eliminate cells exhibiting neoplastic tendencies and/or abnormal function. In a further aspect of the invention, such compounds inhibit the ATPase activity of p97. Another aspect of the invention concerns treatment of malconditions and/or disease such as cancer through use of such compounds.

One aspect of the invention is directed to a substituted monocyclic ring scaffold having pyrimidine or pyridine as the scaffold and a 5:6 bicyclic heteroaryl ring bonded to the 2 position of the pyrimidine or pyridine ring. The scaffold also has an arylalkyl amine group bonded to the 4 position of the pyrimidine scaffold or to the 4 or 6 position of the pyridine scaffold such that for the pyridine scaffold, the arylalkyl amine group is para to the pyridine nitrogen when the heteroaryl group is ortho to the pyridine nitrogen or the arylalkyl amine and heteroaryl groups are both ortho to the pyridine nitrogen. Optional single or multiple aliphatic, functional and/or aromatic components as additional substituents may be bonded to the pyrimidine or pyridine scaffold, to the 5:6 bicyclic heteroaryl ring as well as to the aryl alkyl amine group.

More specifically, this aspect of the invention is directed to a monocyclic pyrimidine or pyridine compound of Formula I.

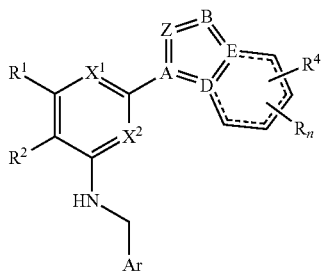

Formula I

The $X^1$ and $X^2$ moieties of Formula I are each independently nitrogen (N) or an $sp^2$ carbon-hydrogen (CH). The A, D and E moieties are each independently C or N, the C being an $sp^2$ carbon. The Z and B moieties are each independently $CR^3$, N, $NR^5$, O or S, the $CR^3$ being an $sp^2$ carbon. The Ar moiety is an aromatic substituent as defined in the following Definitions section. Preferably, Ar is an aryl or heteroaryl substituent as defined in the Definitions section. More preferably, Ar is a phenyl or substituted phenyl substituent.

Several provisos apply to the above moieties so that the scaffold is either a pyrimidine or pyridine scaffold and the 5:6 bicyclic ring is aromatic. The provisos are:

a) At least one of $X^1$ and $X^2$ is N; and,
b) At least one of D and E is C; and,
c) At least one of A, B, D, E and Z is other than C; and,
d) Z and B cannot both be $NR^5$ and both cannot be O or S; and,
e) When one of D and E is N and A is C, Z and B are each independently $CR^3$, N or $NR^5$; and,
f) When both of D and E are C and A is N, Z and B are each independently $CR^3$ or N; and,
g) When all of D, E and A are C, Z and B are each independently $CR^3$, N, $NR^5$, O or S; and,
h) When one of Z and B is O or S, the other is $CR^3$ or N and A, D and E are all C; and,
i) When one of Z and B is NR5, the other is N or CR3, A, D and E are all C.

The substituents $R^1$ and $R^2$ each are independently selected from aliphatic, functional and/or aromatic components as defined in the following Definitions section. Also $R^1$ and $R^2$ do not combine to form another ring of the scaffold. Preferably, substituents $R^1$ and $R^2$ may be independently selected from hydrogen, halogen, straight, branched or cyclo alkyl of 1 to 6 carbons, carboxyl, carboxamide, substituted amino methyl, sulfonyl, sulfonamide, amine, mono, di or trialkyl amine of 1 to 6 carbons, nitrile, N-alkyl carboxamide of 1 to 6 carbons in the alkyl group, perfluoroalkyl of 1 to 3 carbons, alkoxy of 1 to 6 carbons.

The 5:6 bicyclic heteroaryl ring substituent at the two position of the monocyclic scaffold of Formula I is substituted with up to five substituents as designated by $R_n$, $R^3$, $R^4$ and $R^5$. The subscript n for $R_n$ indicates the number of additional substituents of the benzo moiety and is a number selected from 0 or 1 or 2, preferably 0 or 1, more preferably 1, most preferably 0. Each selection of $R_n$ is independent of any other selection of $R_n$. The selection of the substituent $R^5$ bound to N and the substituent $R^3$ bound to C for moieties Z and B are made according to the stability of the resulting molecule under common chemical principles. Each of these substituents may be independently selected from the group consisting of an aliphatic component, a functional component, an aromatic component and any combination thereof. The aliphatic component, functional component and aromatic component are defined in the following Definitions section.

Most preferably, the substituents, $R_n$, $R^1$, $R^2$, $R^3$, $R^4$ and $R^5$ may be independently selected from hydrogen, halogen (preferably fluoro, chloro or bromo, more preferably fluoro or chloro, most preferably fluoro), straight, branched or cyclic alkyl of 1 to 6 carbons, carboxylic acid, carboxyl ester with the ester group being straight, branched or cyclic alkyl of 1 to 6 carbons, N-alkyl amino methyl with the alkyl group being straight, branched or cyclic of 1 to 6 carbons, sulfonic acid, sulfonyl ester with the ester group being straight, branched or cyclic alkyl of 1 to 6 carbons, sulfonamide, amine ($NH_2$), mono, di or trialkyl amine with the alkyl being straight, branched or cyclic of 1 to 6 carbons, nitrile, carboxamide, N-alkyl carboxamide of 1 to 6 carbons in the straight, branched or cyclic alkyl group, perfluoroalkyl of 1 to 3 carbons, straight, branched or cyclic alkoxy of 1 to 6 carbons. When a most preferred substituent is bonded to nitrogen, the substituent is chosen according to principles of chemical stability. For example, for $R^5$, a most preferred substituent for N would not be halogen or amine.

Another aspect of the invention is a subgenus of Formula I and is a monocyclic pyrimidine or pyridine compound of Formula II.

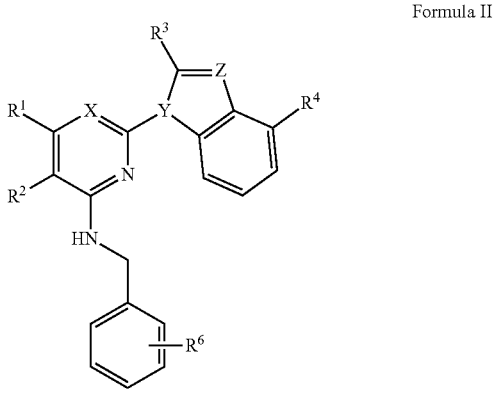

Formula II

The X moiety of Formula II is nitrogen (N) or carbon-hydrogen (CH). The Y moiety is N or CH and the Z moiety is CH or N provided that one of Y and Z is N. As explained in detail in the Detailed Description section, when Y is CH and Z is N, the resulting heterocycle is a tautomer of indole and will rearrange to indole.

The substituents $R^1$, $R^2$, $R^3$, $R^4$ and $R^6$ each are independently selected from aliphatic, functional and/or aromatic components as defined in the following Definitions section. $R^1$ and $R^2$ do not combine to form another ring of the scaffold. Preferably, $R^1$ and $R^2$ are not both methyl and are not both hydrogen.

Most preferably, the substituents, $R^1$, $R^2$, $R^3$, $R^4$ and $R^6$ may be independently selected from hydrogen, halogen (preferably fluoro, chloro or bromo, more preferably fluoro or chloro, most preferably fluoro), straight, branched or cyclic alkyl of 1 to 6 carbons, carboxylic acid, carboxyl ester with the ester group being straight, branched or cyclic alkyl of 1 to 6 carbons, N-alkyl amino methyl with the alkyl group being straight, branched or cyclic of 1 to 6 carbons, sulfonic acid, sulfonyl ester with the ester group being straight, branched or cyclic alkyl of 1 to 6 carbons, sulfonamide, amine ($NH_2$), mono, di or trialkyl amine with the alkyl being straight, branched or cyclic of 1 to 6 carbons, nitrile, carboxamide, N-alkyl carboxamide of 1 to 6 carbons in the straight, branched or cyclic alkyl group, perfluoroalkyl of 1 to 3 carbons, straight, branched or cyclic alkoxy of 1 to 6 carbons.

The benzimidazole/indole/indene substituent at the two position of the monocyclic scaffold of Formula II is substituted with zero, one, two or three substituents each independently selected from the group consisting of an aliphatic component, a functional component, an aromatic component and any combination thereof. The aliphatic component, functional component and aromatic component are defined in the following Definitions section.

An additional aspect of the invention is directed to a pharmaceutical composition of a pharmaceutically acceptable carrier and the above described monocyclic ring scaffold, more specifically the above described monocyclic scaffold of Formula I or Formula II, especially as set forth in the following Detailed Description. A further aspect of the invention is directed to a combination composition of a compound of Formula I or Formula II with a known anti-neoplastic or chemotherapeutic drug, preferably another anti-neoplastic or chemotherapeutic drug of the proteasome inhibitor class, and more preferably a combination composition of a compound of Formula I or Formula II combined with a proteasome inhibitor and a steroid.

Another aspect of the invention is directed to a method of decreasing Valosin containing protein (p97) activity or decreasing degradation of a proteasome system substrate, especially a ubiquitin substrate, by administration to a patient in need an effective therapeutic amount of the foregoing monocyclic scaffold, more specifically the above described monocyclic pyrimidine or pyridine ring scaffold of Formula I or Formula II.

Yet another aspect of the invention is directed to the treatment of neoplastic malconditions, cancer and other malconditions associated with p97 by administration to a patient in need a compound of Formula I or Formula II, the foregoing pharmaceutical composition comprised of Formula I or Formula II or a combination composition of a compound of Formula I or Formula II combined with a known anti-neoplastic or chemotherapeutic drug, preferably another anti-neoplastic or chemotherapeutic drug of the proteasome inhibitor class, and more preferably a combination composition of a compound of Formula I or Formula II combined with a proteasome inhibitor and a steroid.

DETAILED DESCRIPTION OF THE INVENTION

Definitions

Unless defined otherwise, all technical and scientific terms used herein have the same meaning as commonly understood by a person of ordinary skill in the art.

As used in the specification and the appended claims, the singular forms "a," "an" and "the" include plural referents unless the context clearly dictates otherwise.

The term "about" as used herein, when referring to a numerical value or range, allows for a degree of variability in the value or range, for example, within 10%, or within 5% of a stated value or of a stated limit of a range.

All percent compositions are given as weight-percentages, unless otherwise stated.

All average molecular weights of polymers are weight-average molecular weights, unless otherwise specified.

As used herein, "individual" (as in the subject of the treatment) or "patient" means both mammals and non-mammals. Mammals include, for example, humans; non-human primates, e.g. apes and monkeys; and non-primates, e.g. dogs, cats, cattle, horses, sheep, and goats. Non-mammals include, for example, fish and birds.

The term "may" in the context of this application means "is permitted to" or "is able to" and is a synonym for the term "can." The term "may" as used herein does not mean possibility or chance.

The term "disease" or "disorder" or "malcondition" are used interchangeably, and are used to refer to diseases or conditions wherein p97 plays a role in the biochemical mechanisms involved in the disease or malcondition or symptom(s) thereof such that a therapeutically beneficial effect can be achieved by acting on p97. "Acting on" p97, or "modulating" p97, can include binding to p97 and/or inhibiting the bioactivity of p97 and/or allosterically regulating the bioactivity of p97 in vivo.

The expression "effective amount", when used to describe therapy to an individual suffering from a disorder, refers to the amount of a drug, pharmaceutical agent or compound of the invention that will elicit the biological or medical response of a cell, tissue, system, animal or human that is being sought, for instance, by a researcher or clinician. Such responses include but are not limited to amelioration, inhibition or other action on a disorder, malcondition, disease, infection or other issue with or in the individual's tissues wherein the disorder, malcondition, disease and the like is active, wherein such inhibition or other action occurs to an extent sufficient to produce a beneficial therapeutic effect. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

"Treating" or "treatment" within the meaning herein refers to an alleviation of symptoms associated with a disorder or disease, or inhibition of further progression or worsening of those symptoms, or prevention or prophylaxis of the disease or disorder, or curing the disease or disorder. Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result. A therapeutically effective amount is also one in which any toxic or detrimental effects of compounds of the invention are outweighed by the therapeutically beneficial effects.

Phrases such as "under conditions suitable to provide" or "under conditions sufficient to yield" or the like, in the context of methods of synthesis, as used herein refers to reaction conditions, such as time, temperature, solvent, reactant concentrations, and the like, that are within ordinary skill for an experimenter to vary, that provide a useful quantity or yield of a reaction product. It is not necessary that the desired reaction product be the only reaction product or that the starting materials be entirely consumed, provided the desired reaction product can be isolated or otherwise further used.

By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein, in all of their embodiments are intended to include only "chemically feasible" structures, and any recited structures that are not chemically feasible, for example in a structure shown with variable atoms or groups, are not intended to be disclosed or claimed herein.

An "analog" of a chemical structure, as the term is used herein, refers to a chemical structure that preserves substantial similarity with the parent structure, although it may not be readily derived synthetically from the parent structure. A related chemical structure that is readily derived synthetically from a parent chemical structure is referred to as a "derivative."

When a substituent is specified to be an atom or atoms of specified identity, "or a bond", a configuration is referred to when the substituent is "a bond" that the groups that are immediately adjacent to the specified substituent are directly connected to each other in a chemically feasible bonding configuration.

A tautomeric form of a structure is understood to be included by designation of one form of such a structure. Tautomers constitute a set of isomers produced by migration of hydrogen from one atom to another of the chemical compound in question. For example, acetyl acetone and 2-hydroxypent-2-en-4-one are tautomers formed by migration of the hydrogen of the $CH_2$ group of acetyl acetone to the carbonyl oxygen of either the acetyl group or the acetone moiety. Other tautomer pairs exist for indole with migration of the hydrogen from N to C of the pyrrole moiety and for benzimidazole with migration of the hydrogen from N to C or to the other N of the imidazole moiety.

All chiral, diastereomeric, racemic forms of a structure are intended, unless a particular stereochemistry or isomeric form is specifically indicated. In several instances though an individual stereoisomer is described among specifically claimed compounds, the stereochemical designation does not imply that alternate isomeric forms are less preferred, undesired, or not claimed. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

As used herein, the terms "stable compound" and "stable structure" are meant to indicate a compound that is sufficiently robust to survive isolation to a useful degree of purity from a reaction mixture, and formulation into an efficacious therapeutic agent. Only stable compounds are contemplated herein.

Selected substituents within the compounds described herein are present to a recursive degree. In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis. Recursive substituents are an intended aspect of the disclosed subject matter. One of ordinary skill in the art of medicinal and organic chemistry understands the versatility of such substituents. To the degree that recursive substituents are present in a claim of the disclosed subject matter, the total number should be determined as set forth above.

When a group is recited, wherein the group can be present in more than a single orientation within a structure resulting in more than single molecular structure, e.g., a carboxamide group C(=O)NR, it is understood that the group can be present in any possible orientation, e.g., X—C(=O)N(R)—Y or X—N(R)C(=O)—Y, unless the context clearly limits the orientation of the group within the molecular structure.

When a group, e.g., an "alkyl" group, is referred to without any limitation on the number of atoms in the group, it is understood that the claim is definite and limited with respect the size of the alkyl group, both by definition; i.e., the size (the number of carbon atoms) possessed by a group such as an alkyl group is a finite number, less than the total number of carbon atoms in the universe and bounded by the understanding of the person of ordinary skill as to the size of the group as being reasonable for a molecular entity; and by functionality, i.e., the size of the group such as the alkyl group is bounded by the functional properties the group bestows on a molecule containing the group such as solubility in aqueous or organic liquid media. Therefore, a claim reciting an "alkyl" or other chemical group or moiety is definite and bounded, as the number of atoms in the group cannot be infinite.

In general, "substituted" refers to an organic group as defined herein in which one or more bonds to a hydrogen atom contained therein are replaced by one or more bonds to a non-hydrogen atom. More particularly, the term "chemical substituent" refers to any and all aliphatic, aromatic and functional groups listed in this section that can be appended to an organic molecule. A functional group is an inorganic moiety such as halogen, sulfate, nitro, amino and the like as well as monocarbon functional groups such as carboxyl, carbonyl, carboxamide that are ordinary and typical optional substituents of organic molecules. In the context of this invention, recitation of this term without indication of specific groups constitutes the definition given above. Recitation of this term in combination with a Markush recitation of specific groups constitutes a subgenus of the understanding conveyed by the foregoing definition. The term "substituent" generally means any appropriate group named below that has an "yl", "y" or "o" ending to designate that it is appended, attached or covalently bonded to another moiety such as but not limited to an aromatic framework. Examples include but are not limited to, a halogen (i.e., F, Cl, Br, and I); an oxygen atom in groups such as hydroxyl groups, alkoxy groups, aryloxy groups, aralkyloxy groups, oxo (carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents J that can be bonded to a substituted carbon (or other) atom include F, Cl, Br, I, OR', OC(O)N(R')$_2$, CN, NO, NO$_2$, ONO$_2$, azido, CF$_3$, OCF$_3$, R', 0 (oxo), S (thiono), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$N(R')C(O)R', (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted; for example, wherein R' can be hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl or R' can be independently mono- or multi-substituted with J; or wherein two R' groups bonded to a nitrogen atom or to adjacent nitrogen atoms can together with the nitrogen atom or atoms form a heterocyclyl, which can be mono- or independently multi-substituted with J.

In various embodiments, J can be halo, nitro, cyano, OR, NR$_2$, or R, or is C(O)OR, C(O)NR$_2$, OC(O)OR, OC(O)NR$_2$, N(R)C(O)OR, N(R)C(O)NR$_2$ or thio/thiono analogs thereof. By "thio/thiono analogs thereof", with respect to a group containing an O, is meant that any or all O atoms in the group can be replaced by an S atom; e.g., for group C(O)OR, a "thio/thiono analog thereof" includes C(S)OR, C(O)SR, and C(S)SR; e.g., for group OC(O)NR$_2$, a "thio/thiono analog thereof" includes SC(O)NR$_2$, OC(S)NR$_2$, and SC(S)NR$_2$; and so forth.

When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, which can also be written as "CO", "C(O)", or "C(=O)", wherein the C and the O are double bonded. When a carbon atom is substituted with a double-bonded oxygen (=O) group, the oxygen substituent is termed an "oxo" group. When a divalent substituent such as NR is double-bonded to a carbon atom, the resulting C(=NR) group is termed an "imino" group. When a divalent substituent such as S is double-bonded to a carbon atom, the results C(=S) group is termed a "thiocarbonyl" or "thiono" group.

Alternatively, a divalent substituent such as O or S can be connected by two single bonds to two different carbon atoms. For example, O, a divalent substituent, can be bonded to each of two adjacent carbon atoms to provide an epoxide group, or the O can form a bridging ether group, termed an "oxy" group, between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as (CH$_2$)$_n$ or (CR'$_2$)$_n$ wherein n is 1, 2, 3, or more, and each R' is independently selected.

For all substituents, the first atom of the molecular formula of the substituent is the atom bonding the substituent to its corresponding moiety, e.g., for the functional group, N(R$^a$)C(O)R$^a$, the N is bonded to the corresponding moiety substituted by this group. If the substituent is described in words, such as alkenylamine, the phrase ending in "enyl" indicates the carbon atom bonding the substituent to its corresponding moiety. For substituents that display a single bonding site, such as carboxylic acid, sulfonic acid, fluoro, methyl and the like, the bonding arrangement is the expected arrangement.

"Aliphatic substituent, group or component" refers to any organic group that is non-aromatic. Included are acyclic and cyclic organic compounds composed of carbon, hydrogen and optionally of oxygen, nitrogen, sulfur and other heteroatoms. This term encompasses all of the following organic groups except the following defined aromatic and heteroaromatic groups. Examples of such groups include but are not limited to alkyl, alkenyl, alkynyl, corresponding groups with heteroatoms, cyclic analogs, heterocyclic analogs, branched and linear versions and such groups optionally substituted with functional groups, as these groups and others meeting this definition of "aliphatic" are defined below.

"Aromatic substituent, group or component" refers to any and all aromatic groups including but not limited to aryl, aralkyl, heteroalkylaryl, heteroalkylheteroaryl and heteroaryl groups. The term "aromatic" is general in that it encompasses all compounds containing aryl groups optionally substituted with functional groups (all carbon aromatic groups) and all compounds containing heteroaryl groups optionally substituted with functional groups (carbon-heteroatom aromatic groups), as these groups and others meeting this definition of "aromatic" are defined below.

As used herein, the term "optionally" means that the corresponding substituent or thing may or may not be present. It includes both possibilities.

"Alkyl" refers to a straight or branched hydrocarbon chain radical consisting solely of carbon and hydrogen atoms, containing no unsaturation, having from one to ten carbon atoms (e.g., $C_1$-$C_{10}$ alkyl). Whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated. In some embodiments, it is a $C_1$-$C_4$ alkyl group. Typical alkyl groups include, but are in no way limited to, methyl, ethyl, propyl, isopropyl, n-butyl, iso-butyl, sec-butyl isobutyl, tertiary butyl, pentyl, isopentyl, neopentyl, hexyl, septyl, octyl, nonyl, decyl, and the like. The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), 3-methylhexyl, 2-methylhexyl, and the like.

Unless stated otherwise specifically in the specification, an alkyl group is optionally substituted by one or more of substituents as defined above. Such substituents further independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$_a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$ where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkylaryl" refers to an -(alkyl)aryl radical where aryl and alkyl are as disclosed herein and which are optionally substituted by one or more of the substituents described as suitable substituents for aryl and alkyl respectively.

"Alkylhetaryl" refers to an -(alkyl)hetaryl radical where hetaryl and alkyl are as disclosed herein and which are optionally substituted by one or more of the substituents described as suitable substituents for aryl and alkyl respectively.

"Alkylheterocycloalkyl" refers to an -(alkyl) heterocycyl radical where alkyl and heterocycloalkyl are as disclosed herein and which are optionally substituted by one or more of the substituents described as suitable substituents for heterocycloalkyl and alkyl respectively.

An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

"Alkenyl" refers to a straight or branched hydrocarbon chain radical group consisting solely of carbon and hydrogen atoms, containing at least one double bond, and having from two to ten carbon atoms (i.e., $C_2$-$C_{10}$ alkenyl). Whenever it appears herein, a numerical range such as "2 to 10" refers to each integer in the given range; e.g., "2 to 10 carbon atoms" means that the alkenyl group may consist of 2 carbon atoms, 3 carbon atoms, etc., up to and including 10 carbon atoms. In certain embodiments, an alkenyl comprises two to eight carbon atoms. In other embodiments, an alkenyl comprises two to five carbon atoms (e.g., $C_2$-$C_5$ alkenyl). The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like.

Unless stated otherwise specifically in the specification, an alkenyl group is optionally substituted by one or more substituents as defined above. Such substituents further independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocyclylalkyl, heteroaryl or heteroarylalkyl.

"Alkenyl-cycloalkyl" refers to an -(alkenyl)cycloalkyl radical where alkenyl and cyclo alkyl are as disclosed herein and which are optionally substituted by one or more of the substituents described as suitable substituents for alkenyl and cycloalkyl respectively.

"Alkynyl" refers to a straight or branched hydrocarbon chain radical group consisting solely of carbon and hydrogen atoms, containing at least one triple bond, having from two to ten carbon atoms (i.e., C2-C10 alkynyl). Whenever it appears herein, a numerical range such as "2 to 10" refers to each integer in the given range; e.g., "2 to 10 carbon atoms" means that the alkynyl group may consist of 2 carbon atoms, 3 carbon atoms, etc., up to and including 10 carbon atoms. In certain embodiments, an alkynyl comprises two to eight carbon atoms. In other embodiments, an alkynyl has two to five carbon atoms (e.g., C2-C5 alkynyl). The alkynyl is attached to the rest of the molecule by a single bond, for example, ethynyl, propynyl, butynyl, pentynyl, hexynyl, and the like.

Unless stated otherwise specifically in the specification, an alkynyl group is optionally substituted by one or more substituents as defined above. Such substituents further independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)2, —C(O)R$^a$, —C(O)OR$^a$, —C(O)N(R$^a$)2, —C(O)N(R$^a$)2, —N(R$^a$)C(O)OR$^a$, —N(R$^a$)C(O)R$^a$, —N(R$^a$)C(O)N(R$^a$)2, N(R$^a$)C(NR$^a$)N(R$^a$)2, —N(R$^a$)S(O)$_t$R$^a$ (where t is 1 or 2), —S(O)$_t$OR$^a$ (where t is 1 or 2), —S(O)$_t$N(R$^a$)2 (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocyclylalkyl, heteroaryl or heteroarylalkyl.

"Alkynyl-cycloalkyl" refers to refers to an -(alkynyl)cycloalkyl radical where alkynyl and cycloalkyl are as disclosed herein and which are optionally substituted by one or more of the substituents described as suitable substituents for alkynyl and cycloalkyl respectively.

"Carboxaldehyde" refers to a —(C=O)H radical.
"Carboxyl" refers to a —(C=O)OH radical.
"Cyano" refers to a —CN radical.

"Cycloalkyl" refers to a monocyclic or polycyclic radical that contains only carbon and hydrogen, and may be saturated, or partially unsaturated. Cycloalkyl groups include groups having from 3 to 10 ring atoms (i.e., $C_2$-$C_{10}$ cycloalkyl). Whenever it appears herein, a numerical range such as "3 to 10" refers to each integer in the given range; e.g., "3 to 10 carbon atoms" means that the cycloalkyl group may consist of 3 carbon atoms, etc., up to and including 10 carbon atoms. In some embodiments, it is a $C_3$-$C_8$ cycloalkyl radical. In some embodiments, it is a $C_3$-$C_5$ cycloalkyl radical. Illustrative examples of cycloalkyl groups include, but are not limited to the following moieties: cyclopropyl, cyclobutyl, cyclopentyl, cyclopentenyl, cyclohexyl, cyclohexenyl, cycloseptyl, cyclooctyl, cyclononyl, cyclodecyl, norbornyl, and the like.

Unless stated otherwise specifically in the specification, a cycloalkyl group is optionally substituted by one or more substituents as defined above. Such substituents further independently include: alkyl, heteroalkyl, alkenyl, alkynyl, cycloalkyl, heterocyclo alkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocyclylalkyl, heteroaryl or heteroarylalkyl.

"Cycloalkyl-alkenyl" refers to a -(cycloalkyl) alkenyl radical where cycloalkyl and heterocycloalkyl are as disclosed herein and which are optionally substituted by one or more of the substituents described as suitable substituents for heterocycloalkyl and cycloalkyl respectively.

"Cycloalkyl-heterocycloalkyl" refers to a -(cycloalkyl) heterocycyl radical where cycloalkyl and heterocycloalkyl are as disclosed herein and which are optionally substituted by one or more of the substituents described as suitable substituents for heterocycloalkyl and cycloalkyl respectively.

"Cycloalkyl-heteroaryl" refers to a -(cycloalkyl) heteroaryl radical where cycloalkyl and heterocycloalkyl are as disclosed herein and which are optionally substituted by one or more of the substituents described as suitable substituents for heterocycloalkyl and cycloalkyl respectively.

"Alkoxy" refers to the group —O-alkyl, including from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. "Lower alkoxy" refers to alkoxy groups containing one to six carbons. In some embodiments, $C_1$-$C_4$ alkyl is an alkyl group which encompasses both straight and branched chain alkyls of from 1 to 4 carbon atoms.

"Substituted alkoxy" refers to alkoxy wherein the alkyl constituent is substituted (i.e., —O-(substituted alkyl)).

Unless stated otherwise specifically in the specification, the alkyl moiety of an alkoxy group is optionally substituted by one or more substituents as defined above. Such substituents further independently include: alkyl, hetero alkyl, alkenyl, alkynyl, cycloalkyl, heterocycloalkyl, aryl, arylalkyl, hetero aryl, heteroarylalkyl, hydroxy, halo, cyano, trifluoromethyl, trifluoromethoxy, nitro, trimethylsilanyl, —$OR^a$, $SR^a$, —OC(O)—$R^a$, —$N(R^a)_2$, —$C(O)R^a$, —C(O) $OR^a$, —$C(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocyclylalkyl, heteroaryl or heteroarylalkyl.

"Alkoxycarbonyl" refers to a group of the formula (alkoxy)(C=O)— attached through the carbonyl carbon wherein the alkoxy group has the indicated number of carbon atoms. Thus a $C_1$-$C_6$ alkoxycarbonyl group is an alkoxy group having from 1 to 6 carbon atoms attached through its oxygen to a carbonyl linker. "Lower alkoxycarbonyl" refers to an alkoxycarbonyl group wherein the alkoxy group is a lower alkoxy group. In some embodiments, $C_1$-$C_4$ alkoxy, is an alkoxy group which encompasses both straight and branched chain alkoxy groups of from 1 to 4 carbon atoms.

"Substituted alkoxycarbonyl" refers to the group (substituted alkyl)-O—C(O)— wherein the group is attached to the parent structure through the carbonyl functionality.

Unless stated otherwise specifically in the specification, the alkyl moiety of an alkoxycarbonyl group is optionally substituted by one or more substituents as defined above. Such substituents further independently include: alkyl, heteroalkyl, alkenyl, alkynyl, cycloalkyl, heterocycloalkyl, aryl, arylalkyl, hetero aryl, heteroarylalkyl, hydroxy, halo, cyano, trifluoromethyl, trifluoromethoxy, nitro, trimethylsilanyl, —$OR^a$, $SR^a$, —OC(O)—$R^a$, —$N(R^a)_2$, —$C(O)R^a$, —$C(O)OR^a$, —$OC(O)N(R^a)_2$, —$C(O)N(R^a)_2$, —$(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocyclylalkyl, heteroaryl or hetero arylalkyl.

"Acyl" refers to the groups (alkyl)-C(O)—, (aryl)-C(O)—, (heteroaryl)-C(O)—, (heteroalkyl)-C(O)—, and (heterocycloalkyl)-C(O)—, wherein the group is attached to the parent structure through the carbonyl functionality. In some embodiments, it is a $C_1$-$C_{10}$ acyl radical which refers to the total number of chain or ring atoms of the alkyl, aryl, heteroaryl or heterocycloalkyl portion of the acyloxy group plus the carbonyl carbon of acyl, i.e. three other ring or chain atoms plus carbonyl. If the R radical is heteroaryl or heterocycloalkyl, the hetero ring or chain atoms contribute to the total number of chain or ring atoms.

Unless stated otherwise specifically in the specification, the "R" of an acyloxy group is optionally substituted by one or more substituents as defined above. Such substituents further independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, $SR^a$, —OC(O)—$R^a$, —$N(R^a)_2$, —$C(O)R^a$, —C(O) $OR^a$, —$OC(O)N(R^a)_2$, —$C(O)N(R^a)_2$, —$N(R^a)C(O) OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocyclylalkyl, heteroaryl or heteroarylalkyl.

"Acyloxy" refers to a R(C=O)O— radical wherein "R" is alkyl, aryl, heteroaryl, heteroalkyl, or heterocycloalkyl, which are as described herein. In some embodiments, it is a $C_1$-$C_4$ acyloxy radical which refers to the total number of chain or ring atoms of the alkyl, aryl, heteroaryl or heterocycloalkyl portion of the acyloxy group plus the carbonyl carbon of acyl, i.e. three other ring or chain atoms plus carbonyl. If the R radical is heteroaryl or heterocycloalkyl, the hetero ring or chain atoms contribute to the total number of chain or ring atoms.

Unless stated otherwise specifically in the specification, the "R" of an acyloxy group is optionally substituted by one or more substituents as defined above. Such substituents further independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2-S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocyclylalkyl, heteroaryl or heteroarylalkyl.

"Amino" or "amine" refers to a —N(R$^a$)$_2$ radical group, where each R$^a$ is independently hydrogen, alkyl, fluoroalkyl, carbocyclyl, carbocyclylalkyl, aryl, aralkyl, heterocycloalkyl, heterocyclylalkyl, heteroaryl or heteroarylalkyl, unless stated otherwise specifically in the specification. When a —N(R$^a$)$_2$ group has two Ra other than hydrogen they can be combined with the nitrogen atom to form a 4-, 5-, 6-, or 7-membered ring. For example, —N(R$^a$)$_2$ is meant to include, but not be limited to, 1-pyrrolidinyl and 4-morpholinyl.

Unless stated otherwise specifically in the specification, an amino group is optionally substituted by one or more substituents as defined above. Such substituents further independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocyclylalkyl, heteroaryl or heteroarylalkyl and each of these moieties may be optionally substituted as defined herein.

"Substituted amino" also refers to N-oxides of the groups —NHR$^d$, and NR$^d$R$^d$ each as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

An "ammonium" ion includes the unsubstituted ammonium ion NH$_4^+$, but unless otherwise specified, it also includes any protonated or quaternarized forms of amines. Thus, trimethylammonium hydrochloride and tetramethylammonium chloride are both ammonium ions, and amines, within the meaning herein.

"Amide" or "amido" refers to a chemical moiety with formula —C(O)N(R)$_2$ or —NHC(O)R, where R is selected from the group consisting of hydrogen, alkyl, cycloalkyl, aryl, heteroaryl (bonded through a ring carbon) and heteroalicyclic (bonded through a ring carbon), each of which moiety may itself be optionally substituted. In some embodiments it is a C$_1$-C$_4$ amido or amide radical, which includes the amide carbonyl in the total number of carbons in the radical. The R$_2$ of —N(R)$_2$ of the amide may optionally be taken together with the nitrogen to which it is attached to form a 4-, 5-, 6-, or 7-membered ring. Unless stated otherwise specifically in the specification, an amido group is optionally substituted independently by one or more of the substituents as described herein for alkyl, cycloalkyl, aryl, heteroaryl, or heterocycloalkyl. An amide may be an amino acid or a peptide molecule attached to a compound of Formula (I), thereby forming a prodrug. Any amine, hydroxy, or carboxyl side chain on the compounds described herein can be amidified. The procedures and specific groups to make such amides are known to those of skill in the art and can readily be found in reference sources such as Greene and Wuts, Protective Groups in Organic Synthesis, 3rd Ed., John Wiley & Sons, New York, N.Y., 1999, which is incorporated herein by reference in its entirety.

"Aryl" refers to a conjugated pi radical with six or ten ring atoms which has at least one ring having a conjugated pi electron system which is carbocyclic (e.g., phenyl, fluorenyl, and naphthyl). Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. The term includes monocyclic or monocyclic-ring polycyclic (i.e., rings which share adjacent pairs of ring atoms) groups.

Unless stated otherwise specifically in the specification, an aryl moiety is optionally substituted by one or more substituents as defined above. Such substituents further are independently include: alkyl, heteroalkyl, alkenyl, alkynyl, cycloalkyl, heterocyclo alkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocyclylalkyl, heteroaryl or heteroarylalkyl.

"Aralkyl" or "arylalkyl" refers to an (aryl)alkyl radical where aryl and alkyl are as disclosed herein and which are optionally substituted by one or more of the substituents described as suitable substituents for aryl and alkyl respectively.

"Ester" refers to a chemical radical of formula —COOR, where R is selected from the group consisting of alkyl, cycloalkyl, aryl, heteroaryl (bonded through a ring carbon) and heteroalicyclic (bonded through a ring carbon). Any amine, hydroxy, or carboxyl side chain on the compounds described herein can be esterified. The procedures and specific groups to make such esters are known to those of skill in the art and can readily be found in reference sources such as Greene and Wuts, Protective Groups in Organic Synthesis, 3rd Ed., John Wiley & Sons, New York, N.Y., 1999, which is incorporated herein by reference in its entirety.

Unless stated otherwise specifically in the specification, an ester group is optionally substituted by one or more substituents as defined above. Such substituents further independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocyclylalkyl, heteroaryl or heteroarylalkyl.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical may be optionally substituted as defined above for an alkyl group.

"Functional substituent, group or component" refers to a substituent capable of displaying functionality such as hydroxyl, ester, amide, amine, enamine, halogen, cyano, thio, oxidized sulfur, nitrogen or phosphorus groups, alkoxy, olefinic, aldehyde, ketone, carboxylic acid, anhydride, urethane, urea, imine, amidine, hydroxylimine, hydroxylamine, nitrile, organometallic, and any other group capable of displaying dipole interaction and/or reactivity. See *Basic Principles of Organic Chemistry*, Roberts & Casario, W. A. Benjamin, publisher New York, N.Y. 1965, Chapter 10. Additional examples include hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, C(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), —R$^a$—N(R$^a$)$_2$ or PO$_3$(R$^a$)$_2$ where each R$^a$ is independently hydrogen, alkyl, fluoroalkyl, carbocyclyl, carbocyclylalkyl, aryl, aralkyl, heterocyclyl, heterocyclylalkyl, heteroaryl, heteroarylalkyl or any combination thereof.

"Halo", "halide", or, alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

"Hetero alkyl" "heteroalkenyl" and "heteroalkynyl" include optionally substituted alkyl, alkenyl and alkynyl radicals and which have one or more skeletal chain atoms selected from an atom other than carbon, e.g., oxygen, nitrogen, sulfur, phosphorus or combinations thereof. A numerical range may be given, e.g. $C_1$-$C_4$ heteroalkyl which refers to the chain length in total, which in this example is 4 atoms long. For example, a —CH$_2$OCH$_2$CH$_3$ radical is referred to as a "$C_4$" heteroalkyl, which includes the heteroatom center in the atom chain length description. Connection to the rest of the molecule may be through either a heteroatom or a carbon in the heteroalkyl chain.

A heteroalkyl group may be substituted with one or more substituents as defined above. Such substituents further independently include: alkyl, hetero alkyl, alkenyl, alkynyl, cycloalkyl, heterocycloalkyl, aryl, arylalkyl, hetero aryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocyclylalkyl, heteroaryl or hetero arylalkyl.

"Heteroalkylaryl" refers to an -(heteroalkyl)aryl radical where heteroalkyl and aryl are as disclosed herein and which are optionally substituted by one or more of the substituents described as suitable substituents for heteroalkyl and aryl respectively.

"Heteroalkylheteroaryl" refers to an -(heteroalkyl)heteroaryl radical where heteroalkyl and heteroaryl are as disclosed herein and which are optionally substituted by one or more of the substituents described as suitable substituents for heteroalkyl and heteroaryl respectively.

"Hetero alkylheterocyclo alkyl" refers to an -(heteroalkyl)heterocycloalkyl radical where heteroalkyl and heteroaryl are as disclosed herein and which are optionally substituted by one or more of the substituents described as suitable substituents for heteroalkyl and heterocycloalkyl respectively.

"Heteroalkylcycloalkyl" refers to an -(heteroalkyl)cycloalkyl radical where heteroalkyl and cycloalkyl are as disclosed herein and which are optionally substituted by one or more of the substituents described as suitable substituents for heteroalkyl and cycloalkyl respectively.

"Heteroaryl refers to a 5, 6, 7, 8, 9 10 or 11-membered aromatic radical (e.g., $C_5$-$C_{13}$ heteroaryl) that includes one or more ring heteroatoms selected from nitrogen, oxygen and sulfur, and which may be a monocyclic, bicyclic, tricyclic or tetracyclic ring system. Whenever it appears herein, a numerical range refers to each integer in the given range. An N-containing "heteroaromatic" or "heteroaryl" moiety refers to an aromatic group in which at least one of the skeletal atoms of the ring is a nitrogen atom. The polycyclic heteroaryl group may be monocyclic or non-monocyclic. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to adeninyl, azabenzimidazolyl, azaindolyl, azepinyl, acridinyl, benzimidazolyl, benzindolyl, 1,3-benzodioxolyl, benzofuranyl, benzooxazolyl, benzo[d]thiazolyl, benzothiadiazolyl, benzo [b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, imidazopyridinyl, isoxazolopyridinyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thianaphthalenyl, thiapyranyl, triazolyl, tetrazolyl, triazinyl, thieno[2,3-d]pyrimidinyl, thieno[3,2-d]pyrimidinyl, thieno[2,3-c]pyridinyl, and thiophenyl (i.e., thienyl), xanthinyl, guaninyl, quinoxalinyl, and quinazolinyl groups.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

Unless stated otherwise specifically in the specification, a heteraryl moiety is optionally substituted by one or more substituents as defined above. Such substituents further independently include: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocyclylalkyl, heteroaryl or heteroarylalkyl.

Substituted heteroaryl also includes ring systems substituted with one or more oxide (—O—) substituents, such as pyridinyl N-oxides.

"Heterocyclic" refers to any monocyclic or polycyclic moiety comprising at least one heteroatom selected from nitrogen, oxygen and sulfur. As used herein, heterocyclyl moieties can be aromatic or nonaromatic. The moieties heteroaryl and heterocyclyl alkyl are members of the heterocyclic group.

Unless stated otherwise, heterocyclic moieties are optionally substituted by one or more substituents as defined above. Such substituents further independently include: alkyl, heteroalkyl, alkenyl, alkynyl, cycloalkyl, heterocycloalkyl, aryl, arylalkyl, hetero aryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heteroaryl or heteroarylalkyl.

"Heteroarylalkyl" refers to a moiety having an aryl moiety, as described herein, connected to an alkylene moiety, as described herein, wherein the connection to the remainder of the molecule is through the alkylene group.

"Heterocyclylalkyl" refers to a stable 5, 6 or 10-membered non-aromatic ring radical having from one to six heteroatoms selected from nitrogen, oxygen and sulfur. Unless stated otherwise specifically in the specification, the heterocycloalkyl radical is a monocyclic, bicyclic, tricyclic or tetracyclic ring system, which may include monocyclic or bridged ring systems. The heteroatoms in the heterocycloalkyl radical may be optionally oxidized. One or more nitrogen atoms, if present, are optionally quaternized. The heterocycloalkyl radical is partially or fully saturated. The heterocycloalkyl may be attached to the rest of the molecule through any atom of the ring(s). Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl.

Unless stated otherwise specifically in the specification, a heterocycloalkyl moiety is optionally substituted by one or more substituents as defined above. Such substituents further independently include: alkyl, hetero alkyl, alkenyl, alkynyl, cycloalkyl, heterocycloalkyl, aryl, arylalkyl, hetero aryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocyclo alkyl, heteroaryl or heteroarylalkyl.

"Heterocyclylalkyl" also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually with 3 to 7 ring atoms, optionally contains 1-3 heteroatoms independently selected from oxygen, sulfur, and nitrogen and is not aromatic.

The term "($C_x$-$C_y$)perfluoroalkyl," wherein x<y, means an alkyl group with a minimum of x carbon atoms and a maximum of y carbon atoms, wherein all hydrogen atoms are replaced by fluorine atoms. Preferred is —($C_1$-$C_6$)perfluoroalkyl, more preferred is —($C_1$-$C_3$)perfluoroalkyl, most preferred is —$CF_3$.

The term "($C_x$-$C_y$)perfluoroalkylene," wherein x<y, means an alkyl group with a minimum of x carbon atoms and a maximum of y carbon atoms, wherein all hydrogen atoms are replaced by fluorine atoms. Preferred is —($C_1$-$C_6$)perfluoroalkylene, more preferred is —($C_1$-$C_3$)perfluoroalkylene, most preferred is —$CF_2$—.

"Sulfanyl" refers to the groups: —S-(optionally substituted alkyl), —S-(optionally substituted aryl), —S-(optionally substituted heteroaryl), and —S-(optionally substituted heterocycloalkyl).

"Sulfinyl" refers to the groups: —S(O)—H, —S(O)-(optionally substituted alkyl), —S(O)-(optionally substituted amino), —S(O)-(optionally substituted aryl), —S(O)-(optionally substituted heteroaryl), and —S(O)-(optionally substituted heterocycloalkyl).

"Sulfonyl" refers to the groups: —S($O_2$)—H, —S($O_2$)-(optionally substituted alkyl), —S($O_2$)-(optionally substituted amino), —S($O_2$)-(optionally substituted aryl), —S($O_2$)-(optionally substituted heteroaryl), and —S($O_2$)-(optionally substituted heterocycloalkyl).

"Sulfonamidyl" or "sulfonamido" refers to a —S(=O)$_2$—NRR radical, where each R is selected independently from the group consisting of hydrogen, alkyl, cycloalkyl, aryl, heteroaryl (bonded through a ring carbon) and heteroalicyclic (bonded through a ring carbon). The R groups in —NRR of the —S(=O)$_2$—NRR radical may be taken together with the nitrogen to which it is attached to form a 4-, 5-, 6-, or 7-membered ring. In some embodiments, it is a $C_1$-$C_{10}$ sulfonamido, wherein each R in sulfonamido contains 1 carbon, 2 carbons, 3 carbons, or 4 carbons total. A sulfonamido group is optionally substituted by one or more of the substituents described for alkyl, cycloalkyl, aryl, heteroaryl respectively.

"Sulfoxyl" refers to a —S(=O)$_2$OH radical.

"Sulfonate" refers to a —S(=O)$_2$—OR radical, where R is selected from the group consisting of alkyl, cycloalkyl, aryl, heteroaryl (bonded through a ring carbon) and heteroalicyclic (bonded through a ring carbon). A sulfonate group is optionally substituted on R by one or more of the substituents described for alkyl, cycloalkyl, aryl, heteroaryl respectively.

"Azido" refers to an $N_3$ group. An "azide" can be an organic azide or can be a salt of the azide ($N_3^-$) anion. The term "nitro" refers to an $NO_2$ group bonded to an organic moiety. The term "nitroso" refers to an NO group bonded to an organic moiety. The term nitrate refers to an $ONO_2$ group bonded to an organic moiety or to a salt of the nitrate ($NO_3^-$) anion.

"Urethane" ("carbamoyl" or "carbamyl") includes N- and O-urethane groups, i.e., —NRC(O)OR and —OC(O)$NR_2$ groups, respectively.

"Sulfonamide" (or "sulfonamido") includes S- and N-sulfonamide groups, i.e., —$SO_2NR_2$ and —$NRSO_2R$ groups, respectively. Sulfonamide groups therefore include but are not limited to sulfamoyl groups (—$SO_2NH_2$). An organosulfur structure represented by the formula —S(O)(NR)— is understood to refer to a sulfoximine, wherein both the oxygen and the nitrogen atoms are bonded to the sulfur atom, which is also bonded to two carbon atoms.

"Amidine" or "amidino" includes groups of the formula —C(NR)$NR_2$. Typically, an amidino group is —C(NH)$NH_2$.

"Guanidine" or "guanidino" includes groups of the formula —NRC(NR)$NR_2$. Typically, a guanidino group is —NHC(NH)$NH_2$.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as $NH_4^+$ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds of the present invention may take the form of salts. The term "salts" embraces addition salts of free acids or free bases which are compounds of the invention. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge et al. (1977) *"Pharmaceutical Salts", J. Pharm. Sci.* 66: 1-19.)

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. Although pharmaceutically unacceptable salts are not generally useful as medicaments, such salts may be useful, for example as intermediates in the synthesis of Formula (I) compounds, for example in their purification by recrystallization. All of these salts may be prepared by conventional means from the corresponding compound according to Formula (I) by reacting, for example, the appropriate acid or base with the compound according to Formula (I). The term "pharmaceutically acceptable salts" refers to nontoxic inorganic or organic acid and/or base addition salts, see, for example, Lit et al., Salt Selection for Basic Drugs (1986), *Int J. Pharm.,* 33, 201-217, incorporated by reference herein.

A "hydrate" is a compound that exists in a composition with water molecules. The composition can include water in stoichiometric quantities, such as a monohydrate or a dihydrate, or can include water in random amounts. As the term is used herein a "hydrate" refers to a solid form, i.e., a compound in water solution, while it may be hydrated, is not a hydrate as the term is used herein.

A "solvate" is a similar composition except that a solvent other that water replaces the water. For example, methanol or ethanol can form an "alcoholate", which can again be stoichiometric or non-stoichiometric. As the term is used herein a "solvate" refers to a solid form, i.e., a compound in solution in a solvent, while it may be solvated, is not a solvate as the term is used herein.

A "prodrug" as is well known in the art is a substance that can be administered to a patient where the substance is converted in vivo by the action of biochemicals within the patient's body, such as enzymes, to the active pharmaceutical ingredient. Examples of prodrugs include esters of carboxylic acid groups, which can be hydrolyzed by endogenous esterases as are found in the bloodstream of humans and other mammals Conventional procedures for the selection and preparation of suitable prodrug derivatives are described, for example, in "Design of Prodrugs", ed. H. Bundgaard, Elsevier, 1985.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4.

In various embodiments, the compound or set of compounds, such as are used in the inventive methods, can be any one of any of the combinations and/or sub-combinations of the above-listed embodiments.

In various embodiments, a compound as shown in any of the Examples, or among the exemplary compounds, is provided. Provisos may apply to any of the disclosed categories or embodiments wherein any one or more of the other above disclosed embodiments or species may be excluded from such categories or embodiments.

The term "amino protecting group" or "N-protected" as used herein refers to those groups intended to protect an amino group against undesirable reactions during synthetic procedures and which can later be removed to reveal the amine. Commonly used amino protecting groups are disclosed in Protective Groups in Organic Synthesis, Greene, T. W.; Wuts, P. G. M., John Wiley & Sons, New York, N.Y., (3rd Edition, 1999). Amino protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxy-carbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. Amine protecting groups also include cyclic amino protecting groups such as phthaloyl and dithiosuccinimidyl, which incorporate the amino nitrogen into a heterocycle. Typically, amino protecting groups include formyl, acetyl, benzoyl, pivaloyl, t-butylacetyl, phenylsulfonyl, Alloc, Teoc, benzyl, Fmoc, Boc and Cbz. It is well within the skill of the ordinary artisan to select and use the appropriate amino protecting group for the synthetic task at hand.

The term "hydroxyl protecting group" or "O-protected" as used herein refers to those groups intended to protect an OH group against undesirable reactions during synthetic procedures and which can later be removed to reveal the amine. Commonly used hydroxyl protecting groups are disclosed in Protective Groups in Organic Synthesis, Greene, T. W.; Wuts, P. G. M., John Wiley & Sons, New York, N.Y., (3rd Edition, 1999). Hydroxyl protecting groups include acyl groups such as formyl, acetyl, propionyl, pivaloyl, t-butylacetyl, 2-chloro acetyl, 2-bromoacetyl, trifluoroacetyl, trichloroacetyl, o-nitrophenoxyacetyl, oi-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitro benzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. It is well within the skill of the ordinary artisan to select and use the appropriate hydroxyl protecting group for the synthetic task at hand.

At various places in the present specification substituents of compounds of the invention are disclosed in groups or in ranges. It is specifically intended that the invention include each and every individual subcombination of the members of such groups and ranges. For example, the term "C1-C6 alkyl" is specifically intended to individually disclose methyl, ethyl, propyl, isopropyl, n-butyl, sec-butyl, isobutyl, etc. For a number qualified by the term "about", a variance of 2%, 5%, 10% or even 20% is within the ambit of the qualified number.

Standard abbreviations for chemical groups such as are well known in the art are used; e.g., Me=methyl, Et=ethyl, i-Pr=isopropyl, Bu=butyl, t-Bu=tert-butyl, Ph=phenyl, Bn=benzyl, Ac=acetyl, Bz=benzoyl, and the like.

Compounds

The invention is directed to compounds that inhibit ATPase Associated with a variety of Activities (AAA), the ATPase having the descriptive name Valosin containing protein, also known as p97, as well as methods to treat or prevent a disease or condition in a subject or patient that would benefit by inhibition of p97. The compounds embodying of the invention incorporate a monocyclic pyrimidine or pyridine ring scaffold optionally substituted by aliphatic, functional and/or aromatic substituents. Preferably, the scaffold has a heteroaryl group at the 2 position and an arylalkyl amine group at position 4 of the pyrimidine scaffold or at position 4 or 6 of the pyridine scaffold. For the pyridine scaffold, this arrangement places the arylalkyl amine group para to the pyridine nitrogen when the heteroaryl group is ortho to the pyridine nitrogen or places the arylalkyl amine and heteroaryl groups both ortho to the pyridine nitrogen. More preferably, the scaffold is substituted by a benzyl amine group at the 4 position of the pyrimidine scaffold or 4 or 6 position of the pyridine scaffold and a heteroaryl 5:6 bicyclic ring at the 2 position. The scaffold ring as well as the arylalkyl amine and heteroaryl groups may be substituted by optional multiple aliphatic, functional and/or aromatic components described in the foregoing Definitions section.

A preferred embodiment of the monocyclic scaffold of the invention is a monocyclic pyrimidine compound of Formula I:

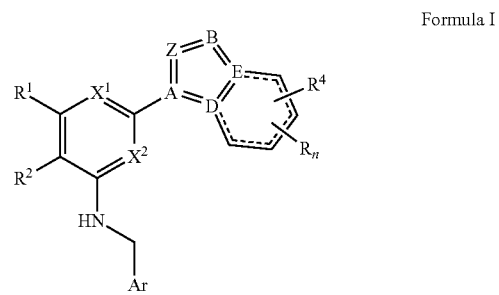

Formula I

The moieties $X^1$, $X^2$, A, B, D, E, Z and Ar are defined above in the Summary section. The definitions and provisos concerning A, B, D, E and Z provide a 5:6 bicyclic heteroaryl group. The 5:6 bicyclic heteroaryl group with symbols A, B, D, E and Z is a subcategory of the aromatic/heteroaromatic group and the heteroaryl group as defined in the foregoing Definitions section. Those embodiments of the heteroaryl group set forth in the Definitions section that constitute a 5:6 bicyclic heteroaryl group are included within the understanding of the 5:6 bicyclic heteraryl group substituent of Formula I. These embodiments are included as the 2 position substituent of the pyrimidine and pyridine scaffold with all optional substitutions defined by $R_n$ and $R_1$-$R_5$ irrespective of whether they meet the provisos associated with A, B, D, E and Z. Also, the position of $R^4$ is preferred to be ortho to E, especially when n of $R_n$ is 0.

Embodiments of the 2-(5:6 Bicyclic Heteroaryl) Scaffolds.

The preferred aromaticity of the 5:6 bicyclic heteroaryl group constituting the 2 position substituent of Formula I establishes that four double bonds are present in this group. This definition and the provisos given in the foregoing Summary produce the following substituted scaffolds as Embodiments. Each of these embodiments as substituted by the groups provided by Formula I is an individually preferred version of Formula I. Each is separate, distinct and is recited as a stand-alone preferred version of Formula I.

In this preferred context calling for aromaticity of the 5:6 bicyclic heteroaryl group, the corresponding five membered ring cannot be formed as an all nitrogen ring nor can it be formed with four nitrogens and one carbon.

With three nitrogens and two carbons, the following structural embodiments are exemplified.

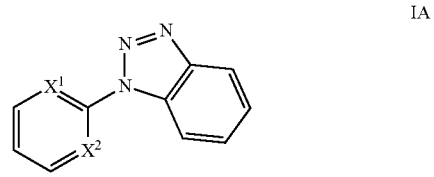

IA

-continued

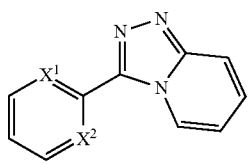
IB

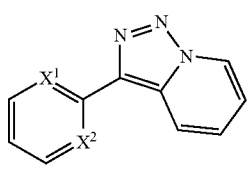
IC

With two nitrogens and three carbons, the following structural embodiments are exemplified.

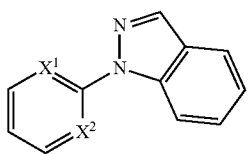
ID

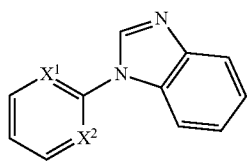
IE

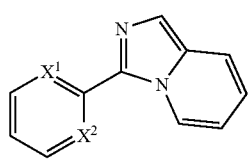
IF

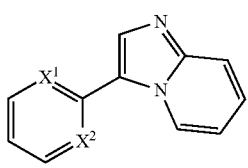
IG

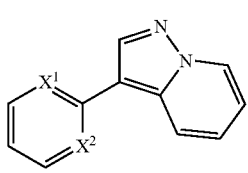
IH

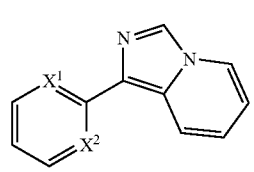
II

With one nitrogen and four carbons, the following structural embodiments are exemplified.

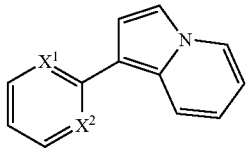
IJ

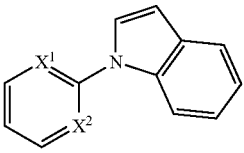
IK

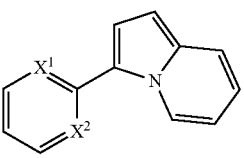
IM

With one nitrogen as NR³, the following structural embodiments are exemplified.

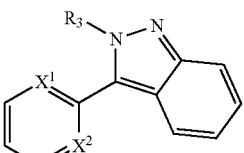
IN

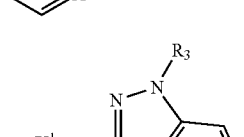
IO

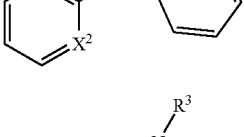
IP

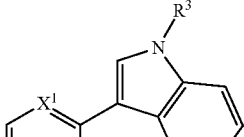
IQ

With O or S, the following structural embodiments are exemplified.

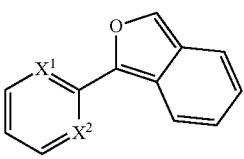
IR

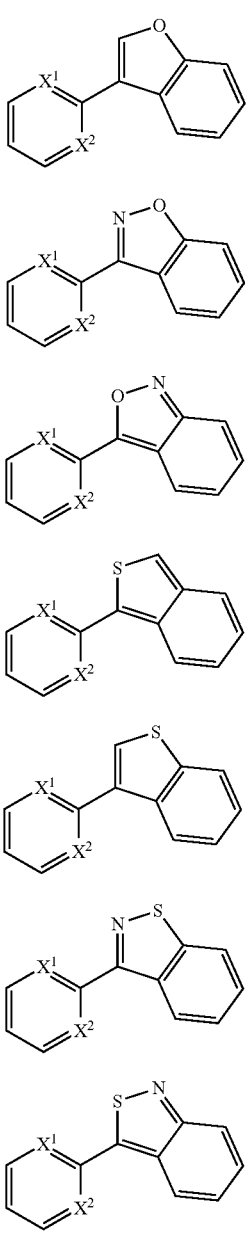

IS

IT

IU

IV

IW

IX

IY

Description of Arylalkyl Amine Substituent at 4 position, $R_n$ and $R^1$, $R^2$, $R^3$, $R^4$ and $R^5$ ($R^1$-$R^5$) for Formulas IA-IY In all of the foregoing structure examples, the arylalkyl amine at the 4 position and $R_n$ and $R^1$-$R^5$ substituents are not shown but are understood to be present as given by foregoing Formula I. These substituents have the same positions and identities as are given for Formula I. Each of these examples IA-IY as substituted by the groups Arylalkyl amine, Rn, and $R_1R_5$ as set forth by Formula I is an individually preferred version of Formula I. Each is separate, distinct and is recited as a stand-alone preferred version of Formula I. The preferred recitations of the substituents Arylalkyl amine, Rn, and $R_1R_5$ also apply to this description of each separate and distinct Formula IA-IY such that the preferred recitations of these substituents constitute preferred subgroups of each separate and distinct Formula IA-IY as if these recitations were fully and completely set forth herein.

Preferences for $X^1$ and $X^2$ of Formulas IA-IY

Preferred embodiments of Formulas IA-IY with the substituents as described above and below for Arylalkyl amine, $R_n$ and $R^1$-$R^5$ (general, preferred, more preferred, especially preferred and most preferred) include those in which $X^1$ and $X^2$ are both N (pyrimidine scaffold). Additional preferred embodiments of Formulas IA-IY with the substituents as described above and below for Arylalkyl amine, $R_n$ and $R^1$-$R^5$ (general, preferred, more preferred, especially preferred and most preferred) include those in which $X^1$ is N and $X^2$ is C (pyridine scaffold) or $X^1$ is C and $X^2$ is N (pyridine scaffold). Especially preferred embodiments of Formulas IA-IY with these same general, preferred, more preferred, especially preferred and most preferred substituent designations for Arylalkyl amine, $R_n$ and $R^1$-$R^5$ include those in which $X^1$ and $X^2$ are both N, and those in which $X^1$ is C and $X^2$ is N. Most especially preferred embodiments of formulas IA-IY with these same general, preferred, more preferred, especially preferred and most especially preferred substituent designations for Arylalkyl amine, $R_n$ and $R^1$-$R^5$ include those in which $X^1$ and $X^2$ are both N (pyrimidine scaffold).

Preferences of Formulas IA-IY with the Foregoing $X^1$ and $X^2$ Designations

Among Formulas IA-IY with the preferences for $X^1$ and $X^2$ and Arylalkyl amine, $R_n$ and $R^1$-$R^5$ given above and below, Formulas IA, ID, IE, IG, IH, IK, IO, IP, IT, IU, IX and IY are preferred. More preferred with the preferences for $X^1$ and $X^2$ and Arylalkyl amine, $R_n$ and $R^1$-$R^5$ given above and below are IA, ID, IE, IG, IH, IK, IP and IS. Most preferred with the preferences for $X^1$ and $X^2$ and Arylalkyl amine, $R_n$ and $R^1$-$R^5$ given above and below are IA, ID, IE, IK, IP and IS.

Description of Formula II

A subgenus of Formula I is Formula II. Formula II incorporates scaffolds JE, IK and IP above with a 5:6 bicyclic heteroaryl group substituted at the 2 position.

The monocyclic pyrimidine or pyridine compound of Formula II has the structure given below wherein $R^1$, $R^2$, $R^3$ and $R^4$ are described in the Summary and have the same general, preferred, more preferred and most preferred substituent definitions as given for Formula I. The substituent $R^6$ is the same as the general, preferred, more preferred and most preferred substituents for Ar of formula I. Especially preferred species for $R^6$ are H and/or F. Preferably for this substitution pattern, $R^1$ and $R^2$ are not both methyl and are not both hydrogen.

Formula II

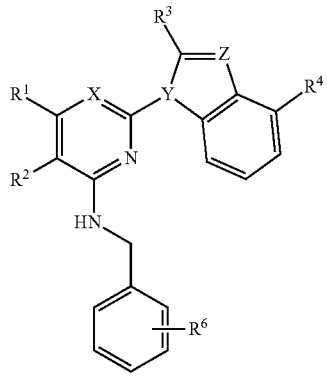

Description of General and Preferred Substituents Arylalkyl amine, $R_n$, and $R^1$, $R^2$, $R^3$, $R^4$, $R^5$, and $R^6$ for Formulas I, II and IA-IY The general and preferred descriptions of Arylalkyl amine, $R_n$ and $R^1$ through $R^5$ for Formula I and $R^1$ through $R^4$ and $R^6$ for Formula II are given above in the Summary of the Invention. The preferred, more preferred, especially preferred and most preferred descriptions of these substituents are given in the following descriptions. These general, preferred, more preferred and most preferred descriptions of Arylalkyl amine, $R_n$ and $R^1$ through $R^5$ for Formula I and $R^1$ through $R^4$ and $R^6$ for Formula II apply also to Formulas IA-IY, to the preferred, especially preferred and most especially preferred embodiments of Formula IA-IY with the $X^1$ and $X^2$ designations given above (the section titled "preferences for $X^1$ and $X^2$ of Formulas IA-IY"); and also to the preferred, more preferred and most preferred selections of Formula IA-IY with the $X^1$ and $X^2$ designations as given above (the section titled "preferences of Formulas IA-IY with the foregoing $X^1$ and $X^2$ designations").

It goes without formal specification that $R^1$ and $R^2$ of Formula I and Formula II do not combine to form a ring. The essential scaffold is the 2-position 5:6 bicyclic heteroaryl monocyclic pyridine or pyrimidine.

For Formula I, the 4 position substituent of the pyrimidine ring or the 2 or 6 position substituent of the pyridine ring is Arylalkyl amine. Preferably, the substituent at the 4 position of the pyrimidine ring or the 2 or 6 position of the pyridine ring of each Formula IA-IY is $NHCH_2Aryl$; more preferably $NHCH_2Ph$ wherein Ph is phenyl and the phenyl may optionally be substituted by one or two groups (preferably one group) ortho, meta or para to the $NHCH_2$ moiety and these substituents may independently be H (i.e., unsubstituted phenyl), halogen (preferably fluoro, chloro or bromo, more preferably fluoro or chloro, most preferably fluoro), $C_1$ to $C_6$ linear, branched or cyclo alkyl or perfluoroalkyl, CN, $CO_2H$, CONHR' or $SO_2R'$ $CO_2R'$ wherein each instance of R' is $C_1$ to $C_6$ linear, branched or cyclo alkyl. The most preferred substituent at the 4 position of each Formula IA-IY is $NHCH_2Ph$ wherein the phenyl is unsubstituted or is fluorophenyl.

For Formulas I and II, substituents $R_n$, $R^1$, $R^2$, $R^3$, $R^4$, $R^5$ and $R^6$ preferably have the following designations. These preferences apply as given to Formulas IA-IY and also with the preferences for Arylalkyl amine as given above, and also to the preferences for $X^1$ and $X^2$ given above (the section titled "preferences for $X^1$ and $X^2$ of Formulas IA-IY") and to the preferences for Formulas IA-IY with the $X^1$ and $X^2$ preferences given above (the section titled "preferences of Formulas IA-IY with the foregoing $X^1$ and $X^2$ designations").

$R^1$ and $R^2$ are each independently selected from the group consisting of hydrogen, $C_1$ to $C_6$ alkyl, branched alkyl or cycloalkyl, $OR^d$, CN, $SR^d$, $OC(O)R^d$, $C(O)R^d$, $C(O)OR^d$, $OC(O)N(R^d)_2$, $C(O)N(R^d)_2$, $N(R^d)C(O)OR^d$, $N(R^d)C(O)R^d$, $-N(R^d)C(O)N(R^d)_2$, $N(R^d)C(NR^d)N(R^d)_2$, $N(R^d)S(O)_tR^d$, $S(O)_tOR^d$, $S(O)_tR^d$, $S(O)_tN(R^d)_2$, $N(R^d)_2$, $(CH_2)_tN(R^d)_2$, $PO_3(R^d)_2$ and $C(O)R^d$, $CF_3$ wherein each $R^d$ is independently hydrogen, alkyl, fluoroalkyl, carbocyclyl, carbocyclylalkyl, aryl, aralkyl, heterocyclyl, heterocyclylalkyl, heteroaryl, heteroarylalkyl alkenyl, alkynyl or any combination thereof.

$R_n$, $R^3$ and $R^4$ are each selected from the group consisting of hydrogen, halogen, $C_1$ to $C_6$ alkyl, branched alkyl or cycloalkyl, $OR^d$, CN, $SR^d$, $OC(O)R^d$, $C(O)R^d$, $C(O)OR^d$, $OC(O)N(R^d)_2$, $C(O)N(R^d)_2$, $N(R^d)C(O)OR^d$, $N(R^d)C(O)R^d$, $-N(R^d)C(O)N(R^d)_2$, $N(R^d)C(NR^d)N(R^d)_2$, $N(R^d)S(O)_tR^d$, $S(O)_tOR^d$, $S(O)_tN(R^d)_2$, $N(R^d)_2$, $(CH_2)_tN(R^d)_2$ and $PO_3(R^d)_2$ wherein each $R^d$ is independently hydrogen, alkyl, fluoroalkyl, carbocyclyl, carbocyclylalkyl, aryl, aralkyl, heterocyclyl, heterocyclylalkyl, heteroaryl, heteroarylalkyl alkenyl, alkynyl or any combination thereof. Each t is independently selected from the group of integers of 1 and 2.

$R^5$ is preferably selected from the group consisting of hydrogen, $C_1$ to $C_6$ alkyl, branched alkyl or cycloalkyl, trifluoromethyl, phenyl, fluorophenyl, furanyl, thiophenyl, tetrahydrofuranyl, tetrahydrothiophenyl, and especially methyl, ethyl, propyl, trifluoromethyl and pentafluoroethyl.

The more preferred substituents of the 5:6 bicyclic heteroaryl group at the two position of the Formula I and Formula II scaffolds (including $R_n$, $R^3$ and $R^4$ of Formulas I and II but not $R^5$ of Formula I) include a functional component selected from the group consisting of hydroxy, halo, cyano, $C_1$ to $C_6$ alkyl, branched alkyl or cycloalkyl, trifluoromethyl, trifluoromethoxy, nitro, trimethylsilanyl, $OR^a$, $SR^a$, $OC(O)$ $R^a$, $N(R^a)_2$, $C(O)R^a$, $C(O)OR^a$, $-OC(O)N(R^a)_2$, $C(O)N(R^a)_2 N(R^a)C(O)OR^a$, $N(R^a)C(O)R^a$, $N(R^a)C(O)N(R^a)_2$, $N(R^a)C(NR^a)N(R^a)_2$, $N(R^a)S(O)_tR^a$, $S(O)_tOR^a$, $S(O)_tN(R^a)_2$, $-R^aN(R^a)_2$, $PO_3(R^a)_2$ and any combination thereof; wherein each $R^a$ is independently hydrogen, alkyl, fluoroalkyl, carbocyclyl, carbocyclylalkyl, aryl, aralkyl, heterocyclyl, heterocyclylalkyl, heteroaryl, heteroarylalkyl or any combination thereof; and wherein each t independently is an integer of 1 or 2.

More preferred embodiments of Formula I include the monocyclic pyrimidine and pyridine compounds of formulas IA, ID, IE, IG, IH, IK, IO, IP, IT, IU IX and IY where $R^1$ and $R^2$ are each independently from, H, Me, OMe, CN, $OCH_2CH_2X$, $N(R^a)_2$, $CO(NR^a)_2$ $SO_2R^a$, $SO_2N(R^a)_2$. $R_n$, R3 and $R^4$ are selected from H, $OCH_2CH_2X$ (wherein X is amino, alkylamino, alkoxy, carboxy, carboxamide, carboxyl ester or N-alkyl carboxyamide), $C_1$ to $C_4$ linear, branched or cycloalkyl, $C_1$ to $C_4$ alkoxy of the same isomerism as given for alkyl, COOH, CONH(Ra), $SO2NH(R_a)$. $R^5$ is selected from H, $C_1$ to $C_4$ alkyl or $COR_a$, $R_a$ being $C_1$ to $C_4$ linear, branched or cyclo alkyl in each instance. The more preferred embodiments of Formula II include these same selections for $R^1$, $R^2$, $R^3$ and $R^4$.

Especially preferred monocyclic pyrimidine and pyridine compounds are represented by Formulas IA, ID, IE, IG, IH, IK, IO, IP, IT, IU, IX IY and by Formula II wherein X is N and Y is N. For these especially preferred compounds of Formulas I and II, $R^1$ and $R^2$ are each independently from H, Me, OMe, $OCH_2CH_2X$ (wherein X is amino, alkylamino, alkoxy, carboxy, carboxamide, carboxyl ester or N-alkyl carboxyamide), $N(R^a)_2$, $CO(NR^a)_2$ $SO_2R^a$, $SO_2N(R^a)_2$. $R^4$ is selected from H, Me, OMe, $OCH_2CH_2X$ (wherein X is amino, alkylamino, alkoxy, carboxy, carboxamide, carboxyl ester or N-alkyl carboxyamide). $R_n$ and $R^3$ are each independently selected from H, Me, OMe, $OCH_2CH_2X$ (wherein X is amino, alkylamino, alkoxy, carboxy, carboxamide, carboxyl ester or N-alkyl carboxyamide), CN, COOH, $CONH(R^a)$, $SO2NH(R^a)$ wherein each $R^a$ is independently hydrogen, alkyl, fluoroalkyl, carbocyclyl, carbocyclylalkyl, aryl, aralkyl, heterocyclyl, heterocyclylalkyl, heteroaryl, heteroarylalkyl or any combination thereof; and wherein each t independently is an integer of 1 or 2. For Formula I, an especially preferred $R^5$ is selected from H, Me, Et, COMe or COEt. For Formula I with these especially preferred designations, the arylalkyl amine substituent is as given above for the preferred, more preferred and most preferred designations. For formula II an especially preferred $R^6$ is H or F.

Preferred Specific Compounds of Formulas I and II

Specific embodiments of the monocyclic pyrimidine and pyridine compounds of Formulas I and II include the specific compounds named in the following List. Almost all monocyclic pyrimidine and pyridine compounds of this List have been synthesized and demonstrate appropriate biological activity in one or more Biological Assays described herein.

The especially preferred species of the monocyclic pyrimidine and pyridine compounds of Formula I include the following synthesized compounds. These compounds are identified by their IUPAC names.

1-[4-(benzylamino)-5-(2-methoxyethoxy)pyrimidin-2-yl]-6-fluoro-2-methyl-1H-indole-4-carboxamide;
1-[4-(benzylamino)-5-(2-methoxyethyl)pyrimidin-2-yl]-6-fluoro-2-methyl-1H-indole-4-carboxamide;
1-[4-(benzylamino)-5-(acetamido methyl)pyrimidin-2-yl]-6-fluoro-2-methyl-1H-indole-4-carboxamide;
1-[4-(benzylamino)-5-(dimethylamino)pyrimidin-2-yl]-6-fluoro-2-methyl-1H-indole-4-carboxamide;
1-[4-(benzylamino)-5-(methoxymethyl)pyrimidin-2-yl]-6-fluoro-2-methyl-1H-indole-4-carboxamide;
1-[4-(benzylamino)-5-(morpholin-4-yl)pyrimidin-2-yl]-6-fluoro-2-methyl-1H-indole-4-carboxamide;
1-[4-(benzylamino)-5-(morpholin-4-ylmethyl)pyrimidin-2-yl]-6-fluoro-2-methyl-1H-indole-4-carboxamide;
1-[4-(benzylamino)-5-(oxetan-3-yl)pyrimidin-2-yl]-6-fluoro-2-methyl-1H-indole-4-carboxamide;
1-[4-(benzylamino)-5-(oxolan-2-yl)pyrimidin-2-yl]-6-fluoro-2-methyl-1H-indole-4-carboxamide;
1-[4-(benzylamino)-5-(piperidin-4-yl)pyrimidin-2-yl]-6-fluoro-2-methyl-1H-indole-4-carboxamide;
1-[4-(benzylamino)-5-(propan-2-yl)pyrimidin-2-yl]-6-fluoro-2-methyl-1H-indole-4-carboxamide;
1-[4-(benzylamino)-5-(propan-2-yloxy)pyrimidin-2-yl]-6-fluoro-2-methyl-1H-indole-4-carboxamide;
1-[4-(benzylamino)-5-(pyrrolidin-2-yl)pyrimidin-2-yl]-6-fluoro-2-methyl-1H-indole-4-carboxamide;
1-[4-(benzylamino)-5-(trifluoromethyl)pyrimidin-2-yl]-6-fluoro-2-methyl-1H-indole-4-carboxamide;
1-[4-(benzylamino)-5-[(dimethylamino)methyl]pyrimidin-2-yl]-6-fluoro-2-methyl-1H-indole-4-carboxamide;
1-[4-(benzylamino)-5-[(methylamino)methyl]pyrimidin-2-yl]-6-fluoro-2-methyl-1 H-indole-4-carboxamide;
1-[4-(benzylamino)-5-[2-(methylamino)ethyl]pyrimidin-2-yl]-6-fluoro-2-methyl-1H-indole-4-carboxamide;
1-[4-(benzylamino)-5-carbamoylpyrimidin-2-yl]-6-fluoro-2-methyl-1H-indole-4-carboxamide;
1-[4-(benzylamino)-5-chloropyrimidin-2-yl]-6-fluoro-2-methyl-1H-indole-4-carboxamide;
1-[4-(benzylamino)-5-ethoxypyrimidin-2-yl]-6-fluoro-2-methyl-1H-indole-4-carboxamide;
1-[4-(benzylamino)-5-methanesulfonylpyrimidin-2-yl]-6-fluoro-2-methyl-1H-indole-4-carboxamide;
1-[4-(benzylamino)-5-methoxy-6-[(methylamino)methyl]pyrimidin-2-yl]-6-fluoro-2-methyl-1H-indole-4-carboxamide;
1-[4-(benzylamino)-5-methoxypyrimidin-2-yl]-6-fluoro-2-methyl-1H-indole-4-carboxamide;
1-[4-(benzylamino)-5-methyl-6-[(methylamino)methyl]pyrimidin-2-yl]-6-fluoro-2-methyl-1H-indole-4-carboxamide;
1-[4-(benzylamino)-5-methylpyrimidin-2-yl]-6-fluoro-2-methyl-1H-indole-4-carboxamide;
1-[4-(benzylamino)-6-(dimethylamino)-5-methylpyrimidin-2-yl]-6-fluoro-2-methyl-1H-indole-4-carboxamide;
1-[4-(benzylamino)-6-fluoro-5-methylpyrimidin-2-yl]-6-fluoro-2-methyl-1H-indole-4-carboxamide;
1-[4-(benzylamino)-6-methylpyrimidin-2-yl]-6-fluoro-2-methyl-1H-indole-4-carboxamide;
1-[5-(azetidin-3-yl)-4-(benzylamino)pyrimidin-2-yl]-6-fluoro-2-methyl-1H-indole-4-carboxamide;
1-[5-amino-4-(benzylamino)pyrimidin-2-yl]-6-fluoro-2-methyl-1H-indole-4-carboxamide;
1-[6-(benzylamino)pyridin-2-yl]-6-fluoro-2-methyl-1H-indole-4-carboxamide;
2-[4-(aminomethyl)-6-fluoro-2-methyl-1H-indol-1-yl]-N-benzyl-5-methoxypyrimidin-4-amine
2-[4-(aminomethyl)-6-fluoro-2-methyl-1H-indol-1-yl]-N-benzyl-5-methylpyrimidin-4-amine
1-(4-(benzylamino)-5-(trifluoromethyl) pyrimidin-2-yl)-6-fluoro-2-methyl-1H-indole-4-carboxamide;
1-[4-(benzylamino)-5-(1-hydroxyethyl)pyrimidin-2-yl]-6-fluoro-2-methyl-1H-indole-4-carboxamide;
1-[4-(benzylamino)-5-(dimethylamino)-6-methylpyrimidin-2-yl]-6-fluoro-2-methyl-1H-indole-4-carboxamide;
1-[4-(benzylamino)-5-(dimethylaminomethyl)pyrimidin-2-yl]-6-fluoro-2-methyl-1H-indole-4-carboxamide;
1-[4-(benzylamino)-5-(methylaminomethyl)pyrimidin-2-yl]-6-fluoro-2-methyl-1 H-indole-4-carboxamide;
1-[4-(benzylamino)-5-(morpholinomethyl)pyrimidin-2-yl]-6-fluoro-2-methyl-1 H-indole-4-carboxamide;
1-[4-(benzylamino)-5-(oxan-4-yl)pyrimidin-2-yl]-6-fluoro-2-methyl-1H-indole-4-carboxamide;
1-[4-(benzylamino)-5-[2-(methylamino)ethyl]pyrimidin-2-yl]-6-fluoro-2-methyl-indole-4-carboxamide;
1-[4-(benzylamino)-5-carbamoyl-pyrimidin-2-yl]-6-fluoro-2-methyl-1H-indole-4-carboxamide;
1-[4-(benzylamino)-5-ethoxy-pyrimidin-2-yl]-6-fluoro 2-methyl-indole-4-carboxamide;
1-[4-(benzylamino)-5-ethylpyrimidin-2-yl]-6-fluoro-2-methyl-1H-indole-4-carboxamide;
1-[4-(benzylamino)-5-isopropoxy-pyrimidin-2-yl]-6-fluoro-2-methyl-H-indole-4-carboxamide;
1-[4-(benzylamino)-5-methoxy-6-(methylaminomethyl)pyrimidin-2-yl]-6-fluoro-2-methyl-1H-indole-4-carboxamide;
1-[4-(benzylamino)-5-methoxy-6-methylpyrimidin-2-yl]-6-fluoro-2-methyl-1H-indole-4-carboxamide;
1-[4-(benzylamino)-5-methyl-6-(methylaminomethyl)pyrimidin-2-yl]-6-fluoro-2-methyl-H-indole-4-carboxamide;
1-[4-(benzylamino)-5-methyl-6-(trifluoromethyl)pyrimidin-2-yl]-6-fluoro-2-methyl-1H-indole-4-carboxamide;
1-[4-(benzylamino)-5-methylsulfonyl-pyrimidin-2-yl]-6-fluoro-2-methyl-1H-indole-4-carboxamide;
1-[4-(benzylamino)-5-morpholino-pyrimidin-2-yl]-6-fluoro-2-methyl-1H-indole-4-carboxamide;
1-[4-(benzylamino)-6-methoxy-5-methylpyrimidin-2-yl]-6-fluoro-2-methyl-1H-indole-4-carboxamide;
1-[4-(benzylamino)-6-methyl-5-(morpholin-4-yl)pyrimidin-2-yl]-6-fluoro-2-methyl-1H-indole-4-carboxamide;
1-[4-(benzylamino)-6-methyl-5-(propan-2-yl)pyrimidin-2-yl]-6-fluoro-2-methyl-1 H-indole-4-carboxamide;
1-[5-(1-aminoeth yl)-4-(benz ylamino)pyrimidin-2-yl]-6-fluoro-2-methyl-1H-indole-4-carboxamide;
1-[5-(2-aminoethoxy)-4-(benz ylamino)pyrimidin-2-yl]-6-fluoro-2-methyl-1H-indole-4-carboxamide;
1-[5-(2-aminoeth yl)-4-(benz ylamino)pyrimidin-2-yl]-6-fluoro-2-methyl-1H-indole-4-carboxamide;
1-[5-(acetamidomethyl)-4-(benzylamino)pyrimidin-2-yl]-6-fluoro-2-methyl-1H-indole-4-carboxamide;
1-[5-(aminomethyl)-4-(benzylamino)pyrimidin-2-yl]-6-fluoro-2-methyl-1H-indole-4-carboxamide;
1-[6-(benzylamino)-2-pyridyl]-6-fluoro-2-methyl-1H-indole-4-carboxamide;
2-(aminomethyl)-1-[4-(benzylamino)-5-(propan-2-yl)pyrimidin-2-yl]-6-fluoro-1H-indole-4-carboxamide;

2-(aminomethyl)-1-[4-(benzylamino)-5-ethylpyrimidin-2-yl]-6-fluoro-1H-indole-4-carboxamide;
2-(aminomethyl)-1-[4-(benzylamino)-5-methoxypyrimidin-2-yl]-6-fluoro-1H-indole-4-carboxamide;
2-(aminomethyl)-1-[4-(benzylamino)-5-methylpyrimidin-2-yl]-6-fluoro-1H-indole-4-carboxamide;
2-[4-(aminomethyl)-2-methyl-6-fluoro-1H-indol-1-yl]-N-benzyl-5-(propan-2-yl)pyrimidin-4-amine
2-[4-(aminomethyl)-2-methyl-6-fluoro-1H-indol-1-yl]-N-benzyl-5, 6-dimethylpyrimidin-4-amine
2-[4-(aminomethyl)-2-methyl-6-fluoro-1H-indol-1-yl]-N-benzyl-5-methoxy-pyrimidin-4-amine
2-[4-(aminomethyl)-2-methyl-6-fluoro-1H-indol-1-yl]-N-benzyl-5-methyl-pyrimidin-4-amine
2-[4-(aminomethyl)-6-fluoro-2-methyl-6-fluoro-1H-indol-1-yl]-N-benzyl-5-methoxypyrimidin-4-amine
1-(4-(benzylamino)-5-(dimethylamino)-6-methylpyrimidin-2-yl)-1H-indazole-4-carboxamide;
1-(4-(benzylamino)-5-isopropyl-6-methylpyrimidin-2-yl)-1H-indazole-4-carboxamide;
1-(4-(benzylamino)-5-methoxypyrimidin-2-yl)-1H-indazole-4-carboxamide;
1-(4-{[(3-fluorophenyl)methyl]amino}-5-methoxypyrimidin-2-yl)-1H-indazole-4-carboxamide;
1-[4-(benzylamino)-5-(1-hydroxyethyl)pyrimidin-2-yl]-1H-indazole-4-carboxamide;
1-[4-(benzylamino)-5-(2-methoxyethoxy)pyrimidin-2-yl]-1H-indazole-4-carboxamide;
1-[4-(benzylamino)-5-(acetamido methyl)pyrimidin-2-yl]-1H-indazole-4-carboxamide;
1-[4-(benzylamino)-5-(dimethylamino)-6-methylpyrimidin-2-yl]-1H-indazole-4-carboxamide;
1-[4-(benzylamino)-5-(dimethylamino)pyrimidin-2-yl]-1H-indazole-4-carboxamide;
1-[4-(benzylamino)-5-(methoxymethyl)pyrimidin-2-yl]-1H-indazole-4-carboxamide;
1-[4-(benzylamino)-5-(propan-2-yl)pyrimidin-2-yl]-1H-indazole-4-carboxamide;
1-[4-(benzylamino)-5-(propan-2-yloxy)pyrimidin-2-yl]-1H-indazole-4-carboxamide;
1-[4-(benzylamino)-5-(trifluoromethyl)pyrimidin-2-yl]-1H-indazole-4-carboxamide;
1-[4-(benzylamino)-5,6-dimethylpyrimidin-2-yl]-1H-indazole-4-carboxamide;
1-[4-(benzylamino)-5-carbamoylpyrimidin-2-yl]-1H-indazole-4-carboxamide;
1-[4-(benzylamino)-5-chloropyrimidin-2-yl]-1H-indazole-4-carboxamide;
1-[4-(benzylamino)-5-ethoxypyrimidin-2-yl]-1H-indazole-4-carboxamide;
1-[4-(benzylamino)-5-ethylpyrimidin-2-yl]-1H-indazole-4-carboxamide;
1-[4-(benzylamino)-5-methanesulfonylpyrimidin-2-yl]-1H-indazole-4-carboxamide;
1-[4-(benzylamino)-5-methoxy-6-methylpyrimidin-2-yl]-1H-indazole-4-carboxamide;
1-[4-(benzylamino)-5-methoxypyrimidin-2-yl]-1H-indazole-4-carboxamide;
1-[4-(benzylamino)-5-methyl-6-(trifluoromethyl)pyrimidin-2-yl]-1H-indazole-4-carboxamide;
1-[4-(benzylamino)-5-methyl-6-[(methylamino)methyl]pyrimidin-2-yl]-1H-indazole-4-carboxamide;
1-[4-(benzylamino)-5-methylpyrimidin-2-yl]-1H-indazole-4-carboxamide;
1-[4-(benzylamino)-6-(dimethylamino)-5-methylpyrimidin-2-yl]-1H-indazole-4-carboxamide;
1-[4-(benzylamino)-6-methoxy-5-methylpyrimidin-2-yl]-1H-indazole-4-carboxamide;
1-[4-(benzylamino)-6-methyl-5-(propan-2-yl)pyrimidin-2-yl]-1H-indazole-4-carboxamide;
1-[4-(benzylamino)-6-methylpyrimidin-2-yl]-1H-indazole-4-carboxamide;
1-[5-(1-aminoeth yl)-4-(benz ylamino)pyrimidin-2-yl]-1H-indazole-4-carboxamide;
1-[5-(aminomethyl)-4-(benzylamino)pyrimidin-2-yl]-1H-indazole-4-carboxamide;
1-[5-(benzylamino)-6-methyl-1,2,4-triazin-3-yl]-1H-indazole-4-carboxamide;
1-[5-amino-4-(benzylamino)pyrimidin-2-yl]-1H-indazole-4-carboxamide;
1-[6-(benzylamino)pyridin-2-yl]-1H-indazole-4-carboxamide;
2-[4-(aminomethyl)-1H-indazol-1-yl]-N-benzyl-5-methoxypyrimidin-4-amine 2-(aminomethyl)-3-[4-(benzylamino)-5-(propan-2-yl)pyrimidin-2-yl]-1H-indole-4-carboxamide;
2-(aminomethyl)-3-[4-(benzylamino)-5-ethylpyrimidin-2-yl]-1H-indole-4-carboxamide;
2-(aminomethyl)-3-[4-(benzylamino)-5-methoxypyrimidin-2-yl]-1H-indole-4-carboxamide;
2-[4-(aminomethyl)-2-methyl-1H-indol-3-yl]-N-benzyl-5-methoxypyrimidin-4-amine;
3-(4-(benzylamino)-5-(dimethylamino)-6-methylpyrimidin-2-yl)-2-methyl-1H-indole-4-carboxamide;
3-(4-(benzylamino)-5-isopropyl-6-methylpyrimidin-2-yl)-2-methyl-1H-indole-4-carboxamide;
3-(4-(benzylamino)-5-methoxypyrimidin-2-yl)-2-methyl-1H-indole-4-carboxamide;
3-[4-(benzylamino)-5-(1-hydroxyethyl)pyrimidin-2-yl]-2-methyl-1H-indole-4-carboxamide;
3-[4-(benzylamino)-5-(2-methoxyethoxy)pyrimidin-2-yl]-2-methyl-1H-indole-4-carboxamide;
3-[4-(benzylamino)-5-(acetamido methyl)pyrimidin-2-yl]-2-methyl-1H-indole-4-carboxamide;
3-[4-(benzylamino)-5-(dimethylamino)-6-methylpyrimidin-2-yl]-1H-indole-4-carboxamide;
3-[4-(benzylamino)-5-(dimethylamino)-6-methylpyrimidin-2-yl]-2-methyl-1H-indole-4-carboxamide;
3-[4-(benzylamino)-5-(dimethylamino)pyrimidin-2-yl]-2-methyl-1H-indole-4-carboxamide;
3-[4-(benzylamino)-5-(methoxymethyl)pyrimidin-2-yl]-2-methyl-1H-indole-4-carboxamide;
3-[4-(benzylamino)-5-(propan-2-yl)pyrimidin-2-yl]-2-methyl-1H-indole-4-carboxamide;
3-[4-(benzylamino)-5-(propan-2-yloxy)pyrimidin-2-yl]-2-methyl-1H-indole-4-carboxamide;
3-[4-(benzylamino)-5-(trifluoromethyl)pyrimidin-2-yl]-2-methyl-1H-indole-4-carboxamide;
3-[4-(benzylamino)-5,6-dimethylpyrimidin-2-yl]-1H-indole-4-carboxamide;
3-[4-(benzylamino)-5-carbamoylpyrimidin-2-yl]-2-methyl-1H-indole-4-carboxamide;
3-[4-(benzylamino)-5-chloropyrimidin-2-yl]-2-methyl-1H-indole-4-carboxamide;
3-[4-(benzylamino)-5-ethoxypyrimidin-2-yl]-2-methyl-1H-indole-4-carboxamide;
3-[4-(benzylamino)-5-ethylpyrimidin-2-yl]-2-methyl-1H-indole-4-carboxamide;
3-[4-(benzylamino)-5-methanesulfonylpyrimidin-2-yl]-2-methyl-1H-indole-4-carboxamide;
3-[4-(benzylamino)-5-methoxy-6-methylpyrimidin-2-yl]-1H-indole-4-carboxamide;

3-[4-(benzylamino)-5-methoxy-6-methylpyrimidin-2-yl]-2-methyl-1H-indole-4-carboxamide;
3-[4-(benzylamino)-5-methoxypyrimidin-2-yl]-2-methyl-1H-indole-4-carboxamide;
3-[4-(benzylamino)-5-methyl-6-(trifluoromethyl)pyrimidin-2-yl]-2-methyl-1H-indole-4-carboxamide;
3-[4-(benzylamino)-5-methyl-6-[(methylamino)methyl]pyrimidin-2-yl]-2-methyl-1H-indole-4-carboxamide;
3-[4-(benzylamino)-5-methylpyrimidin-2-yl]-2-methyl-1H-indole-4-carboxamide;
3-[4-(benzylamino)-6-(dimethylamino)-5-methylpyrimidin-2-yl]-2-methyl-1H-indole-4-carboxamide;
3-[4-(benzylamino)-6-methoxy-5-methylpyrimidin-2-yl]-2-methyl-1H-indole-4-carboxamide;
3-[4-(benzylamino)-6-methyl-5-(propan-2-yl)pyrimidin-2-yl]-2-methyl-1H-indole-4-carboxamide;
3-[4-(benzylamino)-6-methylpyrimidin-2-yl]-2-methyl-1H-indole-4-carboxamide;
3-[5-(1-aminoethyl)-4-(benzylamino)pyrimidin-2-yl]-2-methyl-1H-indole-4-carboxamide;
3-[5-(aminomethyl)-4-(benzylamino)pyrimidin-2-yl]-2-methyl-1H-indole-4-carboxamide;
3-[5-(benzylamino)-6-methyl-1,2,4-triazin-3-yl]-2-methyl-1H-indole-4-carboxamide;
3-[5-amino-4-(benzylamino)pyrimidin-2-yl]-2-methyl-1H-indole-4-carboxamide;
3-[6-(benzylamino)pyridin-2-yl]-2-methyl-1H-indole-4-carboxamide.

The most especially preferred species of the monocyclic pyrimidine and pyridine compounds of Formula I include the following synthesized compounds. These compounds are identified by their IUPAC names.

1-[4-(benzylamino)-5-(1-hydroxyethyl)pyrimidin-2-yl]-6-fluoro-2-methyl-1H-indole-4-carboxamide;
1-[4-(benzylamino)-5-(2-methoxyethoxy)pyrimidin-2-yl]-6-fluoro-2-methyl-1H-indole-4-carboxamide;
1-[4-(benzylamino)-5-(acetamido methyl)pyrimidin-2-yl]-6-fluoro-2-methyl-1H-indole-4-carboxamide;
1-[4-(benzylamino)-5-(dimethylamino)-6-methylpyrimidin-2-yl]-6-fluoro-2-methyl-1H-indole-4-carboxamide;
1-[4-(benzylamino)-5-(dimethylamino)pyrimidin-2-yl]-6-fluoro-2-methyl-1H-indole-4-carboxamide;
1-[4-(benzylamino)-5-(methoxymethyl)pyrimidin-2-yl]-6-fluoro-2-methyl-1H-indole-4-carboxamide;
1-[4-(benzylamino)-5-(propan-2-yl)pyrimidin-2-yl]-6-fluoro-2-methyl-1H-indole-4-carboxamide;
1-[4-(benzylamino)-5-(propan-2-yloxy)pyrimidin-2-yl]-6-fluoro-2-methyl-1H-indole-4-carboxamide;
1-[4-(benzylamino)-5-(trifluoromethyl)pyrimidin-2-yl]-6-fluoro-2-methyl-1H-indole-4-carboxamide;
1-[4-(benzylamino)-5-carbamoylpyrimidin-2-yl]-6-fluoro-2-methyl-1H-indole-4-carboxamide;
1-[4-(benzylamino)-5-chloropyrimidin-2-yl]-6-fluoro-2-methyl-1H-indole-4-carboxamide;
1-[4-(benzylamino)-5-ethoxypyrimidin-2-yl]-6-fluoro-2-methyl-1H-indole-4-carboxamide;
1-[4-(benzylamino)-5-ethylpyrimidin-2-yl]-6-fluoro-2-methyl-1H-indole-4-carboxamide;
1-[4-(benzylamino)-5-methanesulfonylpyrimidin-2-yl]-6-fluoro-2-methyl-1H-indole-4-carboxamide;
1-[4-(benzylamino)-5-methoxy-6-methylpyrimidin-2-yl]-6-fluoro-2-methyl-1H-indole-4-carboxamide;
1-[4-(benzylamino)-5-methoxypyrimidin-2-yl]-6-fluoro-2-methyl-1H-indole-4-carboxamide;
1-[4-(benzylamino)-5-methyl-6-(trifluoromethyl)pyrimidin-2-yl]-6-fluoro-2-methyl-1H-indole-4-carboxamide;
1-[4-(benzylamino)-5-methyl-6-[(methylamino)methyl]pyrimidin-2-yl]-6-fluoro-2-methyl-1H-indole-4-carboxamide;
1-[4-(benzylamino)-5-methylpyrimidin-2-yl]-6-fluoro-2-methyl-1H-indole-4-carboxamide;
1-[4-(benzylamino)-6-(dimethylamino)-5-methylpyrimidin-2-yl]-6-fluoro-2-methyl-1H-indole-4-carboxamide;
1-[4-(benzylamino)-6-methoxy-5-methylpyrimidin-2-yl]-6-fluoro-2-methyl-1H-indole-4-carboxamide;
1-[4-(benzylamino)-6-methyl-5-(propan-2-yl)pyrimidin-2-yl]-6-fluoro-2-methyl-1H-indole-4-carboxamide;
1-[4-(benzylamino)-6-methylpyrimidin-2-yl]-6-fluoro-2-methyl-1H-indole-4-carboxamide;
1-[5-(1-aminoeth yl)-4-(benz ylamino)pyrimidin-2-yl]-6-fluoro-2-methyl-1H-indole-4-carboxamide;
1-[5-(aminomethyl)-4-(benzylamino)pyrimidin-2-yl]-6-fluoro-2-methyl-1H-indole-4-carboxamide;
1-[5-amino-4-(benzylamino)pyrimidin-2-yl]-6-fluoro-2-methyl-1H-indole-4-carboxamide;
1-[6-(benzylamino)pyridin-2-yl]-6-fluoro-2-methyl-1H-indole-4-carboxamide;
2-(aminomethyl)-1-[4-(benzylamino)-5-(propan-2-yl)pyrimidin-2-yl]-6-fluoro-1H-indole-4-carboxamide;
2-(aminomethyl)-1-[4-(benzylamino)-5-ethylpyrimidin-2-yl]-6-fluoro-1H-indole-4-carboxamide;
2-(aminomethyl)-1-[4-(benzylamino)-5-methoxypyrimidin-2-yl]-6-fluoro-1H-indole-4-carboxamide;
2-[4-(aminomethyl)-6-fluoro-2-methyl-1H-indol-1-yl]-N-benzyl-5-methoxypyrimidin-4-amine
1-(4-(benzylamino)-5-isopropyl-6-methylpyrimidin-2-yl)-1H-indazole-4-carboxamide;
1-(4-{[(3-fluorophenyl)methyl]amino}-5-methoxypyrimidin-2-yl)-1H-indazole-4-carboxamide;
1-[4-(benzylamino)-5-(dimethylamino)-6-methylpyrimidin-2-yl]-1H-indazole-4-carboxamide;
1-[4-(benzylamino)-5,6-dimethylpyrimidin-2-yl]-1H-indazole-4-carboxamide;
1-[4-(benzylamino)-5-methoxy-6-methylpyrimidin-2-yl]-1H-indazole-4-carboxamide.

The especially preferred species of the monocyclic pyrimidine and pyridine compounds of Formula II include the following synthesized compounds. These compounds are identified by their IUPAC names.

1-[4-(benzylamino)-5-(2-methoxyethoxy)pyrimidin-2-yl]-2-methyl-1H-indole-4-carboxamide;
1-[4-(benzylamino)-5-(2-methoxyethyl)pyrimidin-2-yl]-2-methyl-1H-indole-4-carboxamide;
1-[4-(benzylamino)-5-(acetamidomethyl)pyrimidin-2-yl]-2-methyl-1H-indole-4-carboxamide;
1-[4-(benzylamino)-5-(dimethylamino)pyrimidin-2-yl]-2-methyl-1H-indole-4-carboxamide;
1-[4-(benzylamino)-5-(methoxymethyl)pyrimidin-2-yl]-2-methyl-1H-indole-4-carboxamide;
1-[4-(benzylamino)-5-(morpholin-4-yl)pyrimidin-2-yl]-2-methyl-1H-indole-4-carboxamide;
1-[4-(benzylamino)-5-(morpholin-4-ylmethyl)pyrimidin-2-yl]-2-methyl-1H-indole-4-carboxamide;
1-[4-(benzylamino)-5-(oxetan-3-yl)pyrimidin-2-yl]-2-methyl-1H-indole-4-carboxamide;
1-[4-(benzylamino)-5-(oxolan-2-yl)pyrimidin-2-yl]-2-methyl-1H-indole-4-carboxamide;
1-[4-(benzylamino)-5-(piperidin-4-yl)pyrimidin-2-yl]-2-methyl-1H-indole-4-carboxamide;
1-[4-(benzylamino)-5-(propan-2-yl)pyrimidin-2-yl]-2-methyl-1H-indole-4-carboxamide;
1-[4-(benzylamino)-5-(propan-2-yloxy)pyrimidin-2-yl]-2-methyl-1H-indole-4-carboxamide;

1-[4-(benzylamino)-5-(pyrrolidin-2-yl)pyrimidin-2-yl]-2-methyl-1H-indole-4-carboxamide;
1-[4-(benzylamino)-5-(trifluoromethyl)pyrimidin-2-yl]-2-methyl-1H-indole-4-carboxamide;
1-[4-(benzylamino)-5-[(dimethylamino)methyl]pyrimidin-2-yl]-2-methyl-1H-indole-4-carboxamide;
1-[4-(benzylamino)-5-[(methylamino)methyl]pyrimidin-2-yl]-2-methyl-1H-indole-4-carboxamide;
1-[4-(benzylamino)-5-[2-(methylamino)ethyl]pyrimidin-2-yl]-2-methyl-1H-indole-4-carboxamide;
1-[4-(benzylamino)-5-carbamoylpyrimidin-2-yl]-2-methyl-1H-indole-4-carboxamide;
1-[4-(benzylamino)-5-chloropyrimidin-2-yl]-2-methyl-1H-indole-4-carboxamide;
1-[4-(benzylamino)-5-ethoxypyrimidin-2-yl]-2-methyl-1H-indole-4-carboxamide;
1-[4-(benzylamino)-5-methanesulfonylpyrimidin-2-yl]-2-methyl-1H-indole-4-carboxamide;
1-[4-(benzylamino)-5-methoxy-6-[(methylamino)methyl]pyrimidin-2-yl]-2-methyl-1H-indole-4-carboxamide;
1-[4-(benzylamino)-5-methoxypyrimidin-2-yl]-2-methyl-1H-indole-4-carboxamide;
1-[4-(benzylamino)-5-methyl-6-[(methylamino)methyl]pyrimidin-2-yl]-2-methyl-1H-indole-4-carboxamide;
1-[4-(benzylamino)-5-methylpyrimidin-2-yl]-2-methyl-1H-indole-4-carboxamide;
1-[4-(benzylamino)-6-(dimethylamino)-5-methylpyrimidin-2-yl]-2-methyl-1H-indole-4-carboxamide;
1-[4-(benzylamino)-6-(methoxymethyl)-5-methylpyrimidin-2-yl]-1H-1,3-benzodiazol-2-amine;
1-[4-(benzylamino)-6-fluoro-5-methylpyrimidin-2-yl]-2-methyl-1H-indole-4-carboxamide;
1-[4-(benzylamino)-6-methylpyrimidin-2-yl]-2-methyl-1H-indole-4-carboxamide;
1-[5-(azetidin-3-yl)-4-(benzylamino)pyrimidin-2-yl]-2-methyl-1H-indole-4-carboxamide;
1-[5-amino-4-(benzylamino)pyrimidin-2-yl]-2-methyl-1H-indole-4-carboxamide;
1-[6-(benzylamino)pyridin-2-yl]-2-methyl-1H-indole-4-carboxamide;
2-[4-(aminomethyl)-2-methyl-1H-indol-1-yl]-N-benzyl-5-methoxypyrimidin-4-amine;
2-[4-(aminomethyl)-2-methyl-1H-indol-1-yl]-N-benzyl-5-methylpyrimidin-4-amine;
6-(benzylamino)-5-methyl-2-(2-methyl-1H-1,3-benzodiazol-1-yl)-3,4-dihydropyrimidin-4-one;
1-(4-(benzylamino)-5-(trifluoromethyl)pyrimidin-2-yl)-2-methyl-1H-indole-4-carboxamide;
1-[4-(benzylamino)-5-(1-hydroxyethyl)pyrimidin-2-yl]-2-methyl-1H-indole-4-carboxamide;
1-[4-(benzylamino)-5-(dimethylamino)-6-methylpyrimidin-2-yl]-2-methoxy-1H-1,3-benzodiazole-4-carboxamide;
1-[4-(benzylamino)-5-(dimethylamino)-6-methylpyrimidin-2-yl]-2-methyl-1H-1,3-benzodiazole-4-carboxamide;
1-[4-(benzylamino)-5-(dimethylamino)-6-methylpyrimidin-2-yl]-2-methyl-1H-indole-4-carboxamide;
1-[4-(benzylamino)-5-(dimethylamino)pyrimidin-2-yl]-2-methoxy-1H-1,3-benzodiazole-4-carboxamide;
1-[4-(benzylamino)-5-(dimethylamino)pyrimidin-2-yl]-2-methyl-1H-1,3-benzodiazole-4-carboxamide;
1-[4-(benzylamino)-5-(dimethylaminomethyl)pyrimidin-2-yl]-2-methyl-1H-indole-4-carboxamide;
1-[4-(benzylamino)-5-(methylaminomethyl)pyrimidin-2-yl]-2-methyl-1H-indole-4-carboxamide;
1-[4-(benzylamino)-5-(morpholinomethyl)pyrimidin-2-yl]-2-methyl-1H-indole-4-carboxamide;
1-[4-(benzylamino)-5-(oxan-4-yl)pyrimidin-2-yl]-2-methyl-1H-indole-4-carboxamide;
1-[4-(benzylamino)-5-(propan-2-yl)pyrimidin-2-yl]-2-methoxy-1H-1,3-benzodiazole-4-carboxamide;
1-[4-(benzylamino)-5-(propan-2-yl)pyrimidin-2-yl]-2-methyl-1H-1,3-benzodiazole-4-carboxamide;
1-[4-(benzylamino)-5-(propan-2-yloxy)pyrimidin-2-yl]-2-methoxy-1H-1,3-benzodiazole-4-carboxamide;
1-[4-(benzylamino)-5-carbamoylpyrimidin-2-yl]-2-methoxy-1H-1,3-benzodiazole-4-carboxamide;
1-[4-(benzylamino)-5-carbamoyl-pyrimidin-2-yl]-2-methyl-1H-indole-4-carboxamide;
1-[4-(benzylamino)-5-ethoxy-6-methylpyrimidin-2-yl]-2-methoxy-1H-1,3-benzodiazole-4-carboxamide;
1-[4-(benzylamino)-5-ethoxypyrimidin-2-yl]-2-methoxy-1H-1,3-benzodiazole-4-carboxamide;
1-[4-(benzylamino)-5-ethoxy-pyrimidin-2-yl]-2-methyl-1H-indole-4-carboxamide;
1-[4-(benzylamino)-5-ethylpyrimidin-2-yl]-2-methoxy-1H-1,3-benzodiazole-4-carboxamide;
1-[4-(benzylamino)-5-ethylpyrimidin-2-yl]-2-methyl-1H-1,3-benzodiazole-4-carboxamide;
1-[4-(benzylamino)-5-ethylpyrimidin-2-yl]-2-methyl-1H-indole-4-carboxamide;
1-[4-(benzylamino)-5-isopropoxy-pyrimidin-2-yl]-2-methyl-1H-indole-4-carboxamide;
1-[4-(benzylamino)-5-methoxy-6-(methylaminomethyl)pyrimidin-2-yl]-2-methyl-1H-indole-4-carboxamide;
1-([4-(benzylamino)-5-methoxypyrimidin-2-yl])-2-methoxy-1H-1,3-benzodiazole-4-carboxamide;
1-[4-(benzylamino)-5-methoxy-6-methylpyrimidin-2-yl]-2-methoxy-1H-1,3-benzodiazole-4-carboxamide;
1-[4-(benzylamino)-5-methoxy-6-methylpyrimidin-2-yl]-2-methyl-1H-1,3-benzodiazole-4-carboxamide;
1-[4-(benzylamino)-5-methoxy-6-methylpyrimidin-2-yl]-2-methyl-1H-indole-4-carboxamide;
1-[4-(benzylamino)-5-methoxypyrimidin-2-yl]-2-methoxy-1H-1,3-benzodiazole-4-carboxamide;
1-[4-(benzylamino)-5-methoxypyrimidin-2-yl]-2-methyl-1H-1,3-benzodiazole-4-carboxamide;
1-[4-(benzylamino)-5-methyl-6-(methylaminomethyl)pyrimidin-2-yl]-2-methyl-1H-indole-4-carboxamide;
1-[4-(benzylamino)-5-methyl-6-(trifluoromethyl)pyrimidin-2-yl]-2-methyl-1H-indole-4-carboxamide;
1-[4-(benzylamino)-5-methylpyrimidin-2-yl]-2-methoxy-1H-1,3-benzodiazole-4-carboxamide;
1-[4-(benzylamino)-5-methylpyrimidin-2-yl]-2-methyl-1H-1,3-benzodiazole-4-carboxamide;
1-[4-(benzylamino)-5-methylsulfonyl-pyrimidin-2-yl]-2-methyl-1H-indole-4-carboxamide;
1-[4-(benzylamino)-5-morpholino-pyrimidin-2-yl]-2-methyl-1H-indole-4-carboxamide;
1-[4-(benzylamino)-6-methoxy-5-methylpyrimidin-2-yl]-2-methyl-1H-indole-4-carboxamide;
1-[4-(benzylamino)-6-methyl-5-(morpholin-4-yl)pyrimidin-2-yl]-2-methyl-1H-indole-4-carboxamide;
1-[4-(benzylamino)-6-methyl-5-(propan-2-yl)pyrimidin-2-yl]-2-methoxy-1H-1,3-benzodiazole-4-carboxamide;
1-[4-(benzylamino)-6-methyl-5-(propan-2-yl)pyrimidin-2-yl]-2-methyl-1H-1,3-benzodiazole-4-carboxamide;
1-[4-(benzylamino)-6-methyl-5-(propan-2-yl)pyrimidin-2-yl]-2-methyl-1H-indole-4-carboxamide;
1-[4-(benzylamino)-6-methyl-5-(propan-2-yloxy)pyrimidin-2-yl]-2-methoxy-1H-1,3-benzodiazole-4-carboxamide;
1-[5-(1-aminoethyl)-4-(benzylamino)pyrimidin-2-yl]-2-methyl-1H-indole-4-carboxamide;

1-[5-(2-aminoethoxy)-4-(benzylamino)pyrimidin-2-yl]-2-methyl-1H-indole-4-carboxamide;
1-[5-(2-aminoethyl)-4-(benzylamino)pyrimidin-2-yl]-2-methyl-1H-indole-4-carboxamide;
1-[5-(acetamidomethyl)-4-(benzylamino)pyrimidin-2-yl]-2-methyl-1H-indole-4-carboxamide;
1-[5-(aminomethyl)-4-(benzylamino)pyrimidin-2-yl]-2-methyl-1H-indole-4-carboxamide;
1-[6-(benzylamino)-2-pyridyl]-2-methoxy-benzimidazole-4-carboxamide;
1-[6-(benzylamino)-2-pyridyl]-2-methyl-1H-indole-4-carboxamide;
2-(aminomethyl)-1-[4-(benzylamino)-5-(propan-2-yl)pyrimidin-2-yl]-1H-indole-4-carboxamide;
2-(aminomethyl)-1-[4-(benzylamino)-5-ethylpyrimidin-2-yl]-1H-indole-4-carboxamide;
2-(aminomethyl)-1-[4-(benzylamino)-5-methoxypyrimidin-2-yl]-1H-indole-4-carboxamide;
2-(aminomethyl)-1-[4-(benzylamino)-5-methylpyrimidin-2-yl]-1H-indole-4-carboxamide;
2-[4-(aminomethyl)-2-methyl-1H-indol-1-yl]-N-benzyl-5-(propan-2-yl)pyrimidin-4-amine;
2-[4-(aminomethyl)-2-methyl-1H-indol-1-yl]-N-benzyl-5,6-dimethylpyrimidin-4-amine;
2-[4-(aminomethyl)-2-methyl-1H-indol-1-yl]-N-benzyl-5-methoxy-pyrimidin-4-amine;
2-[4-(aminomethyl)-2-methyl-1H-indol-1-yl]-N-benzyl-5-methyl-pyrimidin-4-amine;
1-([4-{[(3-fluorophenyl)methyl]amino}-5-methoxypyrimidin-2-yl)-2-methoxy-1H-1,3-benzodiazole-4-carboxamide;
2-(4-(aminomethyl)-2-methyl-1H-indol-1-yl)-N-(3-fluorobenzyl)-5-methoxypyrimidin-4-amine
1-(4-{[(3-fluorophenyl)methyl]amino}-5-(trifluoromethyl)pyrimidin-2-yl)-2-methyl-1H-indole-4-carboxamide;
1-[4-{[(3-fluorophenyl)methyl]amino}-5-(1-hydroxyethyl)pyrimidin-2-yl]-2-methyl-1H-indole-4-carboxamide;
1-[4-{[(3-fluorophenyl)methyl]amino}-5-(2-methoxyethoxy)pyrimidin-2-yl]-2-methyl-1H-indole-4-carboxamide;
1-[4-{[(3-fluorophenyl)methyl]amino}-5-(2-methoxyethyl)pyrimidin-2-yl]-2-methyl-1H-indole-4-carboxamide;
1-[4-{[(3-fluorophenyl)methyl]amino}-5-(acetamidomethyl)pyrimidin-2-yl]-2-methyl-1H-indole-4-carboxamide;
1-[4-{[(3-fluorophenyl)methyl]amino}-5-(dimethylamino)-6-methylpyrimidin-2-yl]-2-methoxy-1H-1,3-benzodiazole-4-carboxamide;
1-[4-{[(3-fluorophenyl)methyl]amino}-5-(dimethylamino)-6-methylpyrimidin-2-yl]-2-methyl-1H-1,3-benzodiazole-4-carboxamide;
1-[4-{[(3-fluorophenyl)methyl]amino}-5-(dimethylamino)-6-methylpyrimidin-2-yl]-2-methyl-1H-indole-4-carboxamide;
1-[4-{[(3-fluorophenyl)methyl]amino}-5-(dimethylamino)pyrimidin-2-yl]-2-methoxy-1H-1,3-benzodiazole-4-carboxamide;
1-[4-{[(3-fluorophenyl)methyl]amino}-5-(dimethylamino)pyrimidin-2-yl]-2-methyl-1H-1,3-benzodiazole-4-carboxamide;
1-[4-{[(3-fluorophenyl)methyl]amino}-5-(dimethylamino)pyrimidin-2-yl]-2-methyl-1H-indole-4-carboxamide;
1-[4-{[(3-fluorophenyl)methyl]amino}-5-(dimethylaminomethyl)pyrimidin-2-yl]-2-methyl-1H-indole-4-carboxamide;
1-[4-{[(3-fluorophenyl)methyl]amino}-5-(methoxymethyl)pyrimidin-2-yl]-2-methyl-1H-indole-4-carboxamide;
1-[4-{[(3-fluorophenyl)methyl]amino}-5-(methylaminomethyl)pyrimidin-2-yl]-2-methyl-indole-4-carboxamide;
1-[4-{[(3-fluorophenyl)methyl]amino}-5-(morpholin-4-yl)pyrimidin-2-yl]-2-methyl-1H-indole-4-carboxamide;
1-[4-{[(3-fluorophenyl)methyl]amino}-5-(morpholin-4-ylmethyl)pyrimidin-2-yl]-2-methyl-1H-indole-4-carboxamide;
1-[4-{[(3-fluorophenyl)methyl]amino}-5-(morpholinomethyl)pyrimidin-2-yl]-2-methyl-1H-indole-4-carboxamide;
1-[4-{[(3-fluorophenyl)methyl]amino}-5-(oxan-4-yl)pyrimidin-2-yl]-2-methyl-1H-indole-4-carboxamide;
1-[4-{[(3-fluorophenyl)methyl]amino}-5-(oxetan-3-yl)pyrimidin-2-yl]-2-methyl-1H-indole-4-carboxamide;
1-[4-{[(3-fluorophenyl)methyl]amino}-5-(oxolan-2-yl)pyrimidin-2-yl]-2-methyl-1H-indole-4-carboxamide;
1-[4-{[(3-fluorophenyl)methyl]amino}-5-(piperidin-4-yl)pyrimidin-2-yl]-2-methyl-1H-indole-4-carboxamide;
1-[4-{[(3-fluorophenyl)methyl]amino}-5-(propan-2-yl)pyrimidin-2-yl]-2-methoxy-1H-1,3-benzodiazole-4-carboxamide;
1-[4-{[(3-fluorophenyl)methyl]amino}-5-(propan-2-yl)pyrimidin-2-yl]-2-methyl-1H-1,3-benzodiazole-4-carboxamide;
1-[4-{[(3-fluorophenyl)methyl]amino}-5-(propan-2-yl)pyrimidin-2-yl]-2-methyl-1H-indole-4-carboxamide;
1-[4-{[(3-fluorophenyl)methyl]amino}-5-(propan-2-yloxy)pyrimidin-2-yl]-2-methoxy-1H-1,3-benzodiazole-4-carboxamide;
1-[4-{[(3-fluorophenyl)methyl]amino}-5-(propan-2-yloxy)pyrimidin-2-yl]-2-methyl-1H-indole-4-carboxamide;
1-[4-{[(3-fluorophenyl)methyl]amino}-5-(pyrrolidin-2-yl)pyrimidin-2-yl]-2-methyl-1H-indole-4-carboxamide;
1-[4-{[(3-fluorophenyl)methyl]amino}-5-(trifluoromethyl)pyrimidin-2-yl]-2-methyl-1H-indole-4-carboxamide;
1-[4-{[(3-fluorophenyl)methyl]amino}-5-[(dimethylamino)methyl]pyrimidin-2-yl]-2-methyl-1H-indole-4-carboxamide;
1-[4-{[(3-fluorophenyl)methyl]amino}-5-[(methylamino)methyl]pyrimidin-2-yl]-2-methyl-1H-indole-4-carboxamide;
1-[4-{[(3-fluorophenyl)methyl]amino}-5-[2-(methylamino)ethyl]pyrimidin-2-yl]-2-methyl-1H-indole-4-carboxamide;
1-[4-{[(3-fluorophenyl)methyl]amino}-5-carbamoylpyrimidin-2-yl]-2-methoxy-1H-1,3-benzodiazole-4-carboxamide;
1-[4-{[(3-fluorophenyl)methyl]amino}-5-carbamoylpyrimidin-2-yl]-2-methyl-1 H-indole-4-carboxamide;
1-[4-{[(3-fluorophenyl)methyl]amino}-5-carbamoyl-pyrimidin-2-yl]-2-methyl-1H-indole-4-carboxamide;
1-[4-{[(3-fluorophenyl)methyl]amino}-5-chloropyrimidin-2-yl]-2-methyl-1H-indole-4-carboxamide;
1-[4-{[(3-fluorophenyl)methyl]amino}-5-ethoxy-6-methylpyrimidin-2-yl]-2-methoxy-1H-1,3-benzodiazole-4-carboxamide;
1-[4-{[(3-fluorophenyl)methyl]amino}-5-ethoxypyrimidin-2-yl]-2-methoxy-1H-1,3-benzodiazole-4-carboxamide;
1-[4-{[(3-fluorophenyl)methyl]amino}-5-ethoxypyrimidin-2-yl]-2-methyl-1H-indole-4-carboxamide;
1-[4-{[(3-fluorophenyl)methyl]amino}-5-ethoxy-pyrimidin-2-yl]-2-methyl-1H-indole-4-carboxamide;
1-[4-{[(3-fluorophenyl)methyl]amino}-5-ethylpyrimidin-2-yl]-2-methoxy-1H-1,3-benzodiazole-4-carboxamide;
1-[4-{[(3-fluorophenyl)methyl]amino}-5-ethylpyrimidin-2-yl]-2-methyl-1H-1,3-benzodiazole-4-carboxamide;
1-[4-{[(3-fluorophenyl)methyl]amino}-5-ethylpyrimidin-2-yl]-2-methyl-1H-indole-4-carboxamide;

1-[4-{[(3-fluorophenyl)methyl]amino}-5-isopropoxy-pyrimidin-2-yl]-2-methyl-1H-indole-4-carboxamide;
1-[4-{[(3-fluorophenyl)methyl]amino}-5-methanesulfonylpyrimidin-2-yl]-2-methyl-1H-indole-4-carboxamide;
1-[4-{[(3-fluorophenyl)methyl]amino}-5-methoxy-6-(methylaminomethyl)pyrimidin-2-yl]-2-methyl-1H-indole-4-carboxamide;
1-[4-{[(3-fluorophenyl)methyl]amino}-5-methoxy-6-[(methylamino)methyl]pyrimidin-2-yl]-2-methyl-1H-indole-4-carboxamide;
1-[4-{[(3-fluorophenyl)methyl]amino}-5-methoxy-6-methylpyrimidin-2-yl]-2-methoxy-1H-1,3-benzodiazole-4-carboxamide;
1-[4-{[(3-fluorophenyl)methyl]amino}-5-methoxy-6-methylpyrimidin-2-yl]-2-methyl-1H-1,3-benzodiazole-4-carboxamide;
1-[4-{[(3-fluorophenyl)methyl]amino}-5-methoxy-6-methylpyrimidin-2-yl]-2-methyl-1H-indole-4-carboxamide;
1-[4-{[(3-fluorophenyl)methyl]amino}-5-methoxypyrimidin-2-yl]-2-methoxy-1H-1,3-benzodiazole-4-carboxamide;
1-[4-{[(3-fluorophenyl)methyl]amino}-5-methoxypyrimidin-2-yl]-2-methyl-1H-1,3-benzodiazole-4-carboxamide;
1-[4-{[(3-fluorophenyl)methyl]amino}-5-methoxypyrimidin-2-yl]-2-methyl-1H-indole-4-carboxamide;
1-[4-{[(3-fluorophenyl)methyl]amino}-5-methyl-6-(methylaminomethyl)pyrimidin-2-yl]-2-methyl-1H-indole-4-carboxamide;
1-[4-{[(3-fluorophenyl)methyl]amino}-5-methyl-6-(trifluoromethyl)pyrimidin-2-yl]-2-methyl-1H-indole-4-carboxamide;
1-[4-{[(3-fluorophenyl)methyl]amino}-5-methyl-6-[(methylamino)methyl]pyrimidin-2-yl]-2-methyl-1H-indole-4-carboxamide;
1-[4-{[(3-fluorophenyl)methyl]amino}-5-methylpyrimidin-2-yl]-2-methoxy-1H-1,3-benzodiazole-4-carboxamide;
1-[4-{[(3-fluorophenyl)methyl]amino}-5-methylpyrimidin-2-yl]-2-methyl-1H-1,3-benzodiazole-4-carboxamide;
1-[4-{[(3-fluorophenyl)methyl]amino}-5-methylpyrimidin-2-yl]-2-methyl-1H-indole-4-carboxamide;
1-[4-{[(3-fluorophenyl)methyl]amino}-5-methylsulfonylpyrimidin-2-yl]-2-methyl-1H-indole-4-carboxamide;
1-[4-{[(3-fluorophenyl)methyl]amino}-5-morpholino-pyrimidin-2-yl]-2-methyl-1H-indole-4-carboxamide;
1-[4-{[(3-fluorophenyl)methyl]amino}-6-(dimethylamino)-5-methylpyrimidin-2-yl]-2-methyl-1H-indole-4-carboxamide;
1-[4-{[(3-fluorophenyl)methyl]amino}-6-(methoxymethyl)-5-methylpyrimidin-2-yl]-1H-1,3-benzodiazol-2-amine
1-[4-{[(3-fluorophenyl)methyl]amino}-6-fluoro-5-methylpyrimidin-2-yl]-2-methyl-1H-indole-4-carboxamide;
1-[4-{[(3-fluorophenyl)methyl]amino}-6-methoxy-5-methylpyrimidin-2-yl]-2-methyl-1H-indole-4-carboxamide;
1-[4-{[(3-fluorophenyl)methyl]amino}-6-methyl-5-(morpholin-4-yl)pyrimidin-2-yl]-2-methyl-1H-indole-4-carboxamide;
1-[4-{[(3-fluorophenyl)methyl]amino}-6-methyl-5-(propan-2-yl)pyrimidin-2-yl]-2-methoxy-1H-1,3-benzodiazole-4-carboxamide;
1-[4-{[(3-fluorophenyl)methyl]amino}-6-methyl-5-(propan-2-yl)pyrimidin-2-yl]-2-methyl-1H-1,3-benzodiazole-4-carboxamide;
1-[4-{[(3-fluorophenyl)methyl]amino}-6-methyl-5-(propan-2-yl)pyrimidin-2-yl]-2-methyl-1H-indole-4-carboxamide;
1-[4-{[(3-fluorophenyl)methyl]amino}-6-methyl-5-(propan-2-yloxy)pyrimidin-2-yl]-2-methoxy-1H-1,3-benzodiazole-4-carboxamide;
1-[4-{[(3-fluorophenyl)methyl]amino}-6-methylpyrimidin-2-yl]-2-methyl-1H-indole-4-carboxamide;
1-[5-(1-aminoethyl)-4-{[(3-fluorophenyl)methyl]amino}pyrimidin-2-yl]-2-methyl-1H-indole-4-carboxamide;
1-[5-(2-aminoethoxy)-4-{[(3-fluorophenyl)methyl]amino}pyrimidin-2-yl]-2-methyl-1H-indole-4-carboxamide;
1-[5-(2-aminoethyl)-4-{[(3-fluorophenyl)methyl]amino}pyrimidin-2-yl]-2-methyl-1H-indole-4-carboxamide;
1-[5-(acetamidomethyl)-4-{[(3-fluorophenyl)methyl]amino}pyrimidin-2-yl]-2-methyl-1H-indole-4-carboxamide;
1-[5-(aminomethyl)-4-{[(3-fluorophenyl)methyl]amino}pyrimidin-2-yl]-2-methyl-1H-indole-4-carboxamide;
1-[5-(azetidin-3-yl)-4-{[(3-fluorophenyl)methyl]amino}pyrimidin-2-yl]-2-methyl-1H-indole-4-carboxamide;
1-[5-amino-4-{[(3-fluorophenyl)methyl]amino}pyrimidin-2-yl]-2-methyl-1H-indole-4-carboxamide;
1-[6-{[(3-fluorophenyl)methyl]amino}-2-pyridyl]-2-methoxy-benzimidazole-4-carboxamide;
1-[6-{[(3-fluorophenyl)methyl]amino}-2-pyridyl]-2-methyl-1H-indole-4-carboxamide;
1-[6-{[(3-fluorophenyl)methyl]amino}pyridin-2-yl]-2-methoxy-1H-1,3-benzodiazole-4-carboxamide;
1-[6-{[(3-fluorophenyl)methyl]amino}pyridin-2-yl]-2-methyl-1H-indole-4-carboxamide;
2-(aminomethyl)-1-[4-{[(3-fluorophenyl)methyl]amino}-5-(propan-2-yl)pyrimidin-2-yl]-1H-indole-4-carboxamide;
2-(aminomethyl)-1-[4-{[(3-fluorophenyl)methyl]amino}-5-ethylpyrimidin-2-yl]-1H-indole-4-carboxamide;
2-(aminomethyl)-1-[4-{[(3-fluorophenyl)methyl]amino}-5-methoxypyrimidin-2-yl]-1H-indole-4-carboxamide;
2-(aminomethyl)-1-[4-{[(3-fluorophenyl)methyl]amino}-5-methylpyrimidin-2-yl]-1H-indole-4-carboxamide;
6-{[(3-fluorophenyl)methyl]amino}-5-methyl-2-(2-methyl-1H-1,3-benzodiazol-1-yl)-3,4-dihydropyrimidin-4-one.

The most especially preferred species of the monocyclic pyrimidine and pyridine compounds of Formula II include the following synthesized compounds. These compounds are identified by their IUPAC names.

1-([4-(benzylamino)-5-methoxypyrimidin-2-yl)-2-methoxy-1H-1,3-benzodiazole-4-carboxamide;
1-[4-(benzylamino)-5-(1-hydroxyethyl)pyrimidin-2-yl]-2-methyl-1H-indole-4-carboxamide;
1-[4-(benzylamino)-5-(2-methoxyethoxy)pyrimidin-2-yl]-2-methyl-1H-indole-4-carboxamide;
1-[4-(benzylamino)-5-(acetamido methyl)pyrimidin-2-yl]-2-methyl-1H-indole-4-carboxamide;
1-[4-(benzylamino)-5-(dimethylamino)-6-methylpyrimidin-2-yl]-2-methoxy-1H-1,3-benzodiazole-4-carboxamide;
1-[4-(benzylamino)-5-(dimethylamino)-6-methylpyrimidin-2-yl]-2-methyl-1H-indole-4-carboxamide;
1-[4-(benzylamino)-5-(dimethylamino)pyrimidin-2-yl]-2-methyl-1H-indole-4-carboxamide;
1-[4-(benzylamino)-5-(methoxymethyl)pyrimidin-2-yl]-2-methyl-1H-indole-4-carboxamide;
1-[4-(benzylamino)-5-(propan-2-yl)pyrimidin-2-yl]-2-methyl-1H-indole-4-carboxamide;
1-[4-(benzylamino)-5-(propan-2-yloxy)pyrimidin-2-yl]-2-methyl-1H-indole-4-carboxamide;

1-[4-(benzylamino)-5-(trifluoromethyl)pyrimidin-2-yl]-2-methyl-1H-indole-4-carboxamide;
1-[4-(benzylamino)-5-carbamoylpyrimidin-2-yl]-2-methyl-1H-indole-4-carboxamide;
1-[4-(benzylamino)-5-chloropyrimidin-2-yl]-2-methyl-1H-indole-4-carboxamide;
1-[4-(benzylamino)-5-ethoxypyrimidin-2-yl]-2-methyl-1H-indole-4-carboxamide;
1-[4-(benzylamino)-5-ethylpyrimidin-2-yl]-2-methyl-1H-indole-4-carboxamide;
1-[4-(benzylamino)-5-(methanesulfonyl)pyrimidin-2-yl]-2-methyl-1H-indole-4-carboxamide;
1-[4-(benzylamino)-5-methoxy-6-methylpyrimidin-2-yl]-2-methyl-1H-indole-4-carboxamide;
1-[4-(benzylamino)-5-methoxypyrimidin-2-yl]-2-methyl-1H-indole-4-carboxamide;
1-[4-(benzylamino)-5-methyl-6-(trifluoromethyl)pyrimidin-2-yl]-2-methyl-1H-indole-4-carboxamide;
1-[4-(benzylamino)-5-methyl-6-[(methylamino)methyl]pyrimidin-2-yl]-2-methyl-1H-indole-4-carboxamide;
1-[4-(benzylamino)-5-methylpyrimidin-2-yl]-2-methyl-1H-indole-4-carboxamide;
1-[4-(benzylamino)-6-(dimethylamino)-5-methylpyrimidin-2-yl]-2-methyl-1H-indole-4-carboxamide;
1-[4-(benzylamino)-6-methoxy-5-methylpyrimidin-2-yl]-2-methyl-1H-indole-4-carboxamide;
1-[4-(benzylamino)-6-methyl-5-(propan-2-yl)pyrimidin-2-yl]-2-methoxy-1H-1,3-benzodiazole-4-carboxamide;
1-[4-(benzylamino)-6-methyl-5-(propan-2-yl)pyrimidin-2-yl]-2-methyl-1H-indole-4-carboxamide;
1-[4-(benzylamino)-6-methylpyrimidin-2-yl]-2-methyl-1H-indole-4-carboxamide;
1-[5-(1-aminoeth yl)-4-(benz ylamino)pyrimidin-2-yl]-2-methyl-1H-indole-4-carboxamide;
1-[5-(aminomethyl)-4-(benzylamino)pyrimidin-2-yl]-2-methyl-1H-indole-4-carboxamide;
1-[5-amino-4-(benzylamino)pyrimidin-2-yl]-2-methyl-1H-indole-4-carboxamide;
1-[6-(benzylamino)pyridin-2-yl]-2-methyl-1H-indole-4-carboxamide;
2-(aminomethyl)-1-[4-(benzylamino)-5-(propan-2-yl)pyrimidin-2-yl]-1H-indole-4-carboxamide;
2-(aminomethyl)-1-[4-(benzylamino)-5-ethylpyrimidin-2-yl]-1H-indole-4-carboxamide;
2-(aminomethyl)-1-[4-(benzylamino)-5-methoxypyrimidin-2-yl]-1H-indole-4-carboxamide;
2-[4-(aminomethyl)-2-methyl-1H-indol-1-yl]-N-benzyl-5-methoxypyrimidin-4-amine;
1-([4-{[(3-fluorophenyl)methyl]amino}-5-methoxypyrimidin-2-yl)-2-methoxy-1H-1,3-benzodiazole-4-carboxamide;
1-[4-{[(3-fluorophenyl)methyl]amino}-5-(1-hydroxyethyl)pyrimidin-2-yl]-2-methyl-1H-indole-4-carboxamide;
1-[4-{[(3-fluorophenyl)methyl]amino}-5-(2-methoxyethoxy)pyrimidin-2-yl]-2-methyl-1H-indole-4-carboxamide;
1-[4-{[(3-fluorophenyl)methyl]amino}-5-(acetamidomethyl)pyrimidin-2-yl]-2-methyl-1H-indole-4-carboxamide;
1-[4-{[(3-fluorophenyl)methyl]amino}-5-(dimethylamino)-6-methylpyrimidin-2-yl]-2-methoxy-1H-1,3-benzodiazole-4-carboxamide;
1-[4-{[(3-fluorophenyl)methyl]amino}-5-(dimethylamino)-6-methylpyrimidin-2-yl]-2-methyl-1H-indole-4-carboxamide;
1-[4-{[(3-fluorophenyl)methyl]amino}-5-(dimethylamino)pyrimidin-2-yl]-2-methyl-1H-indole-4-carboxamide;
1-[4-{[(3-fluorophenyl)methyl]amino}-5-(methoxymethyl)pyrimidin-2-yl]-2-methyl-1H-indole-4-carboxamide;
1-[4-{[(3-fluorophenyl)methyl]amino}-5-(propan-2-yl)pyrimidin-2-yl]-2-methyl-1H-indole-4-carboxamide;
1-[4-{[(3-fluorophenyl)methyl]amino}-5-(propan-2-yloxy)pyrimidin-2-yl]-2-methyl-1H-indole-4-carboxamide;
1-[4-{[(3-fluorophenyl)methyl]amino}-5-(trifluoromethyl)pyrimidin-2-yl]-2-methyl-1H-indole-4-carboxamide;
1-[4-{[(3-fluorophenyl)methyl]amino}-5-carbamoylpyrimidin-2-yl]-2-methyl-1 H-indole-4-carboxamide;
1-[4-{[(3-fluorophenyl)methyl]amino}-5-chloropyrimidin-2-yl]-2-methyl-1H-indole-4-carboxamide;
1-[4-{[(3-fluorophenyl)methyl]amino}-5-ethoxypyrimidin-2-yl]-2-methyl-1H-indole-4-carboxamide;
1-[4-{[(3-fluorophenyl)methyl]amino}-5-ethylpyrimidin-2-yl]-2-methyl-1H-indole-4-carboxamide;
1-[4-{[(3-fluorophenyl)methyl]amino}-5-methane sulfonylpyrimidin-2-yl]-2-methyl-1H-indole-4-carboxamide;
1-[4-{[(3-fluorophenyl)methyl]amino}-5-methoxy-6-methylpyrimidin-2-yl]-2-methyl-1H-indole-4-carboxamide;
1-[4-{[(3-fluorophenyl)methyl]amino}-5-methoxypyrimidin-2-yl]-2-methyl-1H-indole-4-carboxamide;
1-[4-{[(3-fluorophenyl)methyl]amino}-5-methyl-6-(trifluoromethyl)pyrimidin-2-yl]-2-methyl-1H-indole-4-carboxamide;
1-[4-{[(3-fluorophenyl)methyl]amino}-5-methyl-6-[(methylamino)methyl]pyrimidin-2-yl]-2-methyl-1H-indole-4-carboxamide;
1-[4-{[(3-fluorophenyl)methyl]amino}-5-methylpyrimidin-2-yl]-2-methyl-1H-indole-4-carboxamide;
1-[4-{[(3-fluorophenyl)methyl]amino}-6-(dimethylamino)-5-methylpyrimidin-2-yl]-2-methyl-1H-indole-4-carboxamide;
1-[4-{[(3-fluorophenyl)methyl]amino}-6-methoxy-5-methylpyrimidin-2-yl]-2-methyl-1H-indole-4-carboxamide;
1-[4-{[(3-fluorophenyl)methyl]amino}-6-methyl-5-(propan-2-yl)pyrimidin-2-yl]-2-methoxy-1H-1,3-benzodiazole-4-carboxamide;
1-[4-{[(3-fluorophenyl)methyl]amino}-6-methyl-5-(propan-2-yl)pyrimidin-2-yl]-2-methyl-1H-indole-4-carboxamide;
1-[4-{[(3-fluorophenyl)methyl]amino}-6-methylpyrimidin-2-yl]-2-methyl-1H-indole-4-carboxamide;
1-[5-(1-aminoethyl)-4-{[(3-fluorophenyl)methyl]amino}pyrimidin-2-yl]-2-methyl-1H-indole-4-carboxamide;
1-[5-(aminomethyl)-4-{[(3-fluorophenyl)methyl]amino}pyrimidin-2-yl]-2-methyl-1H-indole-4-carboxamide;
1-[5-amino-4-{[(3-fluorophenyl)methyl]amino}pyrimidin-2-yl]-2-methyl-1H-indole-4-carboxamide;
1-[6-{[(3-fluorophenyl)methyl]amino}pyridin-2-yl]-2-methyl-1H-indole-4-carboxamide;
2-(aminomethyl)-1-[4-{[(3-fluorophenyl)methyl]amino}-5-(propan-2-yl)pyrimidin-2-yl]-1H-indole-4-carboxamide;
2-(aminomethyl)-1-[4-{[(3-fluorophenyl)methyl]amino}-5-ethylpyrimidin-2-yl]-1 H-indole-4-carboxamide;
2-(aminomethyl)-1-[4-{[(3-fluorophenyl)methyl]amino}-5-methoxypyrimidin-2-yl]-1H-indole-4-carboxamide;
2-(4-(aminomethyl)-2-methyl-1H-indol-1-yl)-N-(3-fluorobenzyl)-5-methoxypyrimidin-4-amine.

Synthetic Preparation

The novel compounds of the present invention can be prepared in a variety of ways known to one skilled in the art of organic synthesis. The compounds of the present invention can be synthesized using the methods as hereinafter described below, together with synthetic methods known in the art of synthetic organic chemistry or variations thereon as appreciated by those skilled in the art.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene and Wuts, *Protective Groups in Organic Synthesis,* 44th. Ed., Wiley & Sons, 2006, as well as in Jerry March, *Advanced Organic Chemistry,* 4th edition, John Wiley & Sons, publisher, New York, 1992 which are incorporated herein by reference in their entirety.

The monocyclic pyrimidine and pyridine compounds can be prepared by the literature methods cited in the following text. The following schemes depict established, known syntheses of these scaffolds.

The substituents of the monocyclic pyrimidine and pyridine compounds can be synthesized and attached to these scaffolds by the literature methods cited in the following text. The following schemes depict the known techniques for accomplishing this joinder.

General Synthetic Schemes for Monocyclic Pyrimidines

Compounds of the present invention can be synthesized using the following methods. General reaction conditions are given and reaction products can be purified by general known methods including crystallization, silica gel chromatography using various organic solvents such as hexane, cyclohexane, ethyl acetate, methanol and the like, preparative high pressure liquid chromatography or preparative reverse phase high pressure liquid chromatography.

The substituents $R_n$, and $R^1$ through $R^6$ of Formula I and II have alternate designations in the following general schemes 3-21. The position of the substituent indicates its correspondence with $R_n$ and $R^1$ through $R^5$ of Formulas I and II. So as to avoid confusion, the number designations of R in these schemes 3-21 are subscripts instead of the superscripts of the R's of Formulas I and II. For example, for compound 3 of Scheme 3, R is an $R_n$, $R_3$ of the benzo ring is in the position of $R^4$ of Formula I and $R_3$ and $R_4$ of the pyrrole ring are both $R^3$ of Formula I.

In all of these schemes and general syntheses, a 2-chloro-4, 5-disubstituted-6-aminomethylenyl aryl pyridine or 2-chloro-4-aminomethylenyl aryl-5,6-disubstituted pyridine can be substituted for the 2-chloropyrimidine starting material of the scheme or synthesis under consideration and produce the corresponding pyridine compound instead of the pyrimidine compound. In a similar fashion, the nitrile to amide conversion, ester to acid or amide conversion, nitrile to methyl alcohol conversion of schemes 18-21 can be modified by substituting the corresponding pyridine compound for the pyrimidine compound shown (X is N).

Scheme 1
General syntheses of intermediate starting materials (substituted pyrimidines) as for preparation of compounds of Formula I

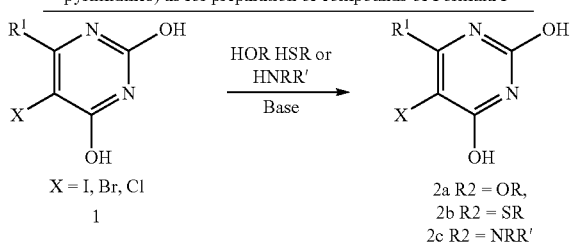

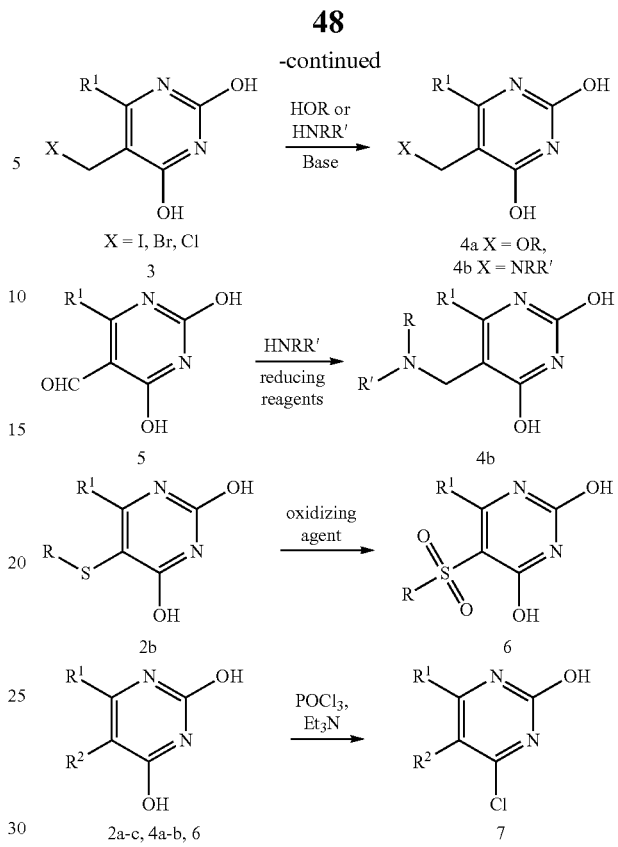

Depending on the nature of substituents $R^1$ and $R^2$ the dicholorpyridine or pyrimidine can be synthesized in several ways. Scheme 1 discloses general methods for the preparation of substituted monocyclic pyrimidines. Pyrimidine diols with a halogen substituent in the 5 position as in compound 1 can be converted to a 5-alkoxy substituted pyrimidine 2a by reacting compound 1 with an alcohol in the presence of a base such as potassium carbonate in an alcohol such as dioxane at reflux. Alternatively, compounds of the general structure 2b can be prepared by reacting a secondary amine in a solvent such as THF at elevated temperature and/or pressure. Similarly compounds of the general structure 2c could be prepared by running the reaction with a thiol in the presence of a base such as potassium carbonate in a solvent such as THF in an oxygen free environment. Reacting a pyrimidine diol of structure 3 substituted with a halogen methyl substituent in the 5 position with an alcohol optionally in the presence of a base such as potassium carbonate at an elevated temperature in a solvent such as THF results in a the preparation of a 5-alkoxy methyl pyrimidine 4a. Alternatively compound 3 can be reacted with a secondary amine at elevated temperature in a solvent such as THF to give a 5-aminomethyl substituted pyrimidine 4b. A compound of the structure 4b can also be prepared by reacting a pyrimidine diol of structure 5 containing an aldehyde in the 5 position with a primary or secondary amine in a solvent such as ethanol in the presence of a reducing agent such as sodium cyanoborohydride at room temperature.

Compound 2b containing a thioether substituent at the 5 position can be reacted with an oxidizing agent such as meta-chloro-perbenzoic acid in a solvent such as DMC. Compounds 2a-c, 4a-b and 6 can be converted to the dichloropyrimidine derivatives by heating them in refluxing $POCl_3$ optionally in the presence of a tertiary amine to give the substituted dichloropyrimidine of structure 7.

Scheme 2. General synthesis of monocyclic pyridine and pyrimidine p97 inhibitors with indolyl and benzimidazolyl substituents at the 2 position.

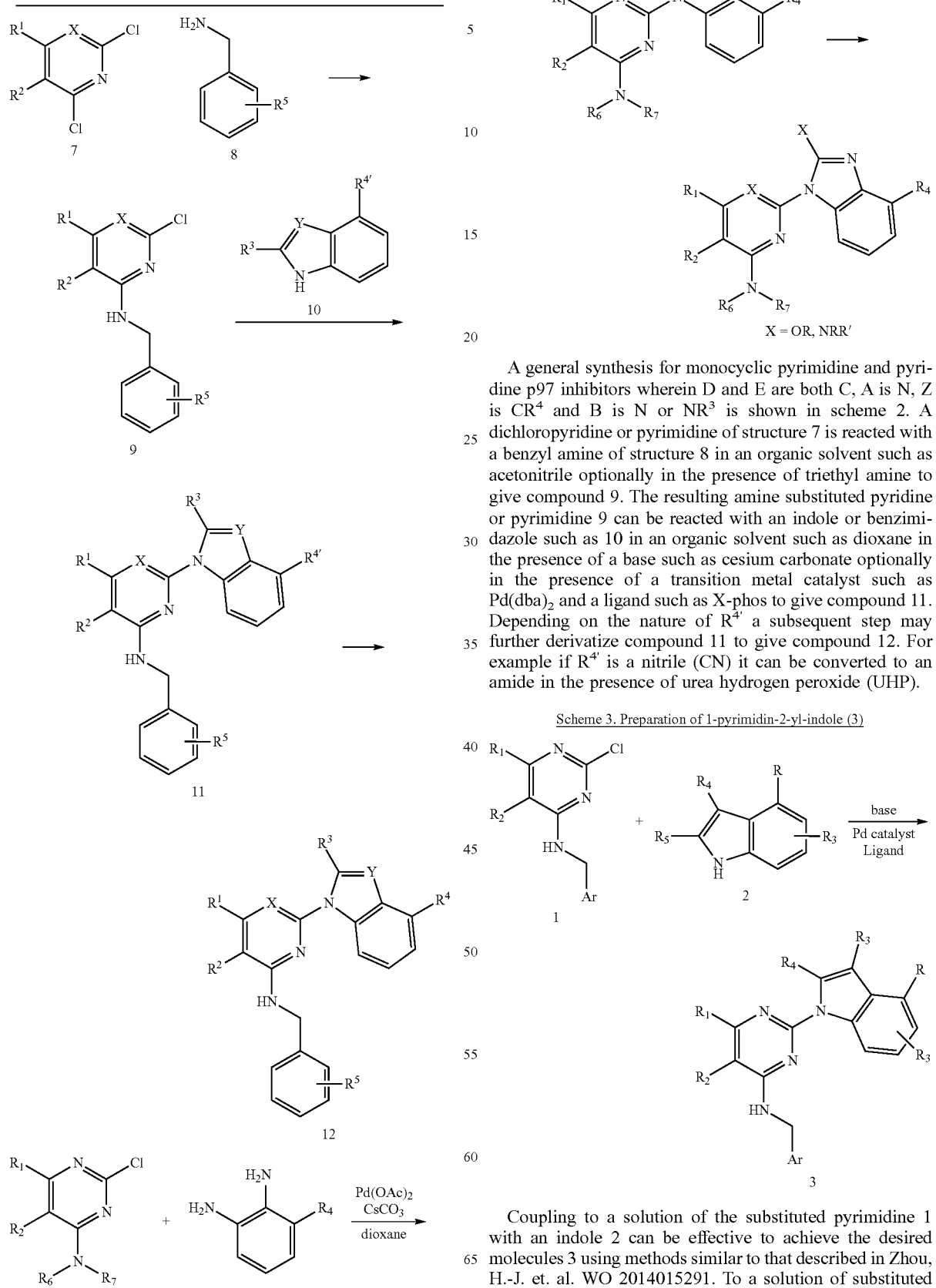

A general synthesis for monocyclic pyrimidine and pyridine p97 inhibitors wherein D and E are both C, A is N, Z is $CR^4$ and B is N or $NR^3$ is shown in scheme 2. A dichloropyridine or pyrimidine of structure 7 is reacted with a benzyl amine of structure 8 in an organic solvent such as acetonitrile optionally in the presence of triethyl amine to give compound 9. The resulting amine substituted pyridine or pyrimidine 9 can be reacted with an indole or benzimidazole such as 10 in an organic solvent such as dioxane in the presence of a base such as cesium carbonate optionally in the presence of a transition metal catalyst such as $Pd(dba)_2$ and a ligand such as X-phos to give compound 11. Depending on the nature of $R^{4'}$ a subsequent step may further derivatize compound 11 to give compound 12. For example if $R^{4'}$ is a nitrile (CN) it can be converted to an amide in the presence of urea hydrogen peroxide (UHP).

Scheme 3. Preparation of 1-pyrimidin-2-yl-indole (3)

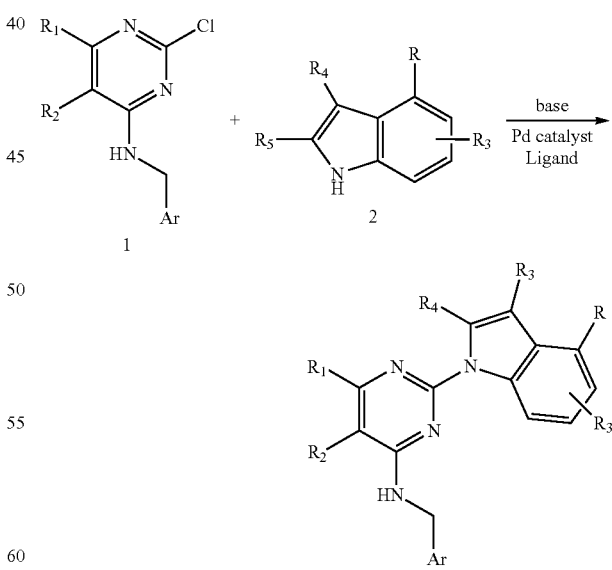

Coupling to a solution of the substituted pyrimidine 1 with an indole 2 can be effective to achieve the desired molecules 3 using methods similar to that described in Zhou, H.-J. et. al. WO 2014015291. To a solution of substituted pyrimidine such as compound 1 is added a indole or a substituted ones such as compound 2 and a base such as sodium carbonate or cesium carbonate, in the presence of a palladium catalyst such as Pd(OAc)2 and a ligand such as triphenylphosphine in a solvent such as dioxane and the reaction can optionally be heated to reflux for up to 48 hours. Water is added and the mixture is extracted with ethyl acetate. The resulting organic layer is dried with drying agent such as Na₂SO₄ and the drying agent is removed by filtration. The organic layer was concentrated under reduced pressure and the resulting residue can optionally be purified by column chromatography to give the 1-pyrimidin-2yl indoles 3.

Scheme 4. Preparation of 1-pyrimidin-2-yl-benzoimidazoles (5)

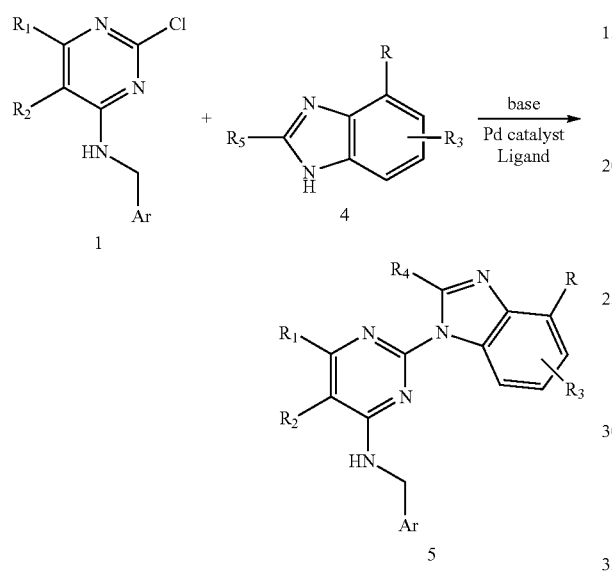

Compounds containing the structure of 1-pyrimidin-2yl benzimidazole 5 can be produced using the methods similar to those described in Zhou, H.-J. et. al. WO 2014015291 and as described above for Scheme 3 by using a substituted benzimidazole 4 in place of substituted indole 2 as shown in Scheme 4.

Scheme 5. Preparation of 1-pyrimidin-2-yl-1,2,3-benzotriazoles (7)

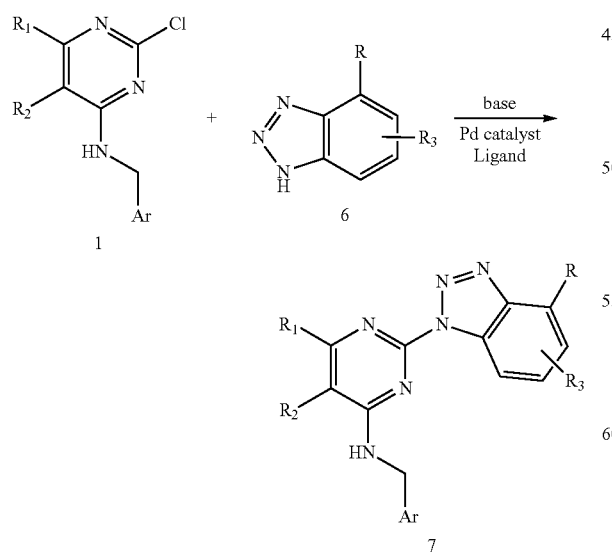

Compounds containing the structure of 1-pyrimidin-2-yl-1,2,3-benzotriazoles 7 can be produced using methods similar to those described in Zhou, H.-J. et. al. WO 2014015291 and Ohlmeyer, Michael J. et al WO 2008060301 and as described above for Scheme 3 by using a substituted 1,2,3-benzotriazole 6 in place of substituted indole 2 as shown in Scheme 3.

Scheme 6. Preparation of 1-pyrimidin-2-yl-1H-indazoles (9)

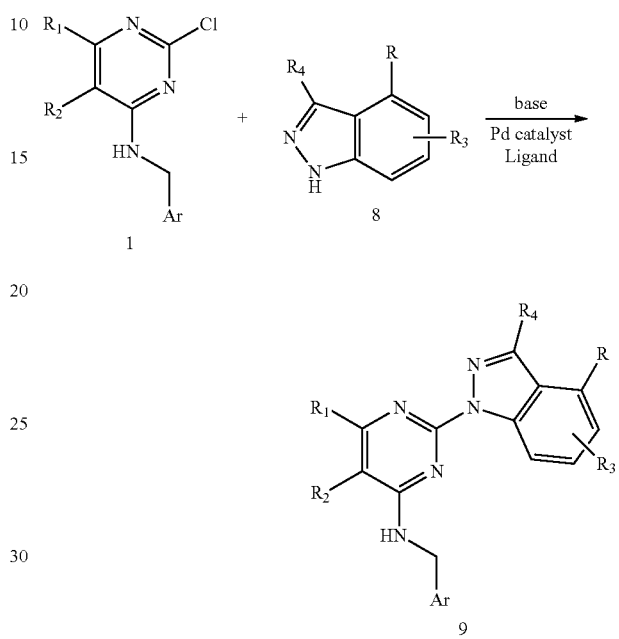

Compounds containing the structure of 1-pyrimidin-2yl-1H-indazoles 9 can be produced using methods similar to those described in Zhou, H.-J. et. al. WO 2014015291 and as described above for Scheme 3 by using a substituted indazole 8 in place of substituted indole 2 as shown in Scheme 6.

Scheme 7. Preparation of 3-pyrimidin-2-yl-[1,2,4]triazolo[4,3-a]pyridines (15)

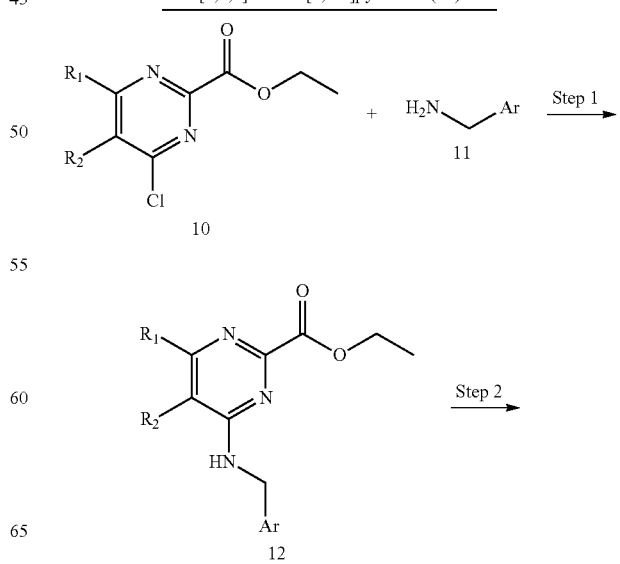

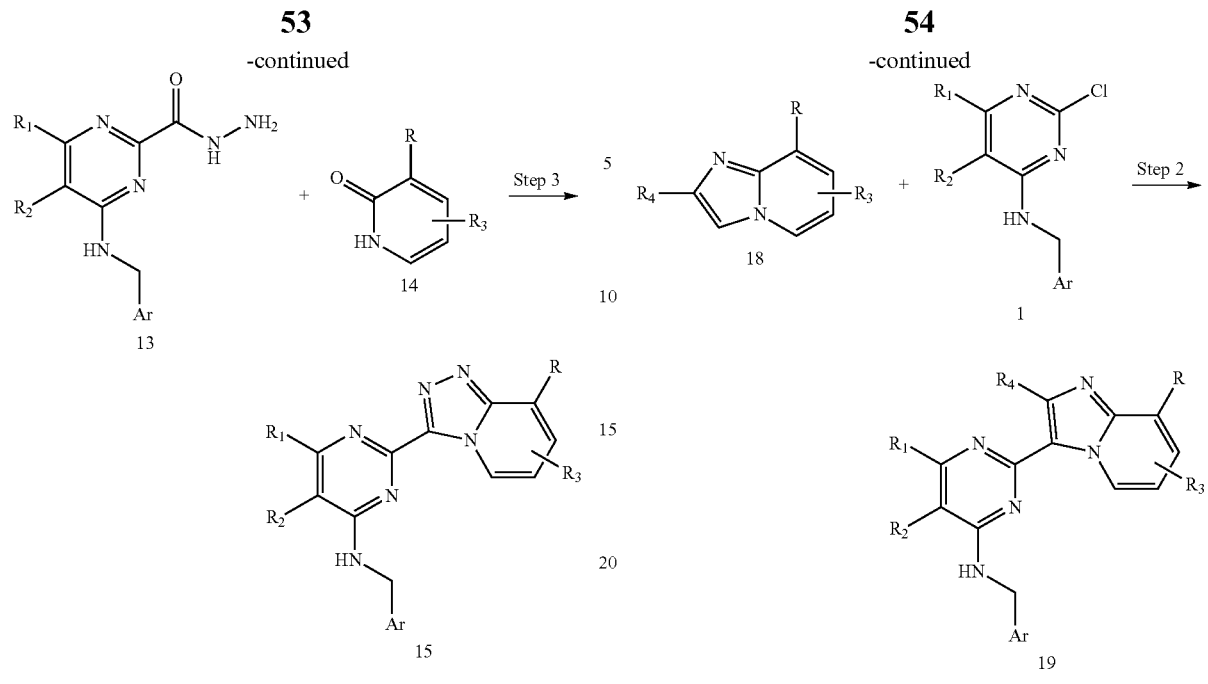

Substituted ethyl 4-chloropyrimidine-2-carboxylates 10 can be prepared by methods similar to those described in described in the references (Honma, Y. et al. *Chemical & Pharmaceutical Bulletin,* 1982, 30, 4314-24 and Armstrong, R. C. et al. WO 2012030918 and Pech, R. Pharmazie 1991, 46, 22-3). A solution of the ethyl 4-chlorolyrimidine carboxylate 10 in a solvent such as acetonitrile is treated with aryl methyl amine 11 and a tertiary amine base such as triethyl amine and the mixture is stirred at room temperature to reflux for a period of 8 to 24 hours. After the reaction is complete the solvent is evaporated and the residue is portioned between a dilute aqueous base such as sodium bicarbonate and an organic solvent such as ethyl acetate. The organic solvent is dried and evaporated and the resulting compound can optionally be purified by column chromatography to give the ethyl 4-aminopyrimidine-2-carboxylate 12.

The aforementioned ethyl 4-aminopyrimidine-2-carboxylate 12 in an organic solvent such as ethanol is treated with hydrazine hydrate and the resulting solution is stirred at a temperature ranging from ambient to reflux for up to 24 hours. The solvents are removed under reduced pressure and the resulting hydrazide 13 which can optionally be used without further purification in the next reaction.

Hydrazide 13 reacted with the substituted pyridine-2-one 14 in a solvent such as acetic acid at a temperature from ambient to reflux. The reaction mixture is poured into an excess of sodium carbonate and is extracted with dichloromethane. The organic extracts are dried and evaporated. The product is isolated form the residue wither by recrystallization or column chromatography to give the desired 3-pyrimidin-2-yl-[1,2,4]triazolo[4,3-a]pyridines 15.

Substituted imidazo[1,2-a]pyridines 18 can be prepared using methodology similar to that outlined in Xiong, Y. et al WO 2009023253. A solution of the 2-amino pyridine 16 reacted with the dimethyl acetal of a bromomethyl ketone 17 in a solvent such as acetonitrile at a temperature between room temperature and reflux. The reaction is cooled and the solvent is evaporated and the resulting residue is optionally purified by column chromatography to give the substituted imidazo[1,2-a]pyridines 18. Compound 1 can be reacted with compound 18 using methodology similar to that described in Eastwood P. R. WO 2011076419. A mixture of substituted 2-chloropyrimidine 1 and the imidazo[1,2-a] pyridine 18 and a base such as potassium carbonate and a phosphine such as triphenyl phosphine in a degassed organic solvent such as acetonitrile is treated with palladium acetate and heated in a sealed tube (optionally using microwave radiation) to 150° C. The reaction is cooled and the solvent is removed under reduced pressure. The resulting residue was partitioned between water and an organic solvent such as ethyl acetate. The organic portion was extracted with a strong aqueous acid such as 2M HCl and the resulting aqueous solution is extracted with an organic solvent such as diethyl ether. The acidic aqueous solution is neutralized with an aqueous base such as sodium carbonate and the formed solid is isolated by filtration to give the desired substituted 3-pyrimidin-2-ylimidazo[1,2-a]pyridines 19.

Scheme 8. Synthesis of 3-pyrimidin-2-ylimidazo[1,2-a]pyridines (19)

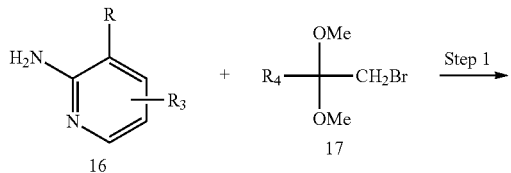

Scheme 9. Synthesis of 3-pyrimidin-2-ylpyrazolo[1,5-a]pyridines (21)

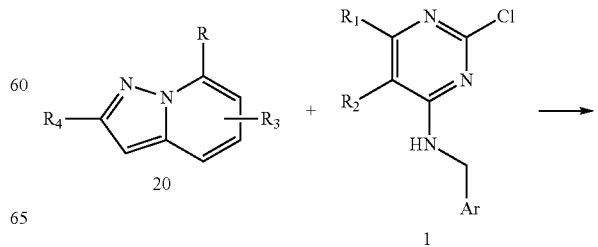

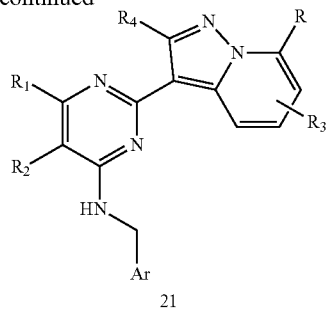

Various methods can be used to prepare substituted 3-pyrimidin-2-ylpyrazolo[1,5-a]pyridines 20 as outlined in Tsuchiya, et. al. Chemical & Pharmaceutical Bulletin 1983, 31, 4568; Hajos, G. and Riedl, Z. Science of Synthesis, 2002, 12, 613 and Aboul-Fadl, T. et al. Synthesis, 2000, 12, 1727-1732. These intermediates can then be coupled with substituted 2-chloro-pyrimidines 1 to yield the desired molecules 21 using methods described in Scheme 8.

Scheme 10. Synthesis of 3-pyrimidin-2-yltriazolo[1,5-a]pyridines (23)

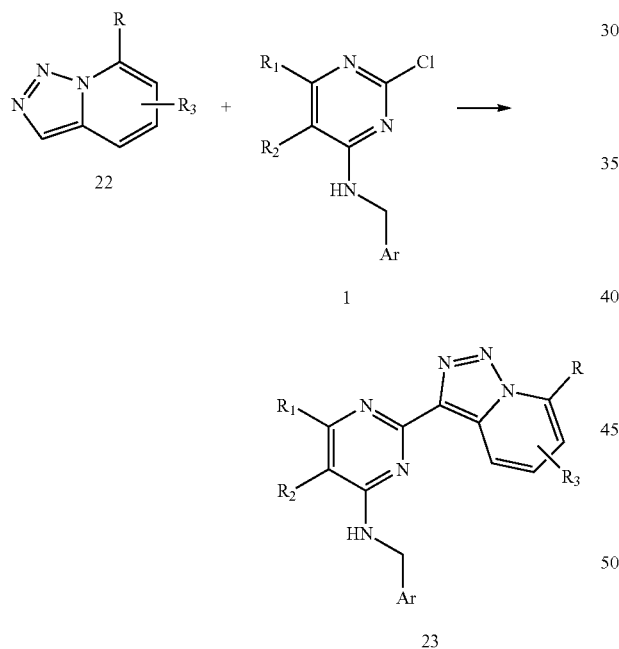

Various methods can be used to prepare 1-pyrimidin-2-ylimidazo[1,5-a]pyridines 22 as outlined in Abarca, B. et al Tetrahedron, 1988, 44, 3005, and Latham, E. Journal of Heterocyclic Chemistry 1995, 32, 787, and Hirayama, T. et al. Chemistry—A European Journal 2014, 20, 4156, as well as Abarca, Belen et al Journal of the Chemical Society, Perkin Transactions 1 1987, 8, 1865. These intermediates can be coupled with substituted 2-chloro-pyrimidines 1 using methods described in Scheme 8 to prepare the desired 3-pyrimidin-2-yltriazolo[1,5-a]pyridines 23.

Scheme 11. Synthesis of 1-pyrimidin-2-ylimidazo[1,5-a]pyridines (27)

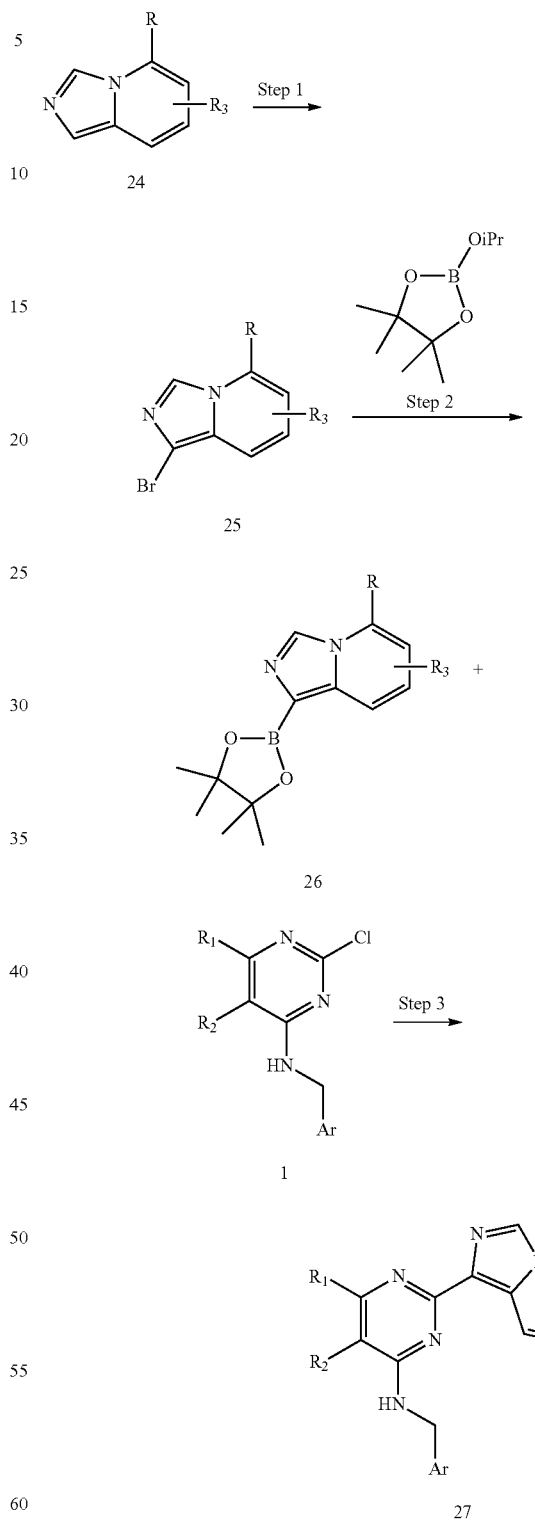

Substituted imidazo[1,5-a]pyridines 24 can be prepared by various methods including those described in Yoshimura, Y. et al. Journal of Antibiotics, 1991, 44, 1394, Linn, D. M. et al. WO 2004039366 and Alcouffe, C. et al. WO 2006097625. 1-Bromo-imidazo[1,5-a]pyridines 25 can be brominated using methodology described in Shibahara, F. et al *Journal of Organic Chemistry*, 2012, 77, 538. Imidazo[1,5-a]pyridine 24 is dissolved an organic solvent such as methylene chloride is cooled to a temperature between 0° C. and −78° C. and treated with N-bromosuccinimide. The cooling bath is removed and the reaction is stirred for a period between 1 and 4 hours. The reaction is quenched with a mild reducing agent such as aq. $Na_2S_2O_3$. The reaction mixture is partitioned between water and dichloromethane and the organic layer was separated, dried with sodium sulfate and evaporated under reduced pressure. The resulting residue was purified using column chromatography to give 1-Bromo-imidazo[1,5-a]pyridine 25. Compound 25 is dissolved in a −78° C. organic solvent such as THF and treated with n-butyl lithium. The mixture is stirred for one hour and is then treated with 2-Isopropoxy-4,4,5,5-tetramethyl-1,3,2-dioxaborolane and the mixture is warmed to room temperature and stirred for two hours. The solvents are evaporated and the reaction mixture is partitioned between ethyl acetate and ammonium chloride. The organic layer was dried and evaporated and the resulting intermediate 26 is used directly in the next reaction. A mixture of the boronic ester 26 is combined with substituted 2-chloropyrimidine 1, cesium fluoride and bis(triphenylphosphine) palladium (II) chloride in and organic solvent such as dimethoxyethane and water. The mixture is back flushed with nitrogen, sealed and heated using microwave irradiation to 150° C. The reaction is cooled to room temperature, filtered and partitioned between ethyl acetate and water. The organic layer is dried and evaporated and the resulting residue is purified by column chromatography to give the target 1-pyrimidin-2-ylimidazo[1,5-a]pyridines 27.

Scheme 12. Preparation of 3-pyrimidin-2-ylimidazol[1,5-a]pyridines (34)

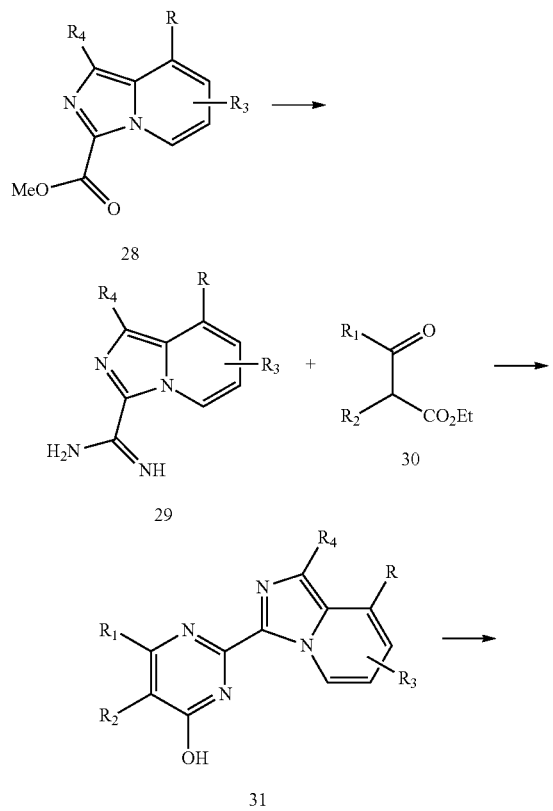

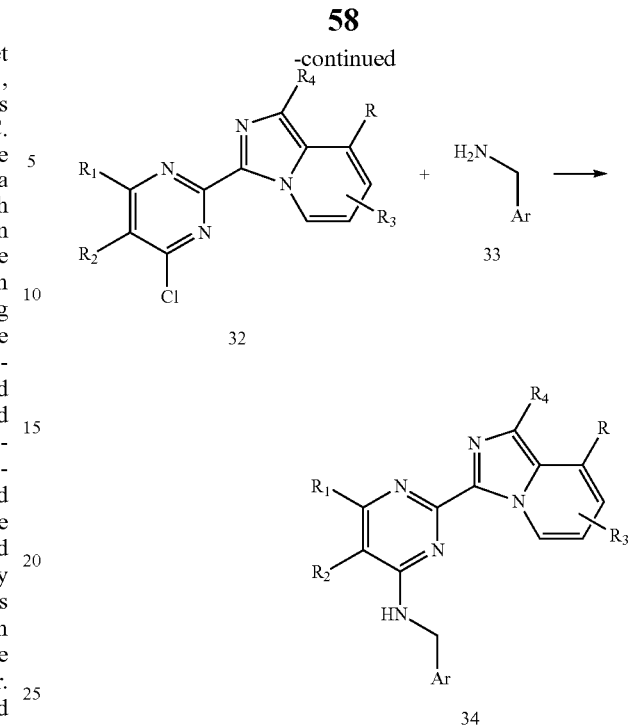

Substituted imidazo[1,5-a]pyridine-3-carboxylate esters 28 can be prepared by various methods including those outlined in Chen, Shaoqing et al WO 2013030138, Bilodeau, and Mark T. et al WO 2008085302. An imidazo[1,5-a]pyridine-3-carboxylate ester 28 can be converted into the corresponding amidine 29 using aminochloromethyl aluminum in an organic solvent such as toluene at a temperate between ambient and 100° C. as described in Brockunier L. et. al. WO 2010065275 and Gargiapati R. S. Tetrahedron Letters 1990, 31, 1969. The resulting imidazo[1,5-a]pyridine-3-carboxamidine 29 can be reacted with ketoester 30 in the presence of a catalytic amount of a base such as sodium ethoxide in ethanol at reflux for 2-6 hours. The reaction mixture was cooled and concentrated under reduced pressure and the residue was portioned between ethyl acetate and aqueous ammonium chloride. The organic layer is dried with brine and sodium sulfate and the solvent is evaporated under reduced pressure to give the pyrimidin-4-ol 31. Compound 32 can be prepared by chlorination of intermediate+with $POCl_3$ or $PCl_5$. The desired molecules 34 can be produced using methods similar to those described in Zhou, H.-J. et. al. WO 2014015291.

Scheme 13. Preparation of 1-pyrimidin-2-yl-3-indoles, or 1-pyrimidin-2-yl-3-benzofurans or 1-pyrimidin-2-yl-3-benzo[b]thiophenes (40)

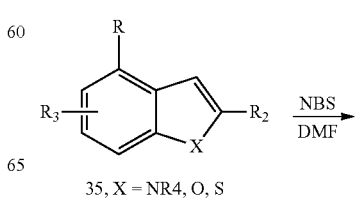

35, X = NR4, O, S

-continued

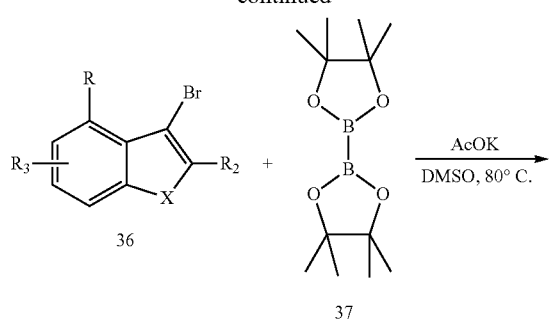

36

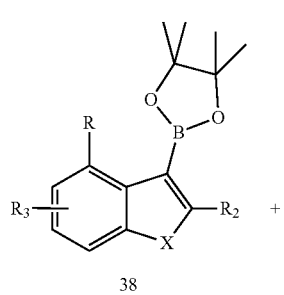

38

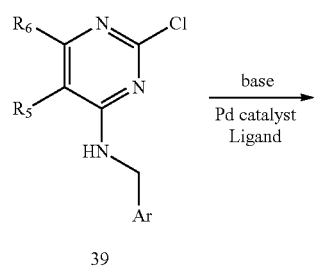

39

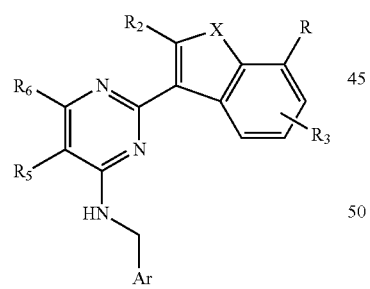

40, X = NR4, O, S

Under various conditions such as NBS in DMF, bromination of 3-unsubstituted intermediates 35 (X=O, S or either substituted nitrogen) would take place region-selectively on their 3-position to yield 3-Br-substituted intermediates 36. They then can be converted into boronic esters 38 by treatment with boronic ester 37 under various conditions. Then Pd-based coupling reaction similar to those described in Zhou, H.-J. et. al. WO 2014015291 between intermediates 38 and 39 provided the desired molecules.

Scheme 14. Preparation of 1-pyrimidin-2-yl-2H-isoindoles (45)

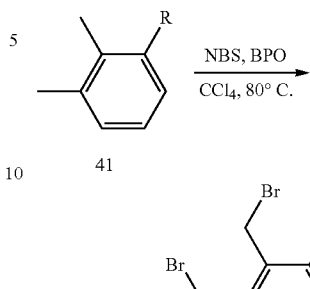

41

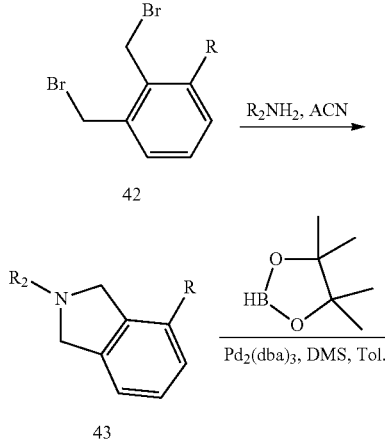

42

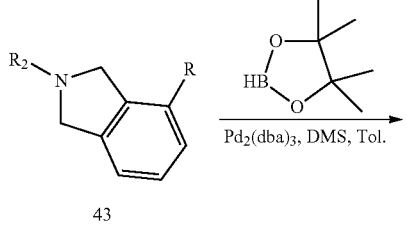

43

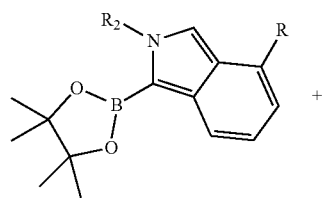

44

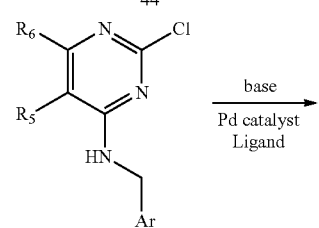

39

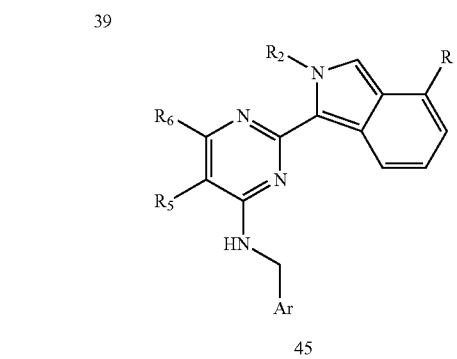

45

The boronic ester of isoindole 44 can prepared from substituted 1,2-dimethylbenzene 41 following the procedure in the reference (Ohmura, Toshimichi et al Journal of the American Chemical Society, 131(17), 6070-6071; 2009). Then Pd-based coupling reaction similar to those described in Zhou, H.-J. et. al. WO 2014015291 between intermediates 39 and 44 provided the desired molecules 45.

Scheme 15. Preparation of 1-pyrimidin-2-yl-benzo[c]thiophenes (49)

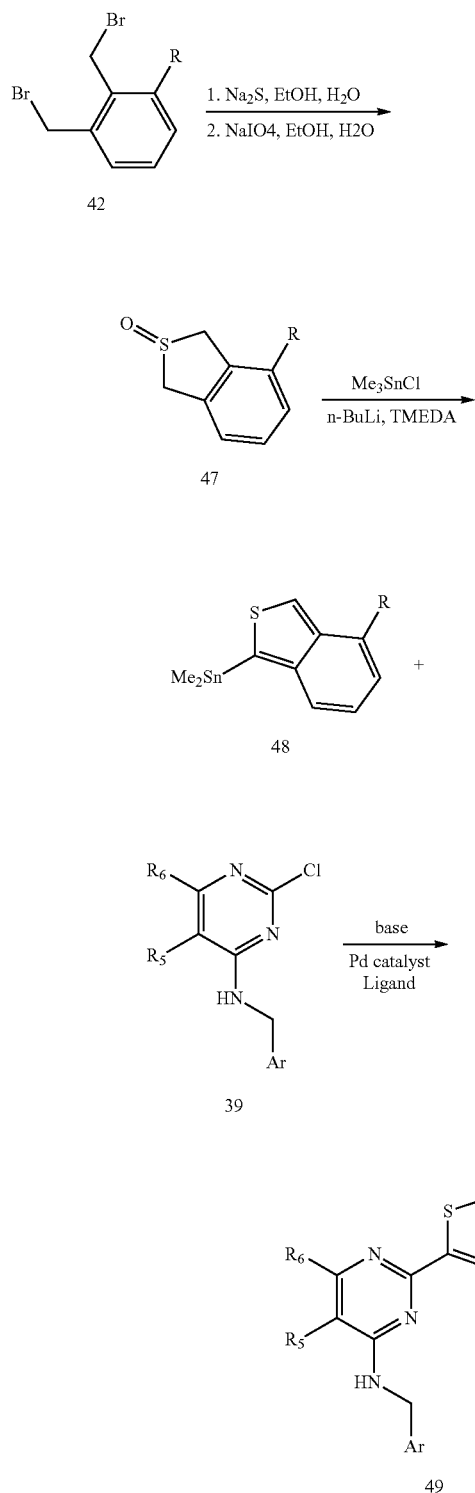

tion similar to those described in Zhou, H.-J. et. al. WO 2014015291 between intermediates 39 and 48 provided the desired molecules 49.

Scheme 16. Preparation of 1-pyrimidin-2-yl-3-1H-indazoles, or 1-pyrimidin-2-yl-3-benzo[d]isoxazoles or 1-pyrimidin-2-yl-3-benzo[d]isothiazoles (52)

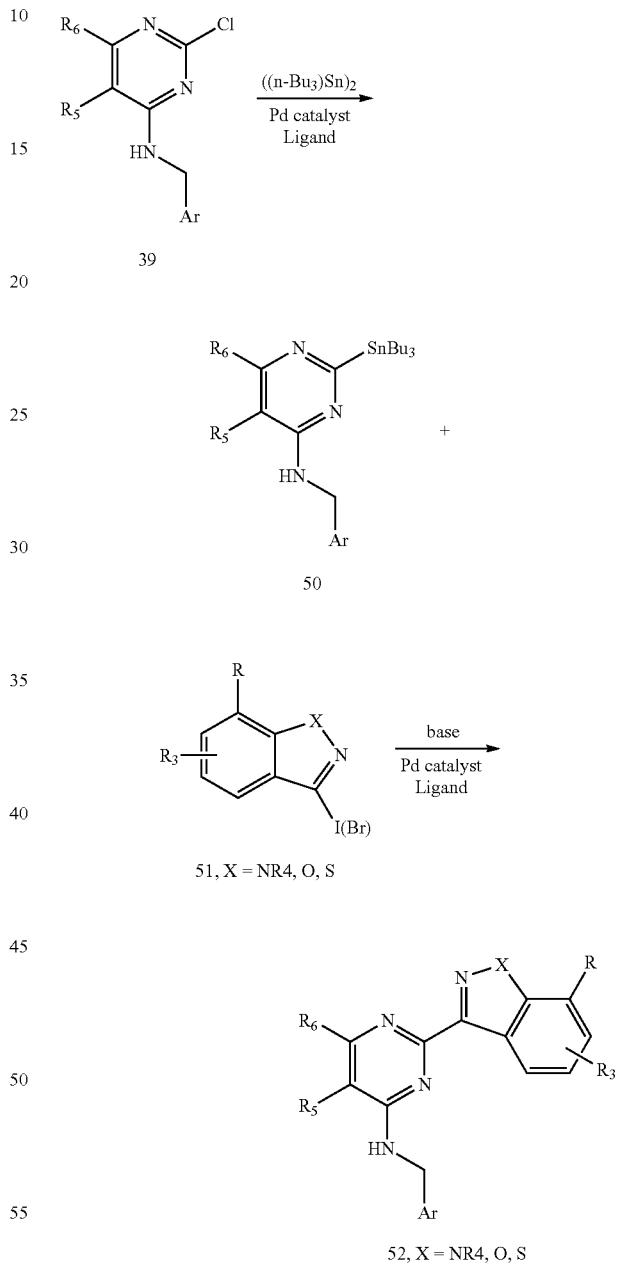

The key intermediates 48, benzo[c]thiophen-1-yltrimethylstannane can prepared from the intermediates 42 following the similar procedure in the reference (Kawabata, Kohsuke and Goto, Hiromasa, Journal of Materials Chemistry, 22(44), 23514-23524; 2012). Then Pd-based coupling reac- The key intermediate 50, tributyl-2-pyrmidinyltin can be prepared from the intermediates 39 following the similar procedure in the reference (Castanedo, Georgette et al, PCT Int. Appl., 2010138589). Then Pd-based coupling reaction similar to those described in Zhou, H.-J. et. al. WO 2014015291 between intermediates 50 and 51 provided the desired molecules 52.

Scheme 17. Preparation of 1-pyrimidin-2-yl-3-2H-indazoles, or 1-pyrimidin-2-yl-3-benzo[c]isoxazoles or 1-pyrimidin-2-yl-3-benzo[c]isothiazoles (54)

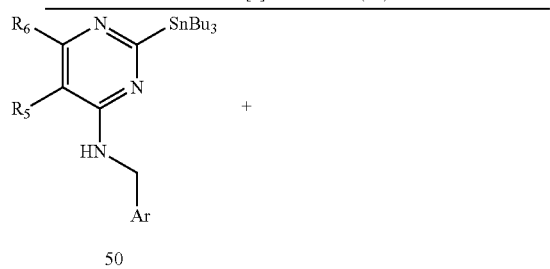

50

+

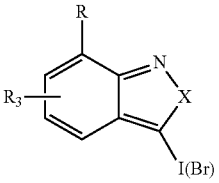

53, X = NR4, O, S

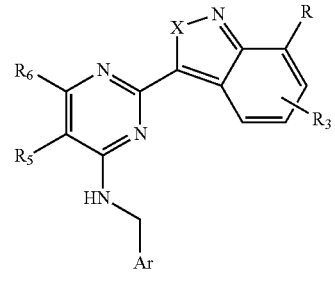

54, X = NR4, O, S

Pd-based coupling reaction similar to those described in Zhou, H.-J. et. al. WO 2014015291 between intermediates 50 and 53 provided the desired molecules 54.

Scheme 18. Conversion of nitriles to amides (56)

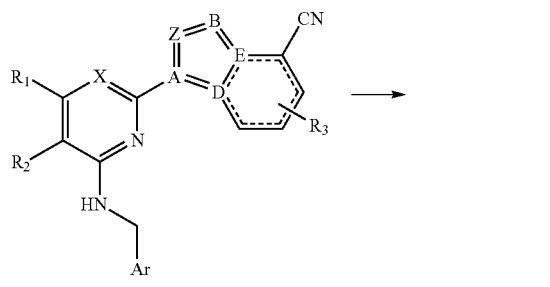

55

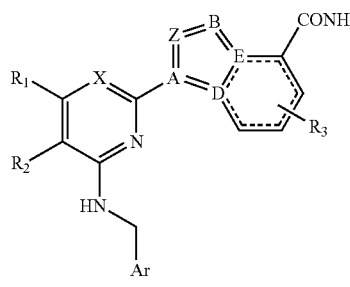

56

The desired compounds 55 prepared in Schemes A-O above can have a nitrile substitution at the position indicated in Scheme P. This substituent can be converted to the corresponding carboxamide. Nitriles 55 are dissolved in a 1/10 ratio of water/DMSO and treated with urea-hydrogen peroxide (UHP) and a base such as potassium carbonate. Reaction mixture is stirred at room temperature for up to 18 hours and then is poured into ice water and stirred for two hours. The resulting solid is filtered, dried and if necessary purified by column chromatography to give the desired amides 56.

Scheme 19. Conversion of nitrile to amino methylamines (57)

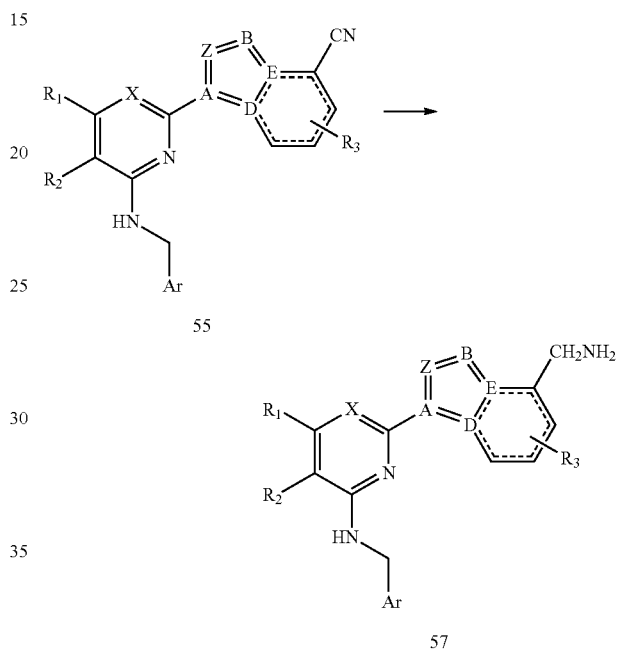

The desired compounds 55 prepared in Schemes 3-17 above can have a nitrile substitution at the position indicated in Scheme 19. This substituent can be converted to the corresponding methylamines 57. A solution of nitrile 55 in an aprotic organic solvent such as THF is treated with LAH and the resulting mixture is stirred for up to 18 hours. The reaction mixture is treated with 15% NaOH in water and the reaction is stirred for one hour and is then filtered. The THF is removed under reduced pressure to give the product 57 which can be further purified by column chromatography.

Scheme 20. Conversion of esters to acids (59) or substituted amides (60)

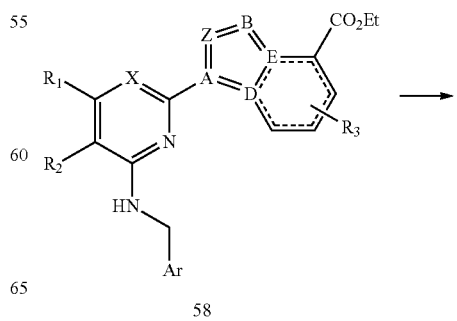

58

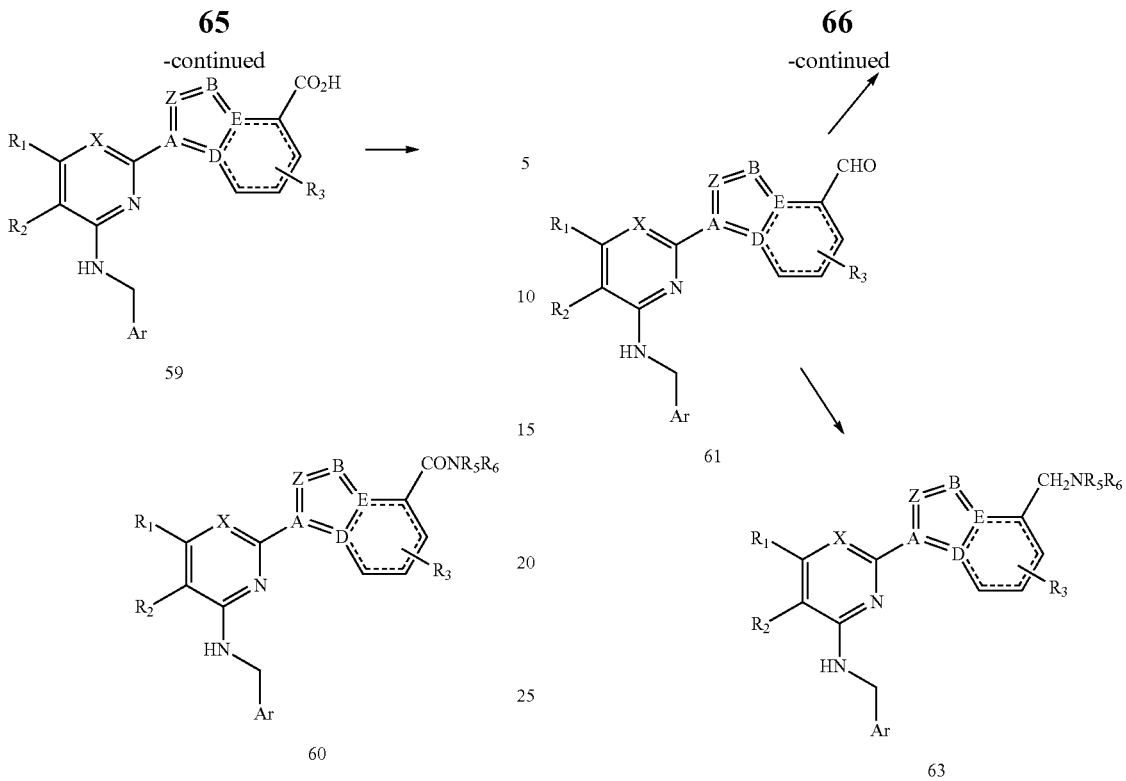

The desired compounds 58 prepared in Schemes 3-17 above can have a carboxylate ester substitution at the position indicated in Scheme 20. This functionality can be readily converted to the corresponding acid 59 or substituted or unsubstituted amide 60 using standard methodology.

Scheme 21. Conversion of nitriles (55) to methyl alcohols (62) or N-substituted amino methyl compounds (63)

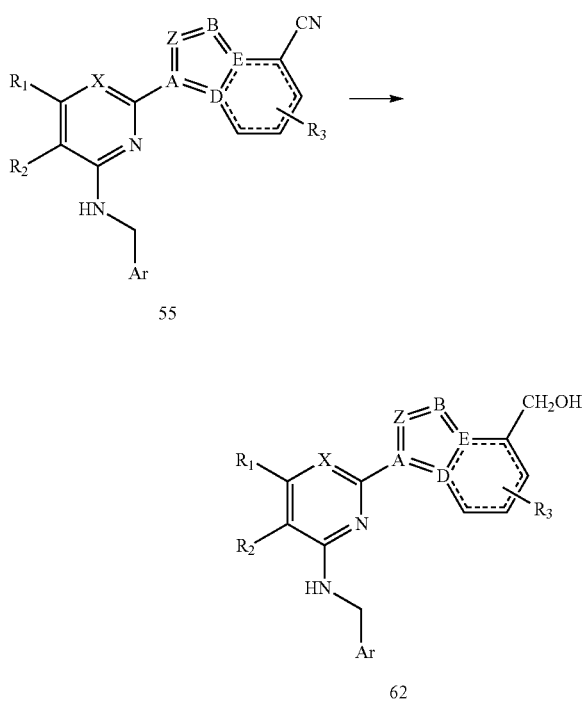

The desired compounds 55 prepared in Schemes 3-17 above can have a nitrile substitution at the position indicated in Scheme 21. This can be converted to methyl alcohols or a variety of amines. The nitrile 55 is dissolved in an aprotic solvent such as dichloromethane, the solution is cooled to −78° C. and treated dropwise with DIBAL. The reaction is stirred for two hours. The reaction is diluted with dichloromethane and extracted with dilute aq. HCl followed by saturated sodium carbonate. The organic extract is dried over magnesium sulfate and evaporated to give the aldehydes 61. Aldehyde 61 can be easily reduced to methyl alcohol 62. Aldehyde 61 is reacted with amines in an alcohol such as methanol in the presence of reducing agent such as sodium cyanoborohydride at room temperature for 3-24 hours. The solvents are removed under reduced pressure and the residue is partitioned between aq. Sodium bicarbonate and dichloromethane. The resulting organic extract is dried with sodium sulfate and evaporated under reduced pressure. The residue is purified by column chromatography to give the desired substituted amine 63.

Biological Assays

The biological activities of the monocyclic pyrimidine and pyridine compounds of the invention can be determined by their examination in assays using protocols well established to identify and select compounds that will exhibit anti-cancer activity. The present invention focuses upon the ability of the monocyclic pyrimidine and pyridine compounds to intersect with the p97 proteosome complex. As described in the Background, the function of the p97 complex is essential for continued cellular viability. Inhibition of the activity of the complex will cause ubiquitinized protein build-up in the cell and consequent apoptosis. The biological assays allow an assessment of the biological activities of the monocyclic pyrimidine and pyridine compounds of the invention.

The primary biological analyses are in vitro assays and cellular based assays for determining the inhibitory capability of the compounds of the invention of the invention against Valosin-containing protein, i.e., p97. The assays also provide a primary indication of bioavailability of the compounds of the invention.

The ability to inhibit the p97 complex is studied through use of a p97 in vitro assay using a tagged p97 substrate pursuant to the method of Christianson in Nat Cell Biol. (2011) 14:93 for a p97 cell-based assay. A cell based assay is used to test the anti-tumor effects of inhibitors on cultured cancer cells. This anti-tumor assay is based upon cultured cancer cells using the commercially available cell titer glo assay provided by Promega. Additional assays enable assessment of bioavailability through art recognized model studies designed to demonstrate the ability of the compounds of the invention to reach target cells in vivo. While all compounds tested displayed a degree of anti-tumor activity, the assays also allow identification of monocyclic pyrimidine compounds as candidates that may be selected for further examination by in vivo anti-tumor testing in mouse, guinea pig and dog models. The selected candidates were shown to have highly desirable pharmacokinetic properties in these in vivo assays.

P97 ATPase Biochemical Assay

The ATPase assay is performed according the following protocol: Purified enzyme (20 nM p97), substrate (20 µM ATP) and a dose titration of compounds are mixed in buffer (50 mM TRIS pH 7.5, 20 mM $MgCl_2$, 0.02% TX-100, 1 mM DTT, 0.2% (v/v) glycerol) and incubated at 37° C. for 15 minutes. The reaction is terminated and the level of product generated is measured using the ADP Glo Assay Kit (Promega, Madison Wis.). Plotting product generated versus compound concentration and using a four-parameter fit model generates an IC50 value for each compounds.

P97 Cell-Based Assay

On target cell-based effects of compounds of the invention are monitored using the reporter cell line HEK-293 TCRα-GFP as described in Christianson et al. Nat. Cell Biol. (2011) 14:93. Inhibition of turnover of the TCRα-GFP reporter is a hallmark of p97 inhibition. The protocol for TCRα-GFP monitoring reporter turnover is as follows: Reporter cells are seeded and incubated with proteasome inhibitor MG132 to accumulate TCRα-GFP. Subsequently, MG132-containing media is removed and a dose titration of compound plus cycloheximide is incubated with the cells. At the end of the incubation, compound and media are removed, cells are fixed and GFP fluorescence is measured by standard epifluorescent microscopy techniques. Plotting fluorescence versus compound concentration and using a four-parameter fit model generates an IC50 value for each compound.

Image-analysis is used to generate quantitative data from these assays that can be fit to a four-parameter sigmoid curve to derive IC50 values. Substrates of the ubiquitin-proteasome system, such as p53, are monitored after tumor cell lines are incubated with compounds for several hours. Accumulation of these proteins indicates an inhibition of proteasome-mediated degradation. Accumulation of lysine-48 chain linkage of poly-ubiquitin is also monitored by immunofluorescence as an indicator of ubiquitin-proteasome system inhibition. Both LC3 and SQSTM1 are mediators of autophagy. The localization and amounts of these proteins are monitored by immunofluorescence and report on the activity and inhibition of autophagy in response to p97 inhibition.

Cultured Cancer Cell Assay

Anti-tumor effects are monitored in cultured cancer cells after several days of compound treatment. The cell titer glo assay (Promega) measures the amount of ATP present as a proxy for cellular viability. Cellular counting is done using high-content microscopy followed by image analysis. A hanging drop 3D-culture system (3D Biomatrix) is used followed by cell titer glo to measure growth in a tumor-like environment.

Absorption Assay

The ability of compounds to be absorbed from the lumen of the gastrointestinal tract after oral administration was assessed by measuring their permeability through Caco-2 cell monolayers. SunD, et al., Curr. Opin. Drug Discov. Develop[(2004) 75. The in vitro permeability of compound (2 µM in Kreb's buffer or HBSS buffer with n=2) was determined using 21-day old Caco-2 cell monolayers. The permeation coefficient was determined for both Apical to Basolateral (A to B) and Basolateral to Apical (B to A) after 120 min at 37° C. The efflux ratio was calculated based on the ratio of permeation coefficient of B to A vs. A to B to determine the potential of compound as substrate for efflux pump (e.g. Pgp). The protocol for this Caco-2 assay and the corresponding detailed description are provided in the following experimental section.

Metabolic Stability Assay

Metabolic stability of compounds can be assessed by measuring their half lives in liver microsomal preparations. Roserts, Sa, et al., Xenobiotica (2001) 37:557. Compounds are applied to a preparation of mouse liver microsomes in the presence of NADPH and their half-lives are determined by measuring the rate of disappearance of the compounds from the preparation by determining the concentration at 0, 15, 30 and 60 minutes using LCMS/MS. The protocol for determining metabolic stability in a mouse liver assay and the corresponding detailed description are provided in the following experimental section.

Nonspecific Binding Assay

Many compounds are known to bind nonspecifically to proteins found in high abundance in the plasma. The fraction of unbound drug (free fraction) is available for interaction with targets found in tissues. Banker, M. J. et al., Curr. Drug Metab. (2008) 9:854. The ability of compounds to escape a chamber containing blood plasma to a chamber containing only buffer can be assessed by measuring the concentration that appears in the buffer chamber and the concentration that remains in the plasma chamber. These measurements can be used to determine the fraction of compound bound to plasma proteins and its free fraction (100-percent bound to plasma proteins). The protocol for determining non-specific protein binding in a plasma protein binding assay and the corresponding detailed description are provided in the following experimental section.

The results of the primary assays conducted with selected monocyclic pyrimidine and pyridine compounds of the invention show that the monocyclic pyrimidine compounds of the invention display significant inhibitory activity ($IC_{50}$) against the enzymatic action of p97 toward its natural substrate. Some of these compounds also have greater potency in cell based assays and have in vitro pharmacokinetic properties consistent with good oral bioavailability.

Table II set forth in the experiment section providing the protocols for these biological assays presents the results of several of these assays conducted upon the monocyclic pyrimidine compounds of the invention.

Mechanism of Action and Medical Treatment

In certain embodiments, the invention is directed to methods of inhibiting p97. Preferred monocyclic pyrimidine compounds and substituted monocyclic pyrimidine or pyridine compounds for use in the methods disclosed herein bind to the active site of p97, e.g., noncovalently or covalently. In certain such embodiments, the covalent binding may be reversible or irreversible.

The compounds of the invention and their pharmaceutical compositions are capable of acting as "inhibitors" of p97 which means that they are capable of blocking or reducing the activity of an enzyme, for example, inhibition of various activities of p97. An inhibitor can act with competitive, uncompetitive, or noncompetitive inhibition. An inhibitor can bind reversibly or irreversibly, and therefore the term includes compounds that are suicide to the enzyme, or it can cause a conformational change elsewhere on the enzyme.

The compounds of the invention and their pharmaceutical compositions function as therapeutic agents in that they are capable of preventing, ameliorating, modifying and/or affecting a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The ability to prevent, ameliorate, modify and/or affect in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a treated population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The compounds of the invention and their pharmaceutical compositions are capable of functioning prophylactically and/or therapeutically and include administration to the host of one or more of the subject compositions. If it is administered prior to clinical manifestation of the unwanted condition (e.g., disease or other unwanted state of the host) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

As used herein, the term "treating" or "treatment" includes reversing, reducing, or arresting the symptoms, clinical signs, and underlying pathology of a condition in manner to improve or stabilize a subject's condition.

The compounds of the invention and their pharmaceutical compositions can be administered in "therapeutically effective amounts" with respect to the subject method of treatment. The therapeutically effective amount is an amount of the compound(s) in a pharmaceutical composition which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

Administration

Compounds prepared as described herein can be administered in various forms, depending on the disorder to be treated and the age, condition, and body weight of the patient, as is well known in the art. As is consistent, recommended and required by medical authorities and the governmental registration authority for pharmaceuticals, administration is ultimately provided under the guidance and prescription of an attending physician whose wisdom, experience and knowledge control patient treatment. For example, where the compounds are to be administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route, they may be formulated as eye drops or eye ointments. These formulations can be prepared by conventional means, and if desired, the active ingredient may be mixed with any conventional additive or excipient, such as a binder, a disintegrating agent, a lubricant, a corrigent, a solubilizing agent, a suspension aid, an emulsifying agent, a coating agent, a cyclodextrin, and/or a buffer. Although the dosage will vary depending on the symptoms, age and body weight of the patient, the nature and severity of the disorder to be treated or prevented, the route of administration and the form of the drug, in general, a daily dosage of from about 1.0 mg to about 4000 mg, preferably about 10 mg to about 3000 mg, more preferably about 20 mg to about 2000 mg, especially more preferably about 40 mg to about 1000 mg, most preferably about 75 mg to about 750 mg of the compound is recommended for an adult human patient, and this may be administered in a single dose or in divided doses. Alternatively, a daily dose can be given according to body weight such as about 14 microgram/kg (μg/kg) to about 60 mg/kg, preferably about 140 μg/kg to about 45 mg/kg, more preferably about 280 μg/kg to about 25 mg/kg, most preferably about 1.0 mg/kg to about 11 mg/kg. The amount of active ingredient which can be combined with a carrier material to produce a single dosage form will generally be that amount of the compound which produces a therapeutic effect.

The precise time of administration and/or amount of the composition that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

A "pharmaceutically acceptable carrier" is a pharmaceutically acceptable material, composition, or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch, potato starch, and substituted or unsubstituted β-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers, and lubricants, such as sodium lauryl sulfate and magnesium stearate, as well as coloring agents, release agents, coating agents, sweetening, flavoring, and perfuming agents, preservatives and antioxidants can also be present in the compositions. Examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert matrix, such as gelatin and glycerin, or sucrose and acacia) and/or as mouthwashes, and the like, each containing a predetermined amount of a compound of the invention as an active ingredient. A composition may also be administered as a bolus, electuary, or paste.

In solid dosage form for oral administration (capsules, tablets, pills, dragees, powders, granules, and the like), a compound of the invention is mixed with one or more pharmaceutically acceptable carriers, such as sodium citrate or dicalcium phosphate, and/or any of the following:

(1) fillers or extenders, such as starches, cyclodextrins, lactose, sucrose, glucose, mannitol, and/or silicic acid;
(2) binders, such as, for example, carboxymethylcellulose, alginates, gelatin, polyvinyl pyrrolidone, sucrose, and/or acacia;
(3) humectants, such as glycerol;
(4) disintegrating agents, such as agar-agar, calcium carbonate, potato or tapioca starch, alginic acid, certain silicates, and sodium carbonate;
(5) solution retarding agents, such as paraffin;
(6) absorption accelerators, such as quaternary ammonium compounds;
(7) wetting agents, such as, for example, acetyl alcohol and glycerol monostearate; (8) absorbents, such as kaolin and bentonite clay;
(9) lubricants, such a talc, calcium stearate, magnesium stearate, solid polyethylene glycols, sodium lauryl sulfate, and mixtures thereof; and
(10) coloring agents. In the case of capsules, tablets, and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols, and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered inhibitor(s) moistened with an inert liquid diluent.

Tablets, and other solid dosage forms, such as dragees, capsules, pills, and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner.

Examples of embedding compositions which can be used include polymeric substances and waxes. A compound of the invention can also be in micro-encapsulated form, if appropriate, with one or more of the above-described excipients.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active inhibitor(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more inhibitor(s) with one or more suitable nonirritating excipients or carriers comprising, for example, cocoa butter, polyethylene glycol, a suppository wax or a salicylate, which is solid at room temperature, but liquid at body temperature and, therefore, will melt in the rectum or vaginal cavity and release the active agent.

Formulations which are suitable for vaginal administration also include pessaries, tampons, creams, gels, pastes, foams, or spray formulations containing such carriers as are known in the art to be appropriate.

Dosage forms for the topical or transdermal administration of an inhibitor(s) include powders, sprays, ointments, pastes, creams, lotions, gels, solutions, patches, and inhalants. The active component may be mixed under sterile conditions with a pharmaceutically acceptable carrier, and with any preservatives, buffers, or propellants which may be required.

The ointments, pastes, creams, and gels may contain, in addition to a compound of the invention, excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to a compound of the invention, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

A compound of the invention can be alternatively administered by aerosol. This is accomplished by preparing an aqueous aerosol, liposomal preparation, or solid particles containing the composition. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of a compound of the invention together with conventional pharmaceutically acceptable carriers and stabilizers. The carriers and stabilizers vary with the requirements of the particular composition, but typically include nonionic surfactants (Tweens, Pluronics, sorbitan esters, lecithin, Cremophors), pharmaceutically acceptable co-solvents such as polyethylene glycol, innocuous proteins like serum albumin, oleic acid, amino acids such as glycine, buffers, salts, sugars, or sugar alcohols. Aerosols generally are prepared from isotonic solutions.

Transdermal patches have the added advantage of providing controlled delivery of a compound of the invention to the body. Such dosage forms can be made by dissolving or dispersing the agent in the proper medium. Absorption enhancers can also be used to increase the flux of the inhibitor(s) across the skin. The rate of such flux can be controlled by either providing a rate controlling membrane or dispersing the inhibitor(s) in a polymer matrix or gel.

Pharmaceutical compositions of this invention suitable for parenteral administration comprise one or more compounds of the invention in combination with one or more pharmaceutically acceptable sterile aqueous or nonaqueous solutions, dispersions, suspensions or emulsions, or sterile powders which may be reconstituted into sterile injectable solutions or dispersions just prior to administration and are typically made isotonic with the blood of the intended recipient. Examples of suitable aqueous and nonaqueous carriers which may be employed in the pharmaceutical compositions of the invention include sterile forms of water, aqueous dextran, Ringer's solution, ethanol, aqueous ethanol, polyols and aqueous forms thereof (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Parenteral administration may be accomplished by subcutaneous, intramuscular, intravenous or other injection route leading to delivery of the compounds and pharmaceutical compositions of the invention to the blood stream. Administration may be accomplished by single dose injection or by continuous intravenous or intra-arterial infusion by catheter or needle delivery to the appropriate vessel. Delivery may also be accomplished by an indwelling portal and catheter permanently implanted in the patient. Continuous infusion will provide a metered dose of the compound or pharmaceutical composition at a rate calculated to deliver the required daily dose as specified above and as adapted for venous or arterial infusion so as to account for a higher serum concentration than is typically achieved by oral administration because of degradation in the alimentary canal and metabolism through the hepatic system.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include tonicity-adjusting agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a compound of the invention, it is desirable to slow the absorption of the compound from subcutaneous or intramuscular injection. For example, delayed absorption of a parenterally administered drug form is accomplished by dissolving or suspending the drug in an oil vehicle.

Injectable depot forms are made by forming microencapsulated matrices of inhibitor(s) in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

The pharmaceutical compositions may be given orally, parenterally, topically, or rectally. They are, of course, given by forms suitable for each administration route. For example, they are administered in tablets or capsule form, by injection, inhalation, eye lotion, ointment, suppository, infusion; topically by lotion or ointment; and rectally by suppositories. Oral administration is preferred.

The phrases "parenteral administration" and "administered parenterally" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection, and infusion.

The pharmaceutical compositions of the invention may be "systemically administered" "administered systemically," "peripherally administered" and "administered peripherally" meaning the administration of a ligand, drug, or other material other than directly into the central nervous system, such that it enters the patient's system and thus, is subject to metabolism and other like processes, for example, subcutaneous administration.

The compound(s) of the invention may be administered to humans and other animals for therapy by any suitable route of administration, including orally, nasally, as by, for example, a spray, rectally, intravaginally, parenterally, intracisternally, and topically, as by powders, ointments or drops, including buccally and sublingually.

Regardless of the route of administration selected, the compound(s) of the invention, which may be used in a suitable hydrated form, and/or the pharmaceutical compositions of the present invention, are formulated into pharmaceutically acceptable dosage forms by conventional methods known to those of skill in the art.

Actual dosage levels of the compound(s) of the invention in the pharmaceutical compositions of this invention may be varied so as to obtain an amount of the active ingredient which is effective to achieve the desired therapeutic response for a particular patient, composition, and mode of administration, without being toxic to the patient.

The concentration of a compound of the invention in a pharmaceutically acceptable mixture will vary depending on several factors, including the dosage of the compound to be administered, the pharmacokinetic characteristics of the compound(s) employed, and the route of administration.

In general, the compositions of this invention may be provided in an aqueous solution containing about 0.1-10% w/v of a compound disclosed herein, among other substances, for parenteral administration. Typical parenteral dose ranges are from about 0.01 mg/kg to about 60 mg/kg, preferably about 0.1 mg/kg to about 45 mg/kg of body weight per day, more preferably about 1 mg/kg to about 15 mg/kg given in 1-4 divided doses. Each divided dose may contain the same or different compounds of the invention. The dosage will be an effective amount depending on several factors including the overall health of a patient, and the formulation and route of administration of the selected compound(s).

Another aspect of the invention provides a conjoint therapy wherein one or more other therapeutic agents are administered with the compounds and compositions of the invention. Such conjoint treatment will achieve the same or similar treatment accounting for the additive effects of the conjoined therapeutic agents other than the compounds of the invention.

In certain embodiments, a compound of the invention is conjointly administered with one or more proteasome inhibitor(s). In certain embodiments, a compound of the invention is conjointly administered with a chemotherapeutic. Suitable chemotherapeutics may include products such as *vinca* alkaloids (i.e., vinblastine, vincristine, and vinorelbine), paclitaxel, epidipodophyllotoxins (i.e., etoposide, tenipo side), antibiotics (dactinomycin (actinomycin D) daunorubicin, doxorubicin and idarubicin), anthracyclines, mitoxantrone, bleomycin, plicamycin (mithramycin) and mitomycin, enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates (busulfan), nitrosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadeno sine); aromatase inhibitors carboplatin), procarbazine, hydroxyurea, mitotane, aminoglutethimide; hormones (i.e. estrogen) and hormone agonists such as leutinizing hormone releasing hormone (LHRH) agonists (goserelin, leuprolide and triptorelin). Other chemotherapeutic agents may include mechlorethamine, camptothecin, ifosfamide, tamoxifen, raloxifene, gemcitabine, navelbine, or any analog or derivative variant of the foregoing. Additional proteasome inhibitors include bortezomib and carfilzomib. Additional chemotherapeutics include lenalidomide, thalidomide and thalidomide derivatives.

In certain embodiments, a compound of the invention is conjointly administered with a steroid. Suitable steroids may include, but are not limited to, 21-acetoxypregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difuprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, paramethasone, prednicarbate, prednisolone, prednisolone 25-diethylaminoacetate, prednisolone, sodium phosphate, prednisone, prednival, prednylidene, rimexolone, tixocortol, triamcinolone, triamcinolone acetonide, triamcinolone benetonide, triamcinolone hexacetonide, and salts and/or derivatives thereof.

In certain embodiments, a compound of the invention is conjointly administered with an immunotherapeutic agent. Suitable immunotherapeutic agents may include, but are not limited to, cyclosporine, thalidomide, and monoclonal antibodies. The monoclonal antibodies can be either naked or conjugated such as rituximab, tositumomab, alemtuzumab, epratuzumab, ibritumomab tiuxetan, gemtuzumab ozogamicin, bevacizumab, cetuximab, erlotinib and trastuzumab.

Combinations of these conjoint chemotherapeutic agents with compounds of the invention can be advantageously administered to a patient in need of treatment of the neoplastic diseases such as the cancers described below. Steroids can be administered before or during administration of the chemotherapeutic agents including the compounds of the invention to promote palliative effects. Preferred combinations for conjoint administration include bortezomib and/or carfilzomib with compounds of Formula I or II or the preferred or more preferred or especially preferred embodiments of Formula I or II. Preferred combinations for conjoint administration include bortezomib and/or carfilzomib and/or lenalidomide with a steroid such as dexamethasone and any one or more of the specifically named compounds of the invention given above. Especially preferred combinations include docetaxel, cabazitaxel, bortezomib, carfilzomib, lenalidomide, rituximab, cetuximab, Herceptin with any one or more of the specifically named compounds of the invention given above optionally with pre or concurrent administration of a palliative steroid such as dexamethasone.

Treatment of Cancer

Exemplary forms of cancer which may be treated by the methods of the invention include, but are not limited to, prostate cancer, bladder cancer, lung cancer (including either small cell or non-small cell cancer), colon cancer, kidney cancer, liver cancer, breast cancer, cervical cancer, endometrial or other uterine cancer, ovarian cancer, testicular cancer, cancer of the penis, cancer of the vagina, cancer of the urethra, gall bladder cancer, esophageal cancer, or pancreatic cancer.

Additional exemplary forms of cancer which may be treated by the methods of the invention include, but are not limited to, cancer of skeletal or smooth muscle, stomach cancer, cancer of the small intestine, cancer of the salivary gland, anal cancer, rectal cancer, thyroid cancer, parathyroid cancer, pituitary cancer, and nasopharyngeal cancer.

The compounds of the present invention and their salts and solvates, thereof, may be employed alone or in combination with other therapeutic agents for the treatment of the diseases or conditions associated with inappropriate P97 activity.

Additional diseases that can be treated according to the methods of the invention include in addition to cancer, auto-immune disorders, metabolic diseases, infection diseases, neurological diseases, graft versus host disease and other hereditary diseases outlined here: abeta-lipoproteinema, acerulopasminemia, alpha-1-antichymotrypsin (ACT) deficiency, aspartylglucosaminuria, autosomal dominant retinitis pigmentosa, brugada syndrome, Charcot-Marie-Tooth syndrome, congenital adrenal hyperplasia, congenital chloride diarrhea, congenital hypothyroidism, congenital long QT syndrome, congenital nephritic syndrome, congenital sucrase-isomaltase deficiency, Crigler-Najjar type II, cystic fibrosis, diabetes mellitus, diastrophic displasia, DubinJohnson syndrome, Fabri disease, familial chylomicronemia, familial glucocorticoid deficiency, familial hypercholesterolemia, Gaucher disease, heavy chain disease, hereditary emphysema, hereditary emphysema with liver injury, hereditary hemochromatosis, hereditary hypofibrinogenemia, hereditary myeloperoxidase, hereditary spherocytosis, hirschprung disease, hypogonadotropic hypogonadism, infantile systemic hyalinosis, infentile neuronal ceroid lipofuscinosis, laron syndrome, liver failure, marfan syndrome, medullary cystic kidney disease, familial juvenile hyperuricemic nephropathy, Menkes disease, nephrogenic diabetes, neurohypophyseal diabetes insipidus, oculocutaneous albinism, osteogenesis imperfect, Pelizaeus-Merzbacher disease, Pendred syndrome, persistent hyperinsulinemic hypoglycemia of infancy, primary hypothyroidism, Protein C deficiency, pseudo achondropla with multiple epiphyseal dysplasia, severe congenital neutropenia, Stargardt-like macular dystrophy, steroid-resistant nephrotic syndrome, TaySachs, Type I hereditary angioedema, tyroxine binding globulin deficiency, von Willebrand disease type IIA, X-linked Charot-Marie-Tooth disease, X-linked hypophosphatemia, Alzheimer disease autosomal recessive juvenile parkinsonism, combined factors V and VIII deficiency, cranio-lenticulo-sutural dysplasia, hypotonia and dysmorphism, inclusion body myopathy Paget's disease of the bone and frontotemporal dementia (IBMPFD), lipid absorption disorders, Marinesco-Sjoegren syndrome, Parkinson, polycystic liver disease, spondyloepiphyseal dysplasia tarda, WalcottRallison syndrome and Lou Gehrig's disease (ALS).

In various embodiments, compounds of the invention may be used to treat neoplastic growth, angiogenesis, infection, inflammation, immune-related diseases, ischemia and reperfusion injury, multiple sclerosis, rheumatoid arthritis, neurodegenerative conditions, or psoriasis.

Neoplastic growth may include cancer. Suitably, the present invention relates to a method for treating or lessening the severity of a cancer selected from: brain (gliomas), glioblastomas, breast, Wilm's tumor, Ewing's sarcoma, rhabdomyosarcoma, ependymoma, medulloblastoma, colon, head and neck, kidney, lung, liver, melanoma, ovarian, pancreatic, prostate, sarcoma, osteosarcoma, giant cell tumor of bone, thyroid, lymphoblastic T cell leukemia, chronic myelogenous leukemia, chronic lymphocytic leukemia, Hairy-cell leukemia, acute lymphoblastic leukemia, acute myelogenous leukemia, chronic neutrophilic leukemia, acute lymphoblastic T cell leukemia, plasmacytoma, immunoblastic large cell leukemia, mantle cell leukemia, multiple myeloma megakaryoblastic leukemia, multiple myeloma, acute megakaryocytic leukemia, promyelocytic leukemia, erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, lung cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer.

In various embodiments, the cancer is selected from brain cancer (gliomas), glioblastomas, breast cancer, colon cancer, head and neck cancer, kidney cancer, lung cancer, liver cancer, melanoma, ovarian cancer, pancreatic cancer, prostate cancer, sarcoma and thyroid cancer.

In various embodiments, the cancer to be treated is associated with the proteasome. See Voorhees et al., The Proteasome as a Target for Cancer Therapy, Clinical Cancer Research, vol. 9, 6316-6325, December 2003, incorporated by reference in its entirety. In various embodiments, the cancer is associated with a particular target, such as NFkB, p44/42 MAPK, P-gp, TopI, TopIIalpha.

In various embodiments, the cancer is a solid tumor. In various embodiments, the cancer is selected from multiple myeloma, metastatic breast cancer, non-small cell lung cancer, prostate cancer, advanced colorectal cancer, ovarian or primary peritoneal carcinoma, hormone refractory prostate cancer, squamous cell carcinoma of the head and neck, metastatic pancreatic adenocarcinoma, gastroesophageal junction or stomach, or non-Hodgkin's lymphoma.

A method of using the compounds described herein for treating a disorder characterized by an inappropriate level of proteasome activity, or in which a reduction of the normal level of proteasome activity yields a clinical benefit. This disorder can include cancer or immune disorders characterized by excessive cell proliferation or cellular signaling. Among cancers, this includes human cancers that overexpress c-Myc or express an oncogenic form of the K-Ras protein.

Neurodegenerative diseases and conditions may include without limitation stroke, ischemic damage to the nervous system, neural trauma (e.g., percussive brain damage, spinal cord injury, and traumatic damage to the nervous system), multiple sclerosis and other immune-mediated neuropathies (e.g., Guillain-Barre syndrome and its variants, acute motor axonal neuropathy, acute inflammatory demyelinating polyneuropathy, and Fisher Syndrome), HIV/AIDS dementia complex, axonomy, diabetic neuropathy, Parkinson's disease, Huntington's disease, ALS, multiple sclerosis, bacterial, parasitic, fungal, and viral meningitis, encephalitis, vascular dementia, multi-infarct dementia, Lewy body dementia, frontal lobe dementia such as Pick's disease, subcortical dementias (such as Huntington or progressive supranuclear palsy), focal cortical atrophy syndromes (such as primary aphasia), metabolic-toxic dementias (such as chronic hypothyroidism or B12 deficiency), and dementias caused by infections (such as syphilis or chronic meningitis). Compounds of the invention may be used to treat Alzheimer's disease, including administering to a subject an effective amount of an agent or composition (e.g., pharmaceutical composition) disclosed herein.

Compounds of the invention may be used to treat cachexia and muscle-wasting diseases. Compounds of the invention may be used to treat such conditions wherein the condition is related to cancer, chronic infectious diseases, fever, muscle disuse (atrophy) and denervation, nerve injury, fasting, renal failure associated with acidosis, diabetes, and hepatic failure.

Compounds of the invention can be used to treat hyperproliferative conditions such as diabetic retinopathy, macular degeneration, diabetic nephropathy, glomerulosclerosis, IgA nephropathy, cirrhosis, biliary atresia, congestive heart failure, scleroderma, radiation-induced fibrosis, and lung fibrosis (idiopathic pulmonary fibrosis, collagen vascular disease, sarcoidosis, interstitial lung diseases and extrinsic lung disorders). The treatment of burn victims is often hampered by fibrosis, thus, an additional embodiment of the application is the topical or systemic administration of the inhibitors to treat burns. Wound closure following surgery is often associated with disfiguring scars, which may be prevented by inhibition of fibrosis. Thus, in certain embodiments, the application relates to a method for the prevention or reduction of scarring.

Compounds of the invention can be used to treat ischemic conditions or reperfusion injury for example acute coronary syndrome (vulnerable plaques), arterial occlusive disease (cardiac, cerebral, peripheral arterial and vascular occlusions), atherosclerosis (coronary sclerosis, coronary artery disease), infarctions, heart failure, pancreatitis, myocardial hypertrophy, stenosis, and restenosis.

Compounds of the invention can be used for the inhibition of TNFalpha to prevent and/or treat septic shock.

Compounds of the invention can be used for inhibiting antigen presentation in a cell, including exposing the cell to an agent described herein. A compound of the invention may be used to treat immune-related conditions such as allergy, asthma, organ/tissue rejection (graft-versus-host disease), and auto-immune diseases, including, but not limited to, lupus, rheumatoid arthritis, psoriasis, multiple sclerosis, and inflammatory bowel diseases (such as ulcerative colitis and Crohn's disease). Thus, a further embodiment is a method for moedulating the immune system of a subject (e.g., inhibiting transplant rejection, allergies, auto-immune diseases, and asthma), including administering to the subject an effective amount of a compound of the invention.

Compounds of the invention can be used in methods for altering the repertoire of antigenic peptides produced by the proteasome or other protein assembly with multicatalytic activity.

Compounds of the invention can be used in methods for inhibiting IKB-alpha degradation, including contacting the cell with an agent identified herein. A further embodiment is a method for reducing the cellular content of NF-KB in a cell, muscle, organ, or subject, including contacting the cell, muscle, organ, or subject with a compound of the invention.

Compounds of the invention can be used in methods for affecting cyclin-dependent eukaryotic cell cycles. Compounds of the invention can be used in methods for treating a proliferative disease in a subject (e.g., cancer, psoriasis, or restenosis). Compounds of the invention can be used for treating cyclin-related inflammation in a subject.

One embodiment is a method for treating p53-related apoptosis, including administering to a subject an effective amount of a compound of the invention.

In another embodiment, the agents of the present application are useful for the treatment of a parasitic infection, such as infections caused by protozoan parasites. In certain such embodiments, the agents are useful for the treatment of parasitic infections in humans caused by a protozoan parasite selected from *Plasmodium* sps., *Trypanosoma* sps., *Leishmania* sps., *Pneumocystis carinii, Toxoplasma gondii, Entamoeba histolytica, Entamoeba invadens*, and *Giardia lamblia*. In certain embodiments, the agents are useful for the treatment of parasitic infections in animals and livestock caused by a protozoan parasite selected from *Plasmodium hermani, Cryptosporidium* sps., *Echinococcus granulosus, Eimeria tenella, Sarcocystis neurona*, and *Neurospora crassa*. Other compounds useful as proteasome inhibitors in the treatment of parasitic diseases are described in WO 98/10779, which is incorporated herein in its entirety.

In particular, the methods of treatment include inhibiting, arresting, ameliorating, minimizing and/or eliminating mal-conditions associated with the inability of cells to metabolize, degrade or otherwise remove ubiquitin tagged proteins and peptides because the tag has been cleaved, degraded, removed or otherwise rendered disfunctional as a result of P97 metalloprotease domain activity. Included are methods in which a human disorder characterized by abnormal regulatory peptide degradation resulting in excessive cell proliferation or cell signaling. The methods are directed to administration of an effective amount of a compound or pharmaceutical formulation disclosed above so that the abnormal regulatory peptide degradation is ameliorated, reduced or inhibited. In particular, the human disorders include a cancer or immune disorder, a cancer resulting from overexpression of c-Myc or expression of an oncogenic form of the K-Ras protein. The methods also include inhibition or amelioration of P97 metalloprotease domain activity in a human patient suffering from abnormal P97 metalloprotease domain activity on ubiquitin modified proteins. As described above, these methods involve administering to the patient an effective amount of a compound or pharmaceutical formulation disclosed above so that the abnormal P97 metalloprotease domain activity is ameliorated, reduced or inhibited.

Additional Embodiments of the Compounds of the Invention

Additional embodiments of the compounds of the invention of Formulas I and II include the following variations of the substituents $R_n$ and $R^1$ to $R^5$ and $R^6$. Each of these variations can be combined with any other variation as is appropriate for the final structure of the monocyclic pyrimidine or pyridine scaffold desired to form a full monocyclic pyrimidine or pyridine compound of the invention. The scaffold embodiments IA-TY as well as the preferred designations of $X^1$ and $X^2$ and the corresponding preferences for scaffold embodiments IA-IY given in foregoing sections titled "Preferences for $X^1$ and $X^2$ of Formulas IA-TY" and "Preferences of Formulas IA-IY with the foregoing $X^1$ and $X^2$ designations" along with the general and preferred designations for the aminoalkylaryl group at position 4 of the scaffold also are alternatively combined with substituents $R_n$ and $R^1$ to $R^5$ and $R^6$ designated below. Each of these substituents may individually be any one of the listings 1-24 below The number designations for the carbons include all integers between the lowest and highest number. Individual numbers of carbon atoms separate and distinct from other numbers of the same group are also included. For example for an alkyl of 1 to 6 carbons, an alkyl group of 1, 2, 3, 4, 5 or 6 carbons is included as well as each individual number designation separate and distinct from other number designations so that an alkyl of 1 to 6 carbons includes separately, methyl, ethyl, propyl, butyl, pentyl and hexyl. Unless otherwise stated, an alkyl group of the following substituent variations includes linear, branched and cyclic isomers and is of 1 to 6 carbons as is appropriate for branching or cyclic isomers.

1) Alkyl and branched alkyl of 1 to 6 carbons,
2) Alkoxy and branched alkoxy of 1 to 6 carbons,
3) Amine and aminoalkyl (e.g., —NHR and —NR$_2$)
4) Carboxylic acid,
5) Carboxylic ester wherein the alkoxy group of the ester is from 1 to 6 branched or straight carbons or the alcohol esterifying group is phenoxy,
6) Branched or straight alkylenyl carboxylic acid or ester of 2 to 7 carbons in the alkylenyl group and 1 to 6 branched or straight carbons in the ester group,
7) Branched or straight alkylenyl amine of 1 to 6 carbons (e.g., —R—NH$_2$),
8) Branched or straight perfluoroalkyl of 1 to 6 carbons,
9) Branched or straight trifluoroalkyl of 1 to 6 carbons wherein the trifluoro group is on the terminating or end carbon,
10) Hydroxyl,
11) Branched or straight alkylenyl hydroxyl of 1 to 6 carbons,
12) Carboxamide e.g., —CONH$_2$
13) Aminocarbonylalkyl, e.g., —NHCOR, wherein R is alkyl of 1 to 6 carbons,
14) A heterocyclic system comprised of one or more of the following and azetidine or substituted azetidine attached through the 1, 2, 3 or 4 positions, pyrrolidine or substituted pyrrolidine attached through the 1, 2, 3, 4 or 5 position, piperidine or substituted piperidine attached through the 1, 2, 3, 4, 5 or 6 position, a piperazine or substituted piperazine attached through the 1, 2, 3, 4, 5 or 6 position, a morpholine or substituted morpholine connected through the 1, 2, 3, 5 or 6 position,
15) Branched or straight alkylenylcarboxyamide of 1 to 6 carbons, e.g., —RCONH$_2$,
16) Alkyleneaminocarbonylalkyl, e.g., —RNHCOR, wherein the alkylenyl is branched or straight and is 1 to 6 carbons and the alkyl is branched or straight and is 1 to 6 carbons,
17) N-substituted carboxamide, wherein the N substituent is an aryl group, heteroaryl group or heterocycle group as defined in the DEFINITIONS section, e.g., —CONHAr or —CONHHet,
18) N-substituted carboxamide wherein the N substituent is an alkaryl group, a alkheteroaryl group or a alkheterocycle group as defined in the DEFINITIONS section, and wherein the "alk" group is an alkylenyl or branched alkylenyl group of 1 to 6 carbons, e.g., —CONH—R—Ar or CONH—R-Het,
19) N-substituted carboxamide wherein the N substituent is a branched or straight alkyl group of 1 to 10 carbons, the polyfluorinated version thereof, or a substituted version thereof, e.g., —CONH—R, wherein the substituent of the alkyl group is halogen, cyano, carboxyl, ester of 1 to 6 branched or straight chain carbons in the alkoxy or phenoxy portion, carboxamide, sulfoxamide, alkoxy of 1 to 6 carbons, urea, carbamate of 1 to 10 carbons, amine, mono or dialkyl amine having from 1 to 6 carbons in the alkyl group with the alkyl group being straight or branched, hydroxyalkyl of 1 to 10 branched or straight chain carbons or a cycloalkyl group as defined in the DEFINITIONS section,
20) Preferred aryl, heteroaryl and heterocycle groups for 17 and 18 include phenyl, halogen substituted phenyl, aminophenyl, benzoic acid, tolyl, xylyl, anisolyl, trifluoromethylphenyl, benzyl, tetrahydrofuran, pyrrolidinyl, tetrahydronaphthalene, cyclohexyl or alkyl substituted cyclohexyl with the alkyl group having 1 to 6 carbons, cyclohexyl or alkyl substituted cyclohexyl with the alkyl group having 1 to 6 carbons, cyclopentyl or alkyl substituted cyclopentyl with the alkyl group having 1 to 6 carbons, pyrazolyl, imidazolyl, piperidinyl, piperazinyl, pyrimidinyl, morpholinyl, pyrrolyl, thiophenyl, substituted versions of any of the foregoing aryl, heteroaryl or heterocycle groups wherein the chemical substituent is halogen, cyano, carboxyl, ester of 1 to 10 branched or straight chain carbons in the alkoxy or phenoxy portion, amine, carboxamide, sulfoxamide, urea, carbamate of 1 to 10 carbons, hydroxyl, thiol, alkoxy, anisolyl, phenyl, benzyl or a cycloalkyl group as defined in the DEFINITIONS section,
21) Derivatives of 15, 16, 17, 18 and 19 wherein the N of the carboxamide has a second substituent and the second substituent is a branched or straight chain alkyl of 1 to 6 carbons,
22) N-substituted carboxamide wherein the N substituent is a mono, di, tri or tetra amino acid and the amino acid moieties include glycinyl, alaninyl, leucinyl, valinyl, phenylalaninyl, lysinyl, argininyl, histidinyl, serinyl, aspariginyl, glutaminyl, aspartic, glutamic such that the amino acid moieties may be combined in any combination of two, three or four moieties including but not limited to a tetramer of four different moieties, a tetramer of two and two different moieties, a tetramer of three of one moiety and one of a different moiety, a trimer of two of one moiety and one of another moiety or a trimer of three different moieties, a dimer of two different moieties of the same moiety, and a monomer of any of the designated moieties. The nitrogen of an amino acid moiety may serve as the nitrogen of the carboxyamide group. The C-terminus of the amino acid monomer, dimer or trimer may be a carboxylic acid or a carboxamide. The order of amino acid moieties in the tetramer, trimer or dimer may be any order.

23) Any of the substituents designated by items 1, 2, 3, 5, 6, 7, 11, 13, 16, 17, 18, 19, 20, 21 or 22 which additionally includes any functional group selected from F, Cl, Br, I, OR', OC(O)N(R')$_2$, CN, NO, NO$_2$, ONO$_2$, azido, CF$_3$, OCF$_3$, R', O (oxo), S (thiono), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$N(R')C(O)R', (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted; for example, wherein R' can be hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl.

24) In addition to the groups of substituents set forth in 1 through 23 above, each individual substituent and individual combination is included separately and individually as if it were individually recited.

25) Additional embodiments of the compounds of the invention further include each individual compound listed on the compound Tables above.

EXAMPLES

The following describes the preparation of representative compounds of the invention in greater detail. The following examples are offered for illustrative purposes, and are not intended to limit the invention in any manner. Those of skill in the art will readily recognize a variety of noncritical parameters which can be changed or modified to yield essentially the same results.

Those skilled in the art will recognize, or be able to ascertain using no more than routine experimentation, numerous equivalents to the syntheses of the compounds and methods of use thereof described herein. Although certain exemplary embodiments are depicted and described herein, it will be appreciated that compound of the invention can be prepared according to the methods generally available to one of ordinary skill in the art. All of the above-cited references and publications are hereby incorporated by reference.

Unless otherwise noted, all solvents, chemicals, and reagents were obtained commercially and used without purification. The $^1$H NMR spectra were obtained in CDCl$_3$, d$_6$-DMSO, CD$_3$OD, or d$_6$-acetone at 25° C. at 300 MHz on an OXFORD (Varian) spectrometer with chemical shift (δ,ppm) reported relative to TMS as an internal standard. HPLC-MS chromatograms and mass spectra were obtained with Shimadzu LC-MS-2020 system. The prep-HPLC instruments used to purify some compounds were either a Gilson GX-281 (Gilson) or a P230 Preparative Gradient System (Elite). Preparative chiral HPLC separations were performed using an Elite P230 Preparative Gradient System, a Thar Prep-80 or Thar SFC X-5. Reactions using microwave irradiation were performed on a CEM Discover SP instrument.

SYNTHETIC EXAMPLES

Example 1

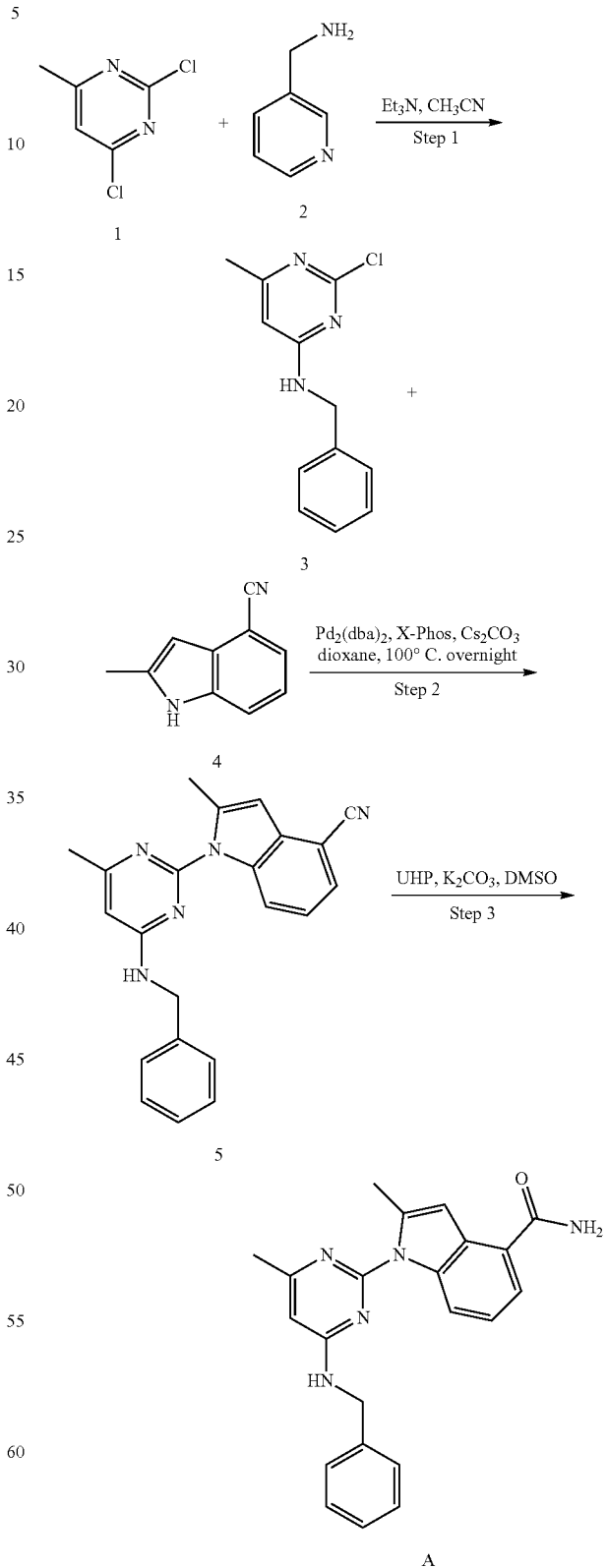

To a solution of 2,4-dichloro-6-methylpyrimidine (0.49 g, 3.0 mmol) in CH$_3$CN (20 mL), was added phenylmethanamine (0.86 g, 8.0 mmol). The mixture was stirred overnight at room temperature. The mixture was concentrated under vacuum, the residue was purified by flash chromatography (3:1 hexane:ethyl acetate) using a mixture of hexane and ethyl acetate to afford N-benzyl-2-chloro-6-methylpyrimidin-4-amine (0.51 g, 73%). LRMS (M+H+) m/z: calcd 234.07. found 234.

A mixture of the aforementioned intermediate 3 (280 mg, 1.2 mmol), 2-methyl-1H-indole-4-carbonitrile 4 (186 mg, 1.2 mmol), tris(dibenzylideneacetone) dipalladium(0) (60 mg), X-phos (60 mg) and $Cs_2CO_3$ (786 mg, 2.4 mmol) in dioxane (10 mL) was heated at 100° C. for 12 hours under nitrogen atmosphere. The reaction mixture was cooled to room temperature and concentrated under vacuum, and the residue was purified by flash chromatography using a mixture of hexane and ethyl acetate to afford 1-[4-(benzylamino)-6-methylpyrimidin-2-yl]-2-methyl-1H-indole-4-carbonitrile 5 (300 mg, 71%). LRMS (M+H$^+$) m/z: calcd 354.16. found 354.

To a 0° C. solution of the aforementioned intermediate 5 (300 mg, 0.85 mmol) in DMSO (20 mL) was added UHP (816 mg, 8.5 mmol) and $K_2CO_3$ (59 mg, 0.43 mmol), was added water (0.5 mL) and the reaction was stirred at room temperature overnight. Water (100 mL) was added to the mixture and the solid formed was filtrated to give the crude product, which was purified by flash chromatography (silica gel, DCM/MeOH=20:1) to afford Example 1.

1-[4-(benzylamino)-6-methylpyrimidin-2-yl]-2-methyl-1H-indole-4-carboxamide, Example 1
(Compound A)

Example 1 was isolated as a white solid. (230 mg, 73%). LRMS (M+H$^+$) m/z: calcd 372.17. found 372. HPLC purity (214 nm): 98%. $^1$HNMR (400 MHz, CD$_3$OD): δ 7.87 (s, 1H), 7.49 (d, J=7.2 Hz, 1H), 7.34-7.24 (m, 5H), 7.06 (m, 1H), 7.04 (t, J=7.2 Hz, 1H), 6.81 (s, 1H), 4.63 (s, 2H), 2.53 (s, 3H), 2.36 (s, 3H).

The following compounds were prepared using similar methodology.

Example 2

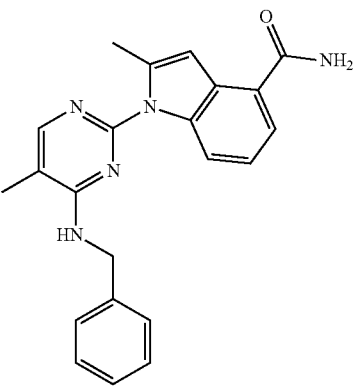

1-[4-(benzylamino)-5-methylpyrimidin-2-yl]-2-methyl-1H-indole-4-carboxamide, Example 2
(Compound B)

Example 2 was isolated as a white solid LRMS (M+H$^+$) m/z: calcd 372.17. found 372. HPLC purity (214 nm): 97%.

$^1$HNMR (400 MHz, CD$_3$OD): δ 8.02 (s, 1H), 7.65 (d, J=8.4 Hz, 1H), 7.44 (d, J=7.6 Hz, 1H), 7.33-7.24 (m, 5H), 6.96 (t, J=8.0 Hz, 1H), 6.77 (s, 1H), 474 (s, 2H), 2.43 (s, 3H), 2.20 (s, 3H).

Example 3

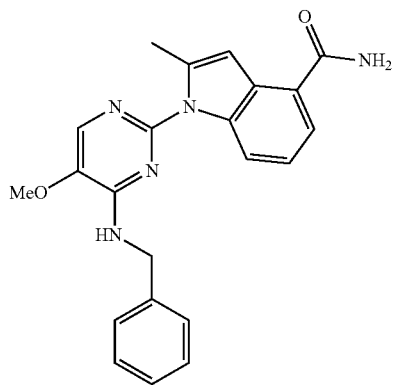

1-[4-(benzylamino)-5-methoxypyrimidin-2-yl]-2-methyl-1H-indole-4-carboxamide, Example 3
(Compound C)

Example 3 was isolated as a solid. LRMS (M+H$^+$) m/z: calcd 388.17. found 388. HPLC purity (214 nm): 100%. $^1$HNMR (300 MHz, CDCl$_3$): δ 7.98 (d, J=8.4 Hz, 1H), 7.82 (s, 1H), 7.50 (d, J=7.5 Hz, 1H), 7.37-7.31 (m, 5H), 7.09 (t, J=8.1 Hz, 1H), 6.81 (s, 1H), 5.91 (t, J=5.7 Hz, 1H), 4.73 (d, J=5.7 Hz, 2H), 3.95 (s, 3H), 2.61 (s, 3H).

Example 4

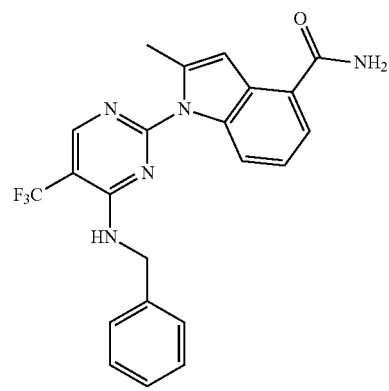

1-[4-(benzylamino)-5-(trifluoromethyl)pyrimidin-2-yl]-2-methyl-1H-indole-4-carboxamide, Example 4
(Compound D)

Example 4 was isolated as a white solid; LRMS (M+H$^+$) m/z: calcd 426.15. found 426.2. $^1$H NMR (300 MHz, CD$_3$OD): δ 8.52 (d, J=0.9 Hz, 1H), 8.02 (d, J=8.4 Hz, 1H), 7.47 (dd, J=0.9, 7.5 Hz, 1H), 7.37-7.21 (m, 5H), 6.97 (t, J=8.0 Hz, 1H), 6.82 (s, 1H), 4.82 (d, J=4.2 Hz, 2H), 2.53 (d, J=0.9 Hz, 3H).

Example 5

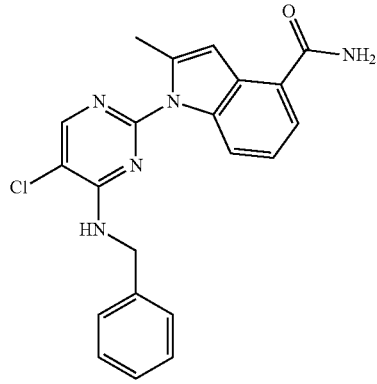

1-[4-(benzylamino)-5-chloropyrimidin-2-yl]-2-methyl-1H-indole-4-carboxamide Example 5 (Compound E)

Example 5 was isolated as a solid (80 mg, 38%); LRMS (M+H⁺) m/z: calcd 391.12. found 391. HPLC purity (214 nm): 99%. ¹HNMR (300 MHz, CDCl₃): δ 8.28 (s, 1H), 8.19 (d, J=8.4 Hz, 1H), 7.51-7.49 (m, 1H), 7.39-7.32 (m, 5H), 7.11 (t, J=8.1 Hz, 1H), 6.88 (s, 1H), 5.87 (t, J=5.7 Hz, 1H), 4.78 (d, J =5.7 Hz, 2H), 2.65 (s, 3H).

Example 6

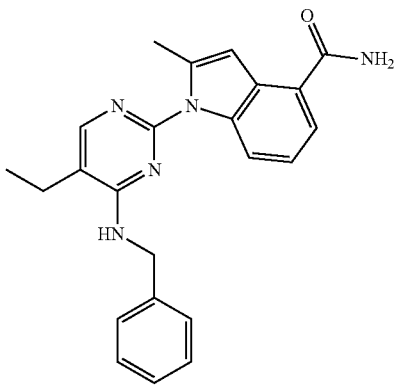

1-[4-(benzylamino)-5-ethylpyrimidin-2-yl]-2-methyl-1H-indole-4-carboxamide, Example 6 (Compound E1)

Example 6 was isolated as a solid, LRMS (M+H⁺) m/z: calcd 386. found 386; ¹HNMR (300 MHz, d₆-DMSO) δ 8.09 (s, 1H), 7.90 (br s, 1H), 7.79 (d, J=8 Hz, 1H), 7.73 (m, 1H), 7.44 (d, J=8 Hz, 1H), 7.37 (m, 5H), 6.90 (t, J=8 Hz, 1H) 6.84 (s, 1H), 4.63 (m, 2H), 2.59 (q, J=7 Hz, 2H) 2.48 (s, 3H), 1.31 (t, J=7 Hz, 3H).

Example 7

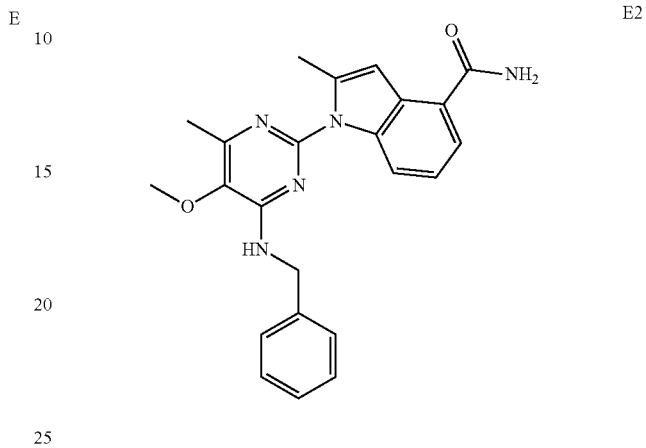

1-[4-(benzylamino)-5-methoxy-6-methylpyrimidin-2-yl]-2-methyl-1H-indole-4-carboxamide, Example 7 (Compound E2)

Example 7 was isolated as a solid. LRMS (M+H⁺) m/z: calcd 402. found 402; ¹H NMR (300 MHz, CD3OD) δ 7.57 (d, J=8 Hz, 1H), 7.45 (d, J=8 Hz, 1H), 7.33 (m, 5H),), 6.97 (t, J=8 Hz, 1H) 6.75 (s, 1H), 4.67 (s, 2H), 3.86 (s, 3H), 2.42 (s, 3H), 2.41 (s, 3H).

Example 8

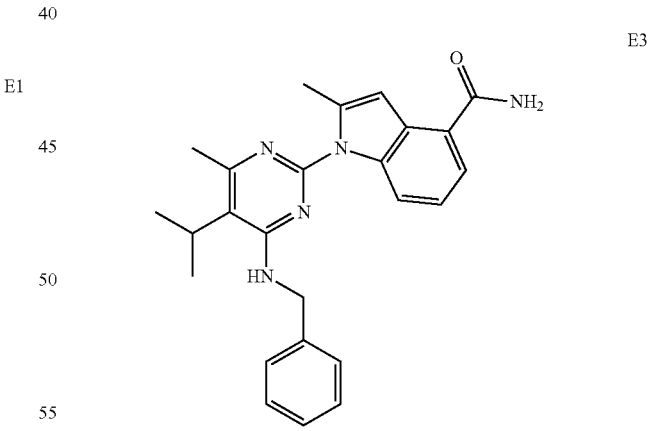

1-[4-(benzylamino)-6-methyl-5-(propan-2-yl)pyrimidin-2-yl]-2-methyl-1H-indole-4-carboxamide, Example 8 (Compound E3)

Example 8 was isolated as a solid. LRMS (M+H⁺) m/z: calcd 414. found 414; ¹H NMR (400 MHz, CDCl₃) δ 8.09 (m, 1H), 7.50 (d, J=8 Hz, 1H), 7.36 (m, 5H), 7.07 (t, J=8 Hz, 1H), 6.82 (s, 1H) 4.78 (d, J=5 Hz, 2H), 3.45 (sept. J=8 Hz, 1H), 2.64 (s, 3H), 2.56 (s, 3H). 1.39 (d, J=8 Hz, 6H)

Example 9

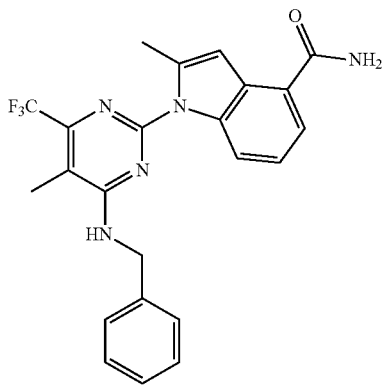

1-[4-(benzylamino)-5-methyl-6-(trifluoromethyl)
pyrimidin-2-yl]-2-methyl-1H-indole-4-carboxamide,
Example 9 (Compound E4)

Example 9 was isolated as a solid. LRMS (M+H$^+$) m/z: calcd 440. found 440; $^1$H NMR (400 MHz, d$_6$-DMSO) δ 8.42 (t, J=7 Hz, 1H), 7.93 (d, J=8 Hz, 1H), 7.77 (br s, 1H), 7.48 (d, J=8 Hz, 1H), 7.32 (m, 5H), 7.26 (br s, 1H), 6.97 (t, J=8 Hz, 1H), 6.91 (s, 1H), 4.74 (d, J=7 Hz, 2H), 2.52 (s, 3H), 2.30 (s, 3H).

Example 10

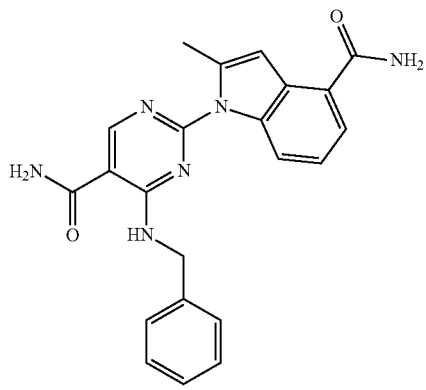

1-[4-(benzylamino)-5-carbamoylpyrimidin-2-yl]-2-
methyl-1H-indole-4-carboxamide, Example 10
(Compound E5)

Example 10 was isolated as a solid. LRMS (M+H$^+$) m/z: calcd 401. found 401; HPLC purity (214 nm): 95.3%. $^1$HNMR (400 MHz, CDCl$_3$): δ 9.48 (br s, 1H), 8.72 (s, 1H), 8.26 (d, J=8 Hz, 1H), 7.48 (d, J=8 Hz, 1H), (7.33 (m, 5H), 7.08 (t, J=8 Hz, 1H), 6.90 (s, 1H), 6.05 (br s 2H), 4.81 (d, J=7 Hz, 2H), 3.59 (br s, 2H), 2.56 (s, 3H).

Example 11

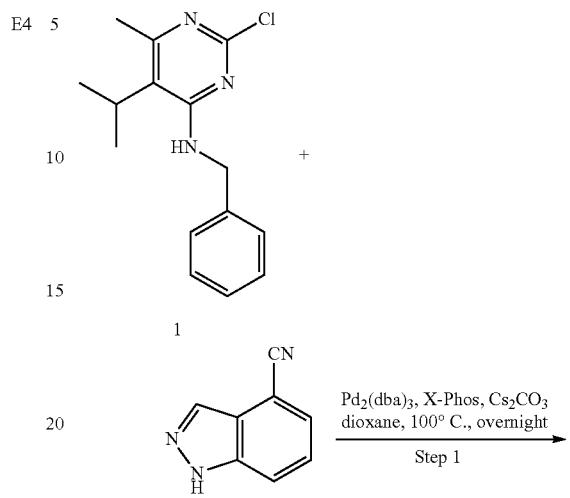

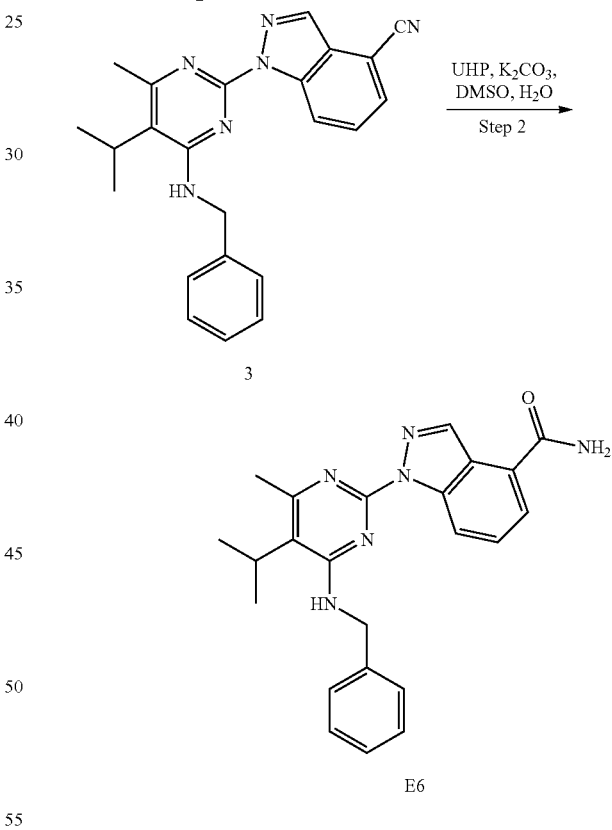

1-(4-(benzylamino)-5-isopropyl-6-methylpyrimidin-
2-yl)-1H-indazole-4-carboxamide, Example 11
(compound E6)

Example 11 (compound E6) was prepared via a similar two-step procedure to Example 1 using intermediate 1 and 4-cyano-indazole (2) as the starting materials. HPLC purity >95%, LRMS (M+H$^+$) m/z: calcd 401.2. found 401.1; $^1$H NMR (400 MHz, DMSO-d$_6$) δ: 8.60 (s, 1H), 8.32 (d, J=7.2 Hz, 1H), 8.09 (br, 1H), 7.67 (d, J=7.2 Hz, 1H), 7.53 (br, 1H), 7.36 (m, 6H), 7.07 (m, 1H), 4.77 (d, J=5.2 Hz, CH$_2$Ph, 2H), 3.36 (m, C$\underline{H}$Me$_2$, 1H), 2.50 (s, Me, 3H). 1.39 (d, J=7.2 Hz, Me$_2$, 6H).

Example 12

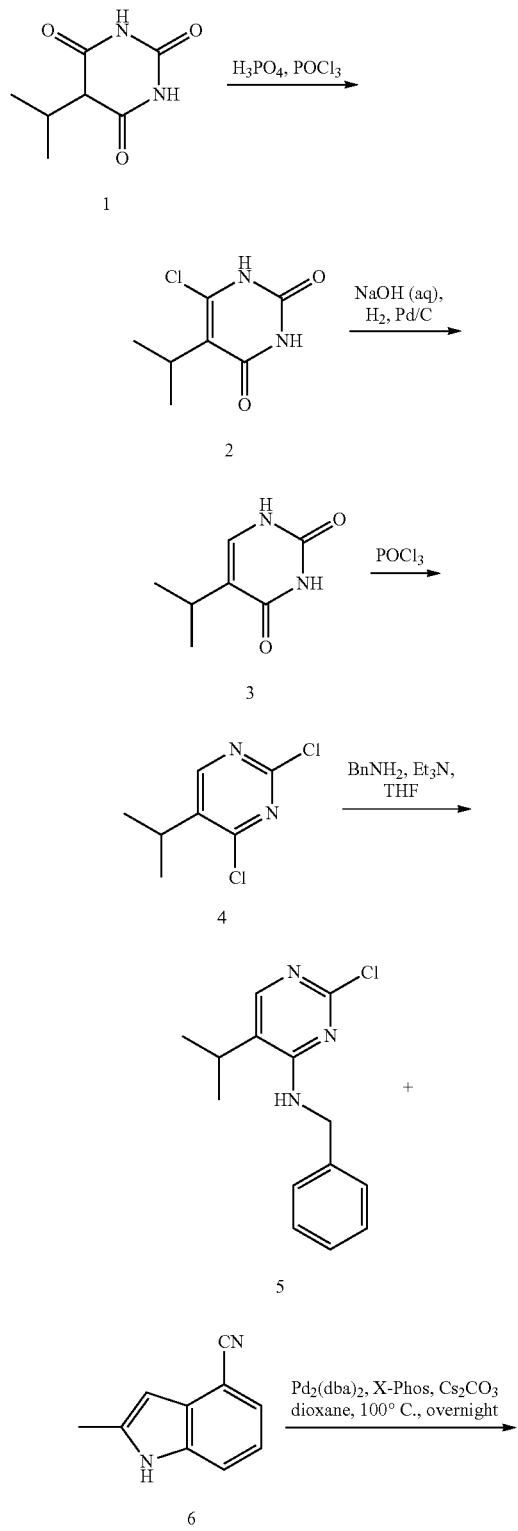

A solution of 5-isopropylpyrimidine-2,4,6(1H,3H,5H)-trione 1 (1.7 g, 10 mmol), H$_3$PO$_4$ (7 mL, 87% aq.), and POCl$_3$ (45 mL) was stirred at 100° C. for 2 hours. The resulting solution was then cooled down to room temperature, and crushed ice (200 g) was added slowly with stirring to decompose unreacted POCl$_3$. The mixture was kept at 0° C. overnight and the precipitated crystalline was collected by filtration, washed well with water, and dried to give 6-chloro-5-isopropylpyrimidine-2,4(1H,3H)-dione 2 (0.6 g, 32%). LRMS (M+H$^+$) m/z: calcd 189.04. found 189.

A mixture of 6-chloro-5-isopropylpyrimidine-2,4(1H,3H)-dione 2 (0.6 g, 3.2 mmol) and 10% Pd/C (500 mg) in NaOH (200 mL, 2N aq.) was shaken in a hydrogen atmosphere for 3 hours with the initial pressure of 40 psi. The catalyst was removed by filtration and the filtrate was acidified with concentrated HCl to pH~2. The resulting precipitate was collected, washed, and dried to give 5-isopropylpyrimidine-2,4(1H,3H)-dione 3 (0.31 g, 63%). LRMS (M+H$^+$) m/z: calcd 155.07. found 155.

A solution of the aforementioned intermediate 3 (0.31 g, 2.0 mmol) in POCl$_3$ (10 mL) was heated to reflux and stirred for 2 h. The mixture was cooled to room temperature and concentrated under vacuum. The residue was diluted with DCM (100 mL) and water (10 mL). The layers were separated, and the aqueous phase was extracted with DCM (50 mL×2). The organic layers were combined and dried over Na$_2$SO$_4$. The Na$_2$SO$_4$ was removed by filtration, and the volatiles were removed under reduced pressure. The resulting residue, 2,4-dichloro-5-isopropylpyrimidine 4 (0.12 g, 32%), which was used in the next step without further purification. LRMS (M+H$^+$) m/z: calcd 191.01. found 191.

To a 0° C. solution of 2,4-dichloro-pyrimidine 4 (0.12 g, 0.63 mmol) in CH₃CN (15 mL) was added benzylamine (0.22 g, 2.0 mmol). The reaction was stirred overnight at room temperature. The resulting mixture was concentrated under vacuum, and the residue was purified by flash chromatography using a mixture of hexane and ethyl acetate to provide N-benzyl-2-chloro-5-isopropylpyrimidin-4-amine 5 (0.10 g, 61%). LRMS (M+H$^+$) m/z: calcd 262.10. found 262.

A mixture of the aforementioned intermediate 5 (100 mg, 0.38 mmol) and 2-methyl-1H-indole-4-carbonitrile 6 (62 mg, 0.4 mmol), tris(dibenzylideneacetone) dipalladium(0) (60 mg), X-phos (60 mg) and Cs₂CO₃ (262 mg, 0.8 mmol) in dioxane (10 mL) was heated at 100° C. for 10 hours under nitrogen atmosphere. The reaction mixture was cooled down to room temperature and concentrated under vacuum, and the residue was purified by flash chromatography (PE/EA=5:3) to afford 1-(4-(benzylamino)-5-(propan-2-yl)pyrimidin-2-yl)-2-methyl-1H-indole-4-carbonitrile 7 (120 mg, 83%). LRMS (M+H$^+$) m/z: calcd 382.20. found 382.

To a 0° C. solution of the aforementioned intermediate 7 (120 mg, 0.31 mmol) in DMSO (5 mL) were added UHP (297 mg, 3.1 mmol), K₂CO₃ (19 mg, 0.14 mmol) and water (0.5 mL), the reaction was stirred at room temperature overnight followed by dilution with water (50 mL). The resulting solid was collected and purified by flash chromatography (DCM/MeOH=20:1) to afford Example 12.

1-(4-(benzylamino)-5-(propan-2-yl)pyrimidin-2-yl)-2-methyl-1H-indole-4-carboxamide, Example 12
(Compound F)

Example 12 was isolated as a yellow solid. (90 mg, 73%). LRMS (M+H$^+$) m/z: calcd 400.21. found 400. HPLC purity (214 nm): 99%. $^1$HNMR (400 MHz, CD₃OD) δ: 8.10 (s, 1H), 7.64 (d, J=8.4 Hz, 1H), 7.44 (d, J=7.2 Hz, 1H), 7.35-7.25 (m, 5H), 6.96 (t, J=8.0 Hz, 1H), 6.77 (s, 1H), 4.77 (s, 2H), 3.08-2.99 (m, 1H), 2.43 (s, 3H), 1.37 (d, J=8.0 Hz, 6H).

Example 13

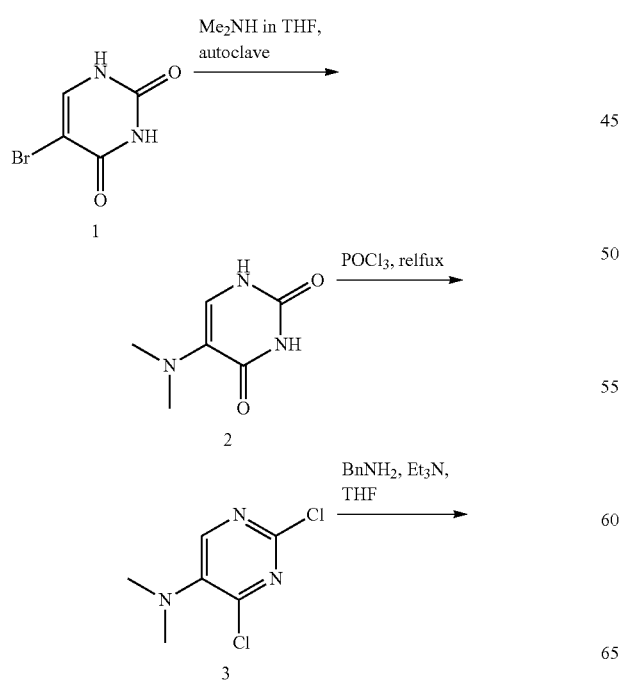

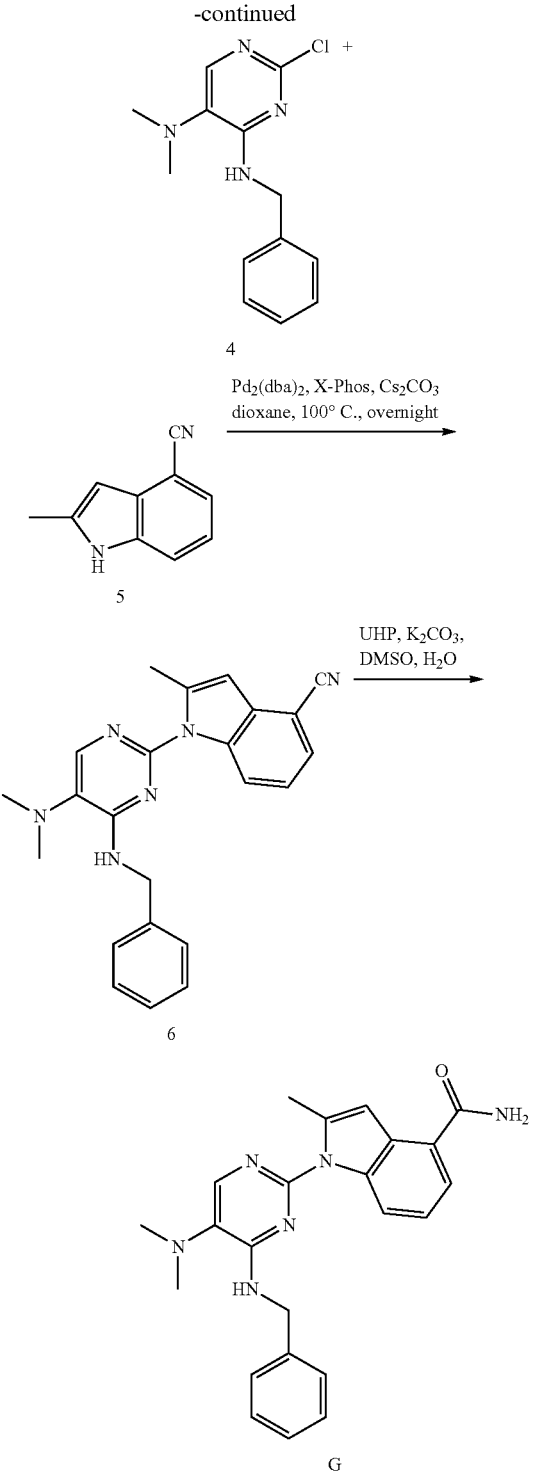

A solution of 5-bromopyrimidine-2,4(1H,3H)-dione 1 (1.5 g, 7.85 mmol) in Me₂NH (15 mL, 2 M in THF) was stirred in autoclave at 100° C. for 16 h. The resulting mixture was cooled down to room temperature and concentrated in vacuum, the residue was washed with water and dried to give 5-(dimethylamino)pyrimidine-2,4(1H,3H)-dione 2 (840 mg, 69%) as a yellow solid. LRMS (M+H$^+$) m/z: calcd 156.07. found 156. $^1$H NMR (300 MHz, DMSO) δ: 11.00 (s, 1H), 10.41 (s, 1H), 6.65 (s, 1H), 2.52 (s, 6H).

A solution of the aforementioned intermediate 2 (400 mg, 2.58 mmol) in POCl₃ (10 mL) was heated to reflux and stirred for 2 h. The mixture was cooled to room temperature and poured slowly into ice-water (100 mL). The aqueous phase was extracted with DCM (50 mL×3). The organic layers were combined and dried over Na₂SO₄. The Na₂SO₄ was removed by filtration, and the volatiles were removed under reduced pressure, and the residue was purified by flash chromatography using a mixture of DCM and THF to give 2,4-dichloro-N,N-dimethylpyrimidin-5-amine 3 (340 mg, 68%) as a yellow oil. LRMS (M+H⁺) m/z: calcd 192.00. found 192.

To a 0° C. solution of 2,4-dichloro-pyrimidine 3 (340 mg, 1.77 mmol) in CH₃CN (20 mL) were added benzylamine (283 mg, 2.65 mmol) and triethylamine (536 mg, 5.31 mmol). The reaction was stirred overnight at room temperature. The resulting mixture was concentrated under vacuum, and the residue was purified by flash chromatography (DCM: MeOH=50:1) to give N⁴-benzyl-2-chloro-N⁵,N⁵-dimethylpyrimidine-4,5-diamine 4 (360 mg, 78%) as a yellow oil. ¹H NMR (300 MHz, CD3OD) δ 7.66 (s, 1H), 7.22-7.35 (m, 5H), 4.63 (s, 2H), 2.64 (s, 6H); LRMS (M+H⁺) m/z: calcd 263.10. found 263.

A mixture of the aforementioned intermediate 4 (150 mg, 0.75 mmol) and 2-methyl-1H-indole-4-carbonitrile 5 (117 mg, 0.75 mmol), tris(dibenzylideneacetone) dipalladium(0) (90 mg, 0.085 mmol), X-phos (78 mg, 0.085 mmol) and Cs₂CO₃ (276 mg, 0.85 mmol) in dioxane (15 mL) was heated at 100° C. for 16 hours under nitrogen atmosphere. The reaction mixture was cooled down to room temperature and concentrated under vacuum, and the residue was purified by flash chromatography (DCM:MeOH=100:1) to give 1-(4-(benzylamino)-5-(dimethylamino)pyrimidin-2-yl)-2-methyl-1H-indole-4-carbonitrile 6 (173 mg, 60%) as a brown solid. 1H NMR (300 MHz, CD3OD) δ 7.97 (s, 1H), 7.72 (d, J=3.0 Hz, 1H), 7.38 (d, J=3.0 Hz, 1H), 7.29-7.33 (m, 4H), 6.98 (t, J=6.0 Hz, 1H), 6.45 (s, 1H), 4.71 (s, 2H), 2.79 (s, 6H), 2.47 (s, 3H); LRMS (M+H+) m/z: calcd 383.19. found 383.

To a 0° C. solution of the aforementioned intermediate 6 (170 mg, 0.44 mmol) in DMSO (5 mL) were added UHP (330 mg, 3.52 mmol), K₂CO₃ (30 mg, 0.22 mmol) and water (0.1 mL), the reaction was stirred at room temperature overnight followed by dilution with water (5 mL). The resulting solid was collected and purified by preparative thin layer chromatography to give Example 13.

1-(4-(benzylamino)-5-(dimethylamino)pyrimidin-2-yl)-2-methyl-1H-indole-4-carboxamide, Example 13 (Compound G)

Example 13 was isolated as a white solid (100 mg, 57%). LRMS (M+H⁺) m/z: calcd 401.20. found 401. ¹H NMR (300 MHz, CD₃OD) δ 7.96 (s, 1H), 7.64 (d, J=4.2 Hz, 1H), 7.44 (d, J=4.0 Hz, 1H), 7.23-7.33 (m, 5H), 6.96 (t, J=7.8 Hz, 1H), 6.76 (s, 1H), 4.70 (s, 2H), 2.75 (s, 6H), 2.43 (s, 3H).

Using similar methods the following examples could be made:

Example 14

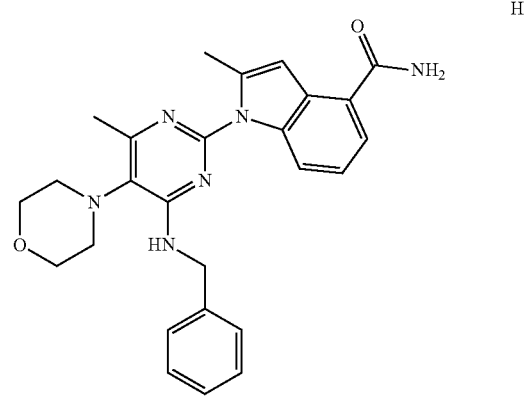 [SMILES: Cc1nc(-n2c(C)cc3c(C(N)=O)cccc32)nc(NCc2ccccc2)c1N1CCOCC1]

1-[4-(benzylamino)-5-(morpholin-4-yl)pyrimidin-2-yl]-2-methyl-1H-indole-4-carboxamide, Example 14 (Compound H)

Example 14 was isolated as a solid. LRMS (M+H⁺) m/z: calcd 443 found 443 ¹H NMR (300 MHz, CD₃OD) δ 8.02 (s, 1H), 7.68 (d, J=9 Hz, 1H), 7.46 (d, J=9 Hz, 1H), 7.32 (m, 5H), 6.96 (t, J=9 Hz, 1H) 6.77 (s, 1H) 4.73 (s, 2H), 3.91 (m, 4H), 3.03 (m, 4H). 2.44 (s, 3H).

Example 15

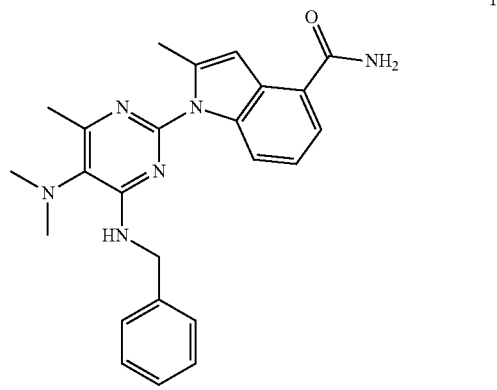

1-[4-(benzylamino)-5-(dimethylamino)-6-methylpyrimidin-2-yl]-2-methyl-1H-indole-4-carboxamide, Example 15 (Compound I)

Example 15 was isolated as a solid. LRMS (M+H⁺) m/z: calcd 415 found 415; ¹H NMR (300 MHz, CD₃OD) δ 7.70 (d, J=9 Hz, 1H), 7.45 (d, J=9 Hz, 1H), 7.26 (m, 5H),), 6.97 (t, J=9 Hz, 1H) 6.77 (s, 1H), 4.68 (s, 2H), 2.85 (s, 6H), 2.46 (s, 3H), 2.41 (s, 3H).

Example 16

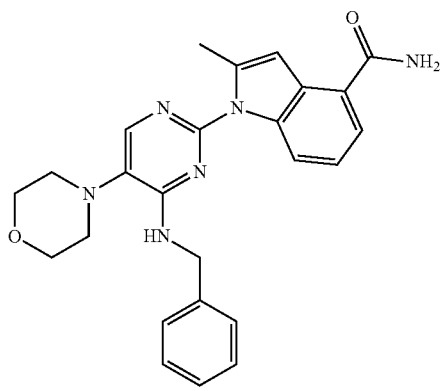

1-[4-(benzylamino)-6-methyl-5-(morpholin-4-yl)
pyrimidin-2-yl]-2-methyl-1H-indole-4-carboxamide,
Example 16 (Compound J)

Example 16 was isolated as a solid. LRMS (M+H$^+$) m/z: calcd 457 found 457; $^1$H NMR (300 MHz, CD$_3$OD) δ 7.74 (d, J=6 Hz, 1H), 7.45 (d, d J=6.1 Hz, 1H), 7.33 (m, 5H), 6.97 (t, J=9 Hz, 1H) 6.77 (s, 1H), 4.72 (s, 2H), 3.90 (m, 4H), 3.33 (m, 2H), 2.83 (m, 2H), 2.47 (s, 6H).

Example 17

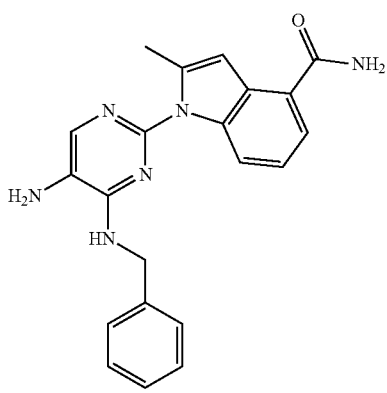

1-[5-amino-4-(benzylamino)pyrimidin-2-yl]-2-
methyl-1H-indole-4-carboxamide; Example 17
(Compound JJ)

Example 17 was isolated as a solid. LRMS (M+H$^+$) m/z: calcd 372 found 372; $^1$H NMR (400 MHz, d$_6$-DMSO) δ 7.69 (s, 2H), 7.59 (d, J=8 hz, 1H), 7.41 (m, 2H), 7.35 (m, 5H), 7.26 (m, 1H), 6.92 (t, J=9 Hz, 1H), 6.77 (s, 1H), 5.00 (s, 2H), 4.64 d, J=5 Hz, 2H), 3.00 (s, 3H).

Example 18

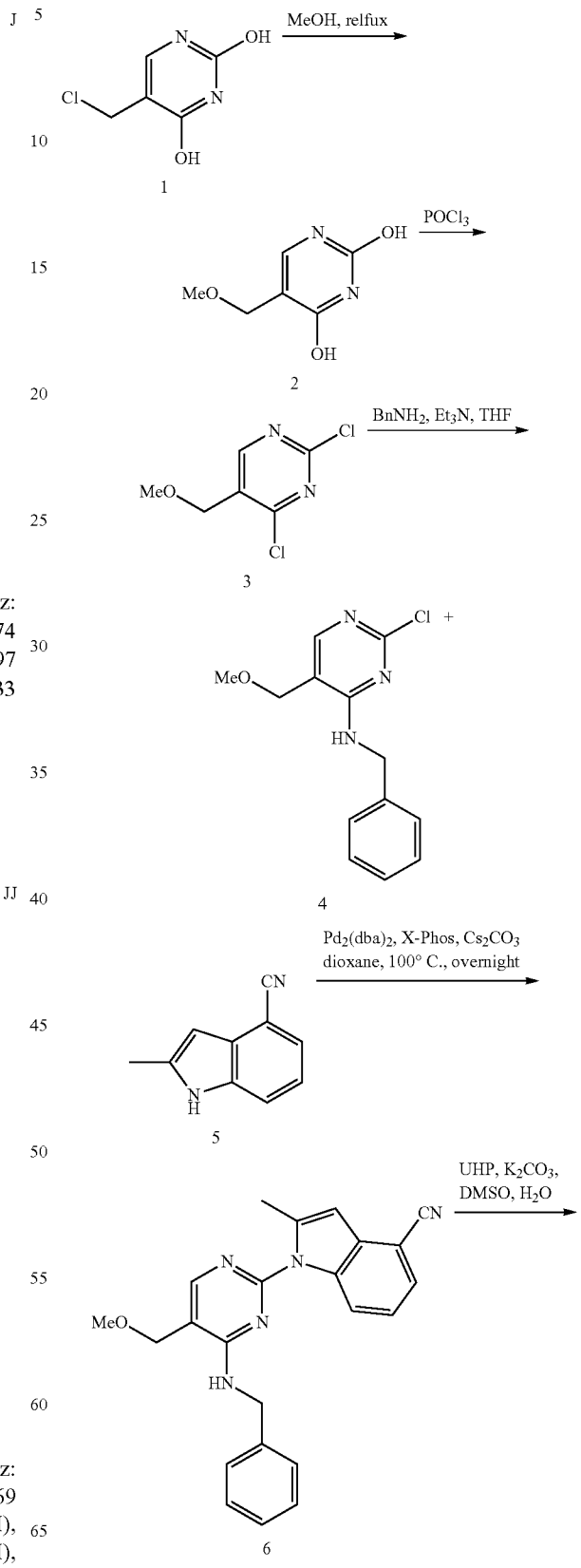

-continued

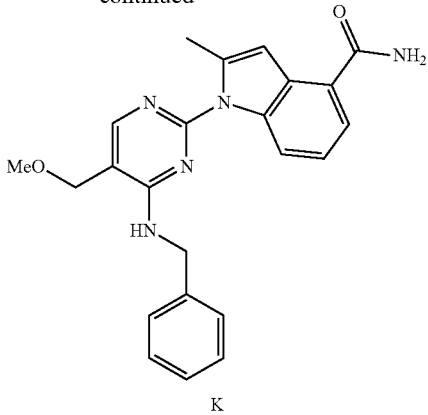

K

A solution of 5-(chloromethyl)pyrimidine-2,4-diol 1 (0.5 g, 3.1 mmol) in MeOH (10 mL) was heated to reflux for 2 h and then cooled down to room temperature, concentrated under vacuum. The resulting residue was dried to afford 5-(methoxymethyl)pyrimidine-2,4-diol 2 (0.46 g, 94%), which was used in the next step without further purification. LRMS (M+H$^+$) m/z: calcd 157.05. found 157.

A solution of the aforementioned intermediate 2 (0.26 g, 1.6 mmol) in POCl$_3$ (10 mL) was heated to reflux and stirred for 2 h. The mixture was cooled to room temperature and concentrated under vacuum. The residue was diluted with DCM (100 mL) and water (10 mL). The layers were separated, and the aqueous phase was extracted with DCM (50 mL×2). The organic layers were combined and dried over Na$_2$SO$_4$. The Na$_2$SO$_4$ was removed by filtration, and the volatiles were removed under reduced pressure. The resulting residue, 2,4-dichloro-5-(methoxymethyl) pyrimidine 3 (0.17 g, 45%) was used in the next step without further purification. LRMS (M+H$^+$) m/z: calcd 192.99. found 193.

To a 0° C. solution of 2,4-dichloro-pyrimidine 3 (0.17 g, 0.88 mmol) in CH$_3$CN (15 mL) was added benzylamine (0.22 g, 2.0 mmol). The reaction was stirred overnight at room temperature. The resulting mixture was concentrated under vacuum, and the residue was purified by flash chromatography using a mixture of hexane and ethyl acetate to afford N-benzyl-2-chloro-5-(methoxymethyl)pyrimidin-4-amine 4 (0.09 g, 39%). LRMS (M+H+) m/z: calcd 264.08. found 264.

A mixture of the aforementioned intermediate 4 (90 mg, 0.34 mmol), 2-methyl-1H-indole-4-carbonitrile 5 (62 mg, 0.4 mmol), tris(dibenzylideneacetone) dipalladium(0) (60 mg), X-phos (60 mg) and Cs$_2$CO$_3$ (262 mg, 0.8 mmol) in dioxane (10 mL) was heated at 100° C. for 10 hours under nitrogen atmosphere. The reaction mixture was cooled down to room temperature and concentrated under vacuum, and the residue was purified by flash chromatography (PE/EA=5:3) to afford 1-1-(4-(benzylamino)-5-(methoxymethyl)pyrimidin-2-yl)-2-methyl-1H-indole-4-carbonitrile 6 (43 mg, 33%). LRMS (M+H$^+$) m/z: calcd 384.17. found 384.

To a 0° C. solution of the aforementioned intermediate 6 (43 mg, 0.11 mmol) in DMSO (5 mL) were added UHP (105 mg, 1.1 mmol), K$_2$CO$_3$ (10 mg, 0.07 mmol) and water (0.5 mL), the reaction was stirred at room temperature overnight followed by dilution with water (50 mL). The resulting solid was collected and purified by flash chromatography (DCM/MeOH=20:1) to afford Example 18.

1-[4-(benzylamino)-5-(methoxymethyl)pyrimidin-2-yl]-2-methyl-1H-indole-4-carboxamide; Example 18 (compound K)

Example 18 was isolated as a yellow solid (9 mg, 20%). LRMS (M+H$^+$) m/z: calcd 402.19. found 402. HPLC purity (214 nm): 99%. $^1$HNMR (400 MHz, CD$_3$OD): δ 8.13 (s, 1H), 7.78 (d, J=8.4 Hz, 1H), 7.45 (d, J=7.2 Hz, 1H), 7.56-7.23 (m, 5H), 6.97 (t, J=8.0 Hz, 1H), 6.79 (s, 1H), 4.74 (s, 2H), 4.49 (s, 2H), 3.43 (s, 3H), 2.47 (s, 3H).

Example 19

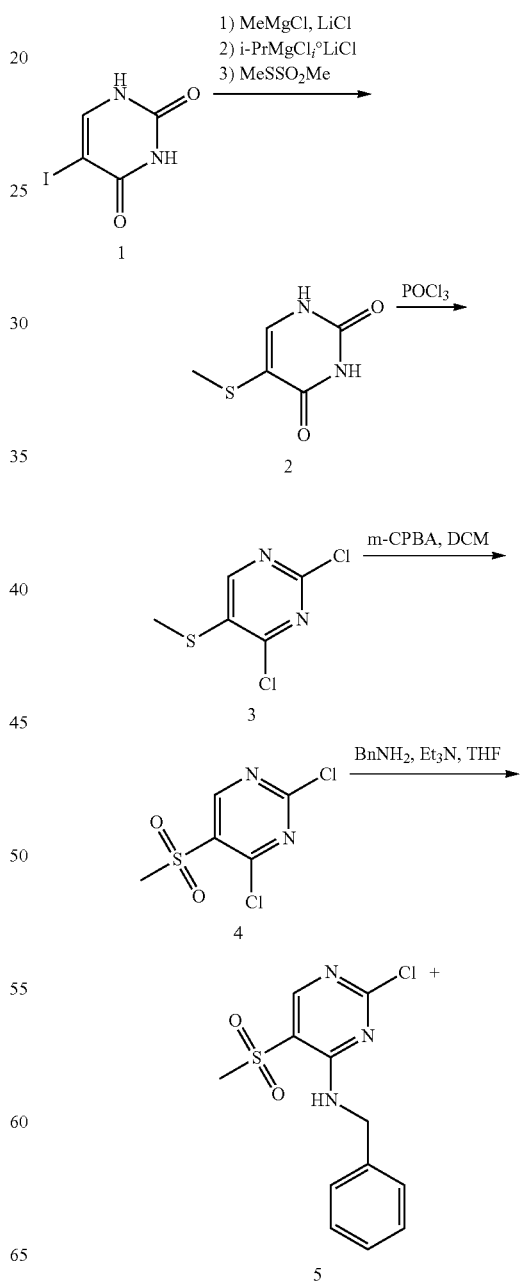

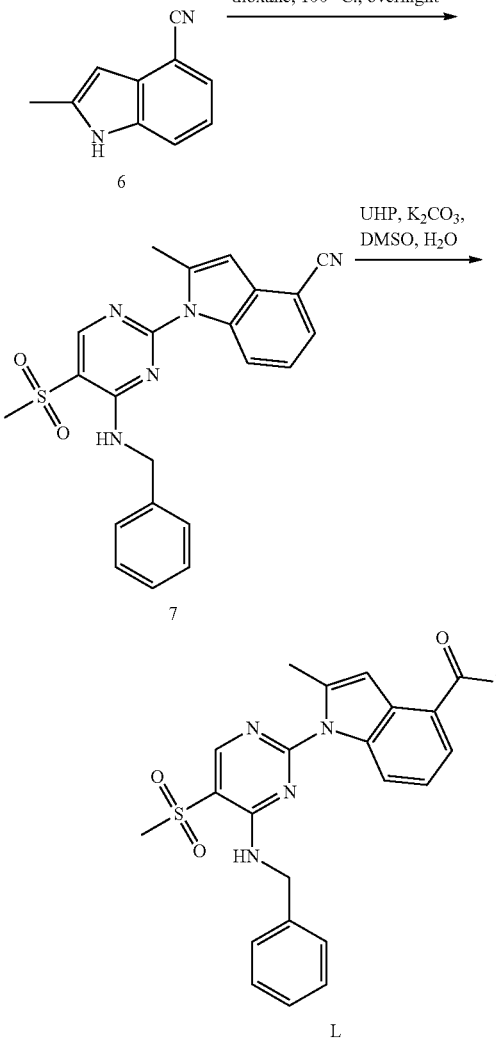

Preparation of 2,4-dichloro-5-(methylthio)pyrimidine 3

A mixture of 5-(methylthio)pyrimidine-2,4(1H,3H)-dione 2 (prepared as in Kopp F, Organic Letters, 2007, 9, 1639-41) (600 mg, 3.8 mmol) in POCl$_3$ (15 ml) was stirred at 100° C. for 16 hours. The reaction was then poured slowly into ice-water and the mixture was extracted with DCM (20 ml×2), dried and evaporated. The residue was purified by column chromatography (DCM:THF=100:0~100) to give 2,4-dichloro-5-(methylthio)pyrimidine 3 520 mg (70% yield) as a yellow oil.

Preparation of 2,4-dichloro-5-(methylsulfonyl)pyrimidine 4

To a solution of 2,4-dichloro-5-(methylthio)pyrimidine 3 (520 mg, 2.66 mmol), and m-CPBA (2.74 g, 15.96 mmol) in DCM (30 ml), the reaction mixture was stirred at room temperature for 16 hours and then concentrated. The residue was purified by column chromatography (DCM:MeOH=100:0-100:1) to give product 4 520 mg (86% yield).

Preparation of N-benzyl-2-chloro-5-(methylsulfonyl)pyrimidin-4-amine 5

A mixture of 2,4-dichloro-5-(methylsulfonyl)pyrimidine 5 (520 mg, 2.29 mmol), Et3N (462 mg, 4.58 mmol) and phenylmethanamine (294 mg, 2.74 mmol) in DCM (20 ml), the reaction mixture was stirred at 20° C. for 3 hours. After the reaction, was TEA removed. The residue was purified by column chromatography to give the product 5 516 mg (76% yield).

Preparation of 1-(4-(benzylamino)-5-(methylsulfonyl)pyrimidin-2-yl)-2-methyl-1H-indole-4-carbonitrile 7

To a solution of N-benzyl-2-chloro-5-(methylsulfonyl)pyrimidin-4-amine 5 (110 mg, 0.37 mmol), 2-methyl-1H-indole-4-carbonitrile 6 (57 mg, 0.37 mmol) and CS2CO3 (178 mg, 0.55 mmol) in DMF (10 ml), Microwave, the reaction mixture was stirred at 100° C. for 30 min. concentrated, the reaction was quenched by adding water and extracted with EA (25 ml×2), dried and concentrated. the residue was purified by column chromatography to give compound 7 106 mg (68% yield).

Example 19 (compound L) was prepared as follows. To a solution of aforementioned 7 (100 mg, 0.24 mmol), UHP (180 mg, 1.92 mmol) and K2CO3 (16 mg, 0.12 mmol) in DMSO (5 ml) and H2O (0.5 ml), the reaction mixture was stirred at 30° C. for 16 h. the reaction was quenched by adding water and extracted with EA (25 ml×2), dried and concentrated. the residue was purified by Prep-TLC to give the product Example 19.

1-[4-(benzylamino)-5-(methylsulfonyl)pyrimidin-2-yl]-2-methyl-1H-indole-4-carboxamide; Example 19 (compound L)

Example 19 was isolated as a solid 74 mg (71% yield). LRMS (M+H$^+$) m/z: calcd 436. found 436; $^1$HNMR (400 MHz, CDCl$_3$): δ 8.76 (s, 1H), 8.45 (d, J=8 Hz, 1H), 7.54 (br s, 1H), 7.50 (d, J=8 Hz, 1H), 7.37 (m, 5H), 7.152 (t, J=8.0 Hz, 1H), 6.98 (s, 1H), 4.82 (d, J=6 Hz, 2H) 3.15 (s, 3H), 2.71, s, 3H), Example 20

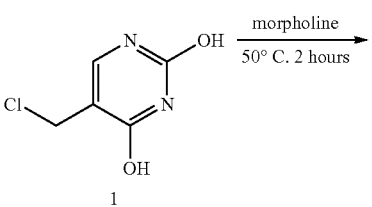

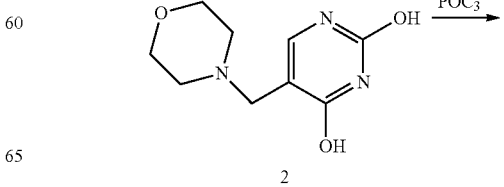

103
-continued

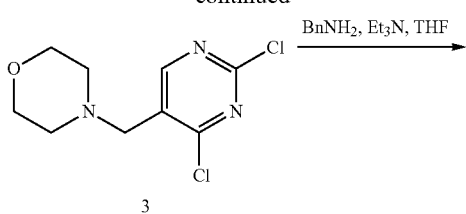

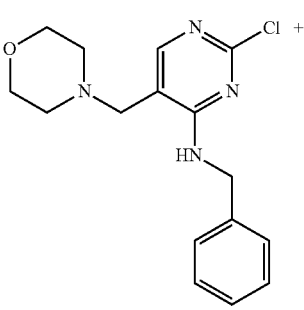

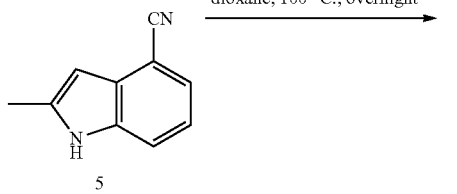

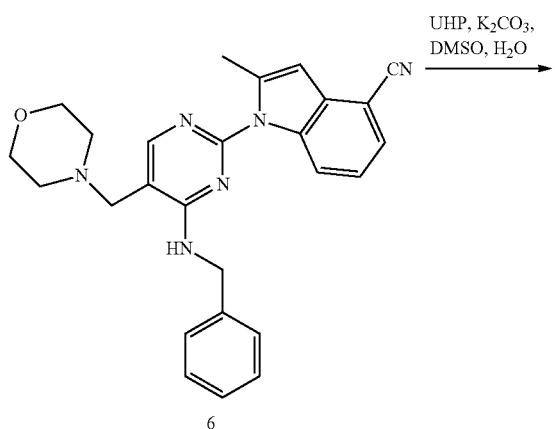

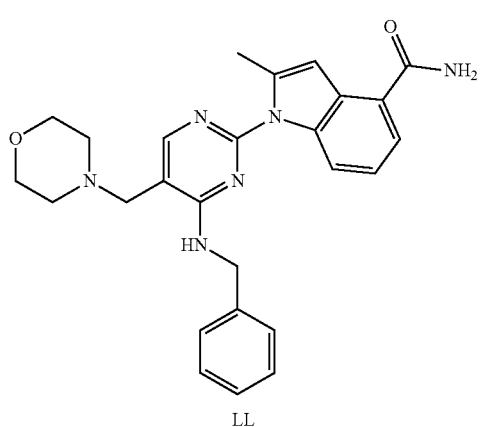 [SMILES: Cc1cc2c(C(N)=O)cccc2n1-c1ncc(CN2CCOCC2)c(NCc2ccccc2)n1]

104

Preparation of 5-(morpholino-4-yl-methyl)pyrimidine-2,4-diol 2

A solution of 1 (320 mg, 2 mmol) in morpholine (8.7 g) was heated at 50° C. for 5 hours and concentrated in vacuo to remove most of the remaining morpholine. The residue was triturated with water to produce white solid, which was filtered and dried to give 3 (150 mg, 35% yield).

Preparation of N-benzyl-2-chloro-5-(morpholino-4-yl-methyl)pyrimidin-4-amine 3

Using methodology disclosed in the previous examples compound 2 was converted to compound 3 using $POCl_3$. Intermediate 3 (110 mg, 0.44 mmol) and N-benzyl amine (1 eq) in THF (20 mL) was treated with $Et_3N$ (2 eq). The resulting mixture was stirred overnight at room temperature. The reaction mixture was concentrated under vacuum, the residue was purified by column chromatography to afford compound 4 (85 mg 60% yield).

Preparation of 1-(4-(benzylamino)-5-(morpholino-4-yl-methyl)pyrimidin-2-yl)-2-methyl-1H-indole-4-carbonitrile 6

To a solution of compound 4 (85 mg, 0.27 mmol), 2-methyl-1H-indole-4-carbonitrile 5 (1 eq), X-phos (0.2 eq), Cs2CO3 (2 eq) in dioxane (10 mL) was added $Pd_2(dba)_3$ (0.2 eq), the mixture heated at 100° C. under $N_2$ atmosphere overnight. The mixture was evaporated in vacuo to dryness and the residue purified by column chromatography to give compound 6 (100 mg, 85% yield)

Example 20 was prepared from intermediate compound 6 as follows.

To a solution of compound 6 (100 mg, 0.23 mmol), $K_2CO_3$ (0.5 eq), UHP (10 eq) in DMSO (5 mL) was added water 0.5 mL, the mixture was stirred at room temperature overnight. The reaction was quenched with water, extracted with DCM and the combined organic extracts were concentrated and purified by column chromatography to give Example 20.

1-[4-(benzylamino)-5-(morpholin-4-ylmethyl)pyrimidin-2-yl]-2-methyl-1H-indole-4-carboxamide; Example 20 (Compound LL)

Example 20 was isolated as a solid (70 mg, 66% yield). LRMS (M+H$^+$) m/z: calcd 457 found 457; $^1$H NMR (300 MHz, CDCl$_3$) δ 8.25 (d, J=8 Hz, 1H) 8.03 (s, 1H), 7.98 (m, 1H), 7.50 (d, J=8 Hz, 1H), 7.36 (m, 5H), 7.11 (t, J=8 Hz, 1H), 6.86 (s, 1H), 4.75 (d, J=6 Hz, 2H), 3.61 (m, 4H), 3.52 (s, 2H), 2.67 (2, 3H), 2.48 (m, 4H).

Using similar methods, example 21, could be made.

Example 21
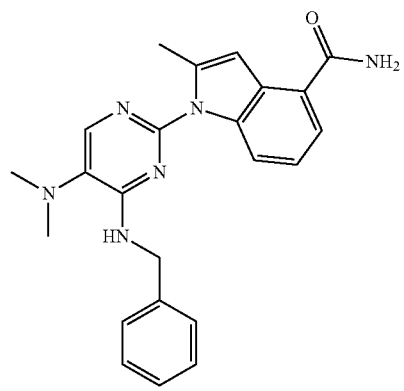
1-[4-(benzylamino)-5-[(dimethylamino)methyl]pyrimidin-2-yl]-2-methyl-1H-indole-4-carboxamide)
Example 21 (Compound M)
Example 21 was isolated as a solid. LRMS (M+H$^+$) m/z: calcd 415 found 415; $^1$H NMR (300 MHz, CD$_3$OD) δ 8.06 (s, 1H), 7.86 (d, J=8 Hz, 1H), 7.49 (d, J=8 Hz, 1H), 7.35 (m, 5H), 7.02, (t, J=8 Hz, 1H), 6.82, (s, 1H), 4.76 (s, 2H), 3.53 (s, 2H), 2.53 (s, 3H), 2.32 (s, 6H).
Example 22
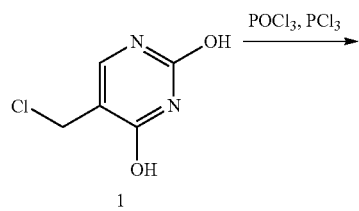
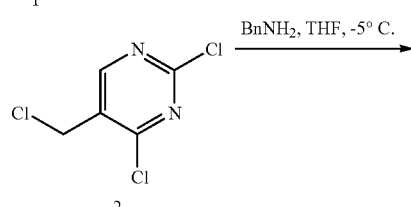
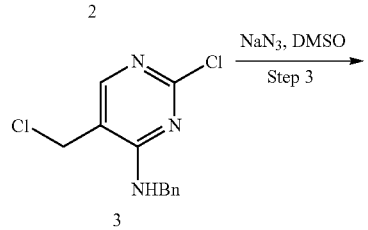
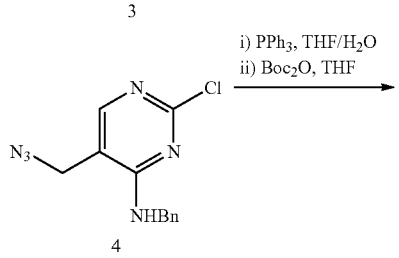
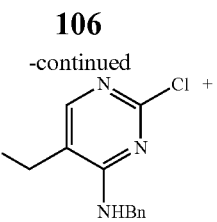
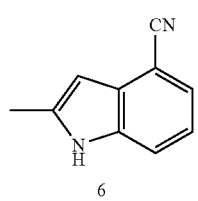
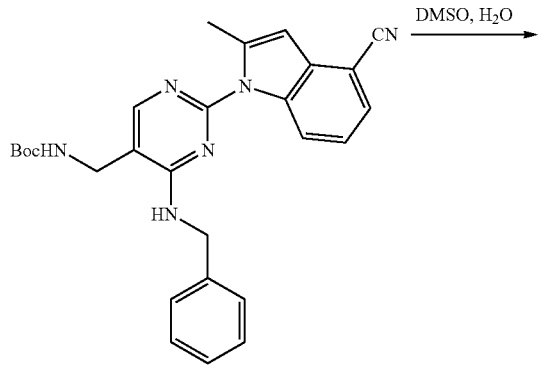
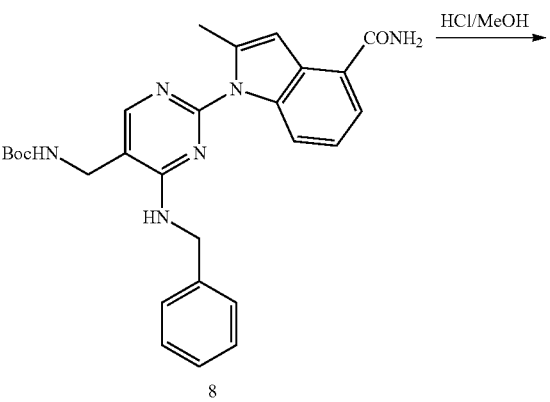
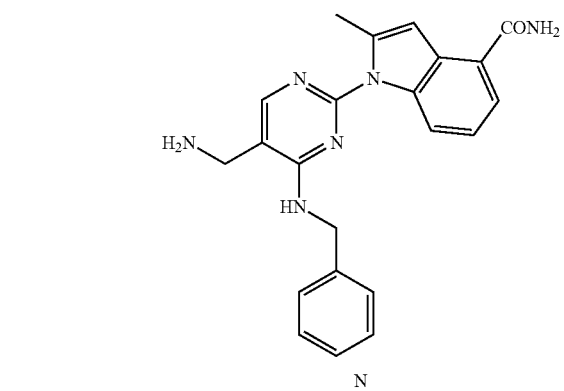

Using methodology outlined in the scheme above, tert-butyl N-[[4-(benzylamino)-2-(4-carbamoyl-2-methyl-indol-1-yl)pyrimidin-5-yl]methyl]carbamate (Intermediate 8) was prepared.

Example 22 was prepared from Intermediate 8 as follows. A solution of N-[[4-(benzylamino)-2-(4-carbamoyl-2-methyl-indol-1-yl)pyrimidin-5-yl]methyl]carbamate (8) (150 mg, 0.31 mmol), 3 N HCl/MeOH (2 mL) in MeOH (5 mL) was stirred at room temperature for 1 h. The mixture was concentrated under vacuum, and the residue was purified by flash chromatograph (DCM/MeOH=10:1) afford Example N.

1-[5-(amino methyl)-4-(benzylamino)pyrimidin-2-yl]-2-methyl-1H-indole-4-carboxamide Example 22 (Compound N)

Example 22 was isolated as a solid (85 mg, 57% yield). LRMS (M+H$^+$) m/z: calcd 387 found 387 $^1$H NMR (300 MHz, CD$_3$OD) δ 8.11 (s, 1H). 7.74 (d, J =8 Hz, 1H), 7.46 (d, J=8 Hz, 1H), 7.33, m, 5H), 6.97 (t, J=8 Hz, 1H), 6.79 (s, 1H), 4.73 (s, 2H), 3.82 (s, 2H), 2.45 (s, 3H).

Example 23

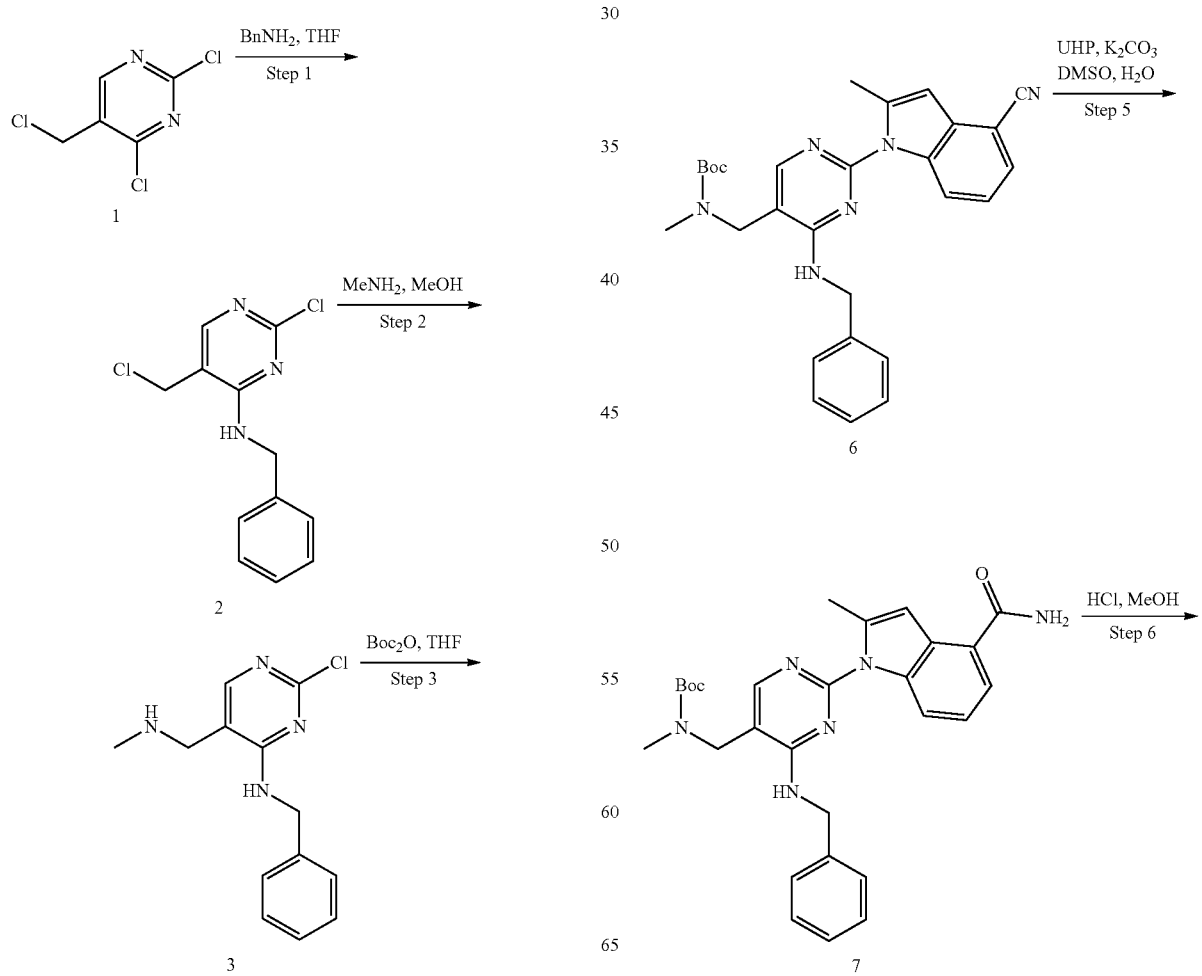

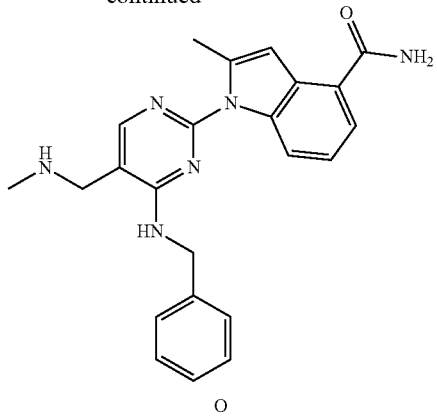

O

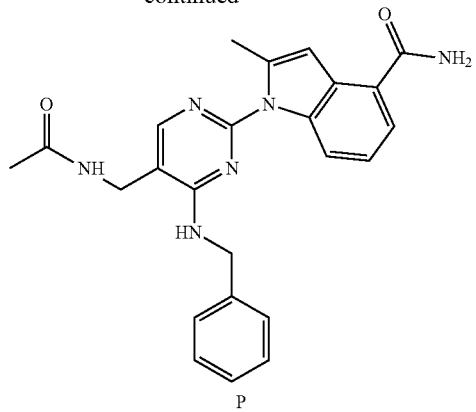

P

Preparation of N-benzyl-2-chloro-5-(chloromethyl)pyrimidin-4-amine 2. To a solution of 2,4-dichloro-5-methyl-pyrimidine (0.2 g, 1.0 mmol) in CH$_3$CN (15 mL), was added phenylmethanamine (0.214 g, 2 mmol). The mixture was stirred overnight at −10° C. The mixture was concentrated under vacuum, the residue was purified by flash chromatography (PE/EA=3:1) to afford N-benzyl-2-chloro-5-(chloromethyl)pyrimidin-4-amine 2 (0.1 g, 38% yield). LRMS (M+H+) m/z: calcd 263. found 263.

Using methodology previously described tert-butyl N-[[4-(benzylamino)-2-(4-carbamoyl-2-methyl-indol-1-yl)pyrimidin-5-yl]methyl]-N-methyl-carbamate 7 was prepared.

Example 23 was prepared from intermediate compound 7 as follows. To a solution of N-[[4-(benzylamino)-2-(4-carbamoyl-2-methyl-indol-1-yl) pyrimidin-5-yl]methyl]-N-methyl-carbamate (7) (60 mg, 0.12 mmol) in DCM (20 mL) was added CF$_3$COOH (5 mL). The mixture was stirred at room temperature for 4 hours. The mixture was evaporated and the resulting residue was purified by column chromatography (DCM/MeOH/NH$_3$H$_2$O=20/1/0.5) to give Example 23

1-[4-(benzylamino)-5-[(methylaminoc)methyl]pyrimidin-2-yl]-2-methyl-1H-indole-4-carboxamide Example 23 (compound O)

Example 23 was isolated as a solid 33 mg, 66% yield). $^1$H NMR (300 MHz, CD$_3$OD) δ 8.13 (s, 1H), 7.82 (d, J=8 Hz, 1H), 7.46 (d, J=8 Hz, 1H), 7.31 (m, 5H), 6.99 (t, J=8 Hz, 1H), 6.80 (s, 1H), 4.76 (s, 2H), 3.87 (s, 2H), 2.52 (s, 3H), 2.50 (s, 3H).

Example 24

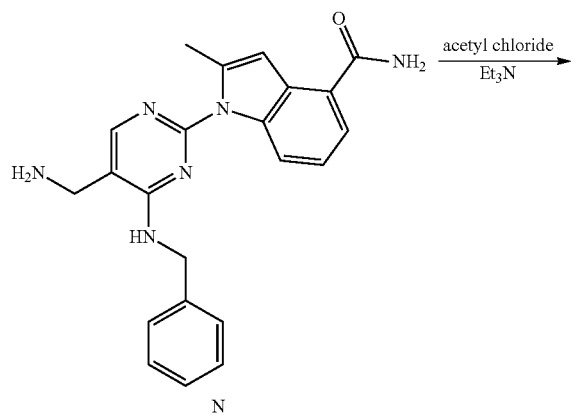

N

Example 24 was prepared from Example N as follows. To a solution of 1-[5-(aminomethyl)-4-(benzylamino)pyrimidin-2-yl]-2-methyl-1H-indole-4-carboxamide Example N (0.050 g, 0.13 mmol) and triethyl amine (0.26 mL in DCM (5 mL), was added AcCl (0.012 g, 0.015 mmol). The mixture was stirred for 2 h at room temperature. The mixture was concentrated under vacuum and the resulting residue was purified by flash chromatography (DCM/MeOH=20:1) to afford Example 24.

1-[4-(benzylamino)-5-(acetamidomethyl)pyrimidin-2-yl]-2-methyl-1H-indole-4-carboxamide Example 24 (Compound P)

Example 24 was isolated as a solid (30 mg, 54% yield). LRMS (M+H$^+$) m/z: calcd 429 found 429; $^1$H NMR (400 MHz, CD$_3$OD) δ 8.10 (s, 1H), 7.83 (d, J=8 Hz, 1H), 7.47 (d, J=8 Hz, 1H), 7.31 (m, 5H), 7.00 (t, J=8 Hz, 1H), 6.80 (s, 1H), 4.73 (s, 2H), 4.34 (s, 2H), 2.49 (s, 3H), 2.00 (s, 3H).

Example 25

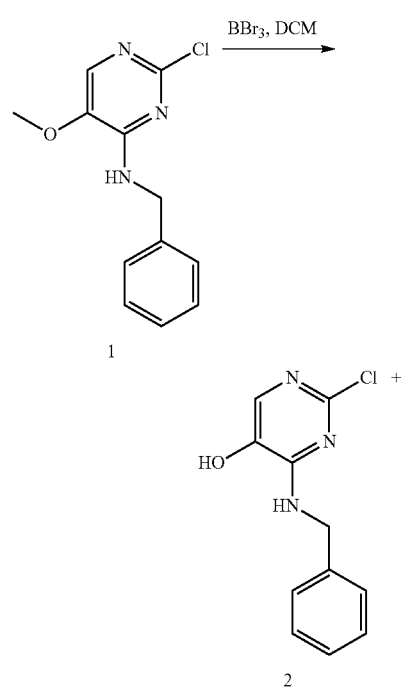

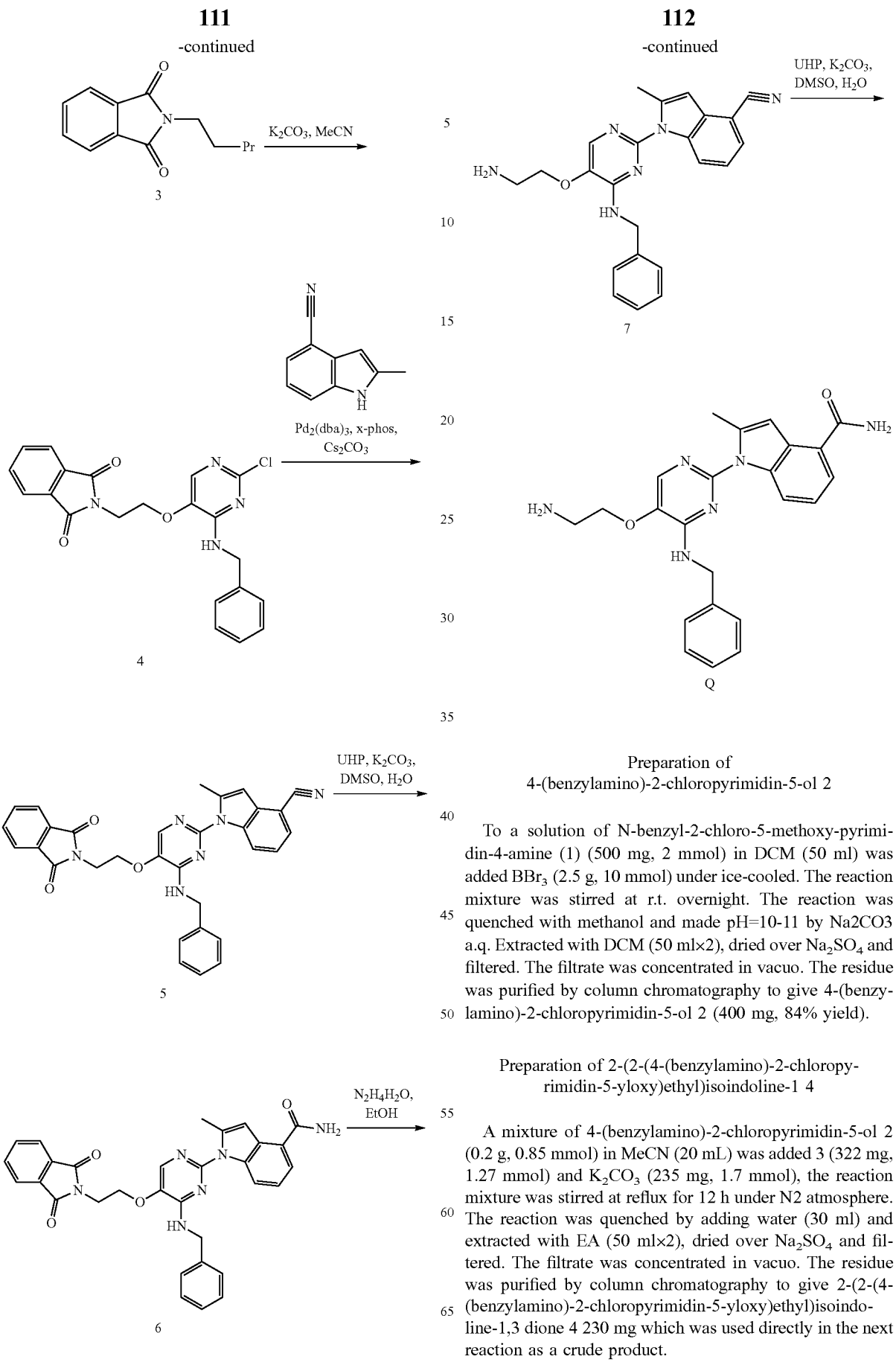

Preparation of 4-(benzylamino)-2-chloropyrimidin-5-ol 2

To a solution of N-benzyl-2-chloro-5-methoxy-pyrimidin-4-amine (1) (500 mg, 2 mmol) in DCM (50 ml) was added BBr$_3$ (2.5 g, 10 mmol) under ice-cooled. The reaction mixture was stirred at r.t. overnight. The reaction was quenched with methanol and made pH=10-11 by Na2CO3 a.q. Extracted with DCM (50 ml×2), dried over Na$_2$SO$_4$ and filtered. The filtrate was concentrated in vacuo. The residue was purified by column chromatography to give 4-(benzylamino)-2-chloropyrimidin-5-ol 2 (400 mg, 84% yield).

Preparation of 2-(2-(4-(benzylamino)-2-chloropyrimidin-5-yloxy)ethyl)isoindoline-1 4

A mixture of 4-(benzylamino)-2-chloropyrimidin-5-ol 2 (0.2 g, 0.85 mmol) in MeCN (20 mL) was added 3 (322 mg, 1.27 mmol) and K$_2$CO$_3$ (235 mg, 1.7 mmol), the reaction mixture was stirred at reflux for 12 h under N2 atmosphere. The reaction was quenched by adding water (30 ml) and extracted with EA (50 ml×2), dried over Na$_2$SO$_4$ and filtered. The filtrate was concentrated in vacuo. The residue was purified by column chromatography to give 2-(2-(4-(benzylamino)-2-chloropyrimidin-5-yloxy)ethyl)isoindoline-1,3 dione 4 230 mg which was used directly in the next reaction as a crude product.

Preparation of 1-[4-(benzylamino)-5-[2-(1,3-dioxoisoindolin-2-yl)ethoxy]pyrimidin-2-yl]-2-methylindole-4-carbonitrile 5

To a solution of give 2-(2-(4-(benzylamino)-2-chloropyrimidin-5-yloxy)ethyl)isoindoline-1,3 dione 4 (236 mg, 0.58 mmol) in dioxane (20 mL) was added 2-methyl-4-cyanoindole (100 mg, 0.64 mmol), Pd₂(dba)₃ (107 mg, 0.116 mmol), X-Phos (56 mg, 0.116 mmol) and CS₂CO₃ (568 mg, 1.74 mmol), the reaction mixture was stirred at 100° C. for 12 h under N2 atmosphere. The reaction was quenched by adding water (20 ml) and extracted with EA (30 ml×2), dried over Na₂SO₄ and filtered. The filtrate was concentrated in vacuo. The residue was purified by column chromatography to give 230 mg of crude product that was used directly in the next reaction.

Preparation of 1-(4-(benzylamino)-5-(2-(1,3-dioxoisoindolin-2-yl)ethoxy)pyrimidin-2-yl)-2-methyl-1H-indole-4-carboxamide 6

1-[4-(benzyl amino)-5-[2-(1,3-dioxoisoindolin-2-yl)ethoxy]pyrimidin-2-yl]-2-methyl-indole-4-carbonitrile 5 (230 mg, 0.43 mmol), UHP (327 mg, 3.48 mmol), K2CO3 (30 mg, 0.215 mmol), H2O (0.5 mL) and DMSO (10 mL) were stirred at r.t. for 12 h. The reaction mixture was poured into ice-water and stirred 30 min, filtered and the solid was washed with water. The solid was purified by column chromatography to give 1-(4-(benzylamino)-5-(2-(1,3-dioxoisoindolin-2-yl)ethoxy)pyrimidin-2-yl)-2-methyl-1H-indole-4-carboxamide 6 (90 mg product, 37% yield).

Preparation of 1-[5-(2-aminoethoxy)-4-(benzylamino)pyrimidin-2-yl]-2-methyl-indole-4-carbonitrile 7

To a solution of 1-(4-(benzylamino)-5-(2-(1,3-dioxoisoindolin-2-yl)ethoxy)pyrimidin-2-yl)-2-methyl-1H-indole-4-carboxamide 6 (110 mg, 0.2 mmol) in EtOH (20 mL) was added N2H4.H2O (1 mL), the mixture was stirred at reflux for 2 hrs. The residue was evaporated to give 18 mg of 1-[5-(2-amino ethoxy)-4-(benzylamino)pyrimidin-2-yl]-2-methyl-indole-4-carbonitrile 7 and used directly in the next reaction.

Example 25 was prepared as follows. A solution of 1-[5-(2-amino ethoxy)-4-(benzylamino)pyrimidin-2-yl]-2-methyl-indole-4-carbonitrile 7 (15 mg, 0.04 mmol), UHP (29 mg, 0.3 mmol), K2CO3 (3 mg, 0.02 mmol), H2O (0.5 mL) and DMSO (5 mL) was stirred at r.t. for 12 h. The reaction mixture was poured into ice-water and stirred 30 min, filtered and the solid was washed with water. The solid was purified column chromatography to give Example 25.

1-[5-(2-aminoethoxy)-4-(benzylamino)pyrimidin-2-yl]-2-methyl-1H-indole-4-carboxamide Example 25 (Compound Q)

Example 25 was isolated as a solid (8 mg, 50% yield). LRMS (M+H⁺) m/z: calcd 417 found 417; ¹H NMR (400 MHz, CD₃OD) δ 7.81 (s, 1H), 7.59 (d, J=8 Hz, 1H), 7.45 (d, J=8 Hz, 1H), 7.31 (m, 5H), 6.98 (t, J=8 Hz, 1H), 6.76 (s, 1H), 4.71 (s, 2H), 4.17 (m, 2H), 3.10 (m, 2H), 2.43 (s, 3H).

Example 26

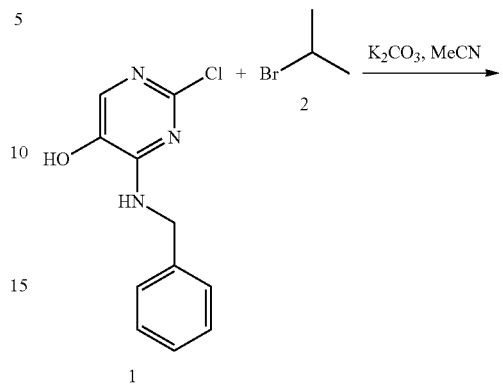

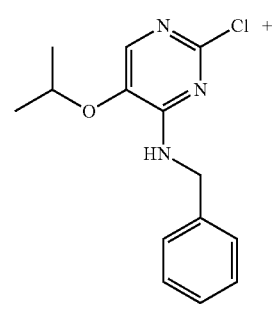

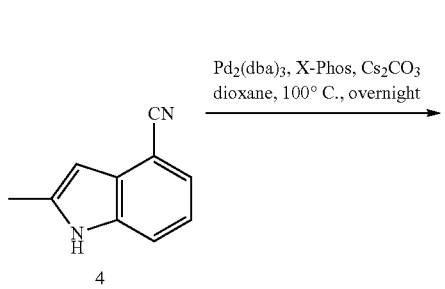

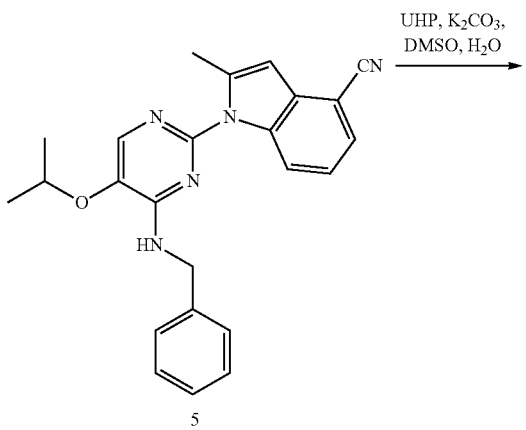

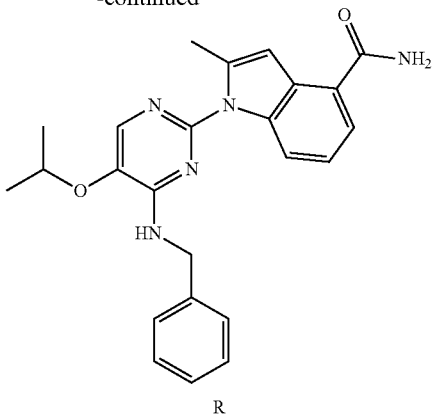

R

Preparation of N-benzyl-2-chloro-5-isopropoxypyrimidin-4-amine 3

To a solution of 4-(benzylamino)-2-chloropyrimidin-5-ol (1) (for preparation see example O) (0.2 g, 0.85 mmol) in MeCN (20 mL) was added isopropyl bromide (208 mg, 1.69 mmol) and K$_2$CO$_3$ (176 mg, 1.27 mmol), the mixture was stirred at 80° C. for 7 hours. The solvent was removed in vacuo and the residue was purified by column chromatography to give N-benzyl-2-chloro-5-isopropoxypyrimidin-4-amine 3 (170 mg, 72% yield)

Preparation of 1-[4-(benzylamino)-5-isopropoxy-pyrimidin-2-yl]-2-methyl-indole-4-carbonitrile (5)

To a solution of N-benzyl-2-chloro-5-isopropoxypyrimidin-4-amine 3 (170 mg, 0.361 mmol) in dioxane (20 ml) was added 2-methyl-4-cyano-indole 4 (96 mg, 0.61 mmol), Pd$_2$(dba)$_3$ (112 mg, 0.122 mmol), X-Phos (58 mg, 0.122 mmol) and t-BuOK (137 mg, 1.22 mmol), the reaction mixture was stirred at 100° C. for 12 h under N$_2$ atmosphere. The reaction was quenched by adding water (20 ml) and extracted with EA (30 ml×2), dried over Na$_2$SO$_4$ and filtered. The filtrate was concentrated in vacuo and the resulting residue was purified by column chromatography to give 1-[4-(benzylamino)-5-isopropoxy-pyrimidin-2-yl]-2-methyl-indole-4-carbonitrile (5) (130 mg, 53% yield)

Example 26 (Compound R) was prepared as follows. A solution of 1-[4-(benzylamino)-5-isopropoxy-pyrimidin-2-yl]-2-methyl-indole-4-carbonitrile (5) (130 mg, 0.33 mmol), UHP (246 mg, 2.62 mmol), K2CO3 (24 mg, 0.17 mmol), H2O (0.5 mL) and DMSO (5 mL) was stirred at r.t. for 12 h. The reaction mixture was poured into ice-water and stirred 30 min, filtered and the solid was washed with water. The solid was purified by column chromatography to give Example 26.

1-[4-(benzylamino)-5-(propan-2-yloxy)pyrimidin-2-yl]-2-methyl-1H-indole-4-carboxamide Example 26 (compound R)

Example 26 was isolated as a solid (90 mg, 66% yield. LRMS (M+H$^+$) m/z: calcd 416 found 416; $^1$H NMR (400 MHz, CD$_3$OD) δ 7.84 (s, 1H), 7.58 (d, J=8 Hz, 1H), 7.45 (d, J=8 Hz, 1H), 7.32 (m, 5H), 6.98 (t, J=8 Hz, 1H), 6.76 (s, 1H), 4.76 (sept. J=6 Hz, 1H), 4.69 (s, 2H), 2.41 (s, 3H), 1.45 (d, J=6 Hz, 6H).

The following examples were prepared using similar methodology

Example 27

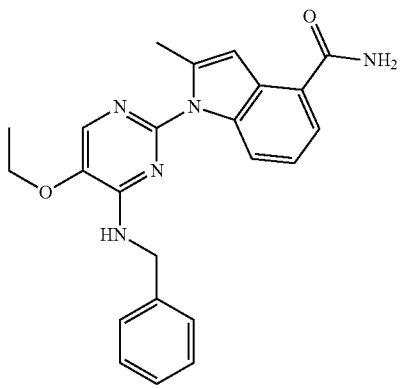

S

1-[4-(benzylamino)-5-ethoxypyrimidin-2-yl]-2-methyl-1H-indole-4-carboxamide Example 27 (Compound S)

Example 27 was isolated as a solid. LRMS (M+H$^+$) m/z: calcd 402 found 402; $^1$H NMR (400 MHz, CD$_3$OD) δ 7.82 (s, 1H), 7.57 (d, J=8 Hz, 1H), 7.45 (d, J=8 Hz, 1H), 7.30 (m, 5H), 6.98 (t, J=8 Hz, 1H), 6.76 (s, 1H), 4.70 (s, 2H), 4.24 (q, J=7 Hz, 2H), 2.41 (s, 3H). 1.52 (t, J=7 Hz, 3H).

Example 28

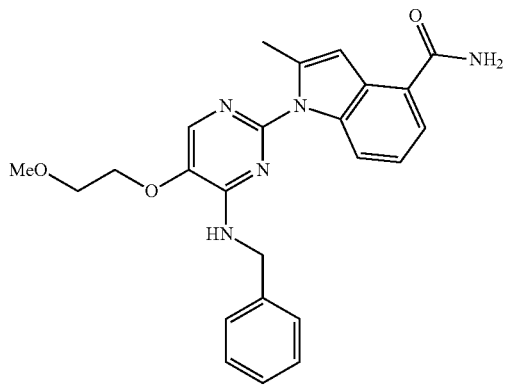

T

1-[4-(benzylamino)-5-(2-methoxyethoxy)pyrimidin-2-yl]-2-methyl-1H-indole-4-carboxamide Example 28 (Compound T)

Example 28 was isolated as a solid. LRMS (M+H$^+$) m/z: calcd 432 found 432; $^1$H NMR (400 MHz, CD$_3$OD) δ 7.88 (s, 1H), 7.63 (d, J=8 Hz, 1H), 7.46 (d, J=8 Hz, 1H), 7.31 (m, 5H), 6.99 (t, J=8 Hz, 1H), 6.77 (s, 1H), 4.70 (s, 2H), 4.30 (t, J=4 Hz, 2H), 3.84 (t, J=4 Hz, 2H), 3.45 (s, 3H), 2.44 (s, 3H).

Example 29

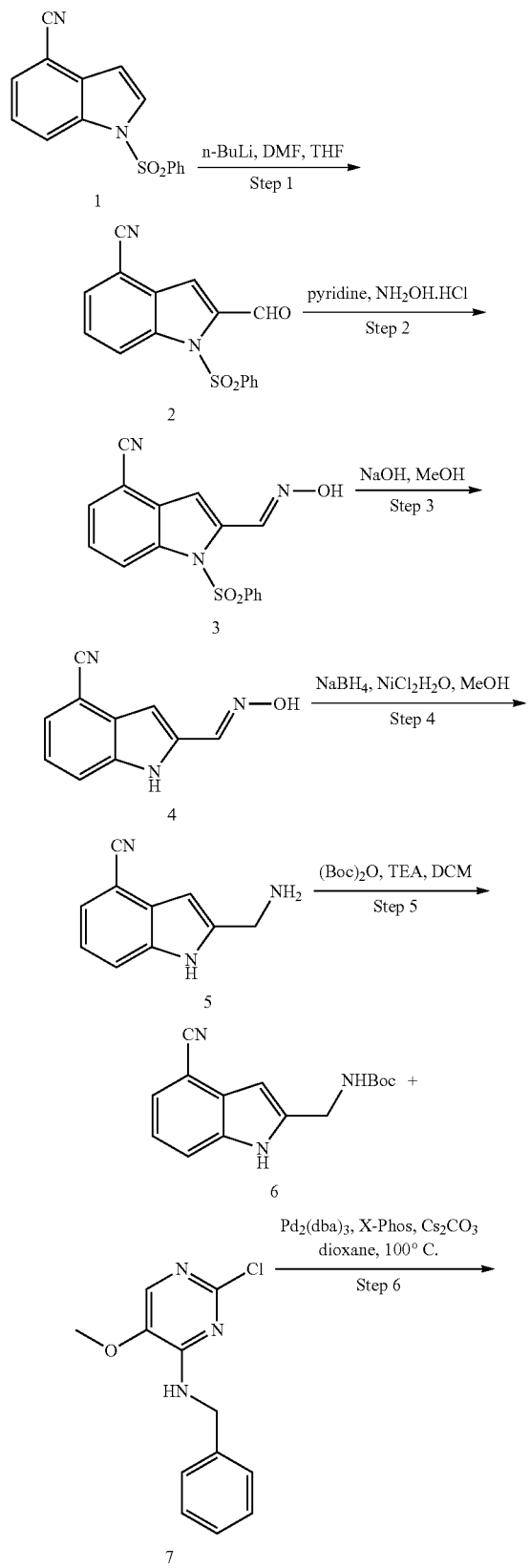

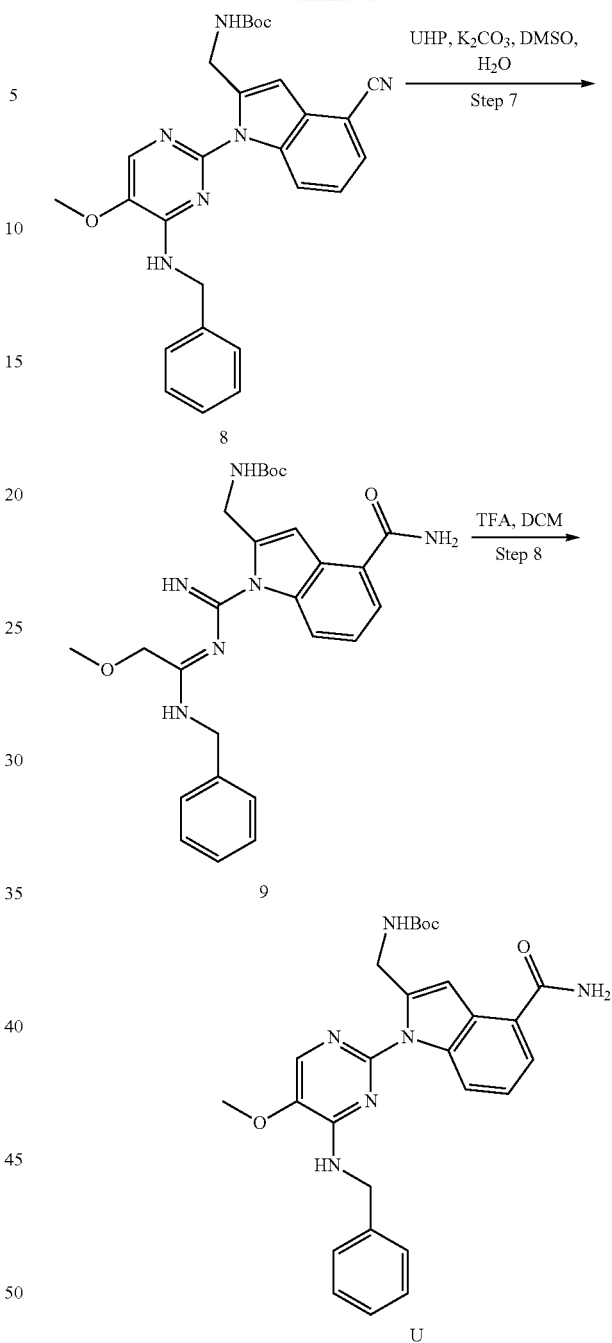

To the solution of 1-(phenylsulfonyl)-1H-indole-4-carbonitrile 1 (16 g, 56.7 mmol) in THF (240 mL) cooled to −78° C. under N2 atmosphere was added n-BuLi (2.4 M in hexane, 28.4 mL, 68.1 mmol) dropwise and the resulting solution was stirred for 1 h. Then DMF (8.3 g, 113.4 mmol) was added dropwise and the resulting solution was stirred at −78° C. for 20 min. The reaction was quenched by saturated NH4Cl solution and the resulting mixture was extracted with EA (3□200 mL). The organic layer was dried over MgSO4 and concentrated in vacuo to give 2-formyl-1-(phenylsulfonyl)-1H-indole-4-carbonitrile 2 (16 g, 91%) as a yellow solid which was used into the next step without further purification. LRMS (M+H+) m/z: calcd 311.33. found 311.

To a solution of 2-formyl-1-(phenylsulfonyl)-1H-indole-4-carbonitrile 2 (16 g, 52 mmol) in pyridine (150 mL) was added hydroxylamine hydrochloride (3.9 g, 57.2 mmol) and the solution was stirred at ambient temperature for 1 hour. The resulting solution was concentrated in vacuo and the residue was diluted with DCM (500 mL). The organic layer was washed successively with water (50 mL×2) and brine (50 mL×2), dried over magnesium sulfate and concentrated in vacuo to give (E)-2-((hydroxyimino)methyl)-1-(phenylsulfonyl)-1H-indole-4-carbonitrile 3 (15 g, 89%) which was used into the next step without further purification. LRMS (M+H+) m/z: calcd 326.05. found 326.

To a solution of (E)-2-((hydroxyimino)methyl)-1-(phenylsulfonyl)-1H-indole-4-carbonitrile 3 (15 g, 46.2 mmol) in methanol (200 mL) was added aqueous sodium hydroxide solution (4 M, 31 mL, 138 mmol). Then the mixture was stirred at 50° C. for 1 hour. The resulting solution was extracted with ethyl acetate, the organic phase was dried, filtered, concentrated and purified by Combiflash (petroleum ether/ethyl acetate=3:1) to give (E)-2-((hydroxyimino)methyl)-1H-indole-4-carbonitrile 4 (6.5 g, 76%). LRMS (M+H+) m/z: calcd 186.06. found 186.

NaBH$_4$ (8 g, 210.6 mmol) and NiCl$_2$.6H2O (8.33 g, 35.1 mmol) were added to a cooled solution of (E)-2-((hydroxyimino)methyl)-1H-indole-4-carbonitrile 4 (6.5 g, 35.1 mmol) in MeOH (200 mL), and the reaction mixture was stirred at room temperature. After 15 min, the reaction mixture was diluted with 1% NH4OH (1 L) and filtered. The filtrate was extracted with EtOAc (3×800 mL), and the organic extract was combined, dried over Na$_2$SO$_4$, and concentrated under reduced pressure. The residue was purified by Combiflash (dichloromethane/methanol=10:1) to give 2-(amino methyl)-1H-indole-4-carbonitrile 5 (2.3 g, 38%). 1HNMR (300 MHz, DMSO): δ 11.58 (s, 1H), 7.64 (d, J=8.1 Hz, 1H), 7.43 (d, J=6.9 Hz, 1H), 7.14 (d, J=7.8 Hz, 1H), 6.42 (s, 1H), 3.89 (s, 2H), 1.97 (br, 2H).

Boc$_2$O (3.5 g, 16.14 mmol) and TEA (5.6 mL, 40.35 mmol) was added to a solution of 2-(amino methyl)-1H-indole-4-carbonitrile 5 (2.3 g, 13.45 mmol) in DCM (120 mL), the mixture was stirred at r.t. for 2 hours. The reaction was diluted with DCM (150 mL), washed with water (50 mL□2) and brine (50 mL), dried over sodium sulfate and concentrated in vacuo. The residue was purified by Combi-Flash (petroleum ether/ethyl acetate=3:1) to give tert-butyl (4-cyano-1H-indol-2-yl)methylcarbamate 6 (3.4 g, 94%). 1HNMR (300 MHz, DMSO): δ 9.41 (s, 1H), 7.51 (d, J=8.4 Hz, 1H), 7.44 (d, J=8.1 Hz, 1H), 7.20 (d, J=8.1 Hz, 1H), 6.54 (s, 1H), 5.16 (br, 1H), 4.41 (d, J=5.1 Hz, 2H), 1.50 (s, 9H).

To a solution of N-benzyl-2-chloro-5-methoxypyrimidin-4-amine 7 (0.78 g, 3.14 mmol) and tert-butyl (4-cyano-1H-indol-2-yl)methylcarbamate 6 (0.85 g, 3.14 mmol) in dioxane (30 mL) was added Pd2(dba)3 (0.57 g, 0.63 mmol), X-Phos (0.6 g, 1.26 mmol) and Cs2CO3 (2 g, 6.28 mmol). The mixture was degassed for 3 times, and then stirred at 100° C. overnight. The resulting mixture was concentrated in vacuo and the residue was purified by Combi-Flash (petroleum ether/ethyl acetate=2:1) to give tert-butyl (1-(4-(benzylamino)-5-methoxypyrimidin-2-yl)-4-cyano-1H-indol-2-yl)methylcarbamate 8 (1.5 g, 99%). LRMS (M+H+) m/z: calcd 485.22. found 485.

To a solution of tert-butyl (1-(4-(benzylamino)-5-methoxypyrimidin-2-yl)-4-cyano-1H-indol-2-yl)methylcarbamate 8 (1.5 g, 3.1 mmol) in DMSO (12 mL) was added UHP (2.3 g, 24.8 mmol) and K2CO3 (214 mg, 1.55 mmol). Then water (0.5 mL) was added to the mixture and stirred at room temperature for 12 hours. Water was added to the mixture, filtrated and the cake was dried to give the crude product, which was purified by column chromatography (dichloromethane/methanol=20:1) to give tert-butyl (1-(4-(benzylamino)-5-methoxypyrimidin-2-yl)-4-carbamoyl-1H-indol-2-yl)methylcarbamate 9 (1.4 g, 90%). LRMS (M+H+) m/z: calcd 493.25. found 493.

Example 29 (Compound U) was prepared as follows. A solution of tert-butyl (1-(4-(benzylamino)-5-methoxypyrimidin-2-yl)-4-carbamoyl-1H-indol-2-yl)methylcarbamate 9 (1.4 g, 27.9 mmol) and HCl in EtOAc (15 mL) was stirred for 2 hours. The resulting solution was concentrated in vacuo. The residue was washed with DCM to give Example 29.

2-(aminomethyl)-1-(4-(benzylamino)-5-methoxypyrimidin-2-yl)-1H-indole-4-carboxamide Example 29 (compound U)

Example 29 was isolated as a solid (1 g, 88%). LRMS (M+H+) m/z: calcd 403.18. found 403. HPLC purity (214 nm): 98%. $^1$HNMR (400 MHz, DMSO): δ 8.51 (br, 3H), 8.33 (t, J=6.0 Hz, 1H), 7.93-7.88 (m, 2H), 7.55 (d, J=7.2 Hz, 1H), 7.39-7.33 (m, 6H), 7.29-7.27 (m, 1H), 7.00 (t, J=6.0 Hz, 1H), 4.65 (d, J=6.4 Hz, 2H), 4.38 (m, 2H), 3.97 (s, 3H).

The following examples were prepared using similar methodology

Example 30

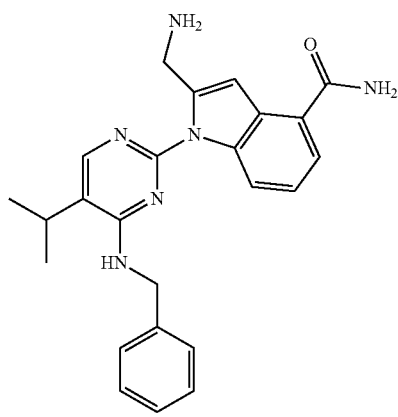

2-(aminomethyl)-1-[4-(benzylamino)-5-(propan-2-yl)pyrimidin-2-yl]-1H-indole-4-carboxamide
Example 30 (Compound V)

Example 30 was isolated as a solid. LRMS (M+H+) m/z: calcd 415. found 415; $^1$11 NMR (400 MHz, DMSO): δ 8.12 (s, 1H), 8.03 (t, J=6.0 Hz, 1H), 7.91 (d, J=8 Hz, 1H), 7.79 (m, 1H), 7.49 (d, J=8 Hz, 1H), 7.39-7.33 (m, 6H), 7.20 (s, 1H), 6.92 (t, J=8.0 Hz, 1H), 4.70 (m, 2H), 4.16 (s, 2H), 3.09 (m, J=6 Hz, 1H), 1.31 (d, J=6 Hz, 6H).

Example 31

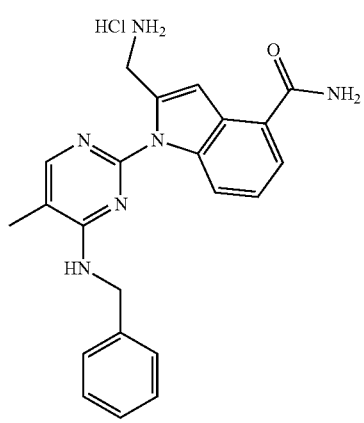

2-(aminomethyl)-1-[4-(benzylamino)-5-methylpyrimidin-2-yl]-1H-indole-4-carboxamide Hydrochloride Example 31 (Compound W)

Example 31 was isolated as a solid. LRMS (M+H+) m/z: calcd 387. found 387; $^1$H NMR (400 MHz, DMSO): δ 8.04 (s, 1H), 8.03 (t, J=6 Hz, 1H), 7.91 (d, J=8 Hz, 1H), 7.79 (m, 1H), 7.49 (d, J=8 Hz, 1H), 7.39-7.33 (m, 6H), 7.20 (s, 1H), 6.92 (t, J=8.0 Hz, 1H), 4.70 (m, 2H), 4.16 (s, 2H), 3.09 (m, J=6 Hz, 1H), 1.31 (d, J=6 Hz, 6H).

Example 32

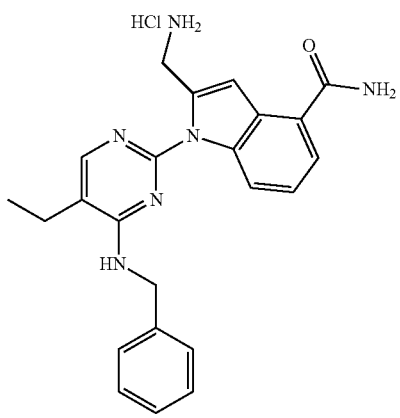

2-(aminomethyl)-1-[4-(benzylamino)-5-ethylpyrimidin-2-yl]-1H-indole-4-carboxamide Example 32 (Compound X)

Example 32 was isolated as a solid. LRMS (M+H+) m/z: calcd 401. found 401; $^1$HNMR (400 MHz, DMSO): δ 8.55 (br s, 2H), 8.21 (br s, 1H), 8.05 (s, 1H), 7.91 (br s, 1H), 7.79 (m, 1H), 7.37 (d, J=8 Hz, 1H), 7.39-7.33 (m, 6H), 7.20 (s, 1H), 6.98 (t, J=8.0 Hz, 1H), 4.71 (m, 2H), 4.36 (m, 2H), 2.61 (q, J=7 Hz, 2H), 1.27 (t, J=7 Hz, 3H).

Example 33

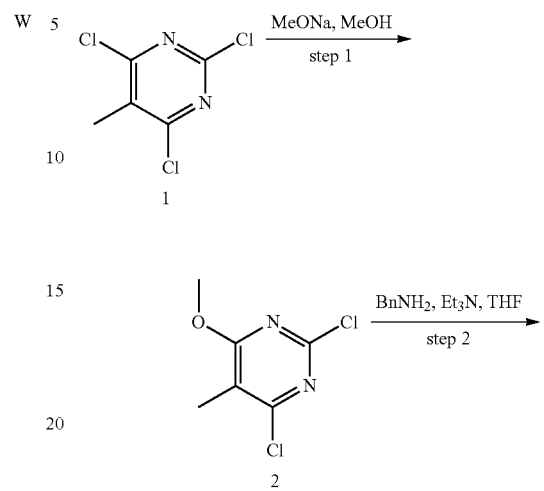

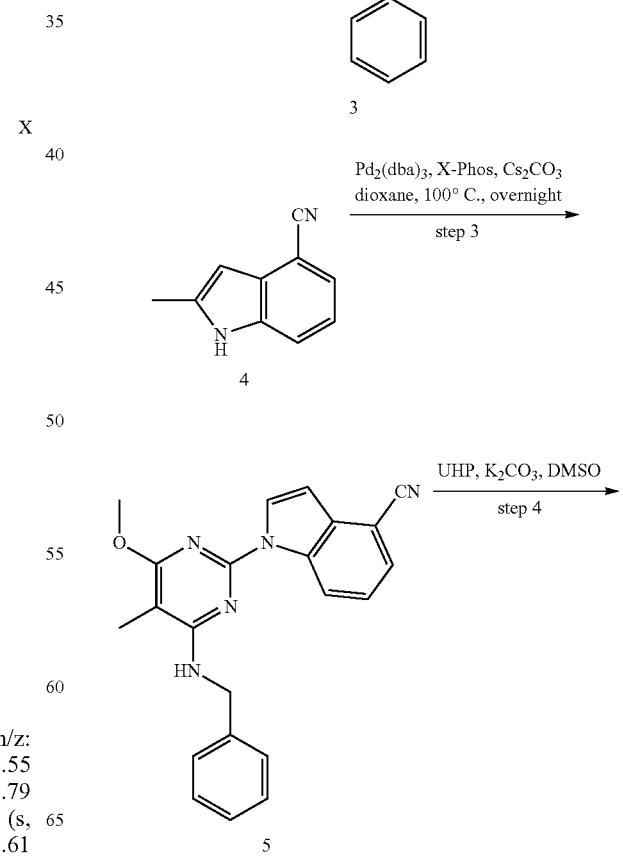

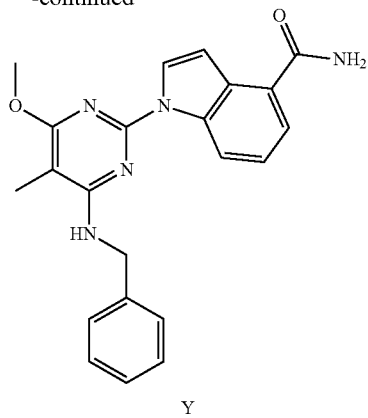

Y

To a solution of 2,4,6-trichloro-5-methylpyrimidine 1 (100 mg, 0.5 mmol) in THF (30 mL) was added sodium methoxide (22 mg, 0.4 mmol) dropwise via syringe at 0° C. The reaction mixture was stirred at 0° C. for additional 40 mins and subsequently warmed up to room temperature over 1 hour. The precipitate was filtered off, and the volatiles were evaporated under reduced pressure to afford the 2,4-dichloro-6-methoxy-5-methylpyrimidine 2 (80 mg, 82%) as white solid that was used in the next step without any further purification. LRMS (M+H+) m/z: calcd 192.99. found 193.

To a solution of 2,4-dichloro-6-methoxy-5-methylpyrimidine 2 (340 mg, 1.77 mmol) in CH₃CN (20 mL) were added benzylamine (283 mg, 2.65 mmol) and triethylamine (536 mg, 5.31 mmol). The reaction was stirred overnight at room temperature. The resulting mixture was concentrated under vacuum, and the residue was purified by flash chromatography (DCM:MeOH=50:1) to give N-benzyl-2-chloro-6-methoxy-5-methylpyrimidin-4-amine 3 (360 mg, 78%) as a yellow oil. LRMS (M+H+) m/z: calcd 264.08. found 264.

A mixture of the N-benzyl-2-chloro-6-methoxy-5-methylpyrimidin-4-amine 3 (420 mg, 1.7 mmol), 2-methyl-1H-indole-4-carbonitrile 4 (248 mg, 1.5 mmol), tris(dibenzylideneacetone) dipalladium(0) (240 mg, 0.3 mol), X-phos (240 mg, 0.5 mmol) and Cs2CO3 (1048 mg, 3.2 mmol) in dioxane (30 mL) was heated at 100° C. for 16 hours under nitrogen atmosphere. The reaction mixture was cooled down to room temperature and concentrated under vacuum, and the residue was purified by flash chromatography (DCM/MeOH=20:1) to afford 1-(4-(benzylamino)-6-methoxy-5-methylpyrimidin-2-yl)-2-methyl-1H-indole-4-carbonitrile 5 (520 mg, 80%). LRMS (M+H+) m/z: calcd 384.17. found 384.

Example 33 (Compound Y) was prepared as follows. To a solution of the 1-(4-(benzylamino)-6-methoxy-5-methylpyrimidin-2-yl)-2-methyl-1H-indole-4-carbonitrile 5 (120 mg, 0.31 mmol) in DMSO (20 mL) were added UHP (297 mg, 3.1 mmol), K2CO3 (19 mg, 0.14 mmol) and water (1 mL), the reaction was stirred at room temperature overnight followed by dilution with water (50 mL). The resulting solid was collected and purified by flash chromatography (DCM:MeOH=20:1) to afford Example 33

1-(4-(benzylamino)-6-methoxy-5-methylpyrimidin-2-yl)-2-methyl-1H-indole-4-carboxamide Example 33 (Compound Y)

Example 33 was isolated as a yellow solid (90 mg, 73%). LRMS (M+H+) m/z: calcd 402.19. found 402. HPLC purity (214 nm): 100%. ¹HNMR (300 MHz, d₆-DMSO): δ 7.88- 7.86 (m, 1H), 7.74-7.73 (m, 1H), 7.56 (s, 1H), 7.45-7.43 (m, 1H), 7.33-7.31 (m, 4H), 7.23 (s, 2H), 6.93-6.90 (m, 1H), 6.87-6.86 (m, 1H), 4.67-4.65 (m, 2H), 3.91 (m, 3H), 2.54-2.51 (m, 3H), 2.03 (s, 3H).

Example 34

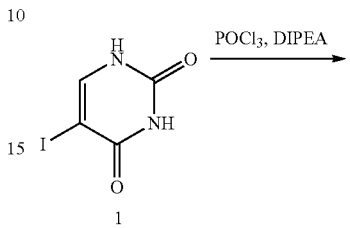

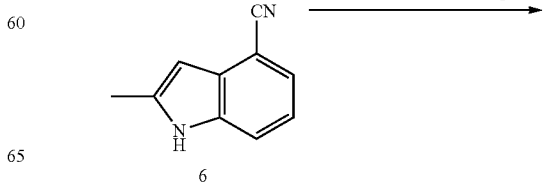

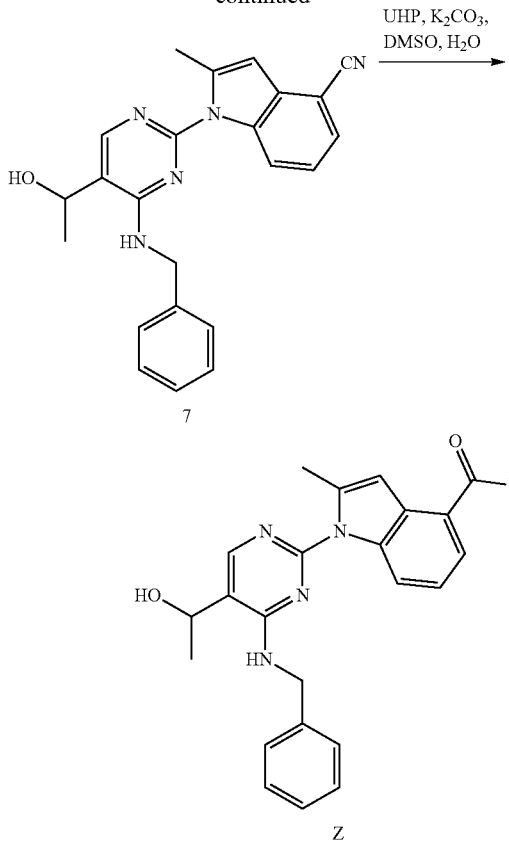

Preparation of 2,4-Dichloro-5-iodo-pyrimidine 2

A mixture of 5-iodo-2,4-pyrimidine-diol (4.76 g, 0.02 mol) and DIPEA (1 mL) in POCl3 (30 mL) was refluxed overnight and then the resulting solution was concentrated under reduced pressure. Saturated NaHCO3 solution was added to adjust the pH to 7 and the resulting mixture was extracted with DCM (3×50 mL). The organic layer was dried over MgSO4 and concentrated in vacuo. The residue was purified by flash chromatography (EA/PE=1:50) to give 2,4-Dichloro-5-iodo-pyrimidine 2 as a white solid (4.38 g, 80% yield).

Preparation of 1-(2,4-dichloropyrimidin-5-yl)ethanol 4

To the solution of 2,4-Dichloro-5-iodo-pyrimidine 2 (2.75 g, 0.01 mol) in THF (50 mL) was added i-PrMgCl (2M in THF, 6 mL, 0.012 mol) dropwise at −78° C. under N2 atmosphere and the resulting solution was stirred at −78° C. for 20 min. Then acetaldehyde 3 (880 mg, 0.02 mmol) was added dropwise and the resulting solution was stirred for 20 min. Saturated NH4Cl solution was added to quench the reaction and the resulting mixture was extracted with ethyl acetate (3×50 mL). The organic layer was dried over MgSO4 and concentrated in vacuo. The residue was purified by chromatography (EA/PE=1:10) to give 1-(2,4-dichloropyrimidin-5-yl)ethanol 4 (710 mg, 37% yield) as a colorless oil.

Preparation of 1-(4-(benzylamino)-2-chloropyrimidin-5-yl)ethanol 5

The solution of 1-(2,4-dichloropyrimidin-5-yl)ethanol 4 (650 mg, 3.37 mmol), BnNH2 (432 mg, 4.04 mmol) and TEA (0.94 mL, 6.74 mmol) in MeCN (5 mL) was stirred overnight. The reaction solution was concentrated under reduced pressure and the residue was purified by flash chromatography (MeOH/DCM=1:100) to give 1-(4-(benzylamino)-2-chloropyrimidin-5-yl)ethanol 5 (440 mg, 49%) as a light yellow oil.

Preparation of 1-(4-(benzylamino)-5-(1-hydroxyethyl)pyrimidin-2-yl)-2-methyl-1H-indole-4-carbonitrile 7

A mixture of 1-(4-(benzylamino)-2-chloropyrimidin-5-yl)ethanol 5 (390 mg, 1.477 mmol), 4-cyano-2-methyl-indole 6 (230 mg, 1.477 mmol), Pd2(dba)3 (135 mg, 0.1477 mmol), X-phos (141 mg, 0.295 mmol) and Cs2CO3 (963 mg, 2.954 mmol) in dioxane (8 mL) was refluxed under N2 atmosphere overnight. The reaction mixture was concentrated under reduced pressure and the residue was purified by flash chromatography (MeOH/DCM=1:100) to give 1-(4-(benzylamino)-5-(1-hydroxyethyl)pyrimidin-2-yl)-2-methyl-1H-indole-4-carbonitrile 7 (440 mg, 78%) as a yellow solid.

Example 34 (compound Z) was prepared as follows. A solution of 1-(4-(benzylamino)-5-(1-hydroxyethyl)pyrimidin-2-yl)-2-methyl-1H-indole-4-carbonitrile 7 (77 mg, 0.2 mmol), UHP (150 mg, 1.6 mmol), K2CO3 (14 mg, 0.1 mmol) in DMSO (4 mL) and H2O (0.5 mL) was stirred at room temp overnight. EA (100 mL) was added and the resulting mixture was washed with H2O (5×20 mL). The organic layer was dried over MgSO4 and concentrated under reduced pressure. The residue was purified by flash chromatography (MeOH/DCM=1:50) to give Example 34.

1-[4-(benzylamino)-5-(1-hydroxyethyl)pyrimidin-2-yl]-2-methyl-1H-indole-4-carboxamide Example 34 (Compound Z)

Example 34 was isolated (40 mg, 50%) as a light yellow solid. LRMS (M+H+) m/z: calcd 402 found 402 HPLC purity (214 nm): 100%; ¹HNMR (300 MHz, d6-DMSO) 8.21 (s, 1H), 7.82 (d, J=8 Hz, 1H), 7.75 (br s, 1H), 7.45 (d, J=8 Hz, 1H), 7.31 (m, 6H) 6.92 (t, J=8 Hz, 1H), 6.85 (s, 1H), 5.57 (d, J=4 Hz, 1H), 4.93 (m, 1H), 3.38 (s, 3H), 1.48 (d, J=6 Hz, 3H).

Example 35

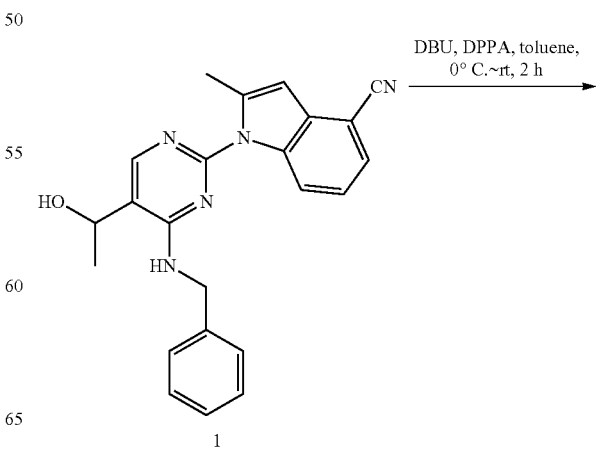

127

-continued

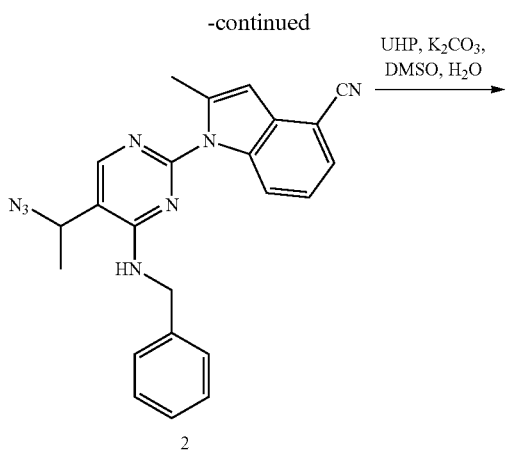

Preparation of 1-(5-(1-azidoethyl)-4-(benzylamino)pyrimidin-2-yl)-2-methyl-1H-indole-4-carbonitrile 2

To a mixture of 1-(4-(benzylamino)-5-(1-hydroxyethyl)pyrimidin-2-yl)-2-methyl-1H-indole-4-carbonitrile 1 (prepared in Example 34 compound 7) (240 mg, 0.627 mmol) and DPPA (414 mg, 1.504 mmol) in toluene (5 mL) at 0° C. was added DBU (208 mg, 1.504 mmol) and the resulting mixture was warmed to room temp and stirred for 2 h. H2O (20 mL) was added and the resulting mixture was extracted with EA (3×20 mL). The organic layer was dried over MgSO4 and concentrated in vacuo. The residue was purified by flash chromatography (EA/PE=1:5) to give 1-(5-(1-azidoethyl)-4-(benzylamino)pyrimidin-2-yl)-2-methyl-1H-indole-4-carbonitrile 2 as a yellow oil (150 mg, 37% yield).

128

Preparation of 1-(5-(1-azidoethyl)-4-(benzylamino)pyrimidin-2-yl)-2-methyl-1H-indole-4-carboxamide 3

A solution of 1-(5-(1-azidoethyl)-4-(benzylamino)pyrimidin-2-yl)-2-methyl-1H-indole-4-carbonitrile 2 (150 mg, 0.368 mmol), UHP (276 mg, 2.94 mmol), K₂CO₃ (25 mg, 0.184 mmol) in DMSO (4 mL) and H2O (0.5 mL) was stirred at RT overnight. EA (100 mL) was added and the resulting mixture was washed with H₂O (5×20 mL). The organic layer was dried over MgSO4 and concentrated under reduced pressure. The residue was purified by flash chromatography (MeOH/DCM=1:100) to give 1-(5-(1-azidoethyl)-4-(benzylamino)pyrimidin-2-yl)-2-methyl-1H-indole-4-carboxamide 3 as a white yellow solid (100 mg, 64% yield).

Example 35 (Compound AA) was prepared as follows. A solution of 1-(5-(1-azidoethyl)-4-(benzylamino)pyrimidin-2-yl)-2-methyl-1H-indole-4-carboxamide 3 (100 mg, 0.235 mmol) in MeOH (5 mL) was treated with Pd/C (20 mg) and the resulting mixture was placed under an atmosphere of hydrogen and was stirred overnight at room temperature. The reaction mixture was concentrated in vacuo and the residue was purified by flash chromatography (MeOH/DCM=1:50) to give Example 35

1-[5-(1-aminoethyl)-4-(benzylamino)pyrimidin-2-yl]-2-methyl-1H-indole-4-carboxamide Example 35 (Compound Z)

Example 35 was isolated as a yellow solid (30 mg, 32% yield). LRMS (M+H+) m/z: calcd 401 found 401 HPLC purity (214 nm): 100%; ¹HNMR (300 MHz, CD₃OD): δ 8.19 (s, 1H), 7.78 (d, J=8 Hz, 1H), 7.46 (d, J=8 Hz, 1H), 7.32 (m, 5H), 6.98 (t, J=8 Hz, 1H), 6.79 (s, 1H), 4.74 (m, 2H), 4.35 (q, J=6 Hz, 1H), 2.48 (s, 3H), 1.55 (d, J=6 Hz, 3H).

Example 36

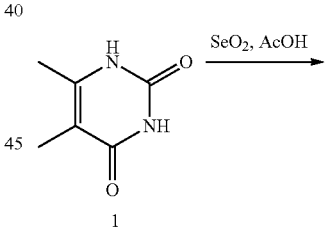

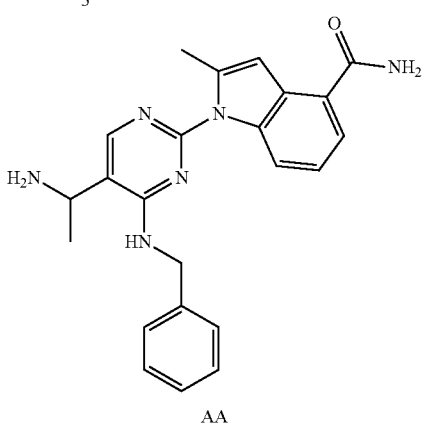

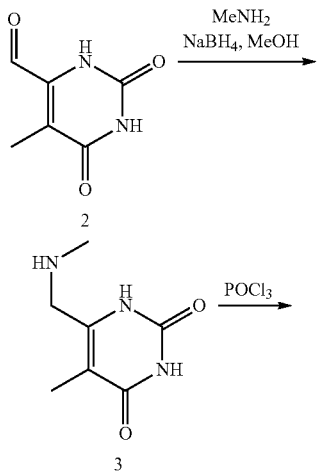

-continued

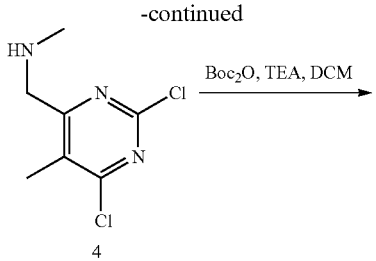
4

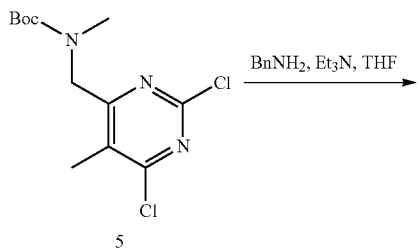
5

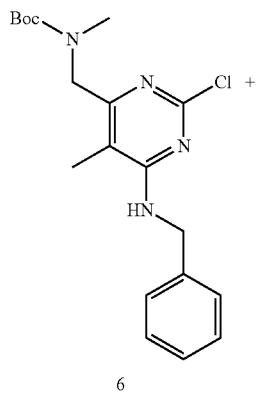
6

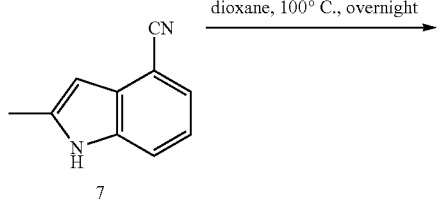
7

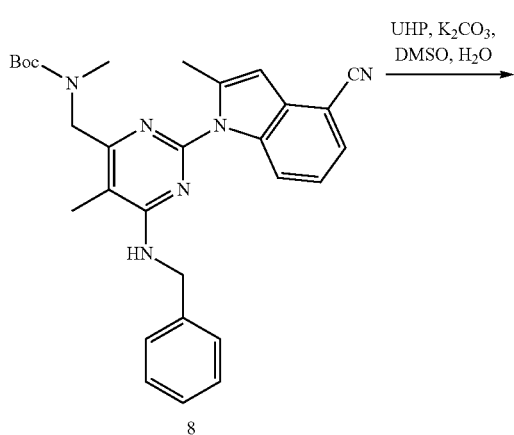
8

-continued

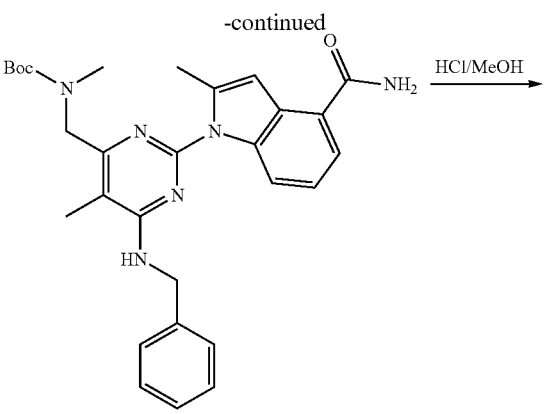
9

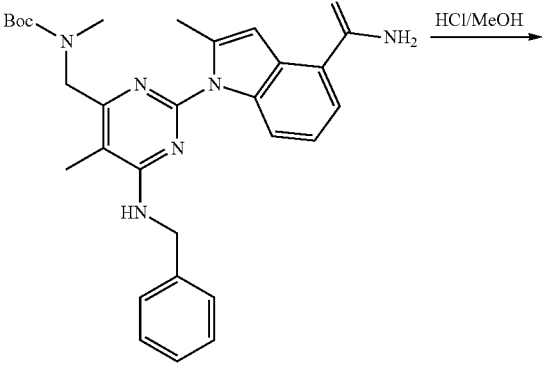
BB

Preparation of 5-methyl-2,6-dioxo-1,2,3,6-tetrahydropyrimidine-4-carbaldehyde 2

A mixture of 4,5-dimethyl-2,6-dioxo-1,2,3,6-tetrahydropyrimidine (5.6 g, 40 mmol) and SeO2 (5.32 g, 48 mmol) in AcOH (80 mL) was stirred at 120° C. for 6 hours. Then the mixture was filtered. The filtrated was concentrated to give yellow oil. The oil was diluted with MeOH (50 mL) and concentrated to give crude product which was used in the next reaction without further purification.

Preparation of 5-methyl-6-((methylamino)methyl)pyrimidine-2,4 (1H,3H)-dione 3

To a solution of SM1 (110 mg crude) in MeOH (10 mL) was added MeNH2 in THF (2M, 1 mL, 2 mmol). After stirred at room temp for 1 hour, NaBH4 (50 mg, 1.3 mmol) was added thereto and stirred at room temp for 1 hour. Then the mixture was quenched with water. The mixture was diluted with DCM (30 mL) and brine (30 mL). The organic layer was concentrated to give crude product. The crude was purified by flash chromatography to give 5-methyl-6-((methylamino)methyl)pyrimidine-2,4(1H,3H)-dione 3 (30 mg, 25% yield over two steps).

Preparation of (2,6-dichloro-5-methylpyrimidin-4-yl)-N-methylmethanamine 4

A mixture of 5-methyl-6-((methylamino)methyl)pyrimidine-2,4(1H,3H)-dione 3 (35 mg, 0.21 mmol) in POCl3 (10 mL) was stirred at 130° C. overnight. After concentrated, the residue was diluted with ice water (20 mL) and DCM (30 mL). The organic layer was washed with brine (30 mL) and concentrated to give crude (2,6-dichloro-5-methylpyrimidin-4-yl)-N-methylmethanamine 4 which was used directly in the next step.

Preparation of tert-butyl (2,6-dichloro-5-methylpyrimidin-4-yl)methyl(methyl) carbamate 5

A solution of crude (2,6-dichloro-5-methylpyrimidin-4-yl)-N-methylmethanamine 4 ((1.3 g, 6.3 mmol) in DCM (100 mL) was added Boc2O (2.75 g, 12.6 mmol). The reaction mixture was stirred at room temp for 2 hrs, then it was concentrated to give crude product that was purified by flash chromatography to give tert-butyl (2,6-dichloro-5-methylpyrimidin-4-yl)methyl(methyl)carbamate 5 (1.2 g, yield 51% over two steps).

Preparation of tert-butyl (6-(benzylamino)-2-chloro-5-methylpyrimidin-4-yl) methyl(methyl)carbamate 6

A solution of tert-butyl (2,6-dichloro-5-methylpyrimidin-4-yl)methyl(methyl) carbamate 5 (1.26 g, 4.1 mmol) in THF (30 mL) was added TEA (0.828 g, 8.2 mmol) and benzyl amine (0.44 g, 4.1 mmol). The mixture was stirred at 50° C. for 5 hrs. Then it was concentrated and diluted with DCM (30 mL) and brine (30 mL). The organic layer was concentrated and the resulting residue was purified by chromatography to give tert-butyl (6-(benzylamino)-2-chloro-5-methylpyrimidin-4-yl) methyl(methyl)carbamate 6 as a yellow solid. (0.6 g, 41% yield).

Preparation of (6-(benzylamino)-2-(4-cyano-2-methyl-1H-indol-1-yl)-5-methylpyrimidin-4-yl)methyl(methyl)carbamate 8

A mixture of tert-butyl (6-(benzylamino)-2-chloro-5-methylpyrimidin-4-yl) methyl(methyl)carbamate 6 (0.53 g, 1.4 mmol), 4-cyano-1-methyl-indole 7 (0.24 g, 1.55 mmol), Pd2(dba)3 (0.192 g, 0.21 mmol) Xphos (0.1 g, 0.021 mmol) and Cs$_2$CO$_3$ (0.913 g, 2.8 mmol) in dioxane (20 mL) was stirred at 100° C. overnight. The reaction was concentrated and purified by flash chromatography to give (6-(benzylamino)-2-(4-cyano-2-methyl-1H-indol-1-yl)-5-methylpyrimidin-4-yl)methyl(methyl)carbamate 8 as a yellow solid (0.58 g, 83% yield).

Preparation of tert-butyl (6-(benzylamino)-2-(4-carbamoyl-2-methyl-1H-indol-1-yl)-5-methylpyrimidin-4-yl)methyl(methyl)carbamate 9

To a solution of (6-(benzylamino)-2-(4-cyano-2-methyl-1H-indol-1-yl)-5-methylpyrimidin-4-yl)methyl(methyl)carbamate 8 (300 mg, 0.6 mmol) in DMSO/H2O (4 mL/0.4 mL) was added K2CO3 (50 mg, 0.36 mmol) and UHP (573 mg, 6 mmol). The reaction mixture was stirred at room temp until all solid dissolved. Then brine (20 mL) was added there to quench the reaction. The mixture was extracted with EA (20×2) and the combined organic layers were concentrated. The resulting residue was purified by flash chromatography to give tert-butyl (6-(benzylamino)-2-(4-carbamoyl-2-methyl-1H-indol-1-yl)-5-methylpyrimidin-4-yl)methyl (methyl)carbamate 9 as a white solid (200 mg, yield 65%).

Example 36 (Compound BB) was prepared as follows. A mixture of tert-butyl (6-(benzylamino)-2-(4-carbamoyl-2-methyl-1H-indol-1-yl)-5-methylpyrimidin-4-yl)methyl (methyl)carbamate 9 (200 mg, 0.39 mmol) was dissolved in ethyl acetate (10 mL) to which HCl/in ethyl acetate (3 mL) was added. The reaction mixture was stirred at overnight at room temperature. H$_2$O (20 mL) was added and the mixture was adjusted to PH=8-9. The organic layer was concentrated and the resulting residue was purified by column chromatography to give Example 36.

1-[4-(benzylamino)-5-methyl-6-[(methylamino)methyl]pyrimidin-2-yl]-2-methyl-1H-indole-4-carboxamide Example 36 (Compound BB)

Example 36 was isolated as a yellow solid (120 mg 74% yield). LRMS (M+H+) m/z: calcd 415 found 415 HPLC purity (214 nm): 100%; $^1$HNMR (400 MHz, CDCl$_3$) δ 8.10 (d, J=8 Hz, 1H), 7.49 (d, J=8 Hz, 1H), 7.36 (m, 5H), 7.08 (t, J=8 Hz, 1H), 6.83 (s, 1H), 5.98 (br s, 1H), 5.75 (br, s 1H), 5.14 (m, 1H), 4.77 (d, J=6 Hz, 2H), 2.64 (s, 3H), 2.55 (s, 3H), 2.11 (s, 3H).

Example 37

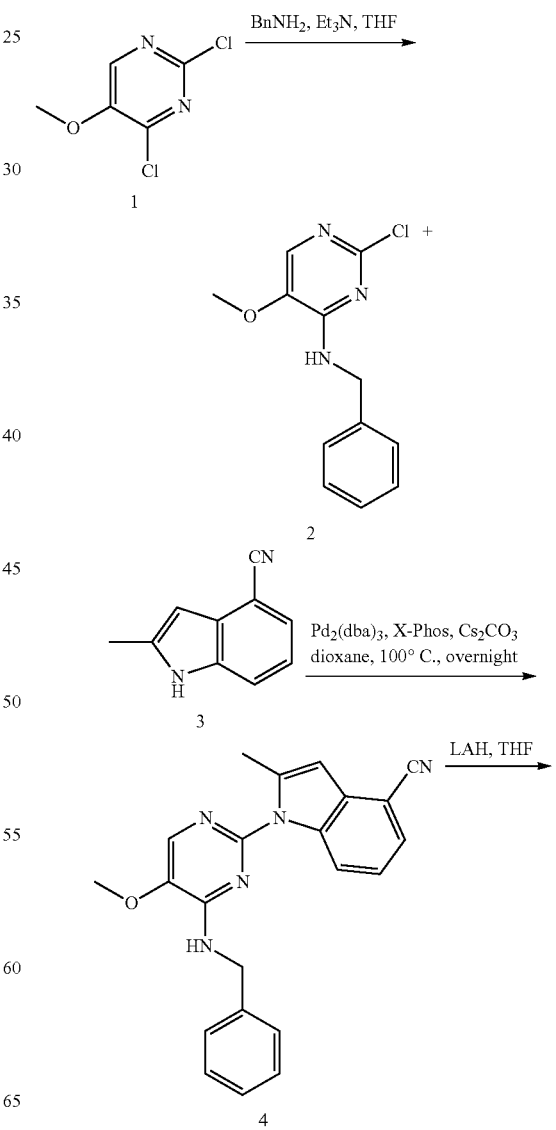

133

-continued

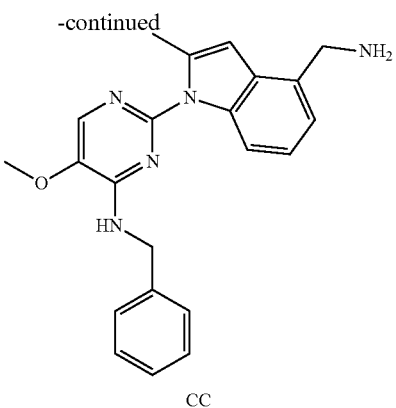

CC

Preparation of
N-benzyl-2-chloro-5-methoxypyrimidin-4-amine 2

To a solution of 2,4-dichloro-5-methoxypyrimidine (1 g, 5.6 mmol) in acetonitrile (60 mL) was added phenylmethanamine (0.72 g, 6.7 mmol) and triethylamine (2.4 mL, 16.8 mmol). Then the reaction solution was stirred at room temperature for 2 hours. The resulting solution was concentrated in vacuo and purified by column chromatography (silica gel, petroleum ether/ethyl acetate=2:1) to give the N-benzyl-2-chloro-5-methoxypyrimidin-4-amine 2 as a white solid (420 mg, 32% yield).

Preparation of 1-[4-(benzylamino)-5-methoxy-pyrimidin-2-yl]-2-methyl-indole-4-carbonitrile 4

To a solution of N-benzyl-2-chloro-5-methoxypyrimidin-4-amine 2 (420 mg, 1.7 mmol) and 2-methyl-1H-indole-4-carbonitrile 3 (263 mg, 1.7 mmol) in dioxane (137 mL) was added Pd2(dba)3 (311 mg, 0.34 mmol), X-Phos (162 mg, 0.34 mmol) and Cs2cO3 (1.1 g, 3.4 mmol). The mixture was degassed for 3 times, then stirred at 100° C. for 12 hours. the resulting mixture was concentrated in vacuo and the residue was purified by column chromatography (silica gel, petroleum ether/ethyl acetate=2:1) to give 1-[4-(benzylamino)-5-methoxy-pyrimidin-2-yl]-2-methyl-indole-4-carbonitrile 4
To a solution of N-benzyl-2-chloro-5-methoxypyrimidin-4-amine 2 (420 mg, 1.7 mmol) and 2-methyl-1H-indole-4-carbonitrile 3 as yellow solid (620 mg, 98% yield).

Example 37 (Compound CC) was prepared as follows. To a solution of 1-(4-(benzylamino)-5-methoxypyrimidin-2-yl)-2-methyl-1H-indole-4-carbonitrile 3 (100 mg, 0.27 mmol) in THF (3 mL) was added LiAlH4 (40 mg, 1.08 mmol) under ice bath. Then the reaction mixture was refluxed for 5 hours. After the mixture was cooled to 0° C., w water (0.4 mL), aqueous NaOH (0.4 mL) and w water (1.2 mL) was added to the mixture, filtered and the filtrate was concentrated and purified by column chromatography to give Example 37

2-[4-(aminomethyl)-2-methyl-1H-indol-1-yl]-N-benzyl-5-methoxypyrimidin-4-amine Example 37 (Compound CC)

Example 37 was isolated as a solid (30 mg, 30% yield). LRMS (M+H+) m/z: calcd 415 found 415 HPLC purity (214 nm): 100%; 1HNMR (400 MHz, CDCl3) δ 7.79 (dd, J=8, 4 Hz, 1H), 7.66 (s, 1H), 7.35 (m, 5H), 7.07 (m, 2H), 6.46 (s, 1H), 5.76 (m, 1H), 4.72 (d, J=8 Hz, 1H), 4.13 (s, 2H), 3.90 (s, 3H), 2.59 (s, 3H).

134

Using similar methodology the following examples could be prepared:

Example 38

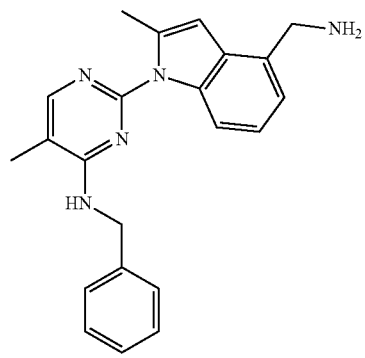

DD

2-[4-(aminomethyl)-2-methyl-1H-indol-1-yl]-N-benzyl-5-methylpyrimidin-4-amine, Example 38 (Compound DD)

Example 38 was isolated as a solid. LRMS (M+H+) m/z: calcd 374 found 374 HPLC purity (214 nm): 97%; 1HNMR (400 MHz, CD3OD) 7.45 (d, J=8 Hz, 1H), 7.32 (m, 5H), 7.01 (d, J=8 Hz, 1H), 6.93 (t, J=8 Hz, 1H), 6.42 (s, 1H), 4.734 (s, 2H), 4.02 (s, 2H), 2.41 (s, 3H), 2.19 (s, 3H).

Example 39

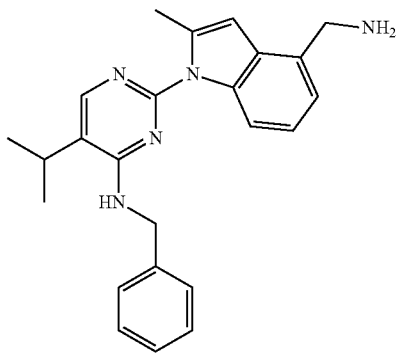

EE

2-[4-(aminomethyl)-2-methyl-1H-indol-1-yl]-N-benzyl-5-(propan-2-yl)pyrimidin-4-amine, Example 39 (Compound EE)

Example 39 was isolated as a solid. LRMS (M+H+) m/z: calcd 386 found 386 HPLC purity (214 nm): 100%; 1HNMR (400 MHz, CD3OD) δ 8.11 (s, 1H), 7.56 (d, J=8 Hz, 1H), 7.29 (m, 5H), 7.12 (d, J=8 Hz, 1H), 6.98 (t, J=8 Hz, 1H), 6.50 (s, 1H), 4.76 (s, 2H), 4.32 (s, 2H), 3.05 (sept. J=7 Hz, 1H) 2.44 (s, 3H), 1.38 (d, J=7 Hz, 3H).

Biological Protocols

The in vitro and in vivo biological assays to determine the anti-cancer properties of the monocyclic pyrimidine compounds of the invention are summarized above. The details of these protocols show how the assays are carried out.

P97 Biochemical Assay Protocol

The p97 assay is an initial screening assay used to determine inhibitory activity of the monocyclic pyrimidine compounds of the invention against the p97 complex. As discussed above, inhibition of activity of the p97 proteosome complex can enable apoptosis and cause elimination of neoplastic cells (cancer cells). The method follows that of Christianson in Nat. Cell Biol., (2011) 14:93.

The Reagents used for the p97 assay include:

Assay Buffer is a mixture of 50 mM TRIS pH 7.5, 20 mM $MgCl_2$, 0.02% TX-100, 1 mM DTT and 0.2% (v/v) Glycerol. The well plate is Platetype: Corning 3674, 384w plate. The identification kit is an ADP glo kit (Promega): stop buffer, detection reagent.

The Assay protocol is conducted as follows:
Serial dilute compound in DMSO in a 1:3.33-fold 10 point serial dilution.
in each well of 384w plate add the following reagents:
0.5 μL compound serial diluted in DMSO (Final Conc. 10%)
2 μL ATP (Final Conc.=20 uM, diluted in assay buffer)
2.5 μL p97 (Final Conc.=20 nM, diluted in assay buffer)
Incubate at 37 degC for 15 min.
Add 5 μL of stop buffer, incubate at RT for 40 min.
Add 10 μL of detection reagent, incubate at RT for 30 min.
Read luminescence on Envision plate reader.
Upon obtaining the data from the luminescence reading, the data may be analyzed as follows:
Normalize luminescence data using no enzyme (full inhibition) and no compound (no inhibition) controls. Plot normalized luminescence data against log-transformed concentration values and fit to a sigmoidal curve to determine IC50 values (done in Collaborative Drug Discovery software).

The results are reported on the following Table for Examples A-EE and the E1-E4 compounds as 50 percent Inhibitory concentration at candidate doses of less than 30 nM, less than 100 nM, less than 300 nM and less than 1000 nM for the p97 inhibition assay.

Caco-2 Permeability Assay

This assay is designed as a model to indicate the permeability of a monocyclic pyrimidine compound of this invention through the gut-blood barrier. The result will yield indications of whether or not the monocyclic pyrimidine compound may be efficiently absorbed into the blood stream of a patient. Efficient, effective absorption of an orally administered drug determines in part its bioavailability. For the monocyclic pyrimidine compounds of the invention, this assay is a model to evaluate the bioavailability of the compounds as a result of their ability to pass through biological barriers to entry into the physiological system of the patient.

The experimental goal of the Caco-2 assay is to measure directional Caco-2 permeability of test compounds in cultured Caco-2 monolayer.

The test compounds are the monocyclic pyrimidine compounds of the invention.

Set-Up

Instruments
Tissue culture $CO_2$ incubator with humidity control
Liquid handler
Orbital shaker
EVOM Epithelial Volt-ohmmeter fitted with planar electrodes (World Precision Instruments, Sarasota, Fla.) required for measuring transepithelial electrical resistance (TEER)
Bench top centrifuge with 96-well plate adaptor
Caco-2 cells (Human colorectal adenocarcinoma, ATCC #37-HTB, passage 30-45)
Cells seeded onto PET membranes (1 μm pore size, 0.31 $cm^2$ surface area) inside Falcon HTS multiwell Insert system using 24-well plates (Becton Dickinson plates, Part #351181, Fisher Scientific, Inc.) at a density of 23,000 cells/well. Cells grown 20-23 days with medium changed every 2-3 days Reagents Ringers buffer solution (pH 7.4 at 25° C.)
Ringers buffer with 1% Methanol
Blk solution: Ringers buffer: Methanol=2:1 (v/v); 100% Methanol including internal standard (IS); 10 mM stock dosing solution in DMSO; 100 μM dosing solution in buffer.

Protocol Summary

Caco-2 permeability: 20-23 day/Passage 30-45
24-well format transwell: 0.31 cm2 surface area
Donor conc: 100 μM including 1% DMSO
A: 300 μL pH 7.4/B: 1200 μL pH 7.4 Ringers buffer
Directionality: A B and B A (N=4)
Donor side sampling: 20 μL at beginning and end (90 min)
Receiver side sampling: 100 μL at 30, 50, 70, and 90 min
Incubation at 50 oscillations per minute, 37° C., 5% $CO_2$, 95% humidity
Analysis: LC-UV, LC-MS, or LSC
Output: Peff (cm/sec)=(dX/dt)/(A*Co*60), dX/dt: transported amount (nmole) versus time (minute) profile in the receiver chamber; A: surface area ($cm^2$); and Co: initial donor concentration (μM)
Positive control: Atenolol and propranolol
Membrane integrity: TEER >200 $Ocm^2$
Amount required: Approximately 1 mg or 100 μL of 10 mM test compound in DMSO
Instruments: $CO_2$ incubator with humidity control, liquid handler, epithelial volt-ohmmeter for TEER, Caco-2 cells (ATCC #37-HTB), and 24-well insert plates (PET membranes, 1 μm pore size, 0.31 $cm^2$ plates, Part #351181) surface area, Becton Dickinson
Throughput: 6 compounds/2 Caco-2 plates/1 FTE/day Preparation

TABLE 24

Preparation of Ringers with Glucose
(Isotonic = 290 mOsm/kg), pH 7.4

| Chemical | Molecular Wt | Concentration | Mass(g) for 1 L | Mass(g) for 2 L | Mass(g) for 4 L |
|---|---|---|---|---|---|
| Ca $SO_4$ $2H_2O$ | 172.2 | 1.25 mM | 0.2152 | 0.4305 | 0.861 |
| $MgSO_4$ $7H_2O$ | 246.5 | 1.1 mM | 0.2712 | 0.5423 | 1.0846 |
| KCl | 74.55 | 5 mM | 0.3728 | 0.7455 | 1.491 |
| $Na_2HPO_4$ | 142.0 | 1.15 mM | 0.1633 | 0.3266 | 0.6532 |
| $NaH_2PO_4$ $H_2O$ | 138.0 | 0.3 mM | 0.0414 | 0.0828 | 0.1656 |

TABLE 24-continued

Preparation of Ringers with Glucose
(Isotonic = 290 mOsm/kg), pH 7.4

| Chemical | Molecular Wt | Concentration | Mass(g) for 1 L | Mass(g) for 2 L | Mass(g) for 4 L |
|---|---|---|---|---|---|
| $NaHCO_3$ | 84.01 | 25 mM | 2.100 | 4.200 | 8.401 |
| Glucose($C_6H_{12}O_6$) | 180.2 | 25 mM | 4.505 | 9.01 | 18.02 |
| NaCl | 58.44 | 110 mM | 6.428 | 12.86 | 25.71 |

Preparation Of 4 Solution

1. To 3.5 distilled water, add Calcium Sulfate and Magnesium Sulfate.
   Note: Add Calcium Sulfate and Magnesium Sulfate first due to low solubility and add the remaining ingredients in the order listed in Table 1.
2. Adjust the final volume of the solution to 4 with distilled water, with continuous stirring.
3. Adjust final solution to a pH of 7.4 using 1N HCl or 1N NaOH.
4. Make the buffer iso-osmotic using NaCl. Measure tonicity of the solution using a tonometer. Given that an isotonic solution is equivalent to 0.9% NaCl (290 mOsm/L), $$Y = \{(290-x)/290\} \times 9 \text{ mg} \times 4000 \text{ mL},$$

where y=NaCl required (in mg) to make the solution isotonic and x=observed tonicity of solution (reported as mOsm/L).

Preparation of Dosing Solution in 15 mL PP Tube 1. 100 μM dosing solution in RG: 140 μL 10 mM stock+(14 mL−140 μL) RG Preparation of Calibration in 96 Shallow Well 1. Prepare 10 μM standard: 100 μL of 100 μM dosing solution+0.9 mL Ringers with 1% Methanol.
2. Prepare analytical standard solutions 10, 5, 2, 1, 0.5, 0.2, 0.1, 0.05, 0.02, 0.01, and 0 μM. (See Table 26)

than or equal to 2000×cm² and those not meeting this criteria are not suitable for permeability evaluations.

3. When studying A to B transport: Fill basolateral side with 1,200 μL of Ringers buffer. Initiate transport experiments by transferring test drug dosing solution (320 μL) to apical side.
4. When studying B to A transport: Fill apical side with 300 μL of Ringers buffer. Initiate transport experiments by transferring test drug dosing solution (1,220 μL) to basolateral side. Transport studies for each direction (A to B, B to A) are performed in quadruplicate for each test drug.
5. Start timer after dosing last donor well.
6. Remove 20 μL aliquots from the donor wells at 0 minutes ($D_O$) and transfer these aliquots to the donor site of the 96-well plate containing 180 μL buffer with 1% Methanol. This step effectively dilutes the $D_0$ ten times.
7. Initiate transport studies by placing plate on orbital shaker maintained inside a prewarmed (37° C.) and humidified (5% $CO_2$) incubator. Studies are performed under stirring conditions at 50 oscillations per minute.
8. Remove 100 μL aliquots from the receiver side of the monolayer at 30, 50, 70, and 90 minutes postdosing and transfer these aliquots to the corresponding 96-well sample plate (See Table 26). Replace with an equivalent volume of prewarmed buffer.
9. Remove 20 μL aliquots from the donor side of the monolayer at 90 minutes postdosing ($D_f$) and transfer these aliquots to a donor site of a 96-well plate containing 180 μL Ringers buffer with 1% Methanol. This step effectively dilutes the $D_f$ ten times.

TABLE 25

Preparation of analytical calibration in 96 shallow well

| | 1 | 2 | 3 | 4 | 5 | 6 | 7 | 8 | 9 | 10 | 11 | 12 |
|---|---|---|---|---|---|---|---|---|---|---|---|---|
| | 0 | 20 μL of 0.1 μM | 20 μL of 0.2 μM | 20 μL of 0.5 μM | 20 μL of 1 μM | 20 μL of 2 μM | 20 μL of 5 μM | 20 μL of 10 μM | 40 μL of 10 μM | 100 μL of 10 μM | 200 μL of 10 μM | Source solution 1% MeOH in buffer |
| | 180 μL | 180 μL | 180 μL | 180 μL | 180 μL | 180 μL | 180 μL | 180 μL | 160 μL | 100 μL | 0 | |
| Comp 1 Comp 2 Comp 3 | Blk | 0.01 μM | 0.02 μM | 0.05 μM | 0.1 μM | 0.2 μM | 0.5 μM | 1 μM | 2 μM | 5 μM | 0 μM | |

Transport Studies

Dosing and Sampling

1. Equilibrate both sides of the monolayers for 10 minutes with prewarmed (37° C.) drug-free Ringers buffer (300 μL apical side, 1,200 μL basolateral side) supplemented with glucose (25 mM).
2. Measure TEER under 37° C. water bath conditions.
   Note: The TEER value serves as a quality control check for monolayer integrity. At 21 days post-seeding, each Caco-2 cell monolayer should have a TEER value of greater 10. Replace both sides of monolayer with fresh, drug-free, prewarmed Ringers buffer (300 μL apical side, 1,200 μL basolateral side) and equilibrate for 10 minutes.
11. Measure TEER under 37° C. water bath conditions.

Sample Handling

The following steps refer to 96-well analytical plate for Caco-2, Table 26.

1. Transfer 20 μL of diluted Do and $D_f$ to corresponding 96-well sample plate with each well containing 80 μL buffer with 1% Methanol.

This step effectively dilutes the samples five times further. Therefore, donor samples are diluted 50 times from their initial concentration.

2. Transfer 100 μL of analytical calibration (from 0 to 10 μM) to the sample plate row 1.
3. Add 50 μL Methanol including IS to all sample wells and mix (standards, samples, and $D_0$ and $D_f$).
4. Transfer 150 μL of Blk solution to the analytical plate row 2.
5. Seal the analytical plate with adhesive sealing film and store samples with label at −80° C. for LC-UV or LC-MS analysis.
6. Analyze 20 μL aliquots of the individual permeability samples and the standards using a suitable analytical instrument.
7. Peff=(dX/dt)/(A×C₀×60), where $P_{eff}$ is the effective permeability in cm/sec, X=mass transported, A is the surface area (cm)² available for transport, $C_0$ is the initial donor drug concentration (μM), and dX/dt is the slope of the best fit line through the transported amount (nmole) versus time (min) profile in the receiver chamber.

TABLE 26

Analytical Plate for Caco-2 (96-well plate)

| 0 Blk | 0.01 μM Blk | 0.02 μM Blk | 0.05 μM Blk | 0.1 μM A to B | 0.2 μM | 0.5 μM | 1 μM B to A | 2 μM Blk | 5 μM Blk | 10 μM Blk | Blk |
|---|---|---|---|---|---|---|---|---|---|---|---|
| 1-30 | 2-30 | 3-30 | 4-30 | | | | | 5-30 | 6-30 | 7-30 | 8-30 |
| 1-50 | 2-50 | 3-50 | 4-50 | | | | | 5-50 | 6-50 | 7-50 | 8-50 |
| 1-70 | 2-70 | 3-70 | 4-70 | | | | | 5-70 | 6-70 | 7-70 | 8-70 |
| 1-90 | 2-90 | 3-90 | 4-90 | | | | | 5-90 | 6-90 | 7-90 | 8-90 |
| 1-Do | 2-Do | 3-Do | 4-Do | | | | | 5-Do | 6-Do | 7-Do | 8-Do |
| 1-Df | 2-Df | 3-Df | 4-Df | | | | | 5-Df | 6-Df | 7-Df | 8-Df |

Positive Control Data

Mean data in Table 27 represent the mean value from 12 separate inter-day experiments.

TABLE 27

$P_{eff}$ (xE-6 cm/sec) in pH 7.4 Caco-2

| | A B | B A |
|---|---|---|
| Atenolol | | |
| Mean | 1.08 | 2.29 |
| Range | 0.69-1.80 | 1.69-2.68 |
| Propranolol | | |
| Mean | 28.53 | 20.91 |
| Range | 18.50-36.80 | 16.30-31.40 |

Mouse Liver Microsome Assay

The liver microsome assay is a model for studying the metabolic stability of the monocyclic pyrimidine compounds of the invention. Metabolic stability is another aspect determining bioavailability. The facility of a compound to be bioabsorbed into the blood stream as shown by the Caco-2 model indicates the degree to which an oral dose of the compound will reach the blood stream. The body efficiently metabolizes substances to rid them from the body and/or to utilize them as nutrients. This aspect of bioavailability can be determined by such model studies as liver microsomal metabolism. Whether by oxidation, conjugation or any other biological pathway, metabolism of a drug determines at least in part the lifetime of the drug in the body.

The mouse liver microsome assay is a model designed to establish drug half-life in vivo. The liver enzymes are responsible to conversion of substances to materials that can be readily excreted by the body. Other routes for such metabolism include kidney metabolism, cellular metabolism and the like.

In this protocol, the compound is combined with a liver microsomal preparation (protein) and NADPH. The mixture is incubated and the rate of disappearance of the compound from the test solution is measured. Measurement is made by screening for the compound concentration at specified times using liquid chromatography in combination with mass spectroscopy.

Concentrations of Reactants Ready for Formulation as the Test Solution:
Protein: 1.0 mg/ml
Compound: 1 um
Organic solvent: 0.4% DMSO Medium: 0.1 M Potassium Phosphate (KB)
1 mM NADPH (sigma N1630, FW 833.3, make freshly)
Prepare test article (TA, i.e., a compound of the invention) by dissolving solid TA in DMSO to make a 0.25 mM solution Amounts of Reactant Solutions to be Combined to Form the Test Solution:

| | |
|---|---|
| 423 ul + | KB (potassium phosphate) |
| 25 ul | MLM (20 mg/ml) (mouse liver microsomal preparation) |
| 448 ul + | |
| 2 ul + | Test compound (a monocyclic pyrimidine compound at 0.25 mM DMSO) |
| 50 ul | NADPH stock (10 mM, 10×) |
| 500 ul | |

Test Protocol for Conducting the Assay
1. Add 423 ul KB to an 8-strip deep well tubes
2. Add 25 ul of MLM for condition 1
3. Place on ice, add 2 ul cpds (250×stock in DMSO, stock at 0.25 mM)
4. Preincubate the reaction mixture at 37 C for 3 to 5 minutes (shaking at 150 rpm)
5. Initiate reaction by adding 50 ul NADPH for condition 1
6. Add 50 ul KB for condition 2
7. An aliquot of samples of 100 ul were collected at 0, 15, 30, and 60 min time point, and 200 ul of acetonitrile mixture containing IS was added to quench the reaction.

8. Centrifuge for 10 min at 4000 rpm
9. The supernatant were injected for liquid chromatographic tandem mass spectrometry (LC-MS/MS) analysis Procedure of Protein Binding Using 96-Well Equilibrium Dialyzer Non-specific protein binding is another facet affecting bioavailability and effectiveness of a drug. To assay a compound for non-specific binding, the compound is combined with human blood plasma and the solution dialyzed against a membrane constructed to prevent passage of larger molecules such as human plasma proteins but allow passage of small molecules such as the compounds of the invention. Typically, such membranes allow passage of such compounds irrespective of their salt or neutral form. The dialysate (solution passing through the membrane) is examined by liquid chromatography mass spectrometric techniques to determine the identity and concentration of the compound present. The concentration of compound in the dialysate compared with the concentration of compound combined with blood plasma indicates whether or not non-specific protein binding has occurred.

Equipment and Reagent:
96-Well Equilibrium Dialyzer (made by: Harvard Apparatus)
Plate Rotator with DIALYZER plates secured in clamp fixture
Buffer: DPBS (gibco, 1×)
Compound Concentration: 1 µM (~0.5 in µg/mL) in Human Plasma Procedure:
1. Seal the empty Sample Side well on the colored side with cap strips.
2. Invert the plate and carefully pipet a volume of buffer, 200 µL equal to the sample volume into the wells on the Buffer Side (clear frame) without touching the membranes by allowing the liquid to flow along the inner side wall of each well.
3. Gently seal the filled buffer wells with cap strips.
4. Invert the plate and carefully remove the cap strips from the sample side wells. Pipet desired samples, without touching the membranes.
5. Reseal the sample wells with the cap strips.
6. Slide the assembled DIALYZER Plate into a Plate Rotator and hand tighten the snobs. Turn on and allow rotating until equilibrium has been reached (24 hours at 37 C), remove the DIALYZER Plate from the Rotator.
7. After equilibrium has been reached, remove the DIALYZER Plate from the rotator.
8. Carefully remove the cap strips from the Buffer Side of the Plated (clear frame) and slowly pipet out the analysis samples from the wells taking care not to touch or puncture the membranes.

Samples will include control at 4 C and stability at 37 C samples in PBS and plasma.

MS Analysis:
Prepare standard range 5, 10, 50, 100, 500 and 1000 ng/mL in Plasma
Pipet 10 µL each of standard and sample into 40 µL of blank buffer/blank plasma them (ratio: 1 plasma/4 DPBS), mix them.
Add 200 µL of Is (internal standard) in ACN, mix well.
Centrifuge the samples and transfer supernatant solution for LC/MS analysis.

The Cell Assay Protocol

The cellular assay provides information about the antineoplastic activity of the compounds of the invention. The compounds are tested against cultured cancer cells to determine whether or not the compounds of the invention are capable of intersecting with cancer cells to minimize or eliminate such cells. The assay involves establishing colonies of such cells and then treating them with the test compound under specified conditions and analysis regime to determine results.

Day 1, Cell Plating to Establish Colonies of Cancer Cells
Cell Plating:
Seed cells ~16 hrs prior to compound treatment
Plate 25 µL of A549 cells in every well of 384-well plate using multidrop.
Two (2) black plates for IF at 2500 cells/well
Let plate sit at room temp for 10-15 minutes prior to putting in incubator to allow cells to stick in middle of plate.
One (1) white plate for viability at 500 cells/well.

Day 2 Treatment of Cultured Cells with Test Compounds
Treat Cells:
Serial dilute compounds with a 10 point 2-fold serial dilution in DMSO to make 250× stock compound solution
Dilute compounds 1:125 in cell culture media to make a 2× solution Add 25 µl of dilution compounds to cell plates in well duplicates
Put cells back in incubator (6 hr incubation for black plates, 72 hr incubation for white plates).

Fix/Stain Black Plates:
Incubate cells in black plates with compound at 37 degC for 6 hrs.
add 15 µL of 16% Paraformaldehyde (PFA) directly into media of each well,
incubate at room temp for 5 min, flick plate and wash in 50 µL of PBS
block in 50 µL of Blocking Buffer for 30 minutes (can go up to several hours)
Blocking buffer: 1×PBS, 1% BSA, 0.3% Triton-X100, Hoechst (1:10,000)
incubate in 25 µL of primary antibody in blocking buffer at 4 degC over night Primary Antibodies:
Plate A K48-Ub 1:20,000 (millipore 05-1307 Lot 2049282)
Rabbit
CHOP/Gadd153 1:2,000 (SC-7351) Mouse
Plate B P53 1:2,000 (SC-6243) Rabbit
p62/SQSTM1 1:2,000 (SC-28359) Mouse
overnight at 4 degC Secondary Antibodies:
AlexaFluor488 Goat anti-Rabbit 1:2,000 (Life Tech A11008)
AlexaFluor555 Goat anti-Mouse 1:2,000 (Life Tech A21422)

Day 3/4
Black Plate Staining (cont):
wash black plates 3× in 50 µL PBS (~5 min each)
incubate in 25 µl of secondary antibody (1:2,000) in blocking buffer for 1-2 hrs at room temp (alexafluor488-anti-Rabbit/alexafluor555-anti-Mouse)
wash 4× in 50 µL PBS (~5 min each)
leave plates in PBS for imaging
clean bottom of plates with 70% EtOH Imaging:
Image plates in high content microscope with 405 nm, 488 nm and 555 nm filters Data Analysis:

Nuclear counts and cellular intensities of each markers are measured using Hoechst as a nuclear marker with an automated image analysis protocol using Matlab software (Math Works)

Day 5

Viability Assay:

Thaw an aliquot of frozen cell titer glo (Promega G7572) at room temperature.

Add 45 mL of NaCl/PBS solution to 5 ml of cell titer glo (10×).

Remove white plates from incubator, leave at room temp for 30 minutes.

Add 25 µl of diluted cell titer glo to each well.

Shake plate for >1 minute.

Incubate plate for >5 minutes to stabilize luminescence.

Luminescence is stable for up to 3 hours.

Read luminescence on plate reader

The results are reported on the following Table I for Examples A-EE and the E1-E4 compounds as 50 percent Inhibitory concentration at candidate doses of less than 1 µM, less than 3 µM and less than 10 µM for both of the K48 antibody and the p53 (CTG) antibody assays

TABLE I

Biological Results of Inhibition of p97 Activity

| Example/compound | p97 IC$_{50}$<br>**** <30 nM<br>*** <100 nM<br>** <300 nM<br>* <1000 nM | A549 CTG IC$_{50}$<br>*** <1 uM<br>** <3 uM<br>* <10 uM | A549 K48 IC$_{50}$<br>*** <1 uM<br>** <3 uM<br>* <10 uM |
|---|---|---|---|
| 1/A | *** | ** | * |
| 2/B | **** | *** | ** |
| 12/F | **** | *** | ** |
| 3/C | **** | *** | *** |
| 4/D | **** | ** | ** |
| 13/G | **** | ** | *** |
| 5/E | **** | ** | ** |
| 18/K | ** | * | ** |
| 19/L | *** | ** | ** |
| 22/N | ** | ND | ND |
| 38/DD |  | ND | ND |
| 37/CC | * | * | ** |
| 25/Q | * |  |  |
| 28/T | *** | * | ** |
| 23/O | * | ND | ND |
| 21/M | * |  |  |
| 24/P | ** | * | * |
| 20/K |  | ND | ND |
| 10/E5 | *** | * | * |
| 16/J |  |  |  |
| 36/BB | *** | * | * |
| 27/S | **** | ** | ** |
| 26/R | *** | ** | ** |
| 7/E2 | **** | ** | ** |
| 8/E3 | **** | ** | *** |
| 15/I | **** | ** | ** |
| 35/AA | *** | * | * |
| 34/Z | **** | ** | ** |
| 14/H |  | ND | ND |
| 30/V | *** | ** | ** |
| 29/U | *** | ** | *** |
| 39/EE | * | ND | ND |
| 9/E4 | **** | ** | ** |
| 33/Y | **** | * | ** |
| 6/E1 | **** | *** | *** |
| 31/W | * | ND | ND |
| 32/X | ** | ND | ND |
| 17/JJ | * | ND | ND |
| 11/E6 | ** | ** | ** |

Table II set forth below presents the results of the Preliminary Biological Assays including p97 cell based assay, the cultured cell assay, the absorption assay, the stability assay and the nonspecific binding assay conducted upon compounds of the invention.

TABLE II

Results of Preliminary Assays

| Example/Compound | R1 | R2 | p97 IC$_{50}$ µM | Cell Titre Glow Assay IC$_{50}$ µM | K48 poly-Ubiquitin Accumulation |
|---|---|---|---|---|---|
| 1/A | Me | H | 0.042 | 2.01 | 3 |
| 2/B | H | Me | 0.022 | 0.97 | 1.6 |
| 3/C | H | OMe | 0.007 | 0.467 | 0.89 |
| 5/E | H | Cl | 0.012 | 1.79 | 1.4 |
| 12/F | H | iPr | 0.009 | 0.73 | 0.64 |

Summary Statements

The inventions, examples, biological assays and results described and claimed herein have may attributes and embodiments include, but not limited to, those set forth or described or referenced in this application.

All patents, publications, scientific articles, web sites and other documents and references mentioned herein are indicative of the levels of skill of those skilled in the art to which the invention pertains, and each such referenced document and material is hereby incorporated by reference to the same extent as if it had been incorporated verbatim and set forth in its entirety herein. The right is reserved to physically incorporate into this specification any and all materials and information from any such paten, publication, scientific article, web site, electronically available information, text book or other referenced material or document.

The written description of this patent application includes all claims. All claims including all original claims are hereby incorporated by reference in their entirety into the written description portion of the specification and the right is reserved to physically incorporate into the written description or any other portion of the application any and all such claims. Thus, for example, under no circumstances may the patent be interpreted as allegedly not providing a written description for a claim on the assertion that the precise wording of the claim is not set forth in haec verba in written description portion of the patent. All features disclosed in this specification may be combined in any order and in any combination with any of the formulas I, II and/or IA-IY.

While the invention has been described in conjunction with the detailed description thereof, the foregoing description is intended to illustrate and not limit the scope of the invention, which is defined by the scope of the appended claims. Thus, from the foregoing, it will be appreciated that, although specific nonlimiting embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred nonlimiting embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in nonlimiting embodiments or examples of the present invention, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed Thus, it will be understood that although the present invention has been specifically disclosed by various non-limiting embodiments and/or preferred nonlimiting embodiments and optional features, any and all modifications and variations of the concepts herein disclosed that may be resorted to by those skilled in the art are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise. Also, the term and/or includes both arrangements, for example, "X and/or Y" means "X" or "Y" and both of "X" and "Y". The letter "s" following a noun designates both the plural and singular forms of that noun.

In addition, where features or aspects of the invention are described in terms of Markush groups, it is intended, and those skilled in the art will recognize, that the invention embraces and is also thereby described in terms of any individual member and any subgroup of members of the Markush group, and the right is reserved to revise the application or claims to refer specifically to any individual member or any subgroup of members of the Markush group.

What is claimed is:

1. A monocyclic pyrimidine compound of Formula IIE, IIK or IIP having a pyrimidine scaffold and a benzimidazole, 1-indole or 3-indole group bound to the P2 position of the scaffold:

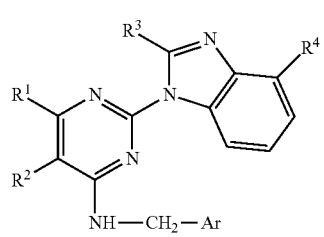

IIE

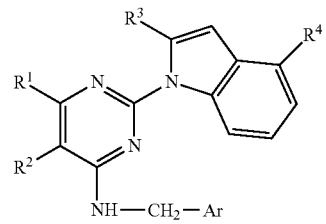

IIK

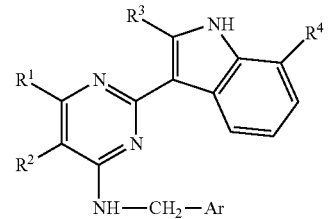

IIP

Wherein:
R$^1$ and R$^2$ are each independently selected from the group consisting of hydrogen, halogen, straight, branched or cyclic alkyl of 1 to 6 carbons, carboxylic acid, carboxyl ester with the ester group being straight, branched or cyclic alkyl of 1 to 6 carbons, N-alkylamino methyl with the alkyl group being straight, branched or cyclic of 1 to 6 carbons, sulfonic acid, sulfonyl ester with the ester group being straight, branched or cyclic alkyl of 1 to 6 carbons, sulfonamide, amine (NH$_2$), mono, di or trialkyl amine with the alkyl being straight, branched or cyclic of 1 to 6 carbons, nitrile, carboxamide, N-alkyl carboxamide of 1 to 6 carbons in the straight, branched or cyclic alkyl group, perfluoroalkyl of 1 to 3 carbons, straight, branched or cyclic alkoxy of 1 to 6 carbons;

Each R$^3$ is independently selected from the group consisting of hydrogen, halogen, straight, branched or cyclic alkyl of 1 to 6 carbons, carboxylic acid, carboxyl ester with the ester group being straight, branched or cyclic alkyl of 1 to 6 carbons, N-alkylamino methyl with the alkyl group being straight, branched or cyclic of 1 to 6 carbons, sulfonic acid, sulfonyl ester with the ester group being straight, branched or cyclic alkyl of 1 to 6 carbons, sulfonamide, amine (NH$_2$), mono, di or trialkyl amine with the alkyl being straight, branched or cyclic of 1 to 6 carbons, nitrile, carboxamide, N-alkyl carboxamide of 1 to 6 carbons in the straight, branched or cyclic alkyl group, perfluoroalkyl of 1 to 3 carbons, straight, branched or cyclic alkoxy of 1 to 6 carbons;

R$^4$ is selected from the group consisting of carboxylic acid, carboxyl ester with the ester group being straight, branched or cyclic alkyl of 1 to 6 carbons, N-alkylaminomethyl with the alkyl group being straight, branched or cyclic of 1 to 6 carbons, sulfonic acid, sulfonyl ester with the ester group being straight, branched or cyclic alkyl of 1 to 6 carbons, sulfonamide, nitrile, carboxamide, N-alkyl carboxamide of 1 to 6 carbons in the straight, branched or cyclic alkyl group, CH$_2$NH$_2$ or CH$_2$OH;

Ar is unsubstituted phenyl or fluorophenyl.

2. A compound of claim 1 wherein R$^4$ is CN, CO$_2$H, CONH$_2$, CH$_2$NH$_2$ or CH$_2$OH.

3. A compound of claim 1 wherein R$^4$ is CONH$_2$ or CH$_2$NH$_2$.

4. A compound of claim 1 wherein R$^4$ is carboxamide (CONH$_2$).

5. A monocyclic pyrimidine compound of claim 1 having the IUPAC name:

1-(4-((3-fluorobenzyl)amino)-5-(2-(methylamino)ethyl)pyrimidin-2-yl)-2-methyl-1H-indole-4-carboxamide; 1-(4-((3-fluorobenzyl)amino)-5-(methoxymethyl)pyrimidin-2-yl)-2-methyl-1H-indole-4-carboxamide; 1-(4-((3-fluorobenzyl)amino)-5-(oxetan-3-yl)pyrimidin-2-yl)-2methyl-1H-indole-4-carboxamide; 1-(4-((3-fluorobenzyl)amino)-5-(piperidin-4-yl)pyrimidin-2-yl)-2-methyl-1H-indole-4-carboxamide; 1-(4-((3-fluorobenzyl)amino)-5-(pyrrolidin-2-yl)pyrimidin-2-yl)-2-methyl-1H-indole-4-carboxamide; 1-(4-((3-fluorobenzyl)amino)-5-(tetrahydro-2H-pyran-4-yl)pyrimidin-2-yl)-2-methyl-1H-indole-4-carboxamide; 1-(4-((3-fluorobenzyl)amino)-5-(tetrahydrofuran-2-yl)pyrimidin-2-yl)-2-methyl-1H-indole-4-carboxamide; 1-(4-((3-fluorobenzyl)amino)-5-(trifluoromethyl)pyrimidin-2-yl)-2-methyl-1H-indole-4-carboxamide; 1-(4-((3-fluorobenzyl)amino)-5-isopropoxy-pyrimidin-2-yl)-2-methyl-1H-indole-4-carboxamide; 1-(4-((3-fluorobenzyl)amino)-5-methoxy-6-methylpyrimidin-2-yl)-2-methyl-1H-indole-4-carboxamide; 1-(4((3-fluorobenzyl)amino)-5-morpholino-pyrimidin-2-yl)-2-methyl-1H-indole-4-carboxamide; 1-(4-(benzylamino)-5-(1 -hydroxyethyl)pyrimidin-2-yl)-2-methyl-1H-indole-4-carboxamide; 1-(4-(benzylamino)-5-(2-(methylamino)ethyl)pyrimidin-2-yl)-2-methyl-1H-indole-4-carboxamide; 1-(4-(benzylamino)-5-(2-methoxyethoxy)pyrimidin-2-yl)-2-methyl-1H-indole-4-carboxamide; 1-(4-(benzylamino)-5-(2-methoxyethyl)pyrimidin-2-yl)-2-methyl-1H-indole-4-carboxamide; 1-(4-(benzylamino)-5-(dimethylamino)-6-methylpyrimidin-2-yl)-2-methyl-1H-indole-4-carboxamide; 1-(4-(benzylamino)-5-(dimethylamino)pyrimidin-2-yl)-2-methoxy-1H-benzo(d)imidazole-4-carboxamide; 1-(4-(benzylamino)-5-(dimethylamino)pyrimidin-2-yl)-2-methyl-1H-indole-4-carboxamide; 1-(4-(benzylamino)-5-(methoxymethyl)pyrimidin-2-yl)-2-methyl-1H-indole-4-carboxamide; 1-(4-(benzylamino)-5-(morpholinomethyl)pyrimidin-2-yl)-2-methyl-1H-indole-4-carboxamide; 1-(4-(benzylamino)-5-(oxetan-3-yl)pyrimidin-2-yl)-2-methyl-1H-indole-4-carboxamide; 1-(4-(benzylamino)-5-(piperidin-4-yl)pyrimidin-2-yl)-2-methyl-1H-indole-4-carboxamide; 1-(4-(benzylamino)-5-(pyrrolidin-2-yl)pyrimidin-2-yl)-2-methyl-1H-indole-4-carboxamide; 1-(4-(benzylamino)-5-(trifluoromethyl)pyrimidin-2-yl)-2-methyl-1H-indole-4-carboxamide; 1-(4-(benzylamino)-5-carbamoylpyrimidin-2-yl)-2-methoxy-1H-benzo(d)imidazole-4-carboxamide; 1-(4-(benzylamino)-5-carbamoyl-pyrimidin-2-yl)-6-fluoro-2-methyl-1H-indole-4-carboxamide; 1-(4-(benzylamino)-5-chloropyrimidin-2-yl)-2-methyl-1H-indole-4-carboxamide; 1-(4-(benzylamino)-5-chloropyrimidin-2-yl)-6-fluoro-2-methyl-1H-indole-4-carboxamide; 1-(4-(benzylamino)-5-ethoxy-6-methylpyrimidin-2-yl)-2-methoxy-1H-1-benzo(d)imidazole-4-carboxamide; 1-(4-(benzylamino)-5-ethoxypyrimidin-2-yl)-2-methoxy-1H-benzo(d)imidazole-4-carboxamide; 1-(4-(benzylamino)-5-ethoxypyrimidin-2-yl)-6-fluoro-2-methyl-1H-indole-4-carboxamide; 1-(4-(benzylamino)-5-ethylpyrimidin-2-yl)-2-methoxy1H-benzo(d)imidazole-4-carboxamide; 1-(4-(benzylamino)-5-ethylpyrimidin-2-yl)-2-methyl-1H-benzo(d)imidazole-4-carboxamide; 1-(4-(benzylamino)-5-ethylpyrimidin-2-yl)-2-methyl-1H-indole-4-carboxamide; 1-(4-(benzylamino)-5-ethylpyrimidin-2-yl)-6-fluoro-2-methyl-1H-indole-4-carboxamide; 1-(4-(benzylamino)-5-methoxy-6-methylpyrimidin-2-yl)-2-methoxy-1H-benzo(d)imidazole-4-carboxamide; 1-(4-(benzylamino)-5-methoxy-6-methylpyrimidin-2-yl)-2-methyl-1H-benzo(d)imidazole-4-carboxamide; 1-(4-(benzylamino)-5-methoxy-6-methylpyrimidin-2-yl)-2-methyl-1H-indole-4-carboxamide; 1-(4-(benzylamino)-5-methoxypyrimidin-2-yl)-2-methoxy-1H-benzo(d)imidazole-4-carboxamide; 1-(4-(benzylamino)-5-methoxypyrimidin-2-yl)-2-methyl-1H-benzo(d)imidazole-4-carboxamide; 1-(4-(benzylamino)-5-methoxypyrimidin-2-yl)-2-methyl-1H-indole-4-carboxamide; 1-(4-(benzylamino)-5-methoxypyrimidin-2-yl)-6-fluoro-2-methyl-1H-indole-4-carboxamide; 1-(4-(benzylamino)-5-methyl-6-(trifluoromethyl)pyrimidin-2-yl)-2-methyl-1H-indole-4-carboxamide; 1-(4-(benzylamino)-5-methylpyrimidin-2-yl)-2-methyl-1H-benzo(d)imidazole-4-carboxamide; 1-(4-(benzylamino)-5-methylpyrimidin-2-yl)-2-methyl-1H-indole-4-carboxamide; 1-(4-(benzylamino)-5-methylpyrimidin-2-yl)-6-fluoro-2-methyl-1H-indole-4-carboxamide; 1-(4-(benzylamino)-6-(dimethylamino)-5-methylpyrimidin-2-yl)-2-methyl-1H-indole-4-carboxamide; 1-(4-(benzylamino)-6-fluoro-5-methylpyrimidin-2-yl)-2-methyl-1H-indole-4-carboxamide; 1-(4-(benzylamino)-6-fluoro-5-methylpyrimidin-2-yl)-6-fluoro-2-methyl-1H-indole-4-carboxamide; 1-(4-(benzylamino)-6-methoxy-5-methylpyrimidin-2-yl)-2-methyl-1H-indole-4-carboxamide; 1-(4-(benzylamino)-6-methylpyrimidin-2-yl)-2-methyl-1H-indole-4-carboxamide; 1-(5-(1-aminoethyl)-4-((3-fluorobenzyl)amino)pyrimidin-2-yl)-2-methyl-1H-indole-4-carboxamide; 1-(5-(1-aminoethyl)-4-(benzylamino)pyrimidin-2-yl)-2-methyl-1H-indole-4-carboxamide; 1-(5-(2-aminoethoxy)-4-(benzylamino)pyrimidin-2-yl)-2-methyl-1H-indole-4-carboxamide; 1-(5-(2-aminoethoxy)-4-(benzylamino)pyrimidin-2-yl)-6-fluoro-2-methyl-1H-indole-4-carboxamide; 1-(5-(2-aminoethyl)-4-(3-fluorobenzylamino)pyrimidin-2-yl)-2-methyl-1H-indole-4-carboxamide; 1-(5-(acetamidomethyl)-4-(benzylamino)pyrimidin-2-yl)-2-methyl-1H-indole-4-carboxamide; 1-(5-(aminomethyl)-4-((3-fluorobenzyl)amino)pyrimidin-2-yl)-2-methyl-1H-indole-4-carboxamide; 1-(5-(aminomethyl)-4-(benzylamino)pyrimidin-2-yl)-2-methyl-1H-indole-4-carboxamide; 1-(5-(azetidin-3-yl)-4-((3-fluorobenzylamino)pyrimidin-2-yl)-2-methyl-1H-indole-4-carboxamide; 1-(5-(azetidin-3-yl)-4-(benzylamino)pyrimidin-2-yl)-2-methyl-1H-indole-4-carboxamide; 1-(5-amino-4-(benzylamino)pyrimidin-2-yl)-2-methyl-1H-indole-4-carboxamide; 1-(6-(benzylamino)pyridin-2-yl)-2-methyl-1H-indole-4-carboxamide; 2-(4-(aminomethyl)-1H-indazol-1-yl)-N-benzyl-5-methoxypyrimidin-4-amine; 2-(4-(aminomethyl)-2-methyl-1H-indol-1-yl)-N-benzyl-5,6-dimethylpyrimidin-4-amine; 2-(4-(aminomethyl)-2-methyl-1H-indol-1H-yl)-N-benzyl-5-methoxy-pyrimidin-4-amine; 2-(4-(aminomethyl)-2-methyl-1H-indol-1-yl)-N-benzyl-5-methyl-pyrimidin-4-amine; 2-(4-(aminomethyl)-2-methyl-1H-indol-3-yl)-N-benzyl-5-methoxypyrimidin-4-amine; 2-(aminomethyl)-1-(4-((3-fluorobenzyl)amino)-5-ethylpyrimidin-2-yl)-1H-indole4-carboxamide; 2-(aminomethyl)-1-(4-((3- fluorobenzyl)amino)-5-isopropylpyrimidin-2-yl)-1H-indole-4-carboxamide; 2-(aminomethyl)-1-(4-((3-fluorobenzyl)amino)-5-methoxypyrimidin-2-yl)-1H-indole-4-carboxamide; 2-(aminomethyl)-1-(4-((3-fluorobenzyl)amino)-5-methylpyrimidin-2-yl)-1H-indole-4-carboxamide; 2-(aminomethyl)-1-(4-(benzylamino)-5-ethylpyrimidin-2-yl)-1H-indole-4-carboxamide; 2-(aminomethyl)-1-(4-(benzylamino)-5-methoxypyrimidin-2-yl)-1H-indole-4-carboxamide; 2-(aminomethyl)-1-(4-(benzylamino)-5-methylpyrimidin-2-yl)-1H-indole-4-carboxamide; 2-(aminomethyl)-3-(4-(benzylamino)-5-ethylpyrimidin-2-yl)-1H-indole-4-carboxamide; 2-(aminomethyl)-3-(4-(benzylamino)-5-methoxypyrimidin-2-yl)-1H-indole-4-carboxamide; 3-(4-(benzylamino)-5-(2-methoxyethoxy)pyrimidin-2-yl)-2-methyl-1H-indole-4-carboxamide; 3-(4-(benzylamino)-5-(dimethylamino)-6-methylpyrimidin-2-yl)-1H-indole-4-carboxamide; 3-(4-(benzylamino)-5-(methoxymethyl)pyrimidin-2-yl)-2-methyl-1H-indole-4-carboxamide; 3-(4-(benzylamino)-5-(trifluoromethyl)pyrimidin-2-yl)-2-methyl-1H-indole-4-carboxamide; 3-(4-(benzylamino)-5-carbamoylpyrimidin-2-yl)-2-methyl-1H-indole-4-carboxamide; 3-(4-(benzylamino)-5-chloropyrimidin-2-yl)-2-methyl-1H-indole-4-carboxamide; 3-(4-(benzylamino)-5-ethoxypyrimidin-2-yl)-2-methyl-1H-indole-4-carboxamide; 3-(4-(benzylamino)-5-ethylpyrimidin-2-yl)-2-methyl-1H-indole-4-carboxamide; 3-(4-(benzylamino)-5-methoxy-6-methylpyrimidin-2-yl)-1H-indole-4-carboxamide; 3-(4-(benzylamino)-5-methyl-6-((methylamino)methyl)pyrimidin-2-yl)-2-methyl-1H-indole-4-carboxamide; 3-(4-(benzylamino)-6-methoxy-5-methylpyrimidin-2-yl)-2-methyl-1H-indole-4-carboxamide; 3-(4-(benzylamino)-6-methylpyrimidin-2-yl)-2-methyl-1H-indole-4-carboxamide; 3-(5-(1-aminoethyl)-4-(benzylamino)pyrimidin-2-yl)-2-methyl-1H-indole-4-carboxamide; 3-(5-(aminomethyl)-4-(benzylamino)pyrimidin-2-yl)-2-methyl-1H-indole4-carboxamide; 3-(5-amino-4-(benzylamino)pyrimidin-2-yl)-2-methyl-1H-indole-4-carboxamide; [4-(benzylamino)-5-methoxypyrimidin-2-yl]-2-methyl-1H-indole-4-carboxamide; 1-(4-((3-fluorobenzyl)amino)-5-((methylamino)methyl)pyrimidin-2-yl)-2-methyl-1H-indole-4-carboxamide; 1-(4-((3-fluorobenzyl)amino)-5-(2-methoxyethoxy)pyrimidin-2-yl)-2-methyl-1H-indole-4-carboxamide; 1-(4-((3-fluorobenzyl)amino)-5-(2-methoxyethyl)pyrimidin-2-yl)-2-methyl-1H-indole-4-carboxamide; 1-(4-((3-fluorobenzyl)amino)-5-(methylsulfonyl)pyrimidin-2-yl)-2-methyl-1H-indole-4-carboxamide; 1-(4((3-fluorobenzyl)amino)-5-(morpholinomethyl)pyrimidin-2-yl)-2-methyl-1H-indole-4-carboxamide; 1-(4-((3-fluorobenzyl)amino)-5-isopropoxypyrimidin-2-yl)-2-methoxy-1H-benzo[d]imidazole-4-carboxamide; 1-4-((3-fluorobenzyl)amino)-5-isopropyl-6-methylpyrimidin-2-yl)-2-methoxy-1H-benzo[d]imidazole-4-carboxamide; 1-(4-((3-fluorobenzyl)amino)-5-isopropyl-6-methylpyrimidin-2-yl)-2-methyl-1H-benzo[d]imidazole-4-carboxamide; 1-(4-((3-fluorobenzyl)amino)-5-isopropyl-6-methylpyrimidin-2-yl)-2-methyl-1H-indole-4-carboxamide; 1-(4-((3-fluorobenzyl)amino)-5-isopropylpyrimidin-2-yl)-2-methoxy-1H-benzo[d]imidazole-4-carboxamide; 1-(4-((3-fluorobenzyl)amino)-5-isopropylpyrimidin-2-yl)-1H-benzo[d]imidazole-4-carboxamide; 1-(4-((3-fluorobenzyl)amino)-5-isopropylpyrimidin-2-yl)-2-methyl-1H-indole-4-carboxamide; 1-(4((3-fluorobenzyl)amino)-5-methoxy-6-((methylamino)methyl)pyrimidin-2-yl)-2-methyl-1H-indole-4-carboxamide; 1-(4-((3-fluorobenzyl)amino)-5-methoxy-6-methylpyrimidin-2-yl)-2-methyl-1H-benzo[d]imidazole-4-carboxamide; 1-(4-((3-fluorobenzyl)amino)-5-methoxypyrimidin-2-yl)-2-methoxy-1H-benzo[d]imidazole-4-carboxamide; 1-4-((3-fluorobenzyl)amino)-5-methyl-6-((methylamino)methyl)pyrimidin-2-yl)-2-methyl-1H-indole-4-carboxamide; 1-(4-((3-fluorobenzyl)amino)-6-methoxy-5-methylpyrimidin-2-yl)-2-methyl-1H-indole-4-carboxamide; 1-(4-(benzylamino)-5-((dimethylamino)methyl)pyrimidin-2-yl)-2-methyl-1H-indole-4-carboxamide; 1-(4-(benzylamino)-5-((dimethylamino)methyl)pyrimidin-2-yl)-6-fluoro-2-methyl-1H-indole-4-carboxamide; 1-(4-(benzylamino)-5-((methylamino)methyl)pyrimidin-2-yl)-2-methyl-1H-indole-4-carboxamide; 1-(4-(benzylamino)-5-((methylamino)methyl)pyrimidin-2-yl)-6-fluoro-2-methyl-1H-indole-4-carboxamide; 1-(4-(benzylamino)-5-(2-(methylamino)ethyl)pyrimidin-2-yl)-6-fluoro-2-methyl-1H-indole-4-carboxamide; 1-(4-(benzylamino)-5-(dimethylamino)-6-methylpyrimidin-2-yl)-2-methoxy-1H-benzo[d]imidazole-4-carboxamide; 1-(4-(benzylamino)-5-(dimethylamino)-6-methylpyrimidin-2-yl)-2-methyl-1H-benzo[d]imidazole-4-carboxamide; 1-(4-(benzylamino)-5-(dimethylamino)-6-methylpyrimidin-2-yl)-6-fluoro-2-methyl-1H-indole-4-carboxamide; 1-(4-(benzylamino)-5-(methylsulfonyl)pyrimidin-2-yl)-2-methyl-1H-indole-4-carboxamide; 1-(4-(benzylamino)-5-(morpholinomethyl)pyrimidin-2-yl)-6-fluoro-2-methyl-1H-indole-4-carboxamide; 1-(4-(benzylamino)-5-(tetrahydro-2H-pyran-4-yl)pyrimidin-2-yl)-2-methyl-1H-indole-4-carboxamide; 1-(4-(benzylamino)-5-(tetrahydro-2H-pyran-4-yl)pyrimidin-2-yl)-6-fluoro-2-methyl-1H-indole-4-carboxamide; 1-(4-(benzylamino)-5-(tetrahydrofuran-2-yl)pyrimidin-2-yl)-2-methyl-1H-indole-4-carboxamide; 1-(4-(benzylamino)-5-carbamoylpyrimidin-2-yl)-2-methyl-1H-indole-4-carboxamide; 1-(4-(benzylamino)-5-ethoxypyrimidin-2-yl)-2-methyl-1H-indole-4-carboxamide; 1-(4-(benzylamino)-5-isopropoxy-6-methylpyrimidin-2-yl)-2-methoxy-1H-benzo[d]imidazole-4-carboxamide; 1-(4-(benzylamino)-5-isopropoxypyrimidin-2-yl)-2-methoxy-1H-benzo[d]imidazole-4-carboxamide; 1-(4-(benzylamino)-5-isopropoxypyrimidin-2-yl)-2-methyl-1H-indole-4-carboxamide; 1-(4-(benzylamino)-5-isopropyl-6-methylpyrimidin-2-yl)-2-methoxy-1H-benzo[d]imidazole-4-carboxamide; 1-(4-(benzylamino)-5-isopropyl-6-methylpyrimidin-2-yl)-2-methyl-1H-benzo[d]imidazole-4-carboxamide; 1-(4-(benzylamino)-5-isopropyl-6-methylpyrimidin-2-yl)-2-methyl-1H-indole-4-carboxamide; 1-(4-(benzylamino)-5-isopropyl-6-methylpyrimidin-2-yl)-6-fluoro-2-methyl-1H-indole-4-carboxamide; 1-(4-(benzylamino)-5-isopropylpyrimidin-2-yl)-2-methyl-1H-benzo[d]imidazole-4-carboxamide; 1-(4-(benzylamino)-5-isopropylpyrimidin-2-yl)-2-methyl-1H-indole-4-carboxamide; 1-(4-(benzylamino)-5-methoxy-6-((methylamino)methyl)pyrimidin-2-yl)-2-methyl-1H-indole-4-carboxamide; 1-(4-(benzylamino)-5-methoxy-6-((methylamino)methyl)pyrimidin-2-yl)-6-fluoro-2-methyl-1H-indole-4-carboxamide; 1-(4-(benzylamino)-5-methyl-6-

((methylamino)methyl)pyrimidin-2-yl)-2-methyl-1H-indole-4-carboxamide; 1-(4-(benzylamino)-5-methyl-6-((methylamino)methyl)pyrimidin-2-yl)-6-fluoro-2-methyl-1H-indole-4-carboxamide; 1-(4-(benzylamino)-5-methyl-6-(trifluoromethyl)pyrimidin-2-yl)-6-fluoro-2-methyl-1H-indole-4-carboxamide; 1-(4-(benzylamino)-5-morpholinopyrimidin-2-yl)-2-methyl-1H-indole-4-carboxamide; 1-(4-(benzylamino)-5-morpholinopyrimidin-2-yl)-6-fluoro-2-methyl-1H-indole-4-carboxamide; 1-(4-(benzylamino)-6-(dimethylamino)-5-methylpyrimidin-2-yl)-6-fluoro-2-methyl-1H-indole-4-carboxamide; 1-(4-(benzylamino)-6-methyl-5-morpholinopyrimidin-2-yl)-2-methyl-1H-indole-4-carboxamide; 1-(4-(benzylamino)-6-methyl-5-morpholinopyrimidin-2-yl)-6-fluoro-2-methyl-1H-indole-4-carboxamide; 1-(4-(benzylamino)-6-methylpyrimidin-2-yl)-6-fluoro-2-methyl-1H-indole-4-carboxamide; 1-(4-(dimethylamino)-6-((3-fluorobenzyl)amino)-5-methylpyrimidin-2-yl)-2-methyl-1H-indole-4-carboxamide; 1-(4-fluoro-6-((3-fluorobenzyl)amino)-5-methylpyrimidin-2-yl)-2-methyl-1H-indole-4-carboxamide; 1-(5-((dimethylamino)methyl)-4-((3-fluorobenzyl)amino)pyrimidin-2-yl)-2-methyl-1H-indole-4-carboxamide; 1-(5-(acetamidomethyl)-4-((3-fluorobenzyl)amino)pyrimidin-2-yl)-2-methyl-1H-indole-4-carboxamide; 1-(5-(dimethylamino)-4-((3-fluorobenzyl)amino)-6-methylpyrimidin-2-yl)-2-methoxy-1H-benzo[d]imidazole-; 4-carboxamide; 1-(5-(dimethylamino)-4-((3-fluorobenzyl)amino)-6-methylpyrimidin-2-yl)-2-methyl-1H-benzo[d]imidazole-4-carboxamide; 1-(5-(dimethylamino)-4-((3-fluorobenzyl)amino)-6-methylpyrimidin-2-yl)-2-methyl-1H-indole-4-carboxamide; 1-(5-(dimethylamino)-4-((3-fluorobenzyl)amino)pyrimidin-2-yl)-2-methoxy-1H-benzo[d]imidazole-4-carboxamide; 1-(5-(dimethylamino)-4-((3-fluorobenzyl)amino)pyrimidin-2-yl)-2-methyl-1H-benzo[d]imidazole-4-carboxamide; 1-(5-(dimethylamino)-4-((3-fluorobenzyl)amino)pyrimidin-2-yl)-2-methyl-1H-indole-4-carboxamide; 1-(5-carbamoyl-4-((3-fluorobenzyl)amino)pyrimidin-2-yl)-2-methyl-1H-indole-4-carboxamide; 1-(5-ethoxy-4-((3-fluorobenzyl)amino)-6-methylpyrimidin-2-yl)-2-methoxy-1H-benzo[d]imidazole-4-carboxamide; 1-(5-ethoxy-4-((3-fluorobenzyl)amino)pyrimidin-2-yl)-2-methoxy-1H-benzo[d]imidazole-4-carboxamide; 1-(5-ethoxy-4-((3-fluorobenzyl)amino)pyrimidin-2-yl)-2-methyl-1H-indole-4-carboxamide; 1-(5-ethyl-4-((3-fluorobenzyl)amino)pyrimidin-2-yl)-2-methoxy-1H-benzo[d]imidazole-4-carboxamide; 1-(5-ethyl-4-((3-fluorobenzyl)amino)pyrimidin-yl)-2-methyl-1H-benzo[d]imidazole-4-carboxamide; 1-(6-(benzylamino)pyridin-2-yl)-2-methoxy-1H-benzo[d]imidazole-4-carboxamide; 2-(4-(aminomethyl)-2-methyl-1H-indol-1-yl)-N-benzyl-5-isopropylpyrimidin-4-amine; 2-(aminomethyl)-1-(4-(benzylamino)-5-isopropylpyrimidin-2-yl)-1H-indole-4-carboxamide; 2-(aminomethyl)-1-(4-(benzylamino)-5-isopropylpyrimidin-2-yl)-6-fluoro-1H-indole-4-carboxamide; 2-(aminomethyl)-3-(4-(benzylamino)-5-isopropylpyrimidin-2-yl)-1H-indole-4-carboxamide; 3-(4-(benzylamino)-5-(methylsulfonyl)pyrimidin-2-yl)-2-methyl-1H-indole-4-carboxamide; 3-(4-(benzylamino)-5,6-dimethylpyrimidin-2-yl)4H-indole-4-carboxamide; 3-(4-(benzylamino)-5-isopropoxypyrimidin-2-yl)-2-methyl-1H-indole-4-carboxamide; 3-(4-(benzylamino)-5-isopropylpyrimidin-2-yl)-2-methyl-1H-indole-4-carboxamide; 3-(5-(acetamidomethyl)-4-(benzylamino)pyrimidin-2-yl)-2-methyl-1H-indole-4-carboxamide.

6. A pharmaceutical composition comprising a pharmaceutically acceptable carrier and a compound of claim 1.

7. A pharmaceutical composition according to claim 6 wherein the compound is present in an amount which is effective as an inhibitor of the AAA family member Valosin containing protein.

8. A method of decreasing Valosin containing protein activity or degradation of a proteasome system substrate comprising administering to a patient an effective amount of a pharmaceutical composition of claim 6.

9. A method according to claim 8 wherein the patient is a human.

10. A compound according to claim 1 wherein $R^3$ is hydrogen, methyl, ethyl, methoxy or ethoxy.

11. A compound according to claim 2 wherein $R^3$ is hydrogen, methyl, ethyl, methoxy or ethoxy.

12. A compound according to claim 4 wherein $R^3$ is hydrogen, methyl, ethyl, methoxy or ethoxy.

* * * * *